(12) United States Patent
Ciccocioppo

(10) Patent No.: US 10,064,850 B2
(45) Date of Patent: Sep. 4, 2018

(54) COMPOSITIONS AND METHODS FOR PROPHYLAXIS AND TREATMENT OF ADDICTIONS

(71) Applicant: Omeros Corporation, Seattle, WA (US)

(72) Inventor: Roberto Ciccocioppo, Camerino (IT)

(73) Assignee: Omeros Corporation, Seattle, WA (US)

( * ) Notice: Subject to any disclaimer, the term of this patent is extended or adjusted under 35 U.S.C. 154(b) by 0 days.

(21) Appl. No.: 15/231,239

(22) Filed: Aug. 8, 2016

(65) Prior Publication Data

US 2017/0027920 A1 Feb. 2, 2017

Related U.S. Application Data

(63) Continuation of application No. 13/853,585, filed on Mar. 29, 2013, now abandoned, which is a continuation of application No. 12/722,429, filed on Mar. 11, 2010, now abandoned, which is a continuation-in-part of application No. 12/101,943, filed on Apr. 11, 2008, now Pat. No. 8,426,439.

(60) Provisional application No. 61/167,824, filed on Apr. 8, 2009, provisional application No. 61/159,377, filed (Continued)

(51) Int. Cl.
| | |
|---|---|
| *A61K 31/4439* | (2006.01) |
| *A61K 31/00* | (2006.01) |
| *A61K 31/137* | (2006.01) |
| *A61K 31/138* | (2006.01) |
| *A61K 31/195* | (2006.01) |
| *A61K 31/35* | (2006.01) |
| *A61K 31/4015* | (2006.01) |
| *A61K 31/4178* | (2006.01) |
| *A61K 31/445* | (2006.01) |
| *A61K 31/485* | (2006.01) |
| *A61K 31/519* | (2006.01) |
| *A61K 31/70* | (2006.01) |
| *A61K 45/06* | (2006.01) |
| *A61K 31/4184* | (2006.01) |
| *A61K 31/425* | (2006.01) |
| *A61K 31/135* | (2006.01) |
| *A61K 31/197* | (2006.01) |
| *A61K 31/426* | (2006.01) |
| *A61K 31/4748* | (2006.01) |
| *A61K 31/55* | (2006.01) |

(52) U.S. Cl.
CPC ......... *A61K 31/4439* (2013.01); *A61K 31/00* (2013.01); *A61K 31/135* (2013.01); *A61K 31/137* (2013.01); *A61K 31/138* (2013.01); *A61K 31/195* (2013.01); *A61K 31/197* (2013.01); *A61K 31/35* (2013.01); *A61K 31/4015* (2013.01); *A61K 31/4178* (2013.01); *A61K 31/4184* (2013.01); *A61K 31/425* (2013.01); *A61K 31/426* (2013.01); *A61K 31/445* (2013.01); *A61K 31/4748* (2013.01); *A61K 31/485* (2013.01); *A61K 31/519* (2013.01); *A61K 31/55* (2013.01); *A61K 31/70* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,572,912 A | 2/1986 | Yoshioka et al. | |
| 4,582,839 A | 4/1986 | Meguro et al. | |
| 4,687,777 A | 8/1987 | Meguro et al. | |

(Continued)

FOREIGN PATENT DOCUMENTS

| | | |
|---|---|---|
| CA | 2 589 393 | 12/2007 |
| CN | 1918164 A | 2/2007 |

(Continued)

OTHER PUBLICATIONS

Feldman, P. et al., "PPAR Modulators and PPAR Pan Agonists for Metabolic Diseases: The Next Generation of Drugs Targeting Peroxisome Proliferator-Activated Receptors?" *Current Topics in Medicinal Chemistry* 8:728-749, 2008.

(Continued)

*Primary Examiner* — Jeffrey S Lundgren
*Assistant Examiner* — Michael J Schmitt
(74) *Attorney, Agent, or Firm* — Marcia S. Kelbon

(57) ABSTRACT

The present invention relates to methods of treating or preventing addiction and relapse use of addictive agents, and treating or preventing addictive or compulsive behavior and relapse practice of an addictive behavior or compulsion, by administering a peroxisome proliferator-activated receptor gamma (PPARγ) agonist, alone or in combination with another therapeutic agent, such as, for example, an opioid receptor antagonist or an antidepressant, or an addictive agent, such as, for example, an opioid agonist. The present invention also includes pharmaceutical compositions for treating or preventing addiction or relapse that include a PPARγ agonist and one or more other therapeutic or addictive agents, as well as unit dosage forms of such pharmaceutical compositions, which contain a dosage effective in treating or preventing addiction or relapse. The methods and compositions of the invention are useful in the treatment or prevention of addiction to any agent, including alcohol, nicotine, marijuana, cocaine, and amphetamines, as well as compulsive and addictive behaviors, including pathological gambling and pathological overeating.

20 Claims, 32 Drawing Sheets

Related U.S. Application Data on Mar. 11, 2009, provisional application No. 60/911,201, filed on Apr. 11, 2007.

(56) References Cited

U.S. PATENT DOCUMENTS

| | | | |
|---|---|---|---|
| 4,725,610 A | 2/1988 | Meguro et al. | |
| 4,775,687 A | 10/1988 | Meguro et al. | |
| 4,812,570 A | 3/1989 | Meguro et al. | |
| 5,217,987 A * | 6/1993 | Berger .................. | A61K 31/00 514/255.04 |
| 5,965,584 A | 10/1999 | Ikeda et al. | |
| 6,011,049 A | 1/2000 | Whitcomb | |
| 6,150,383 A | 11/2000 | Ikeda et al. | |
| 6,294,580 B1 | 9/2001 | Willson et al. | |
| 6,316,465 B1 | 11/2001 | Pershadsingh et al. | |
| 6,437,143 B2 | 8/2002 | Moinet et al. | |
| 6,506,762 B1 | 1/2003 | Horvath et al. | |
| 6,582,738 B2 | 6/2003 | Gubler | |
| 6,620,830 B2 | 9/2003 | Chiang | |
| 6,794,154 B1 | 9/2004 | Yamanouchi et al. | |
| 7,037,910 B2 | 5/2006 | Ewing et al. | |
| 7,067,530 B2 | 6/2006 | Jeppesen et al. | |
| 7,141,561 B2 | 11/2006 | Schwink et al. | |
| 7,312,229 B2 | 12/2007 | Dankulich et al. | |
| 7,319,170 B2 | 1/2008 | Sahoo et al. | |
| 7,326,706 B2 | 2/2008 | Ellsworth et al. | |
| 7,335,799 B2 | 2/2008 | Dasseux et al. | |
| 7,365,064 B2 | 4/2008 | Bhuniya et al. | |
| 7,378,418 B2 | 5/2008 | Yu et al. | |
| 7,381,736 B2 | 6/2008 | Cheruvallath et al. | |
| 7,411,071 B2 | 8/2008 | Yang et al. | |
| 7,429,575 B2 | 9/2008 | Yu et al. | |
| 7,446,110 B2 | 11/2008 | Kaufman et al. | |
| 7,510,728 B2 | 3/2009 | Koike | |
| 7,517,900 B2 | 4/2009 | Pendri et al. | |
| 7,524,975 B2 | 4/2009 | Mae et al. | |
| 7,998,454 B2 | 8/2011 | Akiyama et al. | |
| 2002/0006942 A1 | 1/2002 | Davis | |
| 2002/0077320 A1 | 6/2002 | Lohray et al. | |
| 2003/0069246 A1 | 4/2003 | Darrow et al. | |
| 2003/0100587 A1 | 5/2003 | Moinet et al. | |
| 2003/0220373 A1 | 11/2003 | Jaye et al. | |
| 2004/0024006 A1 | 2/2004 | Simon | |
| 2004/0028735 A1 | 2/2004 | Kositprapa | |
| 2004/0077525 A1 | 4/2004 | Chapman et al. | |
| 2004/0096499 A1 | 5/2004 | Vaya et al. | |
| 2004/0127443 A1 | 7/2004 | Pershadsingh | |
| 2004/0204472 A1 | 10/2004 | Briggs et al. | |
| 2005/0004179 A1 | 1/2005 | Pedersen | |
| 2005/0014786 A1 | 1/2005 | Sun et al. | |
| 2005/0014833 A1 | 1/2005 | Clark et al. | |
| 2005/0096331 A1 | 5/2005 | Das et al. | |
| 2005/0171110 A1 | 8/2005 | Yu et al. | |
| 2006/0009518 A1 | 1/2006 | Campbell et al. | |
| 2006/0024365 A1 | 2/2006 | Vaya et al. | |
| 2006/0035889 A1 | 2/2006 | Tedford et al. | |
| 2006/0084686 A1 | 4/2006 | Barak | |
| 2006/0148721 A1 | 7/2006 | Erondu | |
| 2006/0167045 A1 | 7/2006 | Waldstreicher et al. | |
| 2006/0211749 A1 | 9/2006 | Bobotas et al. | |
| 2006/0252670 A1 | 11/2006 | Fiorucci et al. | |
| 2006/0270722 A1 | 11/2006 | Thornberry et al. | |
| 2007/0037882 A1 | 2/2007 | Kita et al. | |
| 2007/0049576 A1 | 3/2007 | Barlow et al. | |
| 2007/0049613 A1 | 3/2007 | Chen et al. | |
| 2007/0060547 A1 | 3/2007 | Campbell et al. | |
| 2007/0066630 A1 | 3/2007 | Palani et al. | |
| 2007/0099884 A1 | 5/2007 | Erondu et al. | |
| 2007/0112070 A1 | 5/2007 | Aubert et al. | |
| 2007/0167435 A1 | 7/2007 | Mutahi et al. | |
| 2007/0167468 A1 | 7/2007 | Schoenafinger et al. | |
| 2007/0197606 A1 | 8/2007 | Burczynski et al. | |
| 2007/0213359 A1 | 9/2007 | Burstein et al. | |
| 2007/0232573 A1 | 10/2007 | Patel et al. | |
| 2007/0238757 A1 | 10/2007 | Chapman et al. | |
| 2007/0276041 A1 | 11/2007 | Oonuki et al. | |
| 2007/0299047 A1 | 12/2007 | Maher et al. | |
| 2008/0019978 A1 | 1/2008 | Palani et al. | |
| 2008/0045580 A1 | 2/2008 | Madhavan et al. | |
| 2008/0064671 A1 | 3/2008 | Barlow et al. | |
| 2008/0103165 A1 | 5/2008 | Barlow et al. | |
| 2008/0127972 A1 | 6/2008 | Morton | |
| 2008/0220078 A1 | 9/2008 | Morton et al. | |
| 2009/0048232 A1 | 2/2009 | Ciccocioppo | |
| 2010/0184806 A1 | 7/2010 | Barlow et al. | |
| 2010/0234413 A1 | 9/2010 | Ciccocioppo | |

FOREIGN PATENT DOCUMENTS

| | | |
|---|---|---|
| EP | 1 263 438 B1 | 5/2006 |
| EP | 1867994 A2 | 12/2007 |
| JP | 2006-515566 | 6/2006 |
| JP | 200844932 | 2/2008 |
| JP | 2010-502719 | 1/2010 |
| KR | 1020070112580 | 11/2007 |
| WO | WO 98/57941 | 12/1998 |
| WO | WO 99/05161 | 2/1999 |
| WO | WO 99/63983 | 12/1999 |
| WO | WO 01/62238 A2 | 8/2001 |
| WO | WO 01/66098 A2 | 9/2001 |
| WO | WO 02/49626 A2 | 6/2002 |
| WO | WO 02/100341 A2 | 12/2002 |
| WO | WO 03/026586 A2 | 4/2003 |
| WO | WO 03/045918 A1 | 6/2003 |
| WO | WO 2004/000295 A1 | 12/2003 |
| WO | WO 2004/010992 | 2/2004 |
| WO | WO 2004/078113 A2 | 9/2004 |
| WO | WO 2004/092417 A2 | 10/2004 |
| WO | WO 2004/110368 A2 | 12/2004 |
| WO | WO 2004/110375 A2 | 12/2004 |
| WO | WO 2005/000217 A2 | 1/2005 |
| WO | WO 2005/041959 A1 | 5/2005 |
| WO | WO 2005/061509 A1 | 7/2005 |
| WO | WO 2005/063761 A1 | 7/2005 |
| WO | WO 2005/063762 A1 | 7/2005 |
| WO | WO 2005/065654 A1 | 7/2005 |
| WO | WO 2005/065663 A1 | 7/2005 |
| WO | WO 2005/070905 A1 | 8/2005 |
| WO | WO 2005/080343 A2 | 9/2005 |
| WO | WO 2005/080354 A1 | 9/2005 |
| WO | WO 2005/095354 A1 | 10/2005 |
| WO | WO 2005/107713 A2 | 11/2005 |
| WO | WO 2005/108352 A1 | 11/2005 |
| WO | WO 2005/115370 A2 | 12/2005 |
| WO | WO 2006/017292 A1 | 2/2006 |
| WO | WO 2006/028970 A1 | 2/2006 |
| WO | WO 2006/029349 A1 | 3/2006 |
| WO | WO 2006/044391 A1 | 4/2006 |
| WO | WO 2006/056812 A1 | 6/2006 |
| WO | WO 2006/059152 A2 | 6/2006 |
| WO | WO 2006/071762 A2 | 7/2006 |
| WO | WO 2006/074114 A2 | 7/2006 |
| WO | WO 2006/076633 A1 | 7/2006 |
| WO | WO 2006/078037 | 7/2006 |
| WO | WO 2006/078698 A1 | 7/2006 |
| WO | WO 2006/090150 A1 | 8/2006 |
| WO | WO 2006/096564 A1 | 9/2006 |
| WO | WO 2007/007656 A1 | 1/2007 |
| WO | WO 2007/008501 A1 | 1/2007 |
| WO | WO 2007/018956 A2 | 2/2007 |
| WO | WO 2007/032028 A1 | 3/2007 |
| WO | WO 2007/039125 A2 | 4/2007 |
| WO | WO 2007/049050 A2 | 5/2007 |
| WO | WO 2007/075847 A2 | 7/2007 |
| WO | WO 2007/079239 A2 | 7/2007 |
| WO | WO 2007/082206 A2 | 7/2007 |
| WO | WO 2007/083146 A2 | 7/2007 |
| WO | WO 2007/106862 A2 | 9/2007 |
| WO | WO 2007/120605 A2 | 10/2007 |
| WO | WO 2007/121545 A1 | 11/2007 |
| WO | WO 2007/126135 A1 | 11/2007 |
| WO | WO 2007/136607 A2 | 11/2007 |
| WO | WO 2008/000643 A1 | 1/2008 |
| WO | WO 2008/008433 | 1/2008 |

(56) References Cited

FOREIGN PATENT DOCUMENTS

| | | |
|---|---|---|
| WO | WO 2008/017398 A2 | 2/2008 |
| WO | WO 2008/024284 A2 | 2/2008 |
| WO | WO 2008/024456 A2 | 2/2008 |
| WO | WO 2008/030604 A2 | 3/2008 |
| WO | WO 2008/030618 A1 | 3/2008 |
| WO | WO 2008/030651 A1 | 3/2008 |
| WO | WO 2008/036678 A2 | 3/2008 |
| WO | WO 2008/053256 A1 | 5/2008 |
| WO | WO 2008/063842 A2 | 5/2008 |
| WO | WO 2008/095263 A1 | 8/2008 |
| WO | WO 2008/128126 A1 | 10/2008 |
| WO | WO 2008/133884 A2 | 11/2008 |

OTHER PUBLICATIONS

Evans, J. et al., "Novel Approach to Treat Insulin Resistance, Type 2 Diabetes, and the Metabolic Syndrome: Simultaneous Activation of PPARα, PPARγ, and PPARδ," *Current Diabetes Reviews* 1:299-307, 2005.

Rudolph, J. et al., "Indanylacetic Acid Derivatives Carrying 4-Thiazolyl-phenoxy Tail Groups, a New Class of Potent PPAR α/γ/δ Pan Agonists: Synthesis, Structure—Activity Relationship, and In Vivo Efficacy," *J. Med. Chem.* 50:984-1000, 2007.

Kasuga, J. et al., "Improvement of the Transactivation Activity of Phenylpropanoic Acid-type Peroxisome Proliferator-activated Receptor Pan Agonists: Effect of Introduction of Fluorine at the Linker Part," *Bioorganics & Medicinal Chemistry Letters* 18:4525-4528, 2008.

Xu, Y. et al., "Design and Synthesis of Dual Peroxisome Proliferator-Activated Receptors γ and δ Agonists as Novel Euglycemic Agents with a Reduced Weight Gain Profile," *J. Med. Chem.* 49:5649-5652, 2006.

Gonzalez, I. et al., "Design and Synthesis of a Novel Class of Dual PPARγ/δ Agonists," *Bioorganic & Medicinal Chemistry Letters* 17:1052-1055, 2007.

Balakumar, P. et al., "PPAR Dual Agonists: Are they Opening Pandora's Box?" *Pharmacological Research* 56:91-98, 2007.

Adams, A. et al., "Amphipathic 3-Phenyl-7-propylbenzisoxazoles; Human PPaR -65 , δ and α Agonists," *Bioorganic & Medicinal Chemistry Letters* 13:931-935, 2003.

Shah, P. et al., "CoMFA Analysis of Dual/Multiple PPAR Activators," *European Journal of Medicinal Chemistry* 43: 2784-2791, 2008.

Maeda, T. et al., "Peroxisome Proliferator-Activated Receptor Gamma Activation Relieves Expression of Behavioral Sensitization to Methamphetamine in Mice," *Neuropsychopharmacology* 32(5):1133-1140, 2007.

Vetulani, J., "Drug Addiction. Part III. Pharmacotherapy of Addiction," *Polish Journal of Pharmacology* 53:415-434, 2001.

Raby, W., "Gabapentin Therapy for Cocaine Cravings," *Am J Psychiatry* 157(12):2058-2059, 2000.

Chu, K. et al., "Dependence-induced Increases in Ethanol Self-Administration in Mice are Blocked by the $CRF_1$ Receptor Antagonist Antalarmin and by $CRF_1$ Receptor Knockout," *Pharmacol Biochem Behav.* 86(4):813-821, 2007.

Filip, M. et al., "Involvement of Cannabinoid $CB_1$ Receptors in Drug Addiction: Effects of Rimonabant on Behavioral Responses Induced by Cocaine," *Pharmacological Reports* 58:806-819, 2006.

Ang, E. et al., "Induction of Nuclear Factor-kappaB in Nucleus Accumbens by Chronic Cocaine Administration," *J. of Neurochem.* 79:221-224, 2001.

Asanuma, M. et al., "Methamphetamine-induced Increase in Striatal NF-kappaB DNA-binding Activity is Attenuated in Superoxide Dismutase Transgenic Mice," *Molecular Brain Research* 60:305-309, 1998.

Ashby, C. et al., "Acute Administration of the Selective $D_3$ Receptor Antagonist SB-277011A Blocks the Acquisition and Expression of the Conditioned Place Preference Response to Heroin in Male Rats," *Synapse* 48:154-156, 2003.

Barroso, I. et al., "Dominant Negative Mutations in Human PPAR gamma Associated with Severe Insulin Resistance, Diabetes Mellitus and Hypertension," *Nature* 402:880-883, 1999.

Berger, J. et al., "The Machanisms of Action of PPARs," *Annu. Rev. Med.* 53:409-435, 2002.

Bordet, R. et al., "PPAR: a New Pharmacological Target for Neuroprotection in Stroke and Neurodegenerative Diseases," *Biochemical Society* 34(Pt 6):1341-1346, 2006.

Bowers, M. et al., "Forebrain Astroglial Plasticity is Induced Following Withdrawal from Repeated Cocaine Administration," *European Journal of Neuroscience* 17:1273-1278, 2003.

Breidert, T. et al., "Protective Action of the Peroxisome Proliferator-Activated Receptor-Gamma Agonist Pioglitazone in a Mouse Model of Parkinson's Disease," *Journal of Neurochemistry* 82:615-624, 2002.

Burstein, S., "PPAR-gamma: a Nuclear Receptor with Affinity for Cannabinoids," *Life Sciences* 77:1674-1684, 2005.

Butcher, S. et al., "Neuroprotetive Actions of FK506 in Experimentala Stroke: In Vivo Evidence Against an Antiexcitotoxic Mechanism," *The Journal of Neuroscience* 17(18):6939-6946, 1997.

Caito, S. et al., "Rosiglitazone and 15-Deoxy-$\Delta^{12,14}$-Prostaglandin $J_2$, PPARγ Agnonists, Differentially Regulate Cigarette Smoke-Mediated Pro-Inflammatory Cytokine Release in Monocytes/Macrophages," *Antioxidants & Redox Signaling* 10(2):253-260, 2008.

Cernuda-Morollon, E., "PPAR Agonists Amplify iNOS Expression While Inhibiting NF-kappaB: Implications for Mesangial Cell Activation by Cytokines," *J Am Soc Nephrol* 13:2223-2231, 2002.

Chang, F. et al., "Evolution of Peroxisome Proliferator-Activated Receptor Agonists," *The Annals of Pharmacotherapy* 41:973-983, 2007.

Chinetti, G. et al., "Peroxisome Proliferator-Activated Receptors (PPARs): Nuclear Receptors at the Crossroads Between Lipid Metabolism and Inflammation," *Inflamm. res.* 49:497-505, 2000.

Churi, S. et al., "Intrathecal Rosiglitazone Acts at Peroxisome Proliferator-Activated Receptor-gamma to Rapidly Inhibit Neuropathic Pain in Rats," *The Journal of Pain* 9(7):639-649, 2008.

Ciccocioppo, R. et al., "Buprenorphine Reduces Alcohol Drinking Through Activation of the Nociceptin/Orphanin FQ-NOP Receptor System," *Biol Psychiatry* 61:4-12, 2007.

Ciccocioppo, R. et al., "Effect of Nociceptin/Orphanin FQ on the Rewarding Properties of Morphine," *European Journal of Pharmacology* 404:153-159, 2000.

Ciccocioppo, R. et al., "Effect of Nociceptin on Alcohol Intake in Alcohol-preferring Rats," *Psychopharmacology* 141:220-224, 1999.

Ciccocioppo, R. et al., "Cocaine-Predictive Stimulus Induces Drug-Seeking Behaviour and Neural Activation in Limbic Brain Regions after Multiple Months of Abstinence: Reversal by $D_1$ antagonists," *Proc Natl Acad Sci USA* 98(4):1976-1981, 2001.

Cohen, C. et al., "Nicotine-Associated Cues Maintain Nicotine-Seeking Behavior in Rats Several Weeks after Nicotine Withdrawal: Reversal by the Cannabinoid ($CB_1$) Receptor Antagonist, Rimonabant (SR141716)," *Neuropsychopharmacology* 30:145-155, 2005.

Crews, F. et al., "BHT Blocks NF-kappaB activation and Ethanol-Induced Brain Damage," *Alcoholism: Clinical and Experimental Research* 30(11):1938-1949, 2006.

Cristiano, L. et al., "Peroxisome Proliferator-Activated Receptors (PPARs) and Related Transcription Factors in Differentiating Astrocyte Cultures," *Neuroscience* 131:577-587, 2005.

Crosby, M. et al., "Inflammatory Modulation of PPAR Gamma Expression and Activity," *Clinical Immunology* 118:276-283, 2006.

De Souza, E., "Corticotropin-Releasing Factor Receptors: Physiology, Pharmacology, Biochemistry and Role in Central Nervous System and Immune Disorders," *Psychoneuroendocrinology* 20(8):789-819, 1995.

Delva, J. et al., "The Epidemiology of Alcohol, Marijuana, and Cocaine Use Among Mexican American, Puerto Rican, Cuban American, and Other Latin American Eighth-Grade Students in the United States: 1991-2002," *American Journal of Public Health* 95(4): 696-702, 2005.

(56) References Cited

OTHER PUBLICATIONS

Di Chiara, G. et al., "Drugs Abused by Humans Preferentially Increase Synaptic Dopamine Concentrations in the Mesolimbic System of Freely Moving Rats," *Proc. Natl. Acad. Sci. USA* 85:5274-5278, 1988.

Dunn, A. et al., "Physiological and Behavioural Responses to Corticotropin-releasing Factor Administration: is CRF a Mediator of Anxiety or Stress Responses?," *Brain Research Reviews* 15:71-100, 1990.

Enomoto, N. et al., "Prevention of Ethanol-induced Liver Injury in Rats by an Agonist of Peroxisome Proliferator-activated Receptor-gamma, Pioglitazone," *J Pharmacol Exp Ther* 306:846-854, 2003.

Erb, S. et al., "The Role of Corticotropin-Releasing Factor and Corticosterone in Stress- and Cocaine-Induced Relapse to Cocaine Seeking in Rats," *The Journal of Neuroscience* 18(14):5529-5536, 1998.

Feinstein, D., "Therapeutic Potential of Peroxisome Proliferator-Activated Receptor Agonists for Neurological Disease," *Diabetes Technology & Therapeutics* 5(1):67-73, 2003.

Feinstein, D. et al., "Peroxisome Proliferator-Activated Receptor-γ Agonists Prevent Experimental Autoimmune Encephalomyelitis," *Ann Neurol* 51:694-702, 2002.

Fischer, M. et al., "Peroxisome Proliferator-activated Receptor Alpha (PPARalpha) Agonist Treatment Reverses PPARalpha Dysfunction and Abnormalities in Hepatic Lipid Metabolism in Ethanol-fed Mice," *J Biol Chem* 278:27997-28004, 2003.

Flanagan, M., "Metabolic Solutions: PPAR-less Sensitization," *BioCentury: The Bernstein Report on BioBusiness* 17(51):A11, 2009.

Foot, E. et al., "Good Metabolic and Safety Profile of Troglitazone Alone and Following Alcohol in NIDDM Subjects," *Diabetes Research and Clinical Practice* 38:41-51, 1997.

Furukawa, S. et al., "Increased Oxidative Stress in Obesity and its Impact on Metabolic Syndrome," *The Journal of Clinical Investigation* 114(12):1752-1761, 2004.

Garcia-Bueno, B. et al., "Effects of Peroxisome Proliferator-Activated Receptor Gamma Agonists on Brain Glucose and Glutamate Transporters after Stress in Rats," *Neuropsychopharmacology* 32:1251-1260, 2007.

Garcia-Bueno, B. et al., "Peroxisome Proliferator-Activated Receptor Gamma Activation Decreases Neuroinflammation in Brain After Stress in Rats," *Biol Psychiatry* 57:885-894, 2005.

Ghahremani, M. et al., "Inhibition of the Cyclooxygenase Pathway Attenuates Morphine-induced Conditioned Place Preference in Mice." *Pharmacol Biochem Behav.* 85(2):356-361, 2006.

Glatz, A. et al., "Inhibition of Cocaine Self-administration by Fluoxetine or D-fenfluramine Combined with Phentermine," *Pharmacology, Biochemistry and Behavior* 71:197-204, 2002.

Gofflot, F. et al., "Systematic Gene Expression Mapping Clusters Nuclear Receptors According to Their Function in the Brain," *Cell* 131:405-418, 2007.

Gonzalez-Zulueta, M. et al., "Manganese Superoxide Dismutase Protects nNOS Neurons from NMDA and Nitric Oxide-Mediated Neurotoxicity," *The Journal of Neuroscience* 18(6):2040-2055, 1998.

Harris, S. et al., "Prostaglandin $D_2$, its metabolite 15-d-$PGJ_2$, and Peroxisome Proliferator Activated Receptor-γ Agonists Induce Apoptosis in Transformed, but not Normal, Human T Lineage Cells," *Immunology* 105:23-34, 2002.

Heinrichs, S. et al., "Corticotropin-releasing Factor Antagonist Reduces Emotionality in Socially Defeated Rats via Direct Neurotropic Action," *Brain Research* 581:190-197, 1992.

Heneka, M. et al., "PPARs in the Brain," *Biochimica et Biophysica Acta* 1771:1031-1045, 2007.

Heneka, M. et al., "Peroxisome Proliferator-activated Receptor Gamma Agonists Protect Cerebellar Granule Cells from Cytokine-induced Apoptotic Cell Death by Inhibition of Inducible Nitric Oxide Synthase," *Journal of Neuroimmunology* 100:156-168, 1999.

Hofmann, C. et al., "Altered Gene Expression for Tumor Necrosis Factor-α and its Receptors During Drug and Dietary Modulation of Insulin Resistance," *Endocrinology* 134(1):264-270, 1994.

Hollenberg, A. et al., "Functional Antagonism Between CCAAT/Enhancer Binding Protein-α and Peroxisome Proliferator-activated Receptor-γ on the Leptin Promoter," *The Journal of Biological Chemistry* 272(8):5283-5290, 1997.

Hotta, K. et al., "Circulating Concentrations of the Adipocyte Protein Adiponectin Are Decreased in Parallel With Reduced Insulin Sensitivity During the Progression to Type 2 Diabetes in Rhesus Monkeys," *Diabetes* 50:1126-1133, 2001.

Hu, E. et al., "AdipoQ Is a Novel Adipose-specific Gene Dysregulated in Obesity," *The Journal of Biological Chemistry* 271(18):10697-10703, 1996.

Hwang, J. et al., "Peroxisome Proliferator-activated Receptor-Gamma Ligands Regulate Endothelial Membrane Superoxide Production," *Am J Physiol Cell Physiol* 288:C899-C905, 2005.

Jiang, C. et al., "PPAR-γ agonists Inhibit Production of Monocyte Inflammatory Cytokines," *Nature* 391:82-86, 1998.

Jung, T. et al., "Rosiglitazone Relieves Acute Ethanol-Induced Hangover in Sprague-Dawley Rats," *Alcohol and Alcoholism* 41(3):231-235, 2006.

Kainu, T. et al., "Localization of the Peroxisome Proliferator-activated Receptor in the Brain," *NeuroReport* 5:2481-2485, 1994.

Kang, L. et al., "Mirtazapine, a Noradrenergic and Specific Serotonergic Antidepressant, Attenuates Morphine Dependence and Withdrawal in Sprague-Dawley Rats." *Am J Drug Alcohol Abuse* 34(5):541-552, 2008.

Kapadia, R. et al., "Mechanisms of Anti-inflammatory and Neuroprotective Actions of PPAR-Gamma Agonists," *Frontiers in Bioscience* 13:1813-1826, 2008.

Katner, S. et al. "Reinstatement of Alcohol-Seeking Behaviour by Drug-Associated Discriminative Stimuli after Prolonged Extinction in the Rat," *Neuropsychopharmacology* 20(5):471-479, 1999.

Kawaguchi, K. et al., "Pioglitazone Prevents Hepatic Steatosis, Fibrosis, and Enzyme-altered Lesions in Rat Liver Cirrhosis Induced by a Choline-deficient L-amino Acid-defined Diet," *Biochemical and Biophysical Research Communications* 315:187-195, 2004.

Kielian, T. et al., "Effects of Peroxisome Proliferator-Activated Receptor-γ Agonists on Central Nervous System Inflammation," *Journal of Neuroscience Research* 71:315-325, 2003.

Kliewer, S. et al., "A Prostaglandin $J_2$ Metabolite Binds Peroxisome Proliferator-Activated Receptor γ and Promotes Adipocyte Differentiation," *Cell* 83:813-819, 1995.

Koob, G. et al., "Corticotropin Releasing Factor, Stress and Behaviour," *Seminars in the Neurosciences* 6:221-229, 1994.

Koob, G. et al., "Neuroscience of Addiction," *Neuron* 21:467-476, 1998.

Koob, G., "Drugs of abuse: Anatomy, Pharmacology and Function of Reward Pathways," *Trends Pharmacol Sci* 13:177-184, 1992.

Kubota, N., et al., "Pioglitazone Ameliorates Insulin Resistance and Diabetes by Both Adiponectin-dependent and-independent Pathways," *The Journal of Biological Chemistry* 281(13):8748-8755, 2006.

Landreth, G., "PPARγ Agonists as new Therapeutic Agents for the Treatment of Alzheimer's Disease," *Experimental Neurology* 199:245-248, 2006.

Landreth, G. et al., "PPARγ Agonists as Therapeutics for the Treatment of Alzheimer's Disease," *Neurotherapeutics: The Journal of the American Society for Experimental NeuroTherapeutics* 5:481-489, 2008.

Landreth, G., "Anti-inflammatory Actions of the Peroxisome Proliferator-activated Receptor gamma Agonists in Alzheimer's Disease," *Neurobiology of Aging* 22:937-944, 2001.

Le, A. et al., "Reinstatement of Alcohol-seeking by Priming Injections of Alcohol and Exposure to Stress in Rats," *Psychopharmacology* 135:169-174, 1998.

Le, A. et al., "The Role of Corticotrophin-releasing Factor in Stress-induced Relapse to Alcohol-seeking Behaviour in Rats," *Psychopharmacology* 150:317-324, 2000.

(56) References Cited

OTHER PUBLICATIONS

Lee, S. et al., "Peroxisome Proliferator-activated Receptor-γ Inhibits Cigarette Smoke Solution-induced Mucin Production in Human Airway Epithelial (NCI-H292) Cells," *Am J Physiol Lung Cell Mol Physiol* 291:L84-L90, 2006.

Lee, B. et al., "Pharmacological Blockade of $\alpha_2$-Adrenoceptors Induces Reinstatement of Cocaine-Seeking Behavior in Squirrel Monkeys," *Neuropsychopharmacology* 29:686-693, 2004.

Letteron, P. et al., "Acute and Chronic Hepatic Steatosis Lead to in vivo Lipid Peroxidation in Mice," *Journal of Hepatology* 24:200-208, 1996.

Levine, J. et al., "Energy Expenditure in Chronic Alcohol Abuse," *European Journal of Clinical Investigation* 30:779-786, 2000.

Liu, X. et al., "Reinstatement of Ethanol-seeking Behavior by Stress- and Drug-related Cues in Rats with a History of Ethanol-dependence," *Society for Neuroscience* 26:787, 2000.

Liu, X. et al., "Reversal of Ethanol-Seeking Behavior by D1 and D2 Antagonists in an Animal Model of Relapse: Differences in Antagonist Potency in Previously Ethanol-Dependent versus Nondependent Rats," *The Journal of Pharmacology and Experimental Therapeutics* 300(3):882-889, 2002.

Lopez-Liuchi, J. et al., "PPARγ: from Adipose Tissue to the Atherosclerotic Plaque," *European Journal of Endocrinology* 139:363-364, 1998.

Maeda, K. et al., "cDNA Cloning and Expression of a Novel Adipose Specific Collagen-like Factor, apM1 (Adipose Most Abundant Gene Transcript 1)," *Biochemical and Biophysical Research Communications* 221:286-289, 1996.

Maeda, N., et al., "PPARγ Ligands Increase Expression and Plasma Concentrations of Adiponectin, an Adipose-Derived Protein," *Diabetes* 50:2094-2099, 2001.

Magalas, Z. et al., "The Serotonin/naradrenaline Reuptake Inhibitor Venlafaxine Attenuates Acquisition, but not Maintenanace, of Intravenous Self-adminstration of Heroin in Rats." *Eur J Pharmacol.* 528(1-3):103-109. 2005.

Mao, X. et al., "APPL1 Binds to Adiponectin Receptors and Mediates Adiponectin Signalling and Function," *Nature Cell Biology* 8(5):516-523, 2006.

Mas-Nieto, M. et al., "Reduction of Opioid Dependence by the CB(1) Antagonist SR141716A in Mice: Evaluation of the Interest in Pharmacotherapy of Opioid Addiction." *Br J Pharmacol.* 132(8):1809-1816, 2001.

McCusker, C. et al., "The Cue-responsivity Phenomenon in Dependent Drinkers: 'Personality' Vulnerability and Anxiety as Intervening Variables," *British Journal of Addiction* 86:905-912, 1991.

McEwen, B. et al., "Studies of Hormone Action in the Hippocampal Formation Possible Relevance to Depression and Diabetes," *Journal of Psychosomatic Research* 53:883-890, 2002.

Merali, Z. et al., "Aversive and Appetitive Events Evoke the Release of Corticotropin-Releasing Hormone and Bombesin-Like Peptides at the Central Nucleus of the Amygdala," *The Journal of Neuroscience* 18(12):4758-4766, 1998.

Monti, P. et al., "Alcohol Cue Reactivity: Effects of Detoxification and Extended Exposure," *J Stud Alcohol* 54:235-245, 1993.

Moreno, S. et al., "Immunolocalization of Peroxisome Proliferator-Activated Receptors and Retinoid X Receptors in the Adult Rat CNS," *Neuroscience* 123:131-145, 2004.

Naito, H. et al., "Association of V227A PPARalpha polymorphism with altered serum biochemistry and alcohol drinking in Japanese men," *Pharmacogenet. Genomics* 16:569-577, 2006.

Napimoga, M. et al., "15d-prostaglandin $J_2$ Inhibits Inflammatory Hypernociception: Involvement of Peripheral Opioid Receptor," *The Journal of Pharmacology and Experimental Therapeutics* 324(1):313-321, 2007.

Nishikawa, T. et al., "Behavioural Sensitization and Relative Hyper-responsiveness of Striatal and Limbic Dopaminergic Neurons After Repeated Methamphetamine Treatment," *European Journal of Pharmacology* 88:195-203, 1983.

O'Brien, C., "A Range of Research-Based Pharmacotherapies for Addiction," *Science* 278:66-70, 1997.

Oliveira, A. et al., "Antinociceptive and Antiedematogenic Activities of Fenofibrate, an Agonist of PPAR alpha, and Pioglitazone, an Agonist of PPAR gamma," *European Journal of Pharmacology* 561:194-201, 2007.

Organization, W. H., "The World Health Report 2002: Reducing Risks, Promoting Healthy Life," Geneva, World Health Organization, 2002. [substance addiction definition].

Panocka, I. et al., "Effects of the Dopamine $D_1$ Receptor Antagonist SCH 39166 on the Ingestive Behaviour of Alcohol-preferring Rats," *Psychopharmacology* 120:227-235, 1995.

Park, E. et al., "15d-$PGJ_2$ and Rosiglitazone Suppress Janus Kinase—STAT Inflammatory Signaling through Induction of Suppressor of Cytokine Signaling 1 (SOCS1) and SOCS3 in Glia," *The Journal of Biological Chemistry* 278(17):14747-14752, 2003.

Merlo, Pich E. et al., "Increase of Extracellular Corticotropin-Releasing Factor-Like Immunoreactivity Levels in the Amygdala of Awake Rats During Restraint Stress and Ethanol Withdrawal as Measured by Microdialysis," *The Journal of Neuroscience* 15(8):5439-5447, 1995.

Sanchis-Segura, C. et al., "Behavioural Assessment of Drug Reinforcement and Addictive Features in Rodents: an Overview," *Addiction Biology* 11:2-38, 2006.

Sarruf, D. et al., "Expression of Peroxisome Proliferator-Activated Receptor-γ in Key Neuronal Subsets Regulating Glucose Metabolism and Energy Homeostasis," *Endocrinology* 150(2):707-712, 2009.

Sastre, M. et al., "Nonsteroidal Anti-inflammatory Drugs Repress β-secretase Gene Promoter Activity by the Activation of PPARγ," *PNAS*, 103(2):443-448. 2006.

Shalev, U. et al., "Leptin Atneuates Acute Food Deprivation-Induced Relapse to Heroin Seeking," *The Journal of Neuroscience* 21:RC129-RC133, 2001.

Siegal, H. et al., "Probable Relationship Between Opioid Abuse and Heroin Use," *American Academy of Family Physicians* 67(5):942, 2003.

Sorensen, T. et al., "Prospective Evaluation of Alcohol Abuse and Alcoholic Liver Injury in Men as Predictors of Development of Cirrhosis," *The Lancet Ltd*. 2:241-244, 1984.

Sorge, R. et al., "Rats Maintained Chronically on Buprenorphine Show Reduced Heroin and Cocaine Seeking in Tests of Extinction and Drug-Induced Reinstatement," *Neuropsychopharmacology* 30:1681-1692, 2005.

Souza, S. et al., "BRL 49653 Blocks the Lipolytic Actions of Tumor Necrosis Factor-α: A Potential New Insulin Sensitizing Mechanism for Thiazolidinediones," *Diabetes* 47:691-695, 1998.

Steensland, P. et al., "Varenicline, an α4β2 nicotinic acetylcholine receptor partial agonist, selectively decreases ethanol consumption and seeking," *PNAS* 104(30):12518-12523, 2007.

Substance Abuse and Mental Health Services Administration, Emergency Department Trends From the Drug Abuse Warning Network, Final Estimates 1995-2002, Department of Health and Human Services, Office of Applied Statistics, 2003.

Sung, B. et al., "Vasodilatory Effects of Tronglitazone Improve Blood Pressure at Rest and During Mental Stress in Type 2 Diabetes Mellitus," *Hypertension* 34:83-88, 1999.

Swiergiel, A. et al., "Attenuation of Stress-induced Behavior by Antagonism of Corticotropin-releasing Factor Receptors in the Central Amygdala in the Rat," *Brain Research* 623:229-234, 1993.

Takehara, T. et al., "Protective Effect of Hepatocyte Growth Factor on in vitro Hepatitis in Primary Cultured Hepatocytes," *Biomedical Research* 12(5):335-338, 1991.

Tomita, K. et al., "Pioglitazone Prevents Alcohol-Induced Fatty Liver in Rats Through Up-regulation of c-Met," *Gastroenterology* 126:873-885, 2004.

Tontonoz, P. et al., "Fat and Beyond: The Diverse Biology of PPARγ," *Annu. Rev. Biochem.* 77:289-312, 2008.

Tsuchida, A. et al., "Peroxisome Proliferator-Activated Receptor (PPAR)α Activation Increases Adiponectin Receptors and Reduces Obesity-Related Inflammation in Adipose Tissue: Comparison of Activation of PPARα, PPARγ, and Their Combination," *Diabetes* 54:3358-3370, 2005.

(56) References Cited

OTHER PUBLICATIONS

Tzschentke, T. et al., "Effects of Venlafaxine and Desipramine on Heroin-induced Conditioned Place Preference in the Rat." *Addict Biol.* 11(1):64-71, 2006.
van Ree, J. et al., "Vasopressin Neuropeptides and Acquisition of Heroin and Cocaine Self-administration in Rats." *Life Sci.* 42(10):1091-1099, 1988.
Volpicelli, J. et al., "Naltrexone in the Treatment of Alcohol Dependence," *Arch Gen Psychiatry* 49:876-880, 1992.
Weiss, F. et al., "Environmental Stimuli Potently Reinstate Alcohol-Seeking Behavior: Effect of Repeated Alcohol Intoxication," *Society for Neuroscience* 25:1081, 1999.
Weiss, F., et al., "Compulsive Drug-Seeking Behavior and Relapse: Neuroadaptation, Stress, and Conditioning Factors," *Annals New York Academy of Science* 937:1-26, 2001.
Wise, R., "Drug-Activation of Brain Reward Pathways," *Drug and Alcohol Dependence* 51:13-22, 1998.
Woods, J. et al., "Localization of PPARδ in Murine Central Nervous System: Expression in Oligodendrocytes and Neurons," *Brain Research* 975:10-21, 2003.
Wu, Z. et al., "Induction of Peroxisome Proliferator-Activated Receptor γ during the Conversion of 3T3 Fibroblasts into Adipocytes is Mediated by C/EBPβ, C/EPBδ, and Glucocorticoids," *Molecular and Cellular Biology* 16(8):4128-4136, 1996.
Yamauchi, T. et al., "The Fat-Derived Hormone Adiponectin Reverses Insulin Resistance Associated with both Lipoatrophy and Obesity," *Nature Medicine* 7(8):941-946, 2001.
Yamauchi, T. et al., "Cloning of Adiponectin Receptors that Mediate Antidiabetic Metabolic Effects," *Nature* 423:762-769, 2003.
Young, P. et al., "Identification of High-Affinity Binding Sites for the Insulin Sensitizer Rosiglitazone (BRL-49653) in Rodent and Human Adipocytes Using a Radioiodinated Ligand for Peroxisomal Proliferator-Activated Receptor γ," *The Journal of Pharmacology and Experimental Therapeutics* 284(2):751-759, 1998.
Yu, X. et al., "Activation of Cerebral Peroxisome Proliferator-activated Receptors Gamma Exerts Neuroprotection by Inhibiting Oxidative Stress Following Pilocarpine-induced Status Epilepticus," *Brain Research* 1200:146-158, 2008.
Yu, J. et al., "The Effect of Thiazolidinediones on Plasma Adiponectin Levels in Normal, Obese, and Type 2 Diabetic Subjects," *Diabetes* 51:2968-2974, 2002.
Zalcman, S. et al., "Interleukin-6 Increases Sensitivity to the Locomotor-Stimulating Effects of Amphetamine in Rats," *Brain Research* 847:276-283, 1999.
Zarrindast, M. et al., "Effect of Imipramine on the Expression and Acquisition of Morphine-induced Conditioned Place Preference in Mice." *Pharmacol Biochem Behav.* 73(4):941-949, 2002.
Zarrindast, M. et al., "Involvement of GABA(B) Receptors of the Dorsal Hippocampus on the Acquisition and Expression of Morphine-induced Place Preference in Rats." *Physiol Behav.* 87(1):31-38, 2006.
Zhao, M. et al., "15- Deoxy-Δ(12,14)-PGJ2 Inhibits Astrocyte IL-1 Signaling: Inhibition of NF-κB and MAP Kinase Pathways and Suppression of Cytokine and Chemokine Expression," *Journal of Neuroimmunology* 153:132-142, 2004.
Bruno, F., "Buspirone in the Treatment of Alcoholic Patients," *Psychopathology* 22(suppl 1):49-59, 1989.
Holmberg, G. et al., "Yohimbine as an Autonomic Test Drug," *Nature* 193(4822):1313-1314, 1962.
Janiri, L. et al., "Effects of Fluoxetine at Antidepressant Doses on Short-Term Outcome of Detoxified Alcoholics," *International Clinical Psychopharmacology* 11:109-117, 1996.
Derosa, G., et al., "Pioglitazone and Sibutramine Combination Effects on Glucose and Lipid Metabolism in Obese Type 2 Diabetic Patients," *NMCD. Nutrition Metabolism and Cardiovascular Diseases*, Milan Italy, 14(5):310 (2004).
Choi, J. et al., "Exposure to Rosiglitazone and Fluoxetine in the First Trimester of Pregnancy," *Diabetes Care LNKD-PubMed: 16936175*, 29(9):2176 (2006).
Bao, Z. et al., "Influence of Peroxisome Proliferator-activated Receptor Gamma on Airway Inflammation of Guinea Pigs with Asthma," *Chinese Journal of Tuberculosis and Respiratory Diseases*, Zhonghua Yixuehui, Beijing, China, 27(3): 169-173 (English abstract) (2004).
Cohen, C., et al., "$CB_1$ receptor antagonists for the treatment of nicotine addiction," *Pharmacology, Biochemistry and Behavior* 81:387-395 (2005).
ACUROX® (oxycodone HCI, USP and niacin, USP) Tablets, NDA 22-451. Briefing Information for a Joint Meeting of the Anesthetic and Life Support Drugs Advisory Committee and Drug Safety and Risk Management Advisory Committee, Apr. 22, 2010. Acura Pharmaceuticals, Inc.
Omeros Corporation Press Release. Omeros Announces Expansion of Exclusivity License to PDE7 Inhibitors from Daiichi Sankyo: Promising Data for the Treatment of Addiction and Compulsive Disorders. Seattle, Feb. 22, 2011. PRNewswire via COMTEX.
Lallemand, F., et al., "SR147778, a CB1 Cannabinoid Receptor Antagonist, Suppresses Ethanol Preference in Chronically Alcoholized Wistar Rats," *Alcohol* 39(3):125-34 (2006) (Abstract only).
Newton, T.F., et al., "Bupropion Reduces Methamphetamine-induced Subjective Effects and Cue-induced Craving," *Neuropsychopharmacology* 31:1537-1544 (2006).
Compton, W. et al., "Abuse of prescription drugs and the risk of addiction," *Drug and Alcohol Dependence* 83S: S4-S7, 2006.
Deeb, S. et al., "A Pro12Ala Substitution in PPARγ2 Associated with Decreased Receptor Activity, Lower Body Mass Index and Improved Insulin Sensitivity," *Nature Genetics* 20:284-287, 1998.
Compton, W. et al., "Major Increases in Opioid Analgesic Abuse in the United States: Concerns and Strategies," *Drug and Alcohol Dependence* 81:103-107, 2006.
Henke, B., "1 Peroxisome Proliferator-activated receptor gamma (PPARγ) ligands and their therapeutic utility," *Prog.Med.Chem.* 42:1-53 (2004).
Prevention of Smoking Among Children and Adolescents, Feb. 28, 2012. <URL://big-archive.ru/med/tabakokurehnie/20.php.
Alcoholism Prevention, Feb. 28, 2012. <URL://www.russlav.ru/alkogolizm/profilaktika-alkogolizma.html.
Alcoholism Prevention, Feb. 28, 2012. <URL://www.russlav.ru/alkogolizm/profilaktika-alkogolizma.html. (Russian language).
Chuchalinea, A.G., Vyalkova, A.I., Belousova, Yu B., Yasnetsova, V.V. Federal Guidelines on the Use of Drugs. Drugs Used to Treat Nicotine Addiction, 2004.
Chuchalinea, A.G., Vyalkova, A.I., Belousova, Yu B., Yasnetsova, V.V. Federal Guidelines on the Use of Drugs. Drugs Used to Treat Nicotine Addiction, 2004. (Russian language).
International Statistical Classification of Diseases and Related Health Problems, Mar. 2, 2012. <URL://mkb10.ru.
Afif, Hassan et al., "Peroxisome Proliferator-activated Receptor γ1 Expression is Diminished in Human Osteoarthritic Cartilage and is Downregulated by Interleukin-1βin Articular Chondrocytes," *Arthritis Research & Therapy* 9:R31, 2007.
Boileau, Christelle et al., "The Peroxisome Proliferator-Activated Receptor γ Agonist Pioglitazone Reduces the Development of Cartilage Lesions in an Experimental Dog Model of Osteoarthritis: In Vivo Protective Effects Mediated Through the Inhibition of Key Signaling and Catabolic Pathways," *Arthritis & Rheumatism* 56(7):2288-2298, 2007.
Bordji, Karim et al., "Evidence for the Presence of Peroxisome Proliferator-Activated Receptor (PPAR) α and γ and Retinoid Z Receptor in Cartilage: PPARγ Activation Modulates the Effects of Interleukin-1β on Rat Chondrocytes," *The Journal of Biologoical Chemistry* 275(16):12243-12250, 2000.
Cheng, Saranette et al., "Activation of Peroxisome Proliferator-activated Receptor γ Inhibits Interleukin-1β-induced Membrane-associated Prostaglandin $E_2$ Synthase-1 Expression in Human Synovial Fibroblasts by Interfering with Egr-1," *The Journal of Biological Chemistry* 279(21):22057-22065, 2004.
Boyault, Sandrine et al., "15-Deoxy-$\Delta^{12,14}$-$PGJ_2$, but not Troglitazone, Modulates IL-1β Effects in Human Chondrocytes by Inhibiting NF-κB and AP-1 Activation Pathways," *FEBS* 501:24-30, 2001.

(56) References Cited

OTHER PUBLICATIONS

Cheng, S. et al., "Association of Polymorphisms in the Peroxisome Proliferator-activated Receptor γ Gene and Osteoarthritis of the Knee," *Ann Rheum Dis* 65:1394-1397, 2006.

Doi, Shigehiro et al., "Protective Effects of Peroxisome Proliferator-Activated Receptor γ Ligand on Apoptosis and Hepatocyte Growth Factor Induction in Renal Ischemia-Reperfusion Injury," *Transplantation* 84(2):207-213, 2007.

Ciccocioppo, R., et al., "Relapse Induced by Alcohol-Associated Environmental Stimuli After Extinction in Rats," *Alcohol Clin Exp Res* 23(Issue Supplement 5S): 52A, 1999 (Abstract Only).

Fahmi, Hassan et al., Peroxisome Proliferator-Activated Receptor γ Activators Inhibit Interleukin 1β-Induced Nitric Oxide and Matrix Metalloproteianse 13 Production in Human Chondrocytes, *Arthritis Rheum*. 44(3):595-607 (2001).

Fahmi, H., et al., "Peroxisome proliferator-activated receptor gamma activators inhibit MMP-1 production in human synovial fibroblasts likely by reducing the binding of the actiavor protein 1," *Osteoarthritis.Cartilage*. 10(2):100-108 (2002).

Fahmi, H., et al. "15d-PGJ$_2$ is acting as a 'dual agent' on the regulation of COX-2 expression in human osteoarthritic chondrocytes," *Osteoarthritis.Cartilage* 10(11):845-848 (2002).

Farrajota, K., et al. "Inhibition of Interleukin-1β-Induced Cyclooxygenase 2 Expression in Human Synovial Fibroblasts by 15-Deoxy-Δ$^{12,14}$-Prostaglandin J$_2$ Through a Histone Deacetylase-Independent Mechanism," *Arthritis Rheum*. 52(1):94-104 (2005).

Kalajdzic, T., et al., "Nimesulide, a preferential cyclooxygenase 2 inhibitor suppresses peroxisome proliferator-activated receptor induction of cyclooxygenase 2 gene expression in human synovial fibroblasts: evidence for receptor antagonism," *Arthritis Rheum*. 46(2):494-506 (2002).

Kanie, N., et al., "Relationship between peroxisome proliferator-activated receptors (PPARα PPARγ) and endothelium-dependent relaxation in streptozotocin-induced diabetic rats," *Br.J.Pharmacol*. 140(1):23-32 (2003).

Keller, J.M., et al., "Implications of peroxisome proliferator-activated receptors (PPARS) in development, cell life status and disease," *Int J.Dev.Biol*. 44(5):429-442 (2000).

Kobayashi, T., et al., "Pioglitazone, a peroxisome proliferator-activated receptor γ agonist, reduces the progression of experimental osteoarthritis in guinea pigs," *Arthritis Rheum*. 52(2):479-487 (2005).

Koufany, M., et al. "Anti-inflammatory effect of antidiabetic thiazolidnediones prevents bone resorption rather than cartilage changes in experimental polyarthritis," *Arthritis Res. Ther*. 10(1):R6 (2008).

Matsumoto, T., et al., "Mechanisms underlying the chronic pioglitazone treatment-induced improvement in the impared endothelium-dependent relaxation seen in aortas from diabetic rats," *Free Radic.Biol.Med*. 42(7):993-1007 (2007).

Matsumoto, T., et al., "Relationships among ET-1, PPARγ, oxidative stress and endothelial dysfunction in diabetic animals," *J.Smooth Muscle Res*. 44(2):41-55 (2008).

Moulin, D., et al. "Rosiglitazone induces interleukin-1 receptor antagonist in interleukin-1β-stimulated rat synovial fibroblasts via a peroxisome proliferator-activated receptor β/δ -dependent mechanism," *Arthritis Rheum*. 5293):759-769 (2005).

Poleni, P.E. et al. "Agonists of peroxisome proliferators-activated receptors (PPAR) α, β/δ or γ reduce transforming growth factor (TGF)-β-induced proteoglycans' production in chondrocytes," *Osteoarthritis.Cartilage*. 15(5):493-505 (2007).

Simonin, M.A., et al. "PPAR-γ ligands modulate effects of LPS in stimulated rat synogival fibroblasts," *Am.J.Physiol Cell Physiol* 282(1):C125-C133 (2002).

Fahmi, H., et al., "PPARγ ligands as modulators of inflammatory and catabolic responses in arthritis. An overview," *J.Rheumatol*. 29(1):3-14 (2002).

Haraguchi, T., et al., "Cerebroprotective action of telmisartan by inhibition of marcophages/microgila expressing HMGB1 via peroxisome proliferator-activated receptor γ-dependent mechanism," *Neurosci.Lett*. 464(3):151-155 (2009).

Hirano, M., et al. "Rapid improvement of carotid plaque echogenicity within 1 of pioglitazone treatment in partients with acute coronary syndrome," *Atherosclerosis* 203(2):483-488 (2009).

http://www.cwru.edu/med/psychiatry/bipolar/handouts/ Pioglitazone_handout_-_What_is_pioglitazone.pdf, Jun. 2010.

Jouzeau, J.Y., et al., "[Pathophysiological relevance of peroxisome proliferators activated perceptors (PPAR) to joint diseases—the pro and con of agonists]," *J.Soc.Biol*. 202(4):289-312 (2008).

Kobayashi, T., et al., "Changes in peroxisome proliferator-acitvated receptor γ-regulated gene expression and inhibin/activin-follistatin system gene expression in rat testis after an administration of di-η-butyl phthalate," *Toxicol.Lett*. 138(3):215-225 (2003).

Moulin, D., et al., "Effect of peroxisome proliferator activated receptor (PPAR)γ agonists on prostaglandins cascade in joint cells," *Biorheology* 43(3-4):561-575 (2006).

Leavitt, S.B., "Evidence for the efficacy of naltrexone in the treatment of alcohol dependence (alcoholism)," *Addiction Treatment Forum—Naltrexone Clinical Update* Mar. 2002.

Okuyemi, K.S., et al., "Interventions to facilitate smoking cessation," *Am.Fam.Physician* 74(2):262-271 (2006).

Lane, S.D., et al., "Changes in Brain White Matter Integrity After PPAR-GAMMA Agonist Treatment for Cocaine Use Disorder," Poster Abstrast. College on Problem of Drug Dependence. Nov. 16, 2016.

Schmitz, J.M., et al., "Pilot clinical trial of PPAR-Gamma agonist (pioglitazone) for cocaine use disorder," Poster Abstract. College on Problems of Drug Dependence, Jun. 11, 2016.

Miller, W.R., et al., "PPAR Gamma agonism attenuates cocaine cue reactivity," *Addiction Biology*, 1-14 (2016).

Martinez, S., et al., "Effects of Pioglitazone, a PPAR Gamma Agonist, on the Subjective and Reinforcing Effects of Nicotine," Meeting Presentation. Behavior, Biology, and Chemisty Meeting. Mar. 4, 2017.

Jones, J.D., et al., "The Effects of Pioglitazone, a PPAR Gamma Receptor Agonist, on the Abuse Liability of Heroin," Meeting Presentation. Society for Neuroscience Annual Meeting. Nov. 3, 2014.

Jones, J.D., et al., "The effects of pioglitazone, a PPAR Gamma receptors agonist, on the abuse liability of oxycodone among nondependent opioid users," *Physiol Behav* 159:33-39 (2016). Abstract Only.

Cohen, C., et al., "Nicotine-Associated Cues Maintain Nicotine-Seeking Behavior in Rats Several Weeks after Nicotine Withdrawal: Reversal by the Cannabinoid (CB1) Receptor Antagonist, Rimonabant (SR141716)," *Neuropsychopharmacology* 30:145-155 (2005).

Chin, C.T., et al., "Attenuation of methamphetamine-induced behavioral sensitization in mice by systemic administration of naltrexone," *Brain Research Bulletin* 67:100-409 (2005).

Ginawi O.T., et al., "Ondansetron, a selective 5-HT3 antagonist, antagonizes methamphetamine-induced anorexia in mice," *Pharmacological Research* 51:255-259 (2005).

Takamatsu, Y., et al., "Fluoxetine as a Potential Pharmacotherapy for Methamphetamine Dependence—Studies in Mice," *Ann. N.Y. Acad. Sci*. 1074:295-302 (2006).

\* cited by examiner

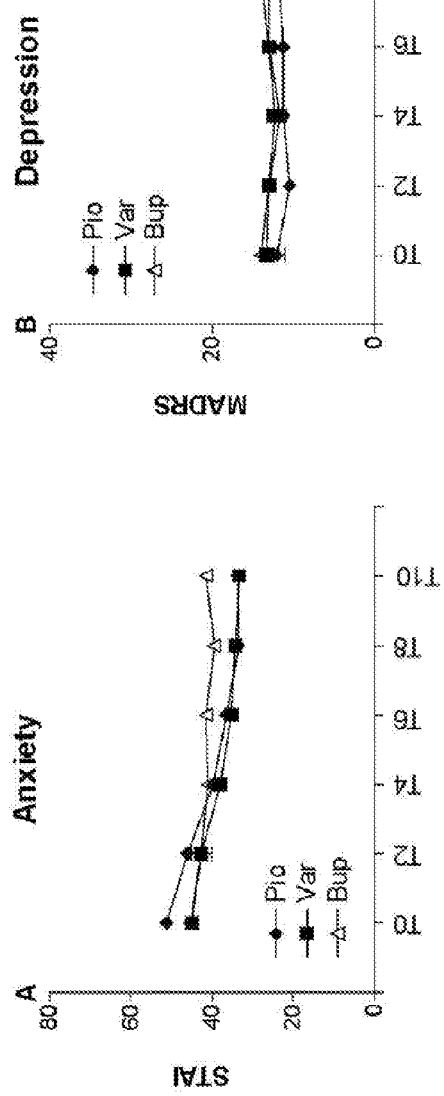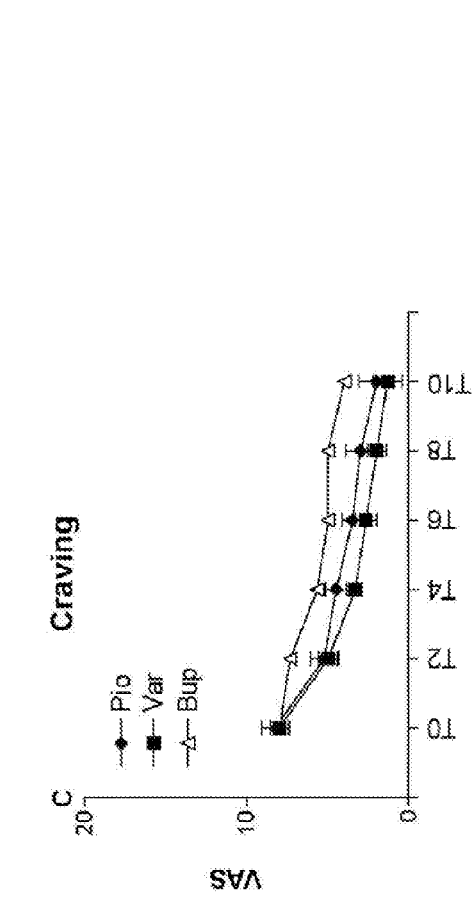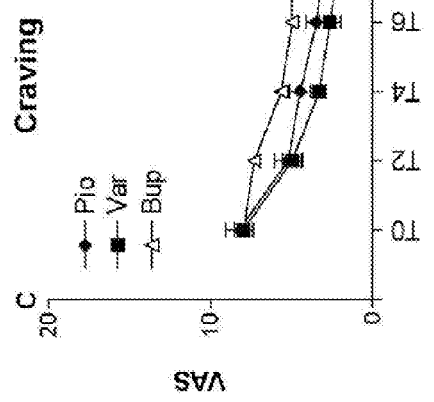
FIG. 25A
FIG. 25B
FIG. 25C

COMPOSITIONS AND METHODS FOR PROPHYLAXIS AND TREATMENT OF ADDICTIONS

CROSS-REFERENCE(S) TO RELATED APPLICATION(S)

This application is a continuation of copending U.S. patent application Ser. No. 13/853,585 filed Mar. 29, 2013, which is a continuation of U.S. patent application Ser. No. 12/722,429 filed Mar. 11, 2010, which is a continuation-in-part of U.S. patent application Ser. No. 12/101,943, filed Apr. 11, 2008, now pending, priority from the filing dates of which is hereby claimed under 35 U.S.C. § 120, and claims the benefit under 35 U.S.C. § 119(e) of U.S. Provisional Patent Application No. 60/911,201 filed Apr. 11, 2007; U.S. Provisional Patent Application No. 61/159,377 filed Mar. 11, 2009; and U.S. Provisional Patent Application No. 61/167,824 filed Apr. 8, 2009, where these (three) provisional application are incorporated herein by reference in their entireties.

BACKGROUND

Technical Field

The present invention is directed generally to the treatment or prevention of addictions using PPARγ agonists, alone or in combination with other therapeutic agents.

Description of the Related Art

The World Health Organization (WHO) defines substance addiction as using a substance repeatedly, despite knowing and experiencing harmful effects. Substance addiction is a chronic, relapsing disease characterized by a loss of control over drug use, compulsive drug seeking and craving for a substance, use that persists despite negative consequences, and physical and/or psychological dependence on the substance. Substance addiction typically follows a course of tolerance, withdrawal, compulsive drug taking behaviour, drug seeking behaviour, and relapse. Substance abuse and addiction are public health issues with significant social and economic impact on both the addict and society by playing a major role in violent crime and the spread of infectious diseases. Addictive substances include alcohol, caffeine, nicotine, *cannabis* (marijuana) and *cannabis* derivatives, opiates and other morphine-like opioid agonists such as heroin, phencyclidine and phencyclidine-like compounds, sedative ipnotics such as benzodiazepines and barbiturates and psychostimulants such as cocaine, amphetamines and amphetamine-related drugs such as dextroamphetamine and methylamphetamine.

Alcohol is one of the most commonly abused substances at a global level. Additionally, alcoholism leads to serious liver and cardiovascular disease and generates dependence resulting in severe mental disorders, social problems and adverse consequences including the division of families, tragic accidents and the reduction of work performance. According to the WHO, alcohol consumption is responsible for 20-30% of oesophageal and liver cancer, liver cirrhosis, homicides, epilepsy, and motor vehicle accidents worldwide. Globally, alcohol abuse leads to about 1.8 million deaths per year. Compulsive behaviour towards the consumption of alcohol is a core symptom of the disorder. In recent years several approaches have been investigated to help alcoholic patients to not only control alcohol drinking but also alcohol cravings and relapse (Monti et al., 1993; Volpicelli et al. 1992; O'Brien et al. 1997).

Medications such as naltrexone, acamprosate, ondansetron, disulfiram, gamma hydroxybutyrate (GHB), and topiramate tested for their potential therapeutic effect on alcohol abuse belong to several classes (Volpicelli et al. 1992; O'Brien et al. 1997). Few of these pharmacotherapeutics, such as naltrexone, acamprosate, and disulfiram, have been proven to be of a certain utility and approved for the treatment of alcoholism. Among these medications, the non-selective opioid antagonist naltrexone is currently considered the pharmacological gold standard. However, despite some promising results none of these medications, including naltrexone, is of sufficient efficacy in alcoholism and prognosis remains poor.

Nicotine is one of the most widely used addictive drugs, and nicotine abuse is the most common form of substance abuse. The WHO estimates that there are 1.25 billion smokers worldwide, representing one third of the global population over the age of 15. The WHO further estimates that 5 million deaths occur each year as a direct result of tobacco use, making nicotine abuse the largest single preventable cause of death worldwide. In industrialized countries, 70-90% of lung cancer, 56-80% of chronic respiratory disease, and 22% of cardiovascular disease instances are attributed to nicotine addiction. Cigarette smoking is associated with 430,000 deaths a year in the US alone and is estimated to cost the nation 80 billion dollars yearly in health care costs. Tobacco use accounts for one third of all cancers, including cancer of the lung, mouth, pharynx, larynx, esophagus, cervix, kidney, ureter, and bladder. The overall rates of death from cancer are twice as high among smokers as among nonsmokers. Smoking also causes lung diseases such as chronic bronchitis and emphysema; exacerbates asthma symptoms; and increases the risk of heart disease, including stroke, heart attack, vascular disease, and aneurysm. An estimated 20% of the deaths from heart disease are attributable to smoking. Expectant women who smoke are at greater risk than nonsmokers for premature delivery, spontaneous abortion, and infants with decreased birth weight.

Nicotine use results in increased levels of the neurotransmitter dopamine, which activates the reward pathways to regulate feelings of pleasure and to mediate the desire to consume nicotine. Symptoms associated with nicotine withdrawal include craving, irritability, anger, hostility, aggression, fatigue, depression, and cognitive impairment, which lead the abuser to seek more nicotine. Environmental conditioning factors and exposure to psychological stress represent additional factors motivating nicotine use in smokers. Repeated nicotine use results in the development of tolerance, requiring higher doses of nicotine to produce the same initial stimulation.

Most therapies developed for nicotine addiction have shown only moderate success in preventing relapse, leading to a high failure rate in attempts to quit smoking. Treatments include the use of nicotine replacement products, antidepressants, anti-hypersensitives, and behavioural therapy.

The National Institute on Drug Abuse estimates that 72 million Americans, about one third of the population, have tried marijuana. Acute effects of marijuana use include memory and learning problems, distorted perception, difficulty problem solving, loss of coordination, and increased heart rate. Long term abuse can cause the same respiratory problems observed in tobacco smokers, such as daily cough, phlegm production, increased risk of lung infections, and an increased chance of developing cancer of the head, neck and lungs. Depression, anxiety, and job-related problems have been associated with marijuana use. Long term marijuana use can result in addiction with compulsive use that interferes with daily activities. Cravings and withdrawal symptoms, such as irritability, increased aggression, sleeplessness, and anxiety make it difficult for addicts to stop using marijuana. There are no pharmaceutical treatments available for treating marijuana addiction and relapse.

According to the WHO, an estimated 13 million people abuse opiates worldwide, including 9 million heroin addicts. More than 25% of opiate abusers die from suicide, homicide, or an infectious disease, such as HIV and hepatitis, within 10-20 years of becoming addicted. Tolerance and physical dependence can develop within two to three days. While abuse and addiction to opioid agents is a known phenomenon, what is new is the worsening of this problem in the recent years (Compton and Volkow 2006; Compton and Volkow 2006). Epidemiological surveys of youth in the United States in 2003 indicated that opioid analgesics were among the most frequently abused illicit drugs among secondary students (12th graders), second only to marijuana (Delva et al. 2005). Furthermore, the past few years have seen a marked increase in the use of opioid medications in the United States and an even greater increase in problems associated with such use. This upsurge in use and problems is particularly concerning because it seems to represent an expanded pathway to opioid addiction (Siegal, Carlson et al. 2003).

According to recent epidemiological data, 4.7% (i.e., 11.0 million) United States household residents over the age of twelve abused an opioid medication in 2002 and 13.7% of these persons (i.e., 1.5 million) endorsed the symptoms of a DSM-IV opioid use disorder (Association 1994; *Substance Abuse and Mental Health Services Administration* 2004). As recently reviewed by Compton and Volkow, the annual incidence of opioid analgesic abuse increased from 628,000 initiates in 1990 to 2.4 million initiates in 2001 (*Administration* 2003; *Substance Abuse and Mental Health Services Administration* 2003). One of the reasons fostering the expansion of opioid addiction is the increased use of analgesic secondary to medical prescription. Short term use of opioid medication is rarely associated with addiction. Conversely, protracted treatments with these agents have been associated with development of addiction in up to 18% of patients.

The goals for treatment of opiate addiction, as with other types of substance addictions, are to discontinue the use of the opiate while minimizing painful withdrawal symptoms and preventing relapse. Current treatments involve replacing the addictive drug with a substitution of an opioid receptor agonist or mixed agonist/antagonist. An alternative approach consists of the use of an opioid receptor antagonist to block the effect of the agonist. Antagonists provide no relief from pain or other withdrawal symptoms; rather, they can precipitate withdrawal, and their therapeutic use was associated with increased accidental opioid agonists overdosing and increased lethality. Use of agonists with a lower affinity for the receptors results in the least severe withdrawal symptoms, but it can lead to a dependence on the substitute opiate. Also, many substitution therapies take 3-6 months, allowing time for addicts to stop treatment midway.

Psychostimulants, such as cocaine and amphetamines, cause euphoria, increased alertness, and increased physical capacity in humans. These substances first increase dopamine transmission, but long term drug usage results in a reduction of dopamine activity, leading to dysregulation of the brain reward system and dysporia. The WHO estimates 33 million people around the world abuse amphetamines.

Chronic cocaine abuse can result in hyperstimulation, tachycardia, hypertension, mydriasis, muscle twitching, sleeplessness, extreme nervousness, hallucinations, paranoia, aggressive behaviour, and depression. Cocaine overdose may lead to tremors, convulsions, delirium, and death resulting from heart arrhythmias and cardiovascular failure. Desipramine, amantadine and bromocriptine have been shown to decrease cocaine withdrawal symptoms.

Amphetamine withdrawal symptoms include EEG changes, fatigue, and mental depression. Tolerance develops over time and may be associated with tachycardia, auditory and visual hallucinations, delusions, anxiety reactions, paranoid psychosis, exhaustion, confusion, memory loss, and prolonged depression with suicidal tendencies. Current treatments for amphetamine addiction include phenothiazines, haloperidol, and chlorpromazine for hallucinations, but potential side effects of these drugs include postural hypotension and severe extrapyramidal motor disorders.

In the past, treatment for substance addictions focused on behavioural therapy, but dependence on many of these highly addictive substances is hard to break. In particular, addictions to alcohol, cocaine, and heroin are considered chronic, relapsing disorders. Also, concurrent abuse of multiple substances, such as nicotine, heroin, cocaine and alcohol, is common.

The long-lasting, chronic nature of many addictions and high rates of recidivism present a considerable challenge for the treatment of drug and alcohol addiction, such that understanding of the neurobiological basis of relapse has emerged as a central issue in addiction research. Emotional and environmental factors (conditioning stimuli) were listed among the main causes of relapse. For example, it is known that specific stress conditions such as loss of work and economic difficulties, or stimuli predictive of the presence of alcohol previously associated with its use such as a bottle of the preferred wine and a bar-like environment, may strongly facilitate relapse in detoxified former alcoholics.

Two major theoretical positions exist to explain the persistence of addictive behaviour and vulnerability to relapse associated with drug and alcohol addiction, homeostatic hypotheses and conditioning hypotheses.

Homeostatic hypotheses relate relapse risk to neuroadaptive changes and disruption of neuroendocrine homeostasis that are thought to underlie anxiety, mood dysregulation and somatic symptoms that accompany acute withdrawal, and that can persist for considerable periods of time during what has been referred to as the "protracted withdrawal" phase. This view, therefore, implicates alleviation of discomfort and negative affect as a motivational basis for relapse.

Conditioning hypotheses are based on observations that relapse is often associated with exposure to drug-related environmental stimuli. This view holds that specific environmental stimuli that have become associated with the rewarding actions of a drug by means of classical conditioning can elicit subjective states that trigger resumption of drug use. The homeostatic and conditioning hypotheses are not mutually exclusive. In fact, homeostatic and conditioning factors are likely to exert additive effects in that exposure to drug-related environmental stimuli may augment vulnerability to relapse conveyed by homeostatic disturbances.

Clearly, there is a need in the art for new methods for treating and preventing addiction and the relapse use of addictive agents. The present invention meets these needs by providing methods and pharmaceutical combinations useful in treating and preventing addiction and recidivism.

BRIEF SUMMARY

The present invention is directed generally to the use of PPARγ agonists, alone or in combination with one or more additional therapeutic agents, for the treatment and prevention of addictions and relapse to addictive use or behavior. Accordingly, the present invention provides methods and related compositions, unit dosage forms, and kits useful for the treatment and prevention of addictions, and for the treatment and prevention of relapse use of addictive agents or practice of addictive or compulsive behaviours.

In one embodiment, the present invention includes a method of treating or preventing an addiction, comprising determining that a subject has or is at risk of developing an addiction, and providing to the subject an amount of an agonist of a peroxisome proliferator-activated receptor gamma (PPARγ agonist) effective for the treatment or prevention of the addiction.

In a related embodiment, the present invention provides a method of treating or preventing an addiction, comprising providing to a subject having an addiction a peroxisome proliferator-activated receptor gamma (PPARγ agonist) and an additional therapeutic agent, wherein each of the PPARγ agonist and the additional therapeutic agent contribute to the effective treatment or prevention of the addiction.

In certain embodiments of the methods of treating or preventing addiction of the present invention, the PPARγ agonist is a thiazolidinedione (TZD). In particular embodiments, the TZD is pioglitazone, rosiglitazone, ciglitazone, troglitazone, englitazone, rivoglitazone, or darglidazone. In certain embodiments, the additional therapeutic agent is an opioid antagonist, a mixed opioid partial agonist/antagonist, an antidepressant, an antiepileptic, an antiemetic, a corticotrophin-releasing factor-1 (CRF-1) receptor antagonist, a selective serotonin-3 (5-HT3) antagonist, a 5-HT$_{2A/2C}$ antagonist, or a cannabinoid-1 (CB1) receptor antagonist. In particular embodiments, the opioid antagonist is naltrexone or nalmefene. In particular embodiments, the antidepressant is fluoxetine, mirtazapine, or bupropion. In particular embodiments, the antiepileptic is topiramate, levetiracetam, or gabapentin. In one embodiment, the CRF-1 receptor antagonist is antalarmin. In another embodiment, the selective serotonin-3 (5-HT3) antagonist is ondansetron. In particular embodiments, the cannabinoid-1 (CB1) receptor antagonist is rimonabant or tanarabant. In one embodiment, the mixed opioid agonist/antagonist is buprenorphine.

In certain embodiments of the methods of the present invention, the subject is addicted to an addictive agent, or at risk for relapse use of an addictive agent. In particular embodiments, the addictive agent is alcohol, nicotine, marijuana, a marijuana derivative, an opioid agonist, a benzodiazepine, a barbiturate, or a psychostimulant. In certain embodiments, the opioid agonist is selected from the group consisting of: morphine, methadone, fentanyl, sufentanil and heroin. In certain embodiments, the psychostimulant is cocaine, amphetamine or an amphetamine derivative. In addition, the subject may be addicted to more than one addictive agent, and the pharmaceutical compositions, unit dosage forms, and kits may be useful for treating or preventing addiction or relapse use of more than one addictive agent.

In other embodiments of the present invention, the subject is addicted to an addictive or compulsive behavior or at risk for relapse practice of an addictive or compulsive behaviour. In particular embodiments, the addictive or compulsive behavior is pathological gambling, pathological overeating, pathological use of electronic devices, pathological use of electronic video games, pathological use of electronic communication devices, pathological use of cellular telephones, addiction to pornography, sex addiction, obsessive compulsive disorder, compulsive spending, anorexia, bulimia, intermittent explosive disorder, kleptomania, pyromania, trichotillomania, compulsive overexercising, and compulsive overworking. In addition, the subject may be addicted to more than one addictive or compulsive behaviour, and the pharmaceutical compositions, unit dosage forms, and kits may be useful for treating or preventing addiction or relapse use of more than one addictive or compulsive behaviour.

In particular embodiments of any of the methods of the present invention, the addictive agent is alcohol and the additional therapeutic agent is an opioid antagonist or a mixed opioid antagonist/partial agonist. In one embodiment, the opioid antagonist is naltrexone. In another embodiment, the mixed opioid partial agonist/antagonist is buprenorphine.

In other particular embodiments of any of the methods of the present invention, the addictive agent is nicotine and the additional therapeutic agent is an antidepressant. In one embodiment, the antidepressant is bupropion.

In further particular embodiments of any of the methods of the present invention, the addictive agent is a psychostimulant and the additional therapeutic agent is an antidepressant. In one embodiment, the antidepressant is bupropion.

In other particular embodiments of any of the present invention, the subject is addicted to two or more addictive agents and the additional therapeutic agent is an opioid antagonist or a mixed opioid partial agonist/antagonist. In certain embodiments, the opioid antagonist is naltrexone or nalmefene. In other embodiments, the mixed opioid partial agonist/antagonist is buprenorphine.

In further related embodiments, the present invention provides a method of preventing relapse use of an addictive agent or practice of an addictive or compulsive behaviour, comprising providing an effective amount of a peroxisome proliferator-activated receptor gamma (PPARγ agonist) to a subject who has undergone a period of abstinence from, or limited or reduced use of, the addictive agent or practice of the addictive or compulsive behaviour. In certain embodiments, the subject has undergone physiological withdrawal from the addictive agent during the period of abstinence from, or limited or reduced use of, the addictive agent or due to no longer being exposed to an effective amount of the anti-addiction treatment. The anti-addiction treatment may be an anti-addiction drug or may be a non-pharmacologic therapy such as counseling, psychotherapy or hypnosis therapy.

In a related embodiment, the present invention includes a method of preventing relapse use of an addictive agent or practice of an addictive or compulsive behaviour, comprising providing an effective amount of a peroxisome proliferator-activated receptor gamma (PPARγ agonist) to a subject who has undergone a period of abstinence from, or limited or reduced use of, the addictive agent or practice of the addictive or compulsive behaviour, and also providing to the subject an additional therapeutic agent, wherein each of the PPARγ agonist and the additional therapeutic agent contribute to the effective prevention of the relapse use or practice. In certain embodiments, the subject has undergone physiological withdrawal from the addictive agent during the period of abstinence from, or limited or reduced use of, the addictive agent or due to no longer being exposed to an effective amount of the anti-addiction treatment.

In another related embodiment, the present invention provides a method of treating relapse use of an addictive agent or practice of an addictive or compulsive behaviour, comprising providing an effective amount of a peroxisome proliferator-activated receptor gamma (PPARγ agonist) to a subject who has undergone a period of abstinence from, or limited or reduced use of, the addictive agent or practice of the addictive or compulsive behaviour. In certain embodiments, the subject has undergone physiological withdrawal from the addictive agent during the period of abstinence from, or limited or reduced use of, the addictive agent or due to no longer being exposed to an effective amount of the anti-addiction treatment.

In a further embodiment, the present invention includes a method of treating relapse use of an addictive agent or practice of an addictive or compulsive behaviour, comprising providing an effective amount of a peroxisome proliferator-activated receptor gamma (PPARγ agonist) to a subject who has undergone a period of abstinence from, or limited or reduced use of, the addictive agent or practice of the addictive or compulsive behaviour, and also providing to the subject an additional therapeutic agent wherein each of the PPARγ agonist and the additional therapeutic agent contribute to the effective treatment of the relapse use or practice. In certain embodiments, the subject has undergone physiological withdrawal from the addictive agent during the period of abstinence from, or limited or reduced use of, the addictive agent or due to no longer being exposed to an effective amount of the anti-addiction treatment.

In another related embodiment, the present invention provides a method of preventing relapse use of an addictive agent or practive of an addictive or compulsive behaviour, comprising providing an effective amount of a peroxisome proliferator-activated receptor gamma (PPARγ agonist) to a subject, wherein the subject previously reduced or eliminated use of the addictive agent or practice of the addictive or compulsive behaviour in response to treatment with an effective amount of an anti-addiction treatment, and wherein the subject is no longer exposed to an effective amount of the anti-addiction treatment. In certain embodiments, the subject is no longer exposed to an effective amount of an anti-addiction agent because the subject has become conditioned to the anti-addiction agent. In certain embodiments, the subject is no longer exposed to an effective amount of the anti-addiction treatment because the subject has reduced or eliminated exposure to the anti-addiction treatment.

In a related embodiment, the present invention provides a method of preventing relapse use of an addictive agent or practive of an addictive or compulsive behaviour, comprising providing an effective amount of a peroxisome proliferator-activated receptor gamma (PPARγ agonist) to a subject, wherein the subject previously reduced or eliminated use of the addictive agent or practice of the addictive or compulsive behaviour in response to treatment with an effective amount of an anti-addiction treatment, and wherein the subject is no longer exposed to an effective amount of the anti-addiction treatment, and also providing to the subject an additional therapeutic agent, wherein each of the PPARγ agonist and the additional therapeutic agent contribute to the effective prevention of the relapse use or practice. In certain embodiments, the subject is no longer exposed to an effective amount of an anti-addiction agent because the subject has become conditioned to the anti-addiction agent. In certain embodiments, the subject is no longer exposed to an effective amount of the anti-addiction treatment because the subject has reduced or eliminated exposure to the anti-addiction treatment.

In additional embodiments, the present invention includes a method of treating relapse use of an addictive agent or practive of an addictive or compulsive behaviour, comprising providing an effective amount of a peroxisome proliferator-activated receptor gamma (PPARγ agonist) to a subject, wherein the subject previously reduced or eliminated use of the addictive agent or practice of the addictive or compulsive behaviour in response to treatment with an effective amount of an anti-addiction treatment, and wherein the subject is no longer exposed to an effective amount of the anti-addiction treatment. In certain embodiments, the subject is no longer exposed to an effective amount of an anti-addiction agent because the subject has become conditioned to the anti-addiction agent. In certain embodiments, the subject is no longer exposed to an effective amount of the anti-addiction treatment because the subject has reduced or eliminated exposure to the anti-addiction treatment.

In a further embodiment, the present invention includes a method of treating relapse use of an addictive agent or practive of an addictive or compulsive behaviour, comprising providing an effective amount of a peroxisome proliferator-activated receptor gamma (PPARγ agonist) to a subject, wherein the subject previously reduced or eliminated use of the addictive agent or practice of the addictive or compulsive behaviour in response to treatment with an effective amount of an anti-addiction treatment, and wherein the subject is no longer exposed to an effective amount of the anti-addiction treatment, and also providing to the subject an additional therapeutic agent, wherein each of the PPARγ agonist and the additional therapeutic agent contribute to the effective treatment of the relapse use or practice. In certain embodiments, the subject is no longer exposed to an effective amount of an anti-addiction agent because the subject has become conditioned to the anti-addiction agent. In certain embodiments, the subject is no longer exposed to an effective amount of the anti-addiction treatment because the subject has reduced or eliminated exposure to the anti-addiction treatment.

In particular embodiments of any of the methods of treating or preventing relapse use or practice of the present invention, the PPARγ agonist is pioglitazone and the additional therapeutic agent is naltrexone.

In particular embodiments of any of the methods of treating or preventing relapse use or practice of the present invention, the relapse use or relapse practice is stress-induced.

In another embodiment, the present invention provides a method of reducing one or more symptoms associated with physiological withdrawal from an addictive agent, comprising providing an effective amount of a peroxisome proliferator-activated receptor gamma (PPARγ) agonist to a subject undergoing physiological withdrawal from an addictive agent.

In a related embodiment, the present invention provides a method of reducing one or more symptoms associated with physiological withdrawal from an addictive agent, comprising providing an effective amount of a peroxisome proliferator-activated receptor gamma (PPARγ) agonist and an additional therapeutic agent to a subject undergoing physiological withdrawal from an addictive agent, wherein each of the PPARγ agonist and the additional therapeutic agent contribute to reducing one or more symptoms associated with physical withdrawal from the addictive agent.

In particular embodiments of methods of reducing one or more symptoms associated with physiological withdrawal from an addictive agent according to the present invention, the PPARγ agonist is a thiazolidinedione (TZD). In certain embodiments, the TZD is pioglitazone, rosiglitazone, ciglitazone, troglitazone, englitazone, rivoglitazone or darglidazone. In certain embodiments, the additional therapeutic agent is an opioid antagonist, a mixed opioid partial agonist/antagonist, an antidepressant, an antiepileptic, an antiemetic, a corticotrophin-releasing factor-1 (CRF-1) receptor antagonist, a selective serotonin-3 (5-HT3) antagonist, a 5-HT$_{2A/2C}$ antagonist, or a cannabinoid-1 (CB1) receptor antagonist.

In another embodiment, the present invention includes a pharmaceutical composition, comprising a peroxisome proliferator-activated receptor gamma (PPARγ) agonist and an additional therapeutic agent, wherein each of the PPARγ agonist and the additional therapeutic agent contribute to the effective treatment or prevention of an addiction. In certain embodiments, the PPARγ agonist is a thiazolidinedione (TZD). In certain embodiments, the TZD is pioglitazone, rosiglitazone, ciglitazone, troglitazone, englitazone, rivoglitazone or darglidazone.

In one embodiment, the pharmaceutical composition is effective in the treatment of an addiction to an addictive agent. In particular embodiments, the addictive agent is alcohol, nicotine, marijuana, a marijuana derivative, an opioid agonist, a benzodiazepine, a barbiturate, or a psychostimulant.

In another embodiment, the pharmaceutical composition is effective in the treatment of an addiction to an addictive or compulsive behaviour. In particular embodiments, the addictive or compulsive behavior is pathological gambling, pathological overeating, pathological use of electronic devices, pathological use of electronic video games, pathological use of electronic communication devices, pathological use of cellular telephones, addiction to pornography, sex addiction, obsessive compulsive disorder, compulsive spending, anorexia, bulimia, intermittent explosive disorder, kleptomania, pyromania, trichotillomania, compulsive over-exercising, and compulsive overworking.

In certain embodiments of pharmaceutical compositions of the present invention, the additional therapeutic agent is an opioid antagonist, a mixed opioid partial agonist/antagonist, an antidepressant, an antiepileptic, an antiemetic, a corticotrophin-releasing factor-1 (CRF-1) receptor antagonist, a selective serotonin-3 (5-HT3) antagonist, a 5-HT$_{2A/2C}$ antagonist, and a cannabinoid-1 (CB1) receptor antagonist. In one embodiment, the opioid antagonist is naltrexone or nalmefene. In one embodiment, the antidepressant is fluoxetine, mirtazapine, or bupropion. In one embodiment, the antiepileptic is selected from the group consisting of: topiramate, levetiracetam, and gabapentin. In one embodiment, the CRF-1 receptor antagonist is antalarmin. In one embodiment, the selective serotonin-3 (5-HT3) antagonist is ondansetron. In one embodiment, the cannabinoid-1 (CB1) receptor antagonist is rimonabant or tanarabant. In one embodiment, the mixed opioid agonist/antagonist is buprenorphine.

In a particular embodiment of a pharmaceutical composition of the present invention, the addictive agent is alcohol and the additional therapeutic agent is an opioid antagonist or a mixed opioid antagonist/partial agonist. In one embodiment, the opioid antagonist is naltrexone. In one embodiment, the mixed opioid partial agonist/antagonist is buprenorphine.

In a particular embodiment of a pharmaceutical composition of the present invention, the addictive agent is nicotine and the additional therapeutic agent is an antidepressant. In one embodiment, the antidepressant is bupropion.

In a particular embodiment of a pharmaceutical composition of the present invention, the addictive agent is a psychostimulant and the additional therapeutic agent is an antidepressant. In one embodiment, the antidepressant is bupropion.

In a particular embodiment of a pharmaceutical composition of the present invention, the addictive agent comprises two or more addictive agents and the additional therapeutic agent is an opioid antagonist or a mixed opioid partial agonist/antagonist. In one embodiment, the opioid antagonist is naltrexone or nalmefene. In one embodiment, the mixed opioid partial agonist/antagonist is buprenorphine.

In a particular embodiment of a pharmaceutical composition of the present invention, the PPARγ agonist is pioglitazone and the additional therapeutic agent is naltrexone.

In further related embodiments, the present invention includes unit dosage forms of a pharmaceutical composition adapted for the treatment of an addiction, wherein said unit dosage form comprises a peroxisome proliferator-activated receptor gamma (PPARγ) agonist and an additional therapeutic agent, wherein said unit dosage form comprises the PPARγ agonist and the additional therapeutic agent in a combined amount effective in the treatment of an addiction, and wherein each of the PPARγ agonist and the additional therapeutic agent contribute to the effective treatment or prevention of the addiction. In particular embodiments, the PPARγ agonist is a thiazolidinedione (TZD). In certain embodiments, the TZD is pioglitazone, rosiglitazone, ciglitazone, troglitazone, englitazone, rivoglitazone or darglidazone. In certain embodiments, the additional therapeutic agent is an opioid antagonist, a mixed opioid partial agonist/antagonist, an antidepressant, an antiepileptic, an antiemetic, a corticotrophin-releasing factor-1 (CRF-1) receptor antagonist, a selective serotonin-3 (5-HT3) antagonist, a 5-HT$_{2A/2C}$ antagonist, or a cannabinoid-1 (CB1) receptor antagonist. In one embodiment, the opioid antagonist is naltrexone or nalmefene. In one embodiment, the antidepressant is fluoxetine, mirtazapine, or bupropion. In one embodiment, the antiepileptic is selected from the group consisting of: topiramate, levetiracetam, and gabapentin. In one embodiment, the CRF-1 receptor antagonist is antalarmin. In one embodiment, the selective serotonin-3 (5-HT3) antagonist is ondansetron. In one embodiment, the cannabinoid-1 (CB1) receptor antagonist is rimonabant or tanarabant. In one embodiment, the mixed opioid agonist/antagonist is buprenorphine.

In one particular embodiment of a unit dosage form of the present invention, the PPARγ agonist is pioglitazone and the additional therapeutic agent is naltrexone.

In another related embodiment, the present invention includes a kit useful for the treatment or prevention of an addiction, comprising: a first container comprising a peroxisome proliferator-activated receptor gamma (PPARγ) agonist; and a second container comprising an additional therapeutic agent, wherein each of the PPARγ agonist and the additional therapeutic agent contribute to the effective treatment of prevention of an addiction. In particular embodiments, the PPARγ agonist is a thiazolidinedione (TZD). In certain embodiments, the TZD is pioglitazone, rosiglitazone, ciglitazone, troglitazone, englitazone, rivoglitazone or darglidazone. In certain embodiments, the additional therapeutic agent is an opioid antagonist, a mixed opioid partial agonist/antagonist, an antidepressant, an antiepileptic, an antiemetic, a corticotrophin-releasing factor-1 (CRF-1) receptor antagonist, a selective serotonin-3 (5-HT3) antagonist, a 5-HT$_{2A/2C}$ antagonist, or a cannabinoid-1 (CB1) receptor antagonist. In one embodiment, the opioid antagonist is naltrexone or nalmefene. In one embodiment, the antidepressant is fluoxetine, mirtazapine, or bupropion. In one embodiment, the antiepileptic is selected from the group consisting of: topiramate, levetiracetam, and gabapentin. In one embodiment, the CRF-1 receptor antagonist is antalarmin. In one embodiment, the selective serotonin-3 (5-HT3) antagonist is ondansetron. In one embodiment, the cannabinoid-1 (CB1) receptor antagonist is rimonabant or tanarabant. In one embodiment, the mixed opioid agonist/antagonist is buprenorphine.

In one particular embodiment of a kit of the present invention, the PPARγ agonist is pioglitazone and the additional therapeutic agent is naltrexone.

In one particular embodiment of a kit of the present invention, the addictive agent is alcohol and the additional therapeutic agent is an opioid antagonist or a mixed opioid antagonist/partial agonist. In one embodiment, the opioid antagonist is naltrexone. In one embodiment, the mixed opioid partial agonist/antagonist is buprenorphine.

In one particular embodiment of a kit of the present invention, the addictive agent is nicotine and the additional therapeutic agent is an antidepressant. In one embodiment, the antidepressant is bupropion.

In one particular embodiment of a kit of the present invention, the addictive agent is a psychostimulant and the additional therapeutic agent is an antidepressant. In one embodiment, the antidepressant is bupropion.

In one particular embodiment of a kit of the present invention, the addictive agent comprises two or more addictive agents and the additional therapeutic agent is an opioid antagonist or a mixed opioid partial agonist/antagonist. In one embodiment, the opioid antagonist is naltrexone or nalmefene. In one embodiment, the mixed opioid partial agonist/antagonist is buprenorphine.

In a further embodiment, the present invention includes a kit comprising one or more unit dosage forms of a peroxisome proliferator-activated receptor gamma (PPARγ) agonist and one or more unit dosage forms of nicotine. In one embodiment, the one or more unit dosage forms of nicotine comprise two or more different amounts of nicotine. In one embodiment, the PPARγ agonist is a thiazolidinedione (TZD). In one embodiment, the TZD is pioglitazone, rosiglitazone, ciglitazone, troglitazone, englitazone, rivoglitazone or darglidazone.

In additional embodiment, the present invention includes a method of preventing a subject from becoming addicted, or reducing the likelihood that a subject will become addicted, to an addictive therapeutic agent, comprising providing to a subject in need thereof an addictive therapeutic agent, and an effective amount of a peroxisome proliferator-activated receptor gamma (PPARγ agonist), wherein the effective amount of the PPARγ agonist is an amount effective in preventing the subject from becoming addicted, or reducing the likelihood that the subject will become addicted, to the addictive therapeutic agent. In particular embodiment, this method further comprises providing to the subject an additional therapeutic agent, wherein each of the PPARγ agonist and the additional therapeutic agent contribute to preventing the subject from becoming addicted, or reducing the likelihood that the subject will become addicted, to the addictive therapeutic agent. In one embodiment, the addictive therapeutic agent is an opioid agonist. In certain embodiments, the opioid agonist is codeine, morphine, noscapapine, hydrocodone, hydromorphone, oxycodone, tramadol, fentanyl, sufentanil, alfentanil, propoxyphene, methadone, butorphanol, destropropoxyphene, diamorphine, levorphanol, meptazinol, nalbuphine, pentazocine, dezocine, meperidine, or buprenorphine. In one embodiment, the PPARγ agonist is a TZD. In particular embodiments, the TZD is pioglitazone, rosiglitazone, ciglitazone, troglitazone, englitazone, rivoglitazone or darglidazone. In one embodiment, the PPARγ agonist is pioglitazone, and the addictive therapeutic agent is oxycodone. In another embodiment, the the PPARγ agonist is pioglitazone, and the addictive therapeutic agent is hydrocodone. In a further embodiment, the PPARγ agonist is rosiglitazone, and the addictive therapeutic agent is oxycodone. In a further embodiment, the PPARγ agonist is rosiglitazone, and the addictive therapeutic agent is hydrocodone. In another embodiment, the PPARγ agonist is pioglitazone, and the addictive therapeutic agent is fentanyl. In a further embodiment, the PPARγ agonist is rosiglitazone, and the addictive therapeutic agent is fentanyl.

In related embodiments, the present invention also includes pharmaceutical compositions, and unit dosage forms thereof, comprising an effective amount of an addictive therapeutic agent and an effective amount of a PPARγ agonist, wherein the effective amount of the PPARγ agonist is an amount effective in preventing the subject from becoming addicted, or reducing the likelihood that the subject will become addicted, to the addictive therapeutic agent. In one embodiment, the addictive therapeutic agent is an opioid agonist. In particular embodiments, the opioid agonist is alfentanil, allylprodine, alphaprodine, anileridine, apomorphine, benzylmorphine, beta-hydroxy 3-methylfentanyl, bezitramide, buprenorphine, butorphanol, carfentanil, clonitazene, codeine, desomorphine, destropropoxyphene, dextromoramide, dezocine, diacetylmorphine (heroin), diamorphine, diampromide, dihydrocodeine, dihydroetorphine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, etorphine, fentanyl, hydrocodone, hydromorphone, hydroxypethidine, isomethadone, ketobemidone, LMM, levorphanol, levophenacylmorphan, lofentanil, meperidine, meptizinol, metapon, metazocine, methadone, methadyl acetate, metopon, morphine, myrophine, nalbuphine, narceine, nicomorphine, norlevorphanol, normethadone, normorphine, norpipanone, noscapine, opium, oxycodone, oxymorphone, papaverine, pentazocine, phenadoxone, phenomorphan, phenoperidine, piminodine, piritramide, propheptazine, promedol, properidine, propoxyphene, remifentanil, sufentanil, thebaine, tildine, or tramadol, or any combination thereof. In particular embodiments, the TZD is pioglitazone, rosiglitazone, ciglitazone, troglitazone, englitazone, rivoglitazone or darglidazone. In one embodiment, the PPARγ agonist is pioglitazone, and the addictive therapeutic agent is oxycodone. In another embodiment, the the PPARγ agonist is pioglitazone, and the addictive therapeutic agent is hydrocodone. In a further embodiment, the PPARγ agonist is rosiglitazone, and the addictive therapeutic agent is oxycodone. In a further embodiment, the PPARγ agonist is rosiglitazone, and the addictive therapeutic agent is hydrocodone. In another embodiment, the PPARγ agonist is pioglitazone, and the addictive therapeutic agent is fentanyl. In a further embodiment, the PPARγ agonist is rosiglitazone, and the addictive therapeutic agent is fentanyl. In one embodiment, the combination of a PPARγ agonist, such as pioglitazone or rosiglitazone, and fentanyl may be delivered transdermally, e.g., using a patch comprising both agents. Alternatively, each agent may be delivered via a different route.

In certain embodiments of the methods of the present invention, the subject is addicted to an addictive agent, or at risk for relapse use of an addictive agent. In various embodiments, the pharmaceutical compositions, unit dosage forms, and kits of the present invention are useful for the treatment or prevention of addiction to an addictive agent or relapse use of an addictive agent. In particular embodiments, the addictive agent is alcohol, nicotine, marijuana, a marijuana derivative, an opioid agonist, a benzodiazepine, a barbiturate, or a psychostimulant. In certain embodiments, the opioid agonist is selected from the group consisting of: morphine, methadone, fentanyl, sufentanil and heroin. In certain embodiments, the psychostimulant is cocaine, amphetamine or an amphetamine derivative. In addition, the subject may be addicted to more than one addictive agent, and the pharmaceutical compositions, unit dosage forms, and kits may be useful for treating or preventing addiction or relapse use of more than one addictive agent.

In other embodiments of the present invention, the subject is addicted to an addictive or compulsive behavior or at risk for relapse practice of an addictive or compulsive behaviour. In various embodiments, the pharmaceutical compositions, unit dosage forms, and kits of the present invention are useful for the treatment or prevention of addiction to an addictive or compulsive behaviour or relapse use of an addictive or compulsive behaviour. In particular embodiments, the addictive or compulsive behavior is pathological gambling, pathological overeating, pathological use of electronic devices, pathological use of electronic video games, pathological use of electronic communication devices, pathological use of cellular telephones, addiction to pornography, sex addiction, obsessive compulsive disorder, compulsive spending, anorexia, bulimia, intermittent explosive disorder, kleptomania, pyromania, trichotillomania, compulsive overexercising, and compulsive overworking. In addition, the subject may be addicted to more than one addictive or compulsive behaviour, and the pharmaceutical compositions, unit dosage forms, and kits may be useful for treating or preventing addiction or relapse use of more than one addictive or compulsive behaviour.

In a further related embodiment, the present invention includes a kit comprising one or more unit dosage forms of a peroxisome proliferator-activated receptor gamma (PPARγ agonist) and one or more unit dosage forms of nicotine. In one embodiment, the PPARγ agonist is a thiazolidinedione (TZD). In certain embodiments, the TZD is selected from the group consisting of pioglitazone, rosiglitazone, ciglitazone, troglitazone, englitazone, rivoglitazone and darglidazone.

In another related embodiment, the present invention includes a delivery system comprising an amount of nicotine and an amount of a peroxisome proliferator-activated receptor gamma (PPARγ agonist) effective for the treatment of nicotine addition. In various embodiments, the amount of nicotine and the amount of the PPARγ agonist are present in a transdermal patch, an oral lozenge, or a chewing gum.

In a further related embodiment, the present invention includes a method of preventing a subject from becoming addicted, or reducing the likelihood that a subject will become addicted, to an addictive therapeutic agent, comprising providing to a subject in need thereof an addictive therapeutic agent and an effective amount of a thiazolidinedione (TZD), wherein the effective amount of the TZD is an amount effective in preventing the subject from becoming addicted, or reducing the likelihood that the subject will become addicted, to the addictive therapeutic agent.

In a related embodiment, the present invention provides a unit dosage form of a pharmaceutical composition, wherein said unit dosage form comprises an effective amount of an addictive therapeutic agent and an effective amount of a thiazolidinedione (TZD), wherein the effective amount of the TZD is an amount effective in preventing the subject from becoming addicted, or reducing the likelihood that the subject will become addicted, to the addictive therapeutic agent. In particular embodiments, the addictive therapeutic agent is an opioid agonist.

In a further related embodiment, the present invention includes a delivery system comprising an amount of nicotine and an amount of a thiazolidinedione (TZD) effective for the treatment of nicotine addition.

BRIEF DESCRIPTION OF THE SEVERAL VIEWS OF THE DRAWINGS

FIG. 3D shows daily food intake measured at 24 hour intervals. Significant difference from controls is indicated: *p<0.05.

FIG. 4D shows daily food intake measured at 24 hour intervals. Significant difference from controls is indicated: *p<0.05.

Each lever response resulted in the delivery of 0.1 ml of 10% ethanol. Significant difference from controls (Veh) is indicated: *P<0.05.

Figure 8:
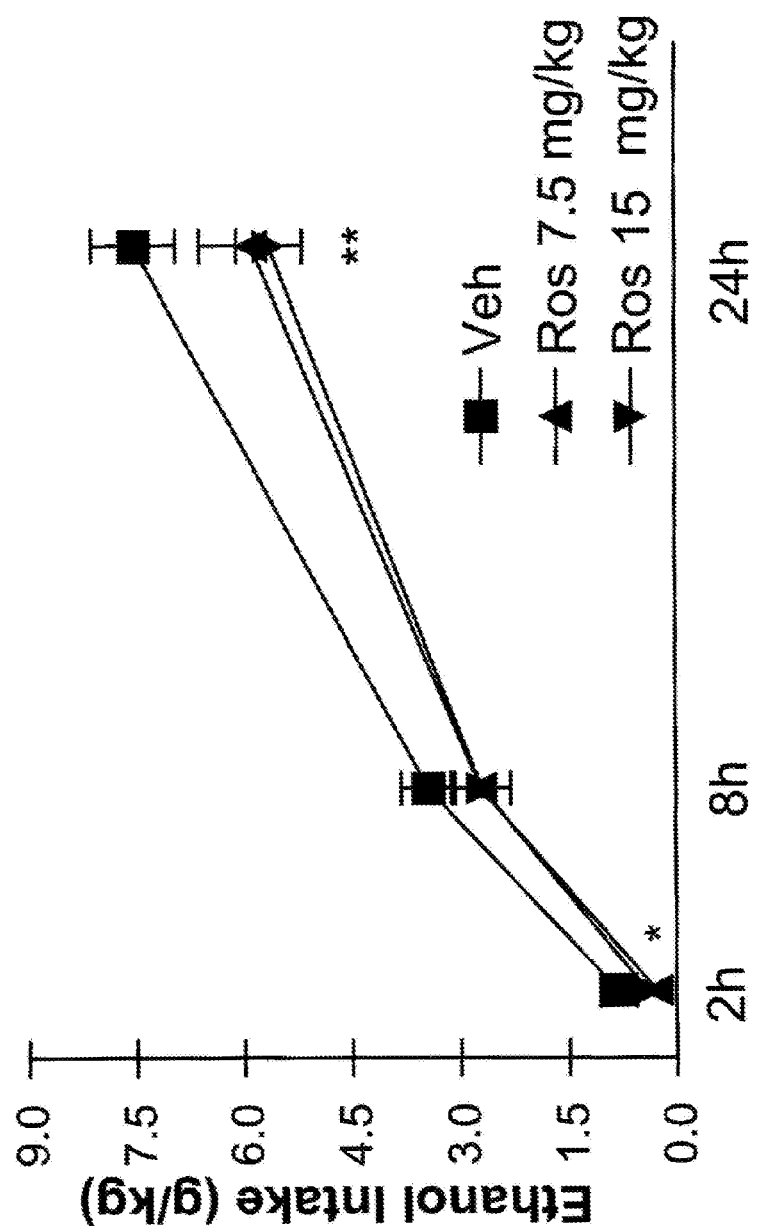

FIG. 8 is a graph the effect of administration of 7.5 or 15.0 mg/kg of rosiglitazone (Ros) on alcohol intake in msP rats. Controls were treated with the drug vehicle (Veh). Values represent the mean±sem of alcohol intake (g/kg) at the indicated time points. Significant difference from controls is indicated: **<0.01 and *p<0.05.

Figure 9A:
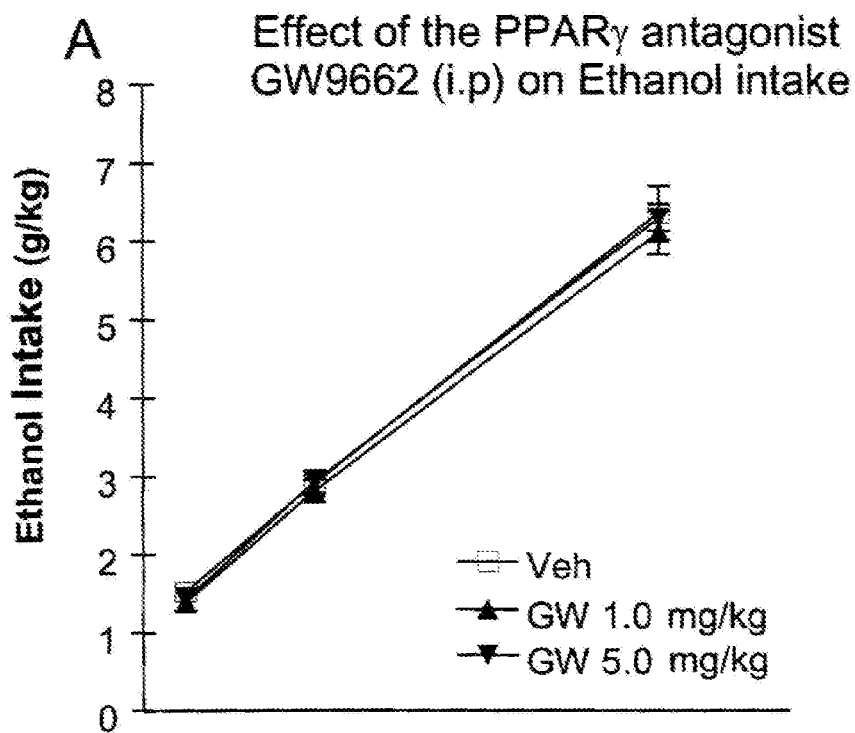
Figure 9B:
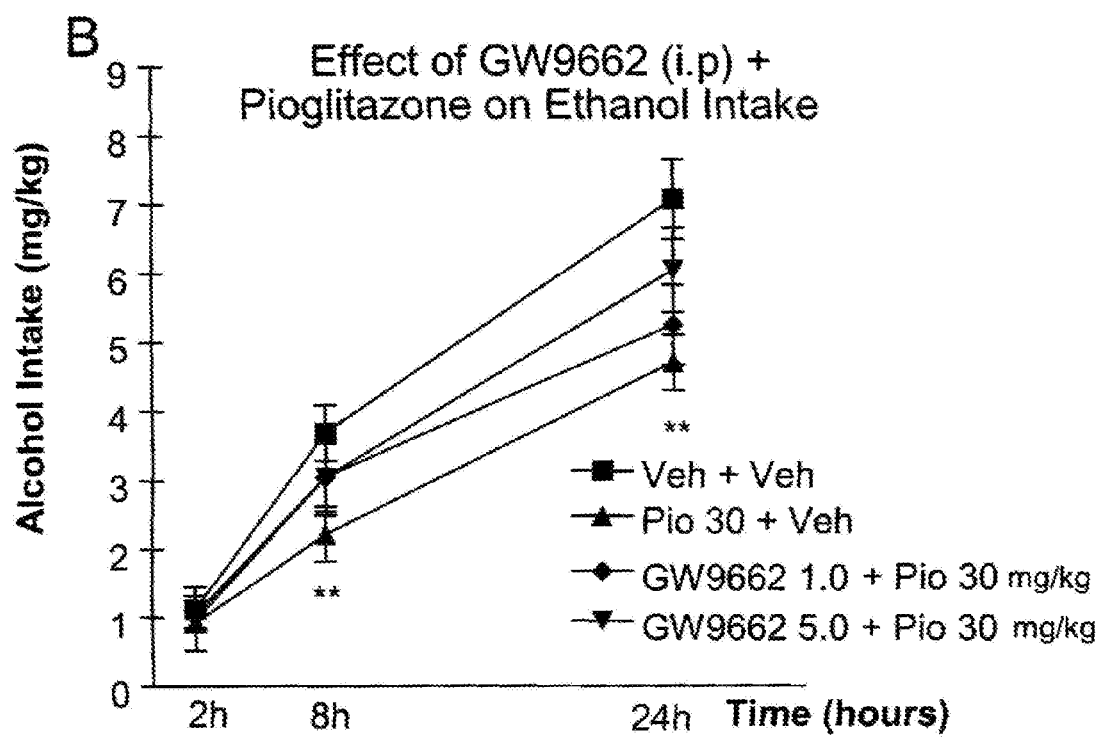

FIGS. 9A and 9B are graphs depicting the effect of pre-treatment with the PPARγ antagonist GW9662 on pioglitazone induced reduction of ethanol drinking. FIG. 9A represents the effect of GW9662 (GW) given alone (1.0 and 5.0 mg/kg) on ethanol intake in msP rats. FIG. 9B describes the effect of pre-treatment with GW9662 on animals injected with 30 mg/kg pioglitazone (Pio) or its vehicle. The control group received vehicles of both drugs (Veh+Veh). Values represent the mean±sem of alcohol intake (g/kg). Significant difference from controls is indicated: **p<0.01.

Figure 10:
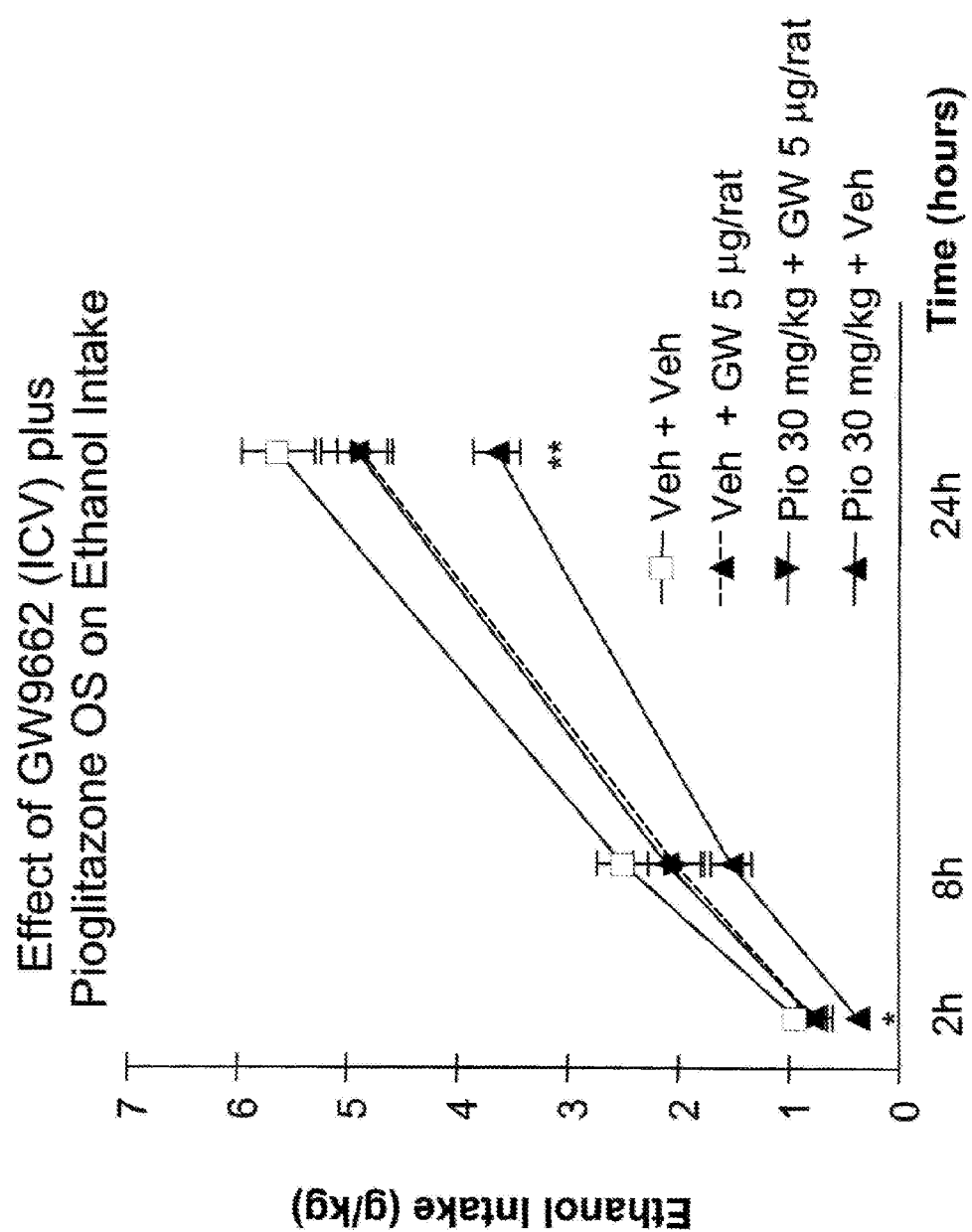

FIG. 10 is a graph depicting the effect of pre-treatment with the PPARγ antagonist GW9662 given ICV on pioglitazone-induced reduction of ethanol drinking. MsP rats received 5.0 µg/rat of GW9662 (GW) alone, 30 mg/kg of pioglitazone (Pio) alone or their combination. Control group received vehicles of both drugs (Veh+Veh). Values represent the mean±sem of alcohol intake (g/kg). Significant difference from controls is indicated: *p<0.05 and **p<0.01.

Figure 11:
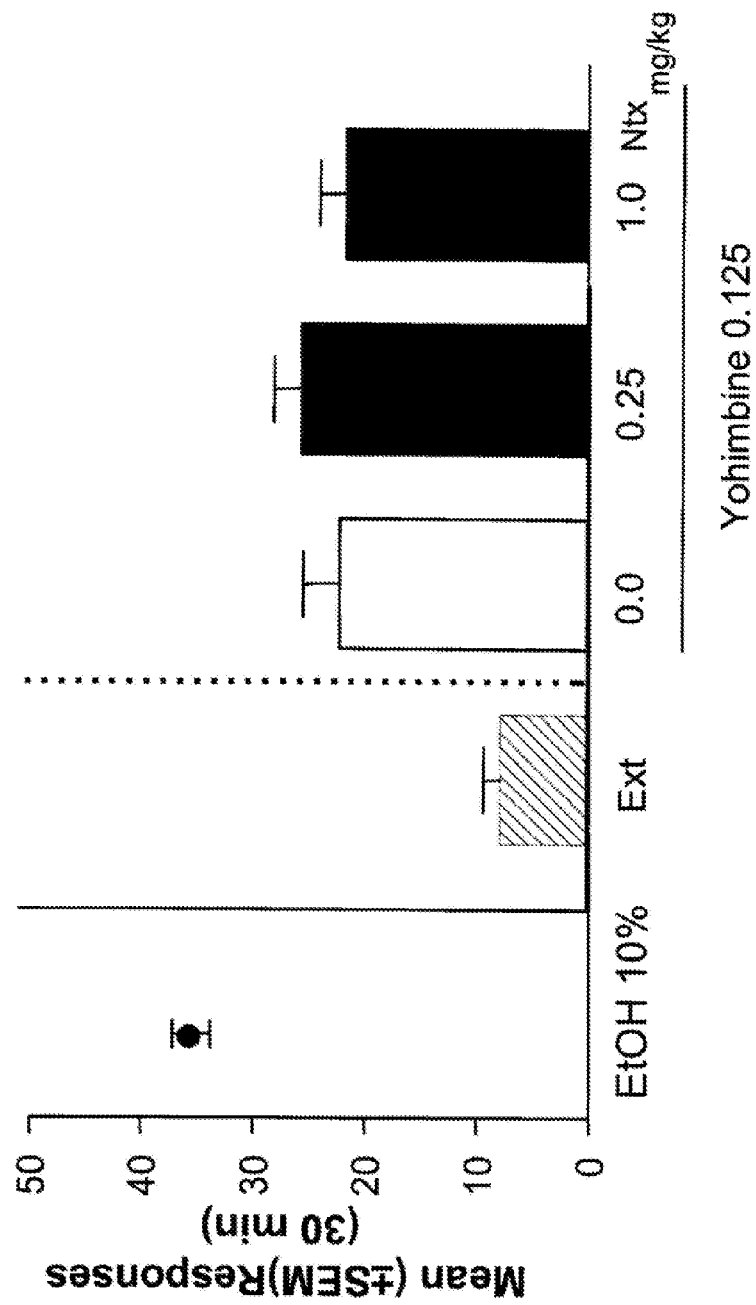

FIG. 11 is a graph depicting the effect of naltrexone (Ntx) on yohimbine-induced reinstatement of alcohol seeking. Compared to extinction (Ext) yohimbine elicited a significant reinstatement of responding that was not modified by pre-treatment with 0.25 and 1.0 mg/kg of naltrexone. Values represent the mean (±SEM) number of responses at the active lever. Difference from controls (0.0) was not significant.

Figure 12:
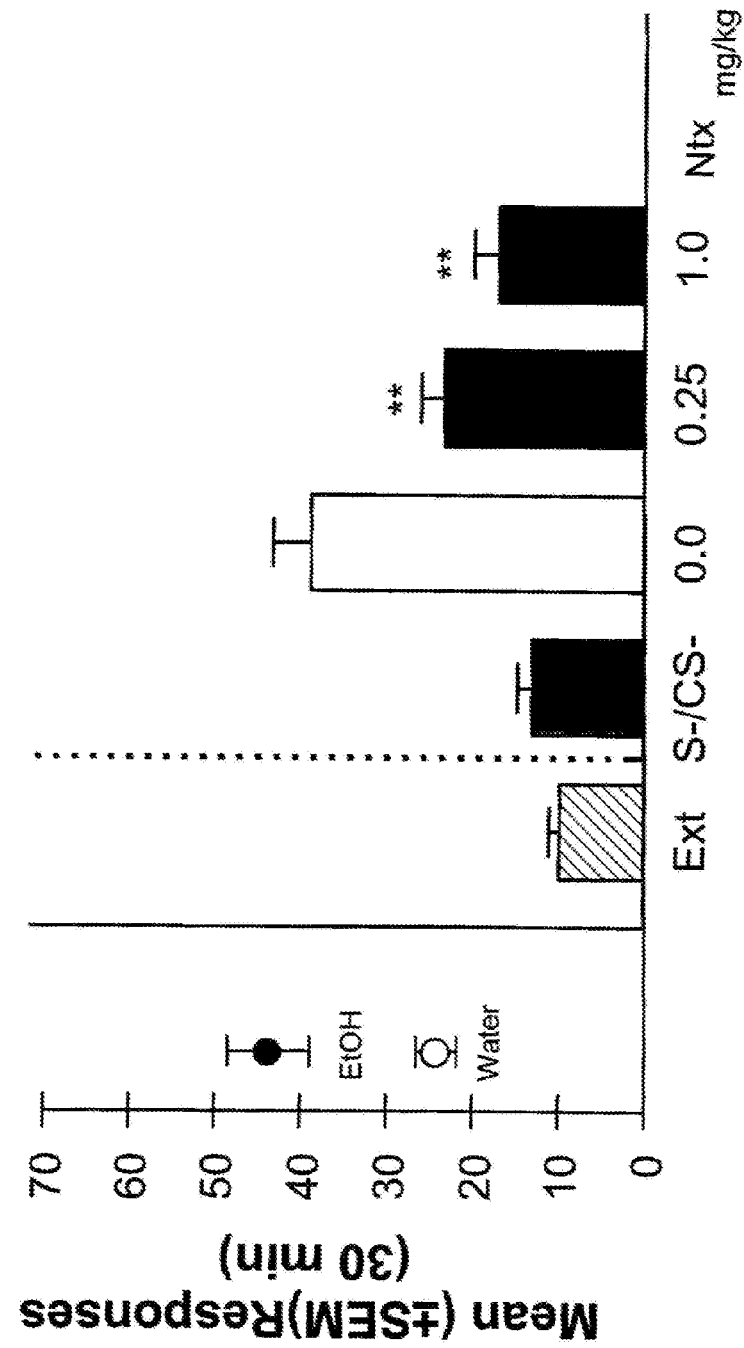

FIG. 12 is a graph depicting the effect of naltrexone (Ntx) on cue-induced reinstatement of alcohol seeking. Values represent the mean (±SEM) number of responses at the active lever. Conditioning: responses of the last 10% alcohol (filled circle) and water (open circle) session of the discrimination phase. Extinction (Ext): responses during the last day of this phase. Reinstatement: responses in rats exposed to stimuli predictive of alcohol ($S^+/CS^+$) or water ($S^-/CS^-$) availability. Treatment with 0.25 and 1.0 mg/kg of naltrexone significantly reduced cue-induced reinstatement of alcohol-seeking; **p<0.01.

Figure 13A:
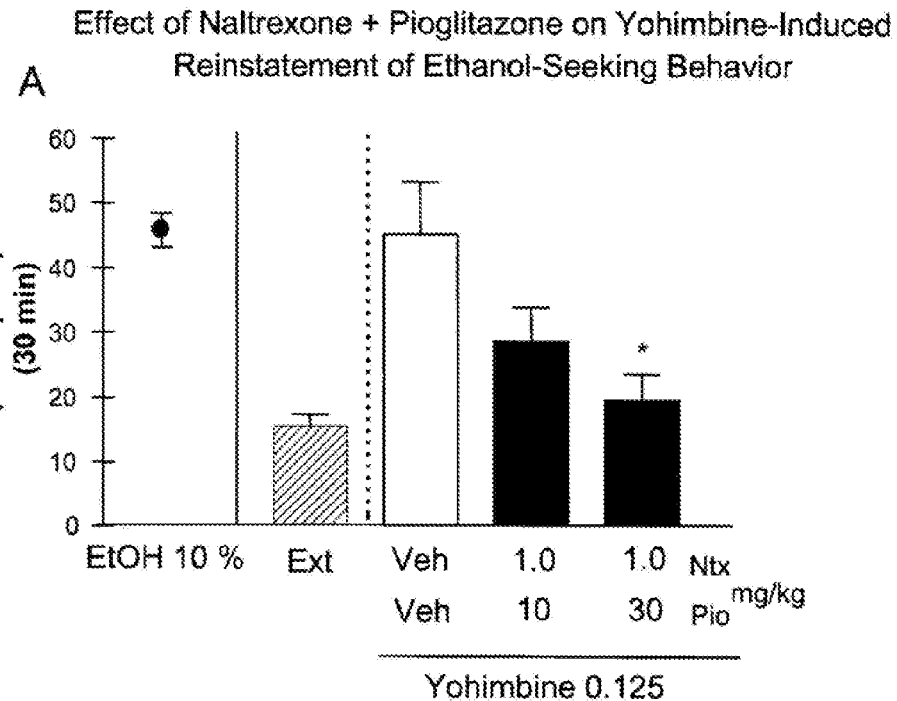
Figure 13B:
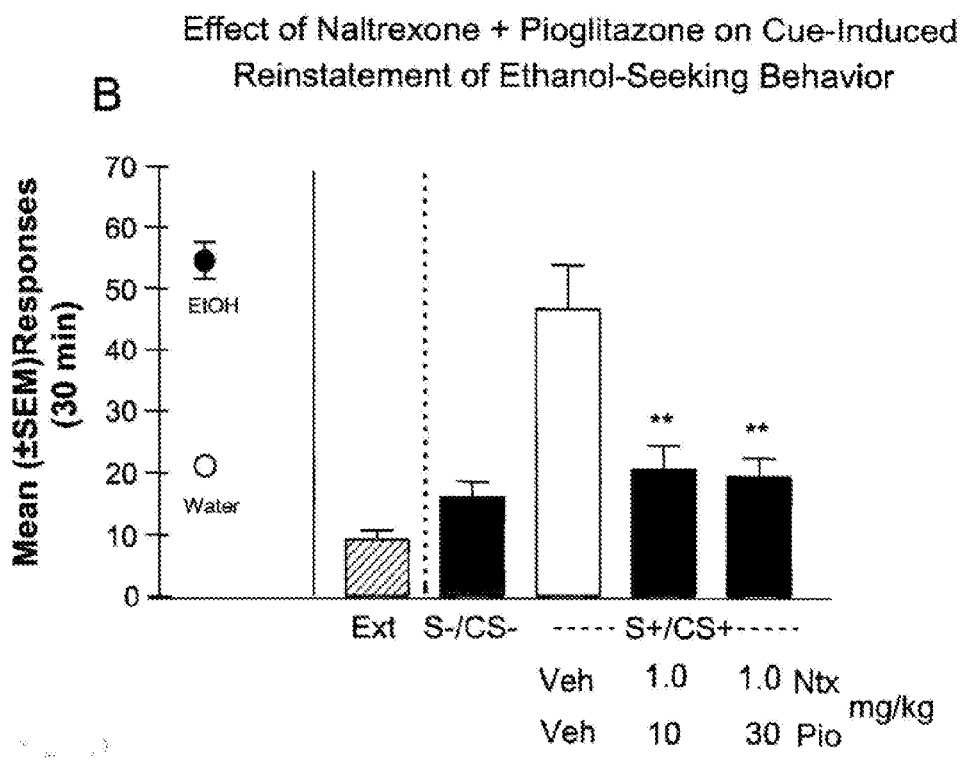

FIGS. 13A and 13B are graphs depicting the effect of naltrexone (ntx) plus pioglitazone (Pio) combination on: yohimbine-induced reinstatement of alcohol seeking (FIG. 13A) or cue-induced reinstatement of alcohol seeking (FIG. 13B). Compared to extinction (Ext), yohimbine elicited a significant reinstatement of responding. The combination of Naltrexone (1.0 mg/kg) plus pioglitazone (10 and 30 mg/kg) significantly inhibited yohimbine-induced reinstatement of alcohol seeking (FIG. 13A). Treatment with 1.0 mg/kg of naltrexone in combination with Pioglitazone (10.0 and 30.0 mg/kg) also significantly reduced cue-induced reinstatement of alcohol-seeking. Conditioning: responses of the last 10% alcohol (filled circle) and water (open circle) session of the discrimination phase. Extinction (Ext): responses during the last day of this phase. Reinstatement: responses in rats exposed to stimuli predictive of alcohol ($S^+/CS^+$) or water ($S^-/CS^-$) availability. Values represent the mean (±SEM) number of responses at the active lever. Significant difference from Ext is indicated: *P<0.05, **p<0.01.

Figure 14:
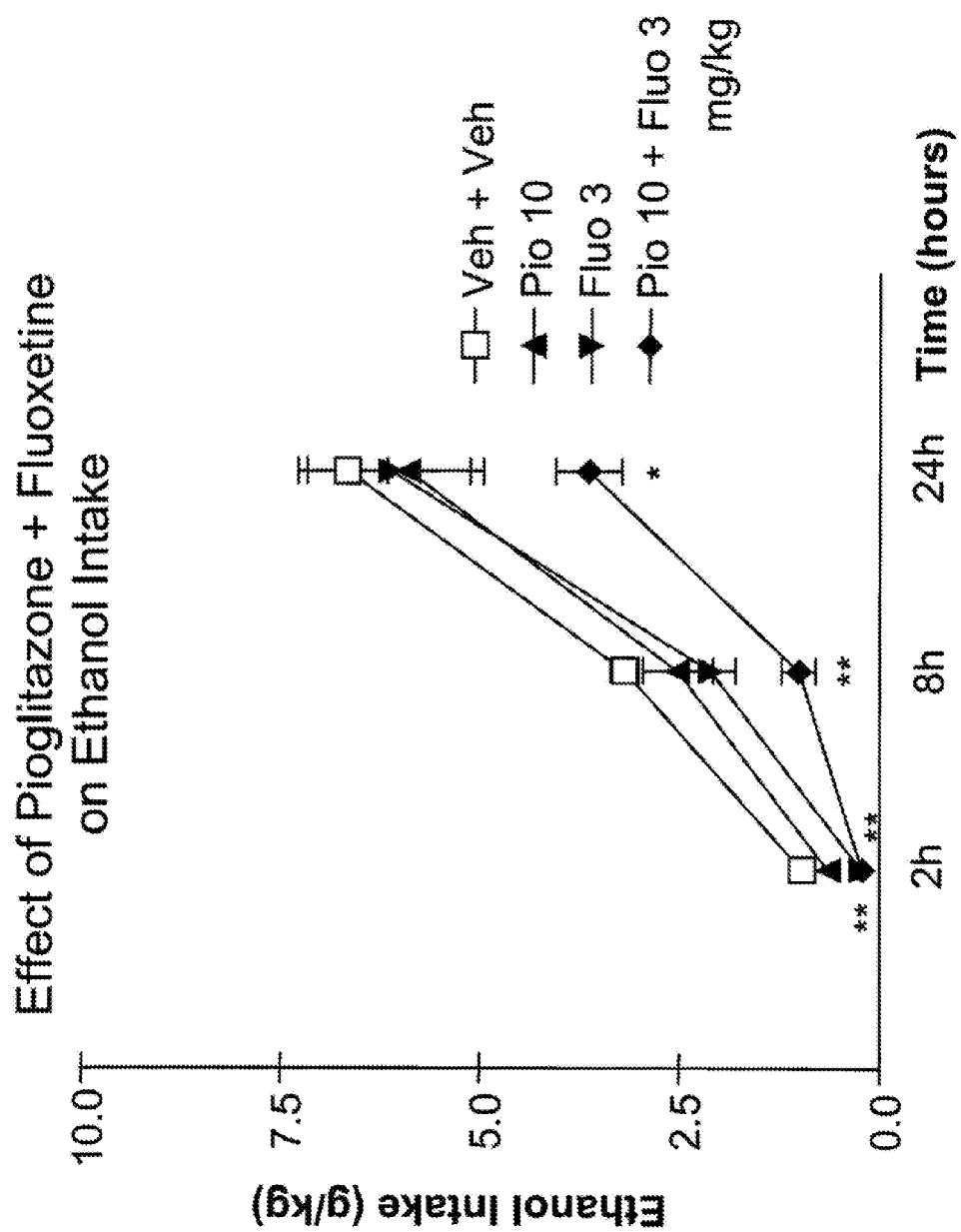

FIG. 14 is a graph depicting the effect of administration of 10 mg/kg of pioglitazone (Pio) alone or 3 mg/kg of fluoxetine alone or their combination on alcohol intake in msP rats. Controls were treated with the drug vehicles (Veh+Veh). Values represent the mean±sem of alcohol intake (g/kg). Significant difference from controls is indicated: *p<0.05 and **p<0.01.

Figure 15:
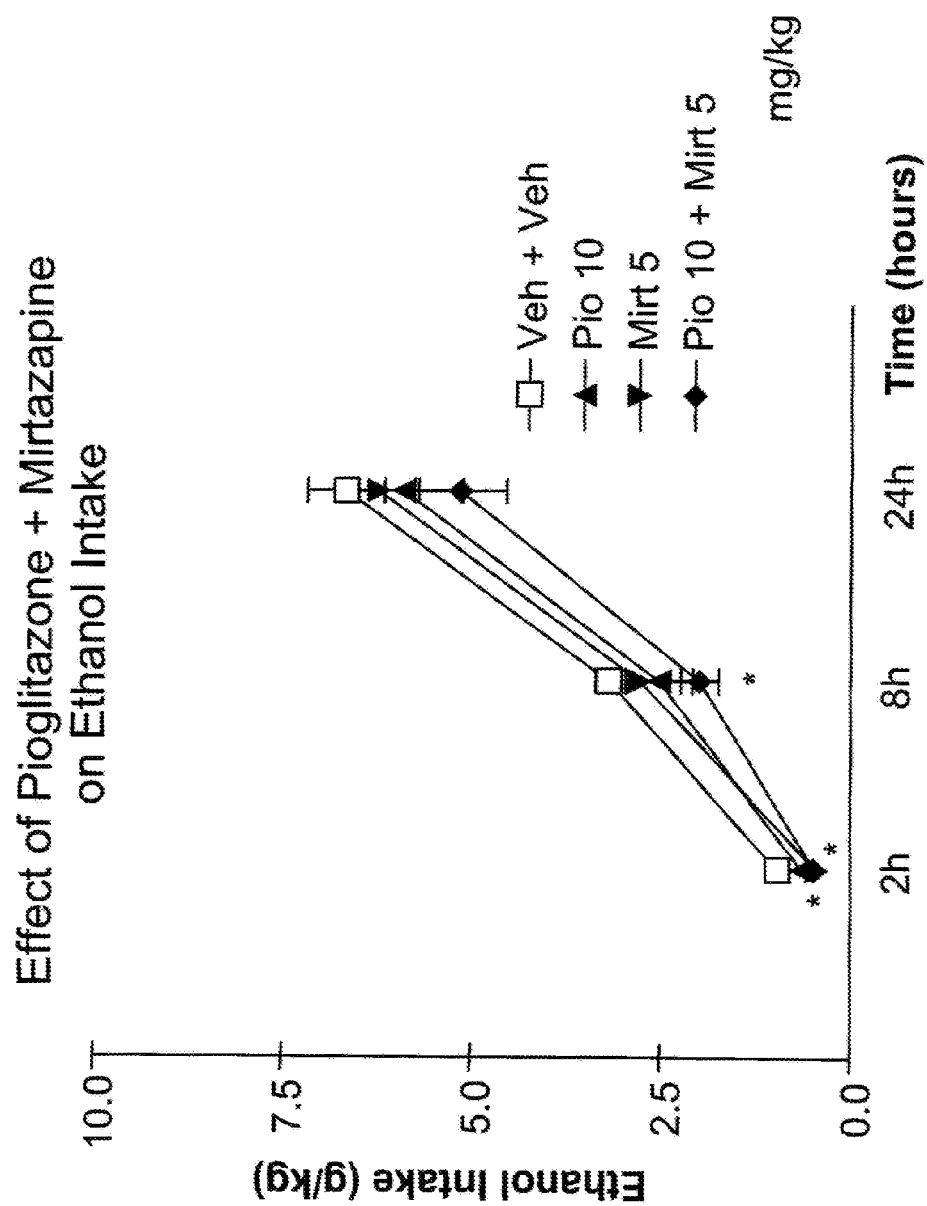

FIG. 15 is a graph depicting the effect of administration of 10 mg/kg of pioglitazone (Pio) alone or 5 mg/kg of mirtazapine alone or their combination on alcohol intake in msP rats. Controls were treated with the drug vehicles (Veh+Veh). Values represent the mean±sem of alcohol intake (g/kg). Significant difference from controls is indicated: *p<0.05.

Figure 16:
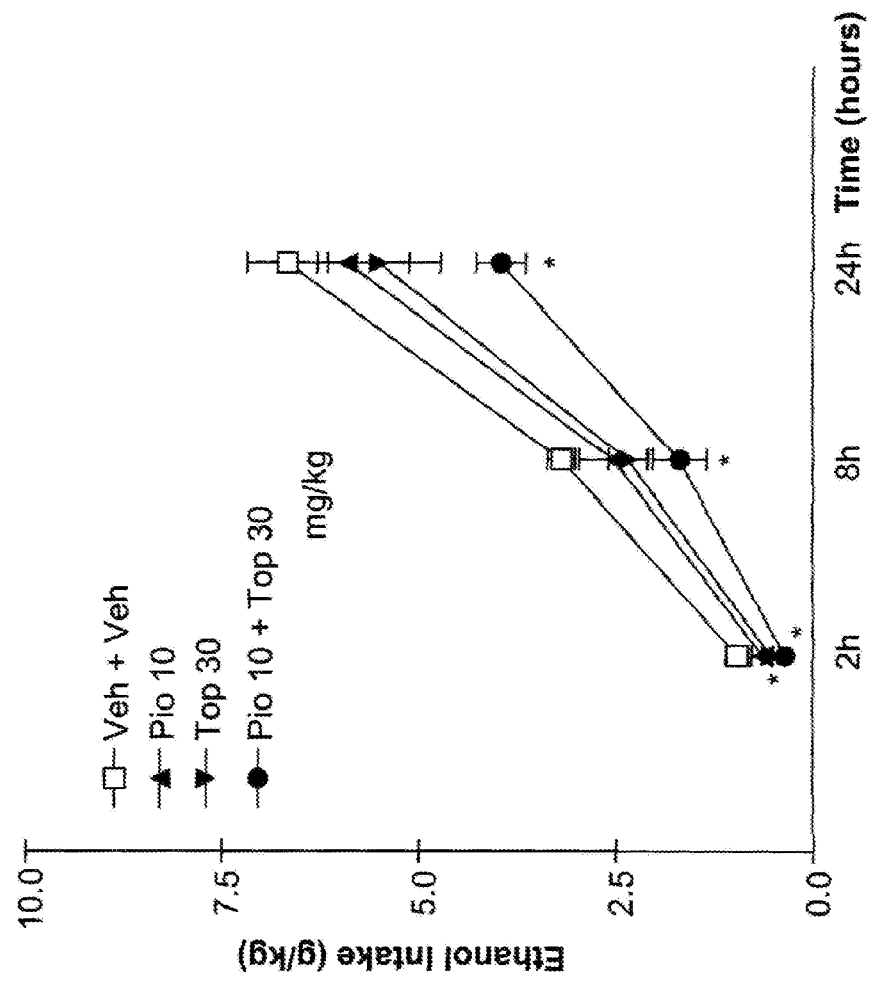

FIG. 16 is a graph depicting the effect of administration of 10 mg/kg of pioglitazone (Pio) alone or 30 mg/kg of topiramate alone or their combination on alcohol intake in msP rats. Controls were treated with the drug vehicles (Veh+Veh). Values represent the mean±sem of alcohol intake (g/kg). Significant difference from controls is indicated: *p<0.05.

Figure 17:
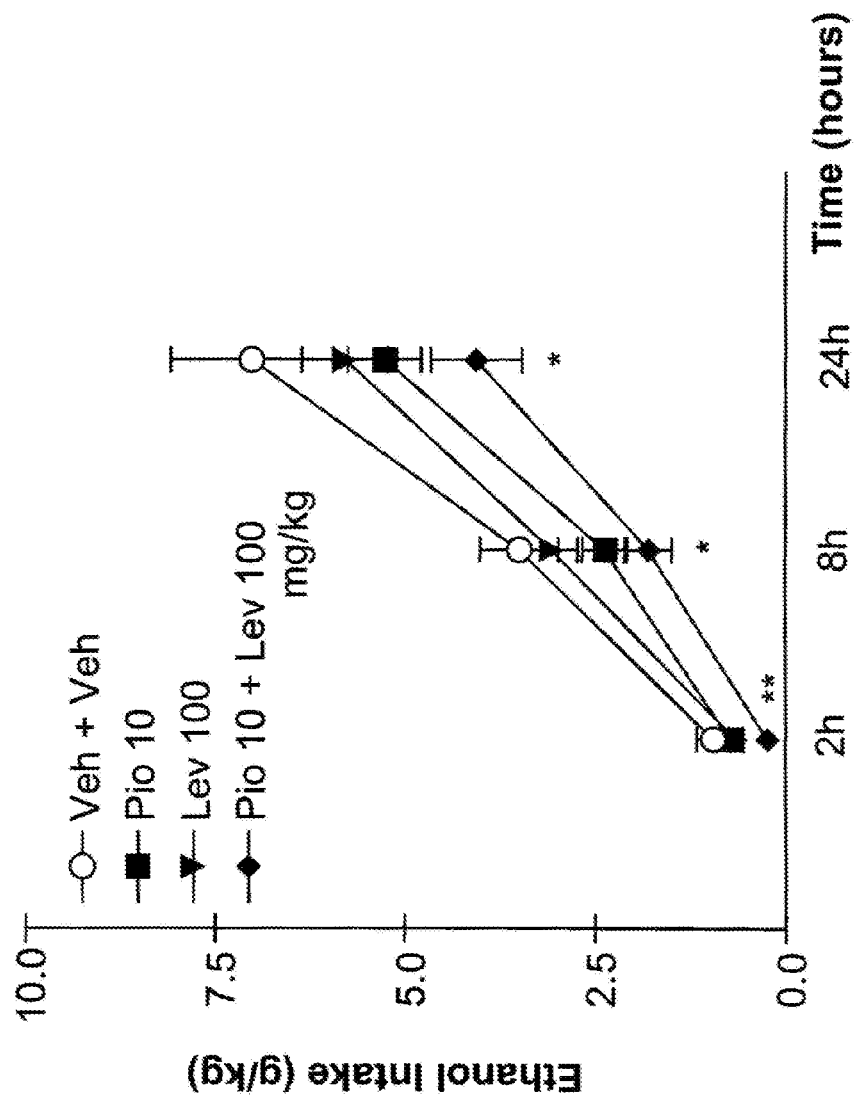

FIG. 17 is a graph depicting the effect of administration of 10 mg/kg of pioglitazone (Pio) alone or 100 mg/kg of levetiracetam (Leve) alone or their combination on alcohol intake in msP rats. Controls were treated with vehicles alone (Veh+Veh). Values represent the mean±sem of alcohol intake (g/kg). Significant difference from controls is indicated: *p<0.05 and **p<0.01.

Figure 18:
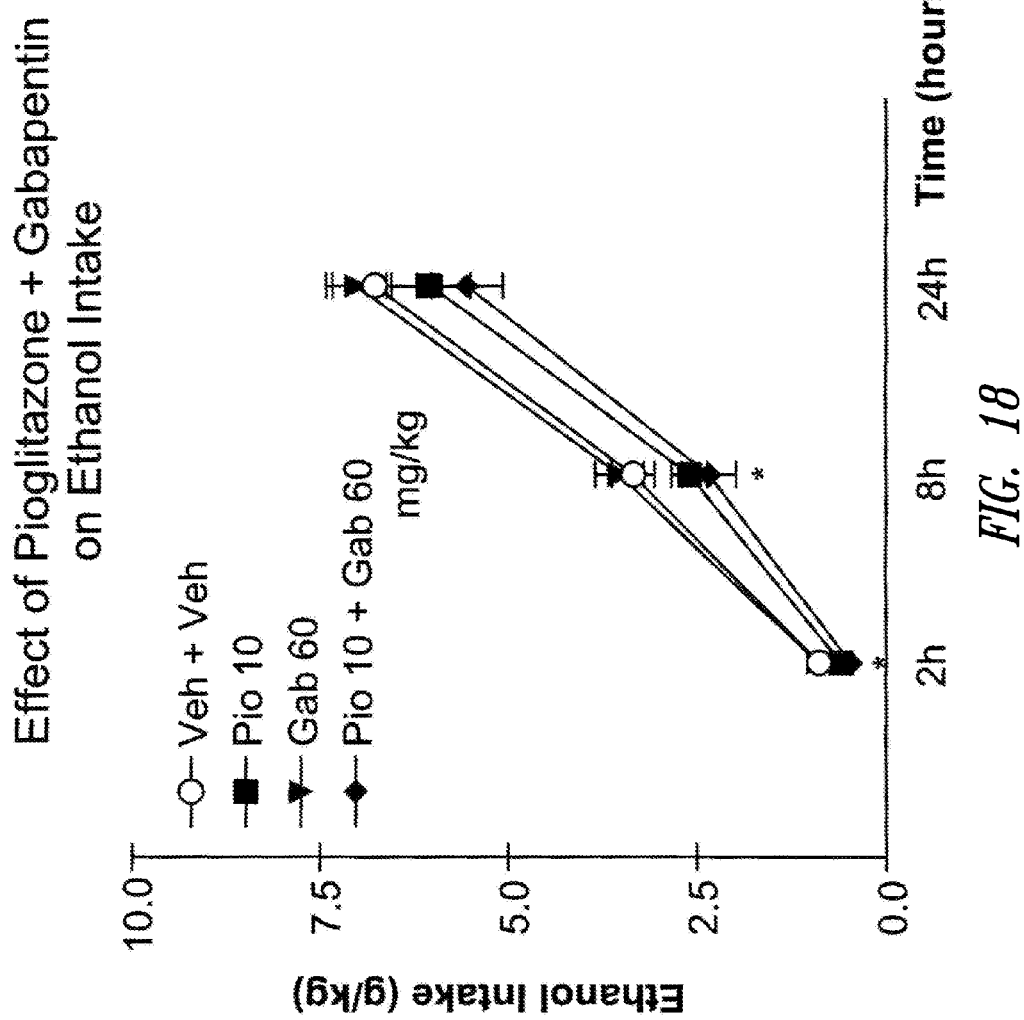

FIG. 18 is a graph depicting the effect of administration of 10 mg/kg of pioglitazone (Pio) alone or 30 mg/kg of gabapentin alone or their combination on alcohol intake in msP rats. Controls were treated with vehicles (Veh+Veh). Values represent the mean±sem of alcohol intake (g/kg). Significant difference from controls is indicated: **p<0.01 and *p<0.05.

Figure 19:
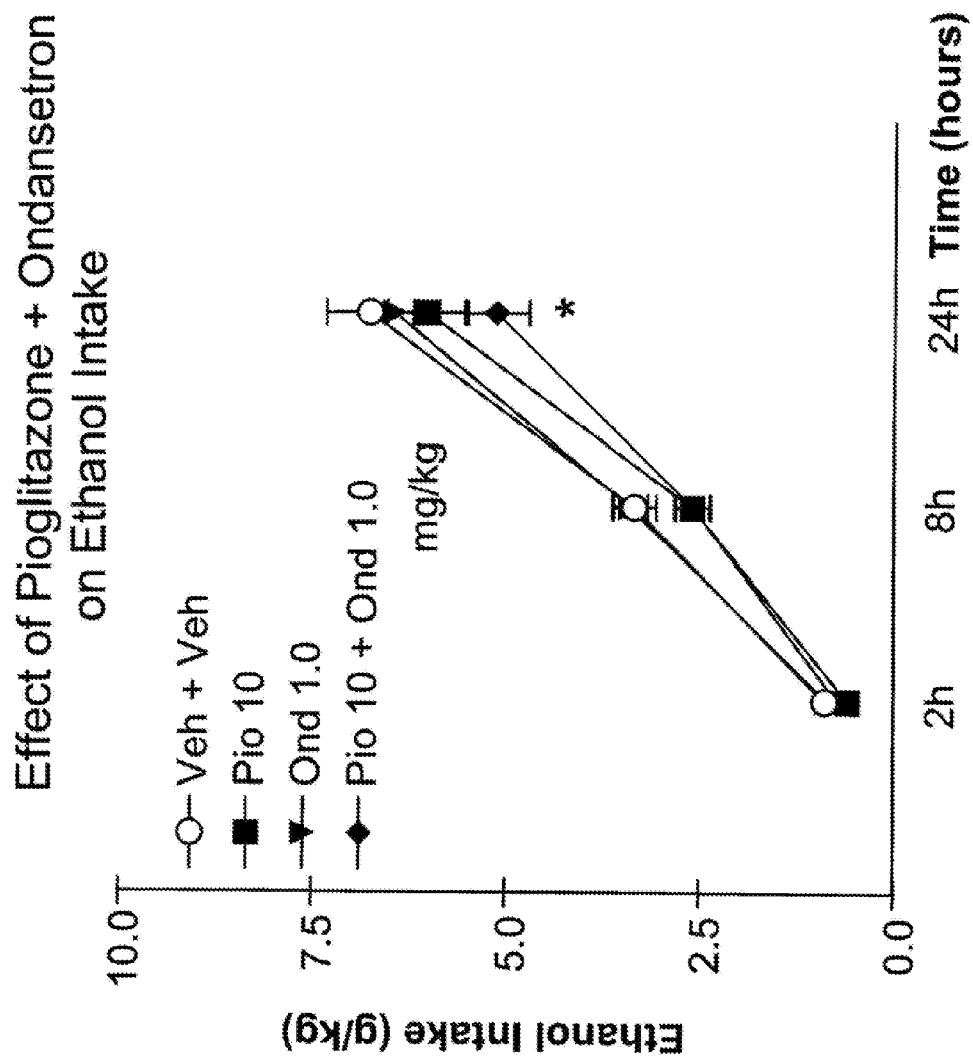

FIG. 19 is a graph depicting the effect of administration of 10 mg/kg of pioglitazone (Pio) alone or 1.0 mg/kg of ondansetron alone or their combination on alcohol intake in msP rats. Controls were treated with the drug vehicles (Veh+Veh). Values represent the mean±sem of alcohol intake (g/kg). Significant difference from controls is indicated: **p<0.01 and *p<0.05.

Figure 20:
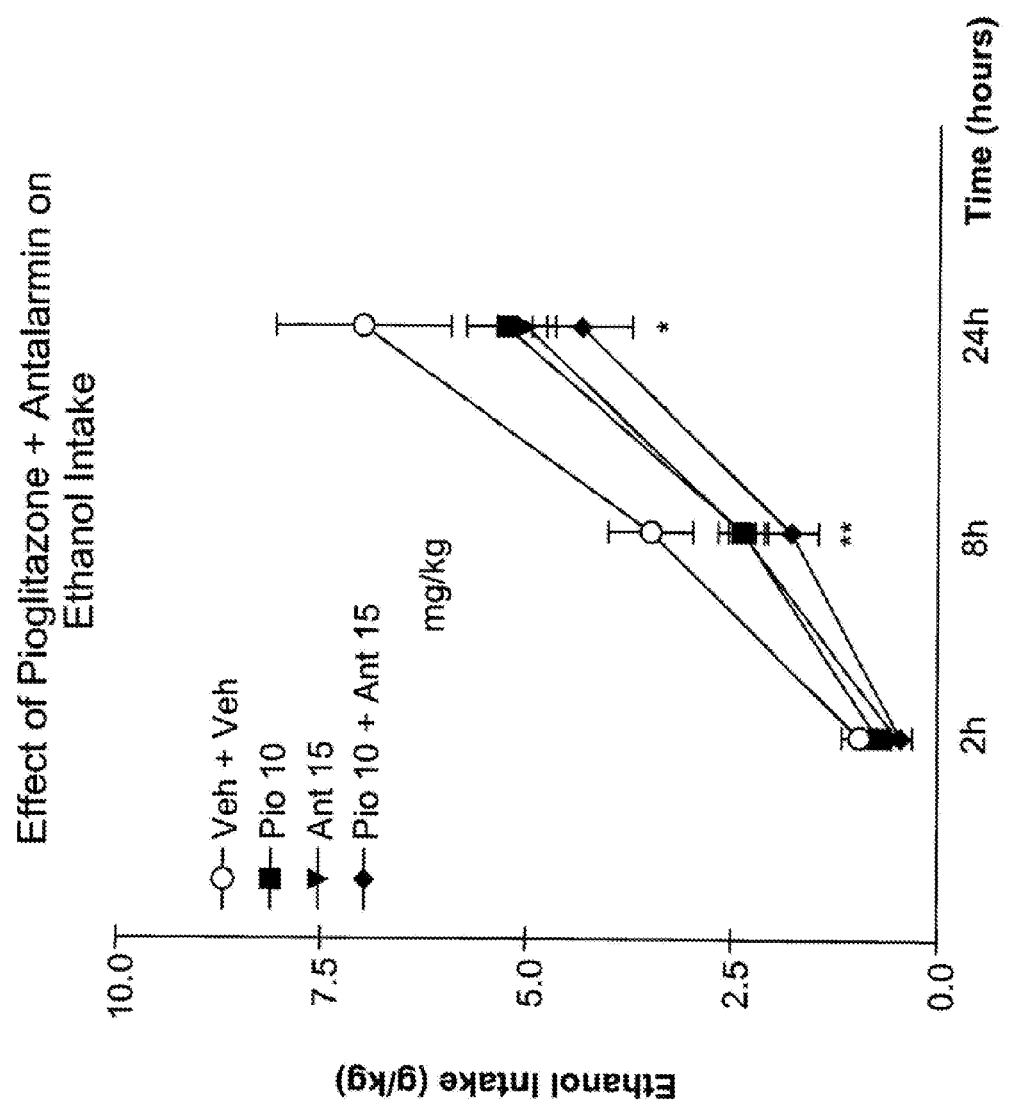

FIG. 20 is a graph depicting the effect of administration of 10 mg/kg of pioglitazone (Pio) alone or 15 mg/kg of antalarmin alone or their combination on alcohol intake in msP rats. Controls were treated with vehicles (Veh+Veh). Values represent the mean±sem of alcohol intake (g/kg). Significant difference from controls is indicated: *p<0.05 and **p<0.01.

Figure 21:
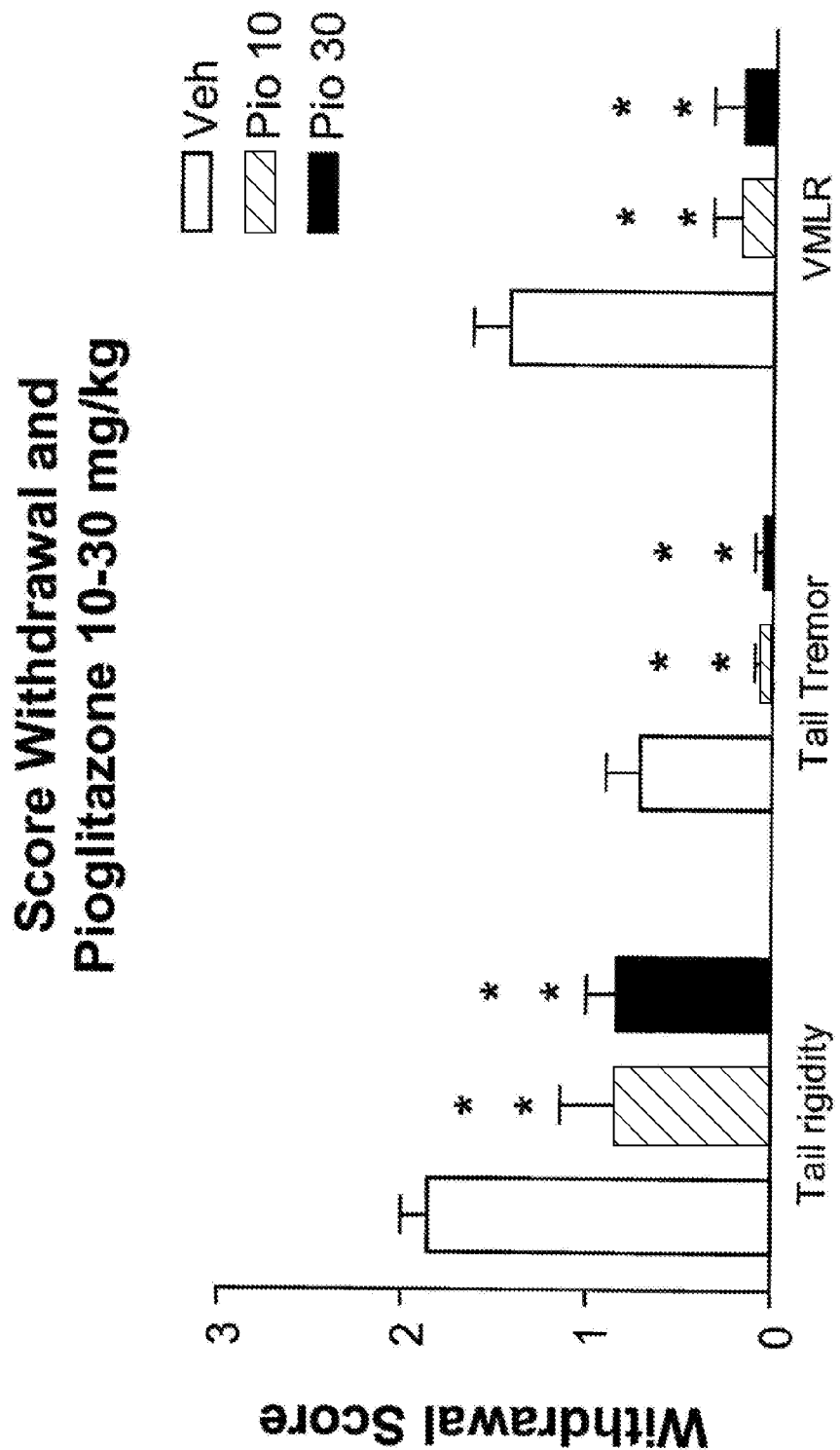

FIG. 21 is a graph depicting the effect of administration of 10 and 30 mg/kg of pioglitazone (Pio) on an alcohol withdrawal score in Wistar rats. Controls received oral administration of alcohol vehicle. Values represent the mean±sem of total withdrawal score. Significant difference from controls is indicated: **p<0.01.

Figure 22A:
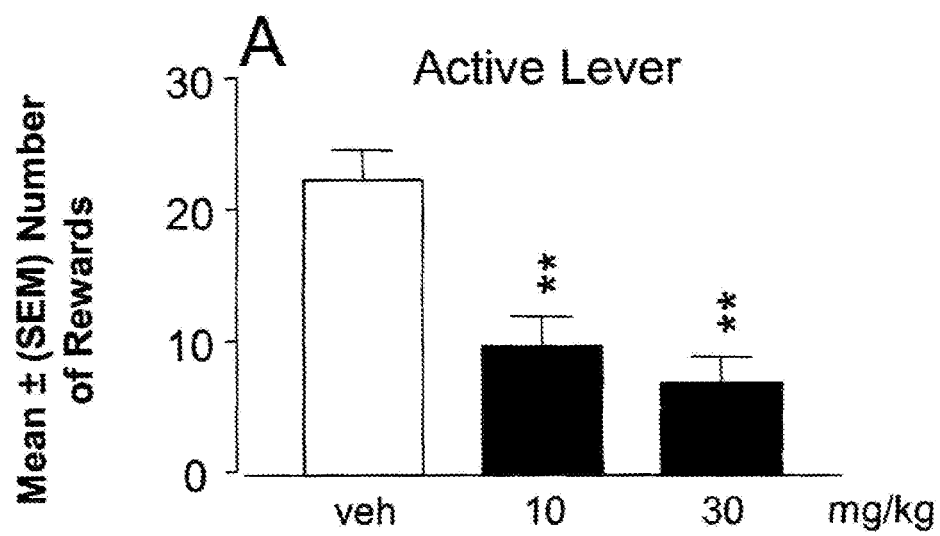
Figure 22B:
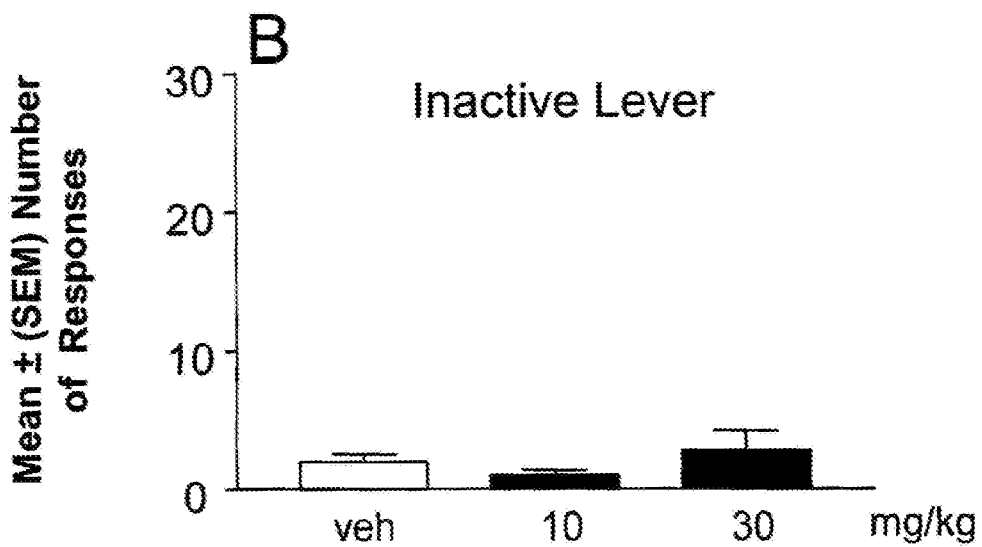

FIGS. 22A and 22B are graphs depicting the effect of treatment with 10.0 or 30.0 mg/kg pioglitazone (10 or 30, respectively) or its vehicle (veh) on FR5 cocaine self-administration in Wistar rats. FIG. 22A shows the number of rewards at the active lever, with each five lever response resulting in the delivery of one reward (0.25 mg/0.1 ml of cocaine). FIG. 22B shows the number of responses at the left inactive lever. Significant difference from controls (Veh) is indicated: **p<0.01.

Figure 23A:
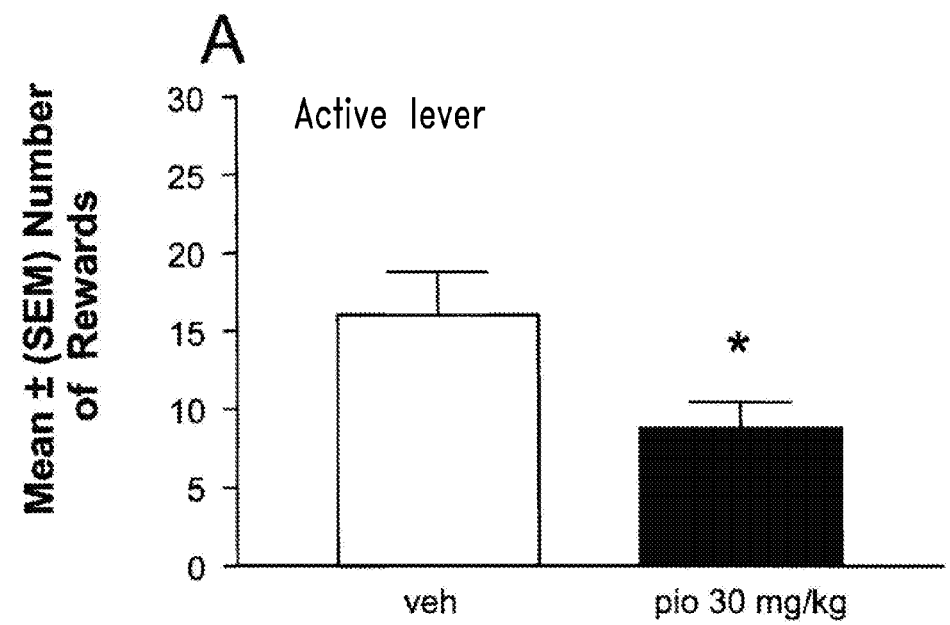
Figure 23B:
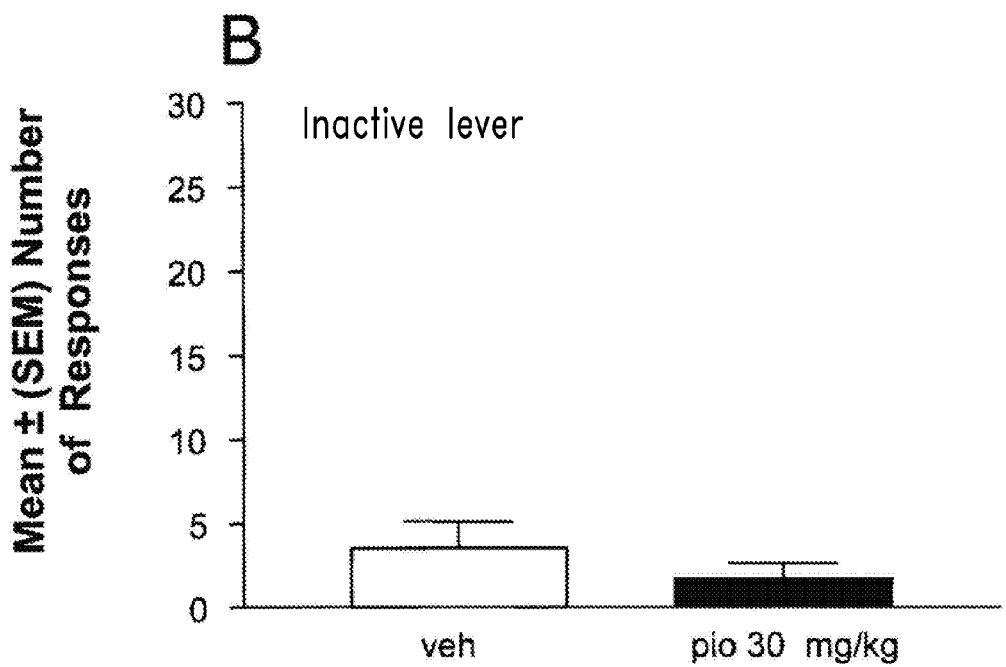

FIGS. 23A and 23B are graphs depicting the effect of treatment with pioglitazone (30.0 mg/kg) or its vehicle (veh) on FR5 nicotine self-administration in Wistar rats. FIG. 23A shows the number of rewards at the active lever, with each five lever response resulting in the delivery of 0.25 mg/0.03 ml of nicotine. FIG. 23B shows the number of responses at the left inactive lever. Significant difference from controls (Veh) is indicated: *p<0.05.

Figures 24A, 24B:
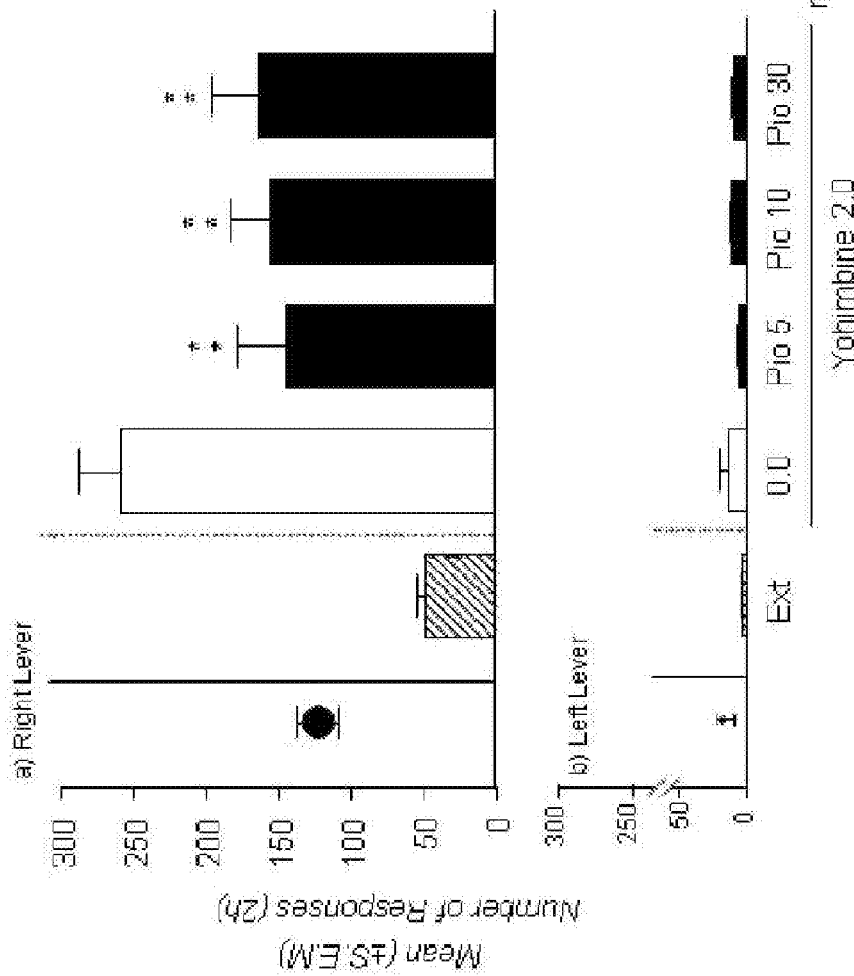

FIGS. 24A and 24B are graphs showing the effect of 5 mg/kg (Pio 5), 10 mg/kg (Pio 10) or 30 mg/kg of (Pio 30) of pioglitazone on yohimbine-induced reinstatement of nicotine. Black filled circles indicate the number of lever presses of the last nicotine self-administration day. Extinction (Ext) value represents the mean value of the last 3 extinction days. Compared to extinction, yohimbine elicited a significant reinstatement of responding that was prevented by treatment with all pioglitazone doses. Values represent the mean (±SEM) number of responses at the active lever (FIG. 24A) or inactive lever (FIG. 24B). Significant difference from controls (Veh) is indicated: **p<0.01.

FIGS. 25A, 25B, and 25C are graphs showing the effect of treatment with pioglitazone (Pio), varenicline (Var) and bupropione (Bup) on: anxiety (FIG. 25A); depression (FIG. 25B); and craving (FIG. 25C), as measured by Spielberger State-Trait Anxiety Inventory (STAI), Montgomery Asberg Depression Rating Scale (M.A.D.R.S 10 Item, and Visual Analogic Scale of Craving.

Figure 26:
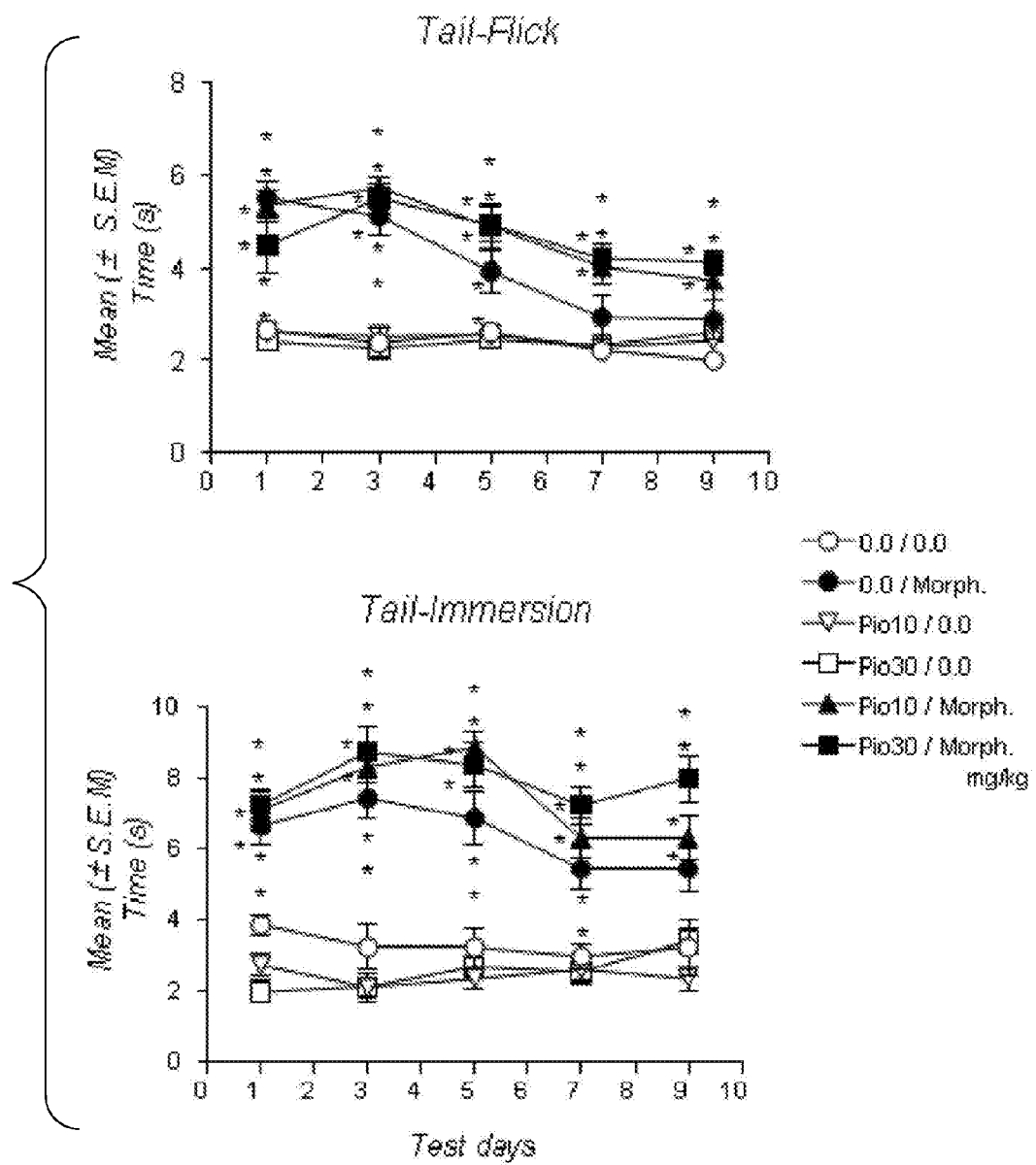

FIG. 26 shows the effect of morphine, pioglitazone or their combination on the tail-flick test (upper panel) or the tail-immersion test (lower panel). Mice were divided into 6 groups. Group 1 (n=8) received drug vehicles (v/v). Group 2 (n=9) received pioglitazone vehicle plus 30 mg/kg morphine. Group 3 (n=8) and Group 4 (n=8) received 10 (pio 10) or 30 mg/kg (pio 30) of pioglitazone followed by morphine vehicle. Group 5 (n=8) and Group 6 (n=7) received 10 (pio 10/morphine) or 30 mg/kg (pio 10/morf) of pioglitazone followed by morphine administration. Animals were treated twice daily (between 9:00 and 10:00 a.m. and 9:00 and 10:00 p.m.). Statistical difference from controls (v/v): **P<0.01 and *P<0.05.

Figure 27:
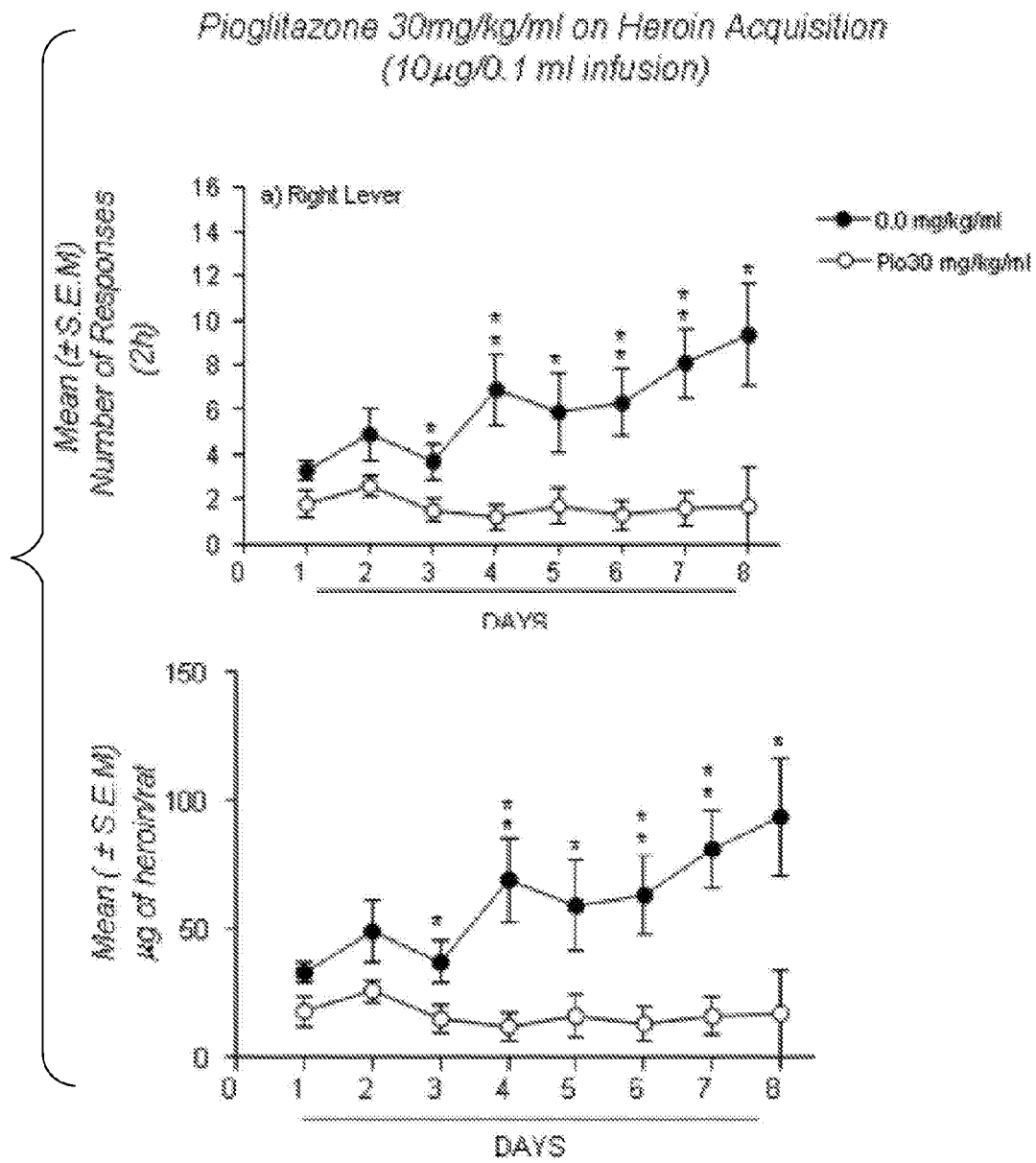

FIG. 27 shows the effect of pioglitazone (Pio30) or its vehicle (0.0) on acquisition of heroin self-administration. Rats were divided into two groups. Group 1 (n=10) received drug vehicles (0.0 mg/kg/ml) and self-administered heroin. Group 2 (n=10) received pioglitazone (30 mg/kg/ml) and self-administered heroin. Animals were treated twice daily. The upper panel shows the mean number of reinforced active lever responses. The lower panel depicts the total daily dose of heroine self-administered by rats. Statistical difference from controls (0.0 mg/kg/ml): **P<0.01 and *P<0.05.

Figure 28:
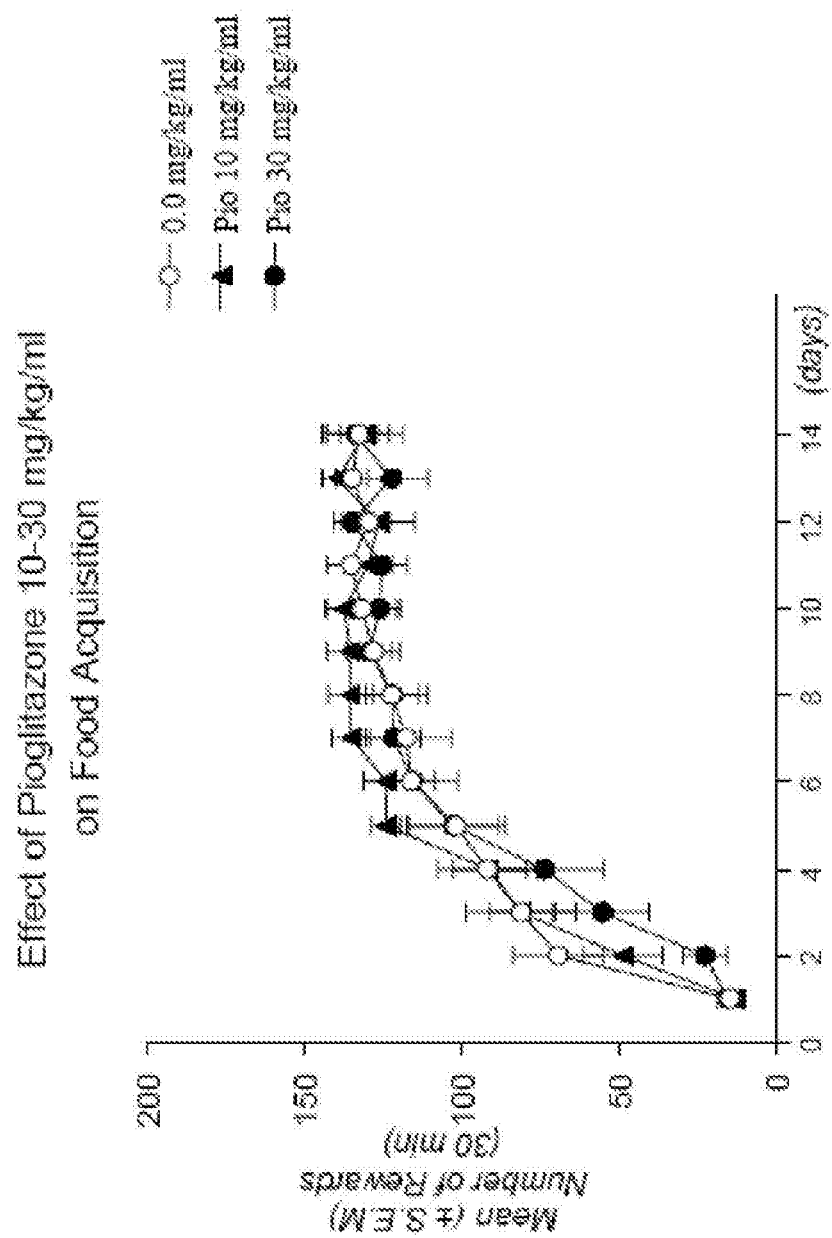

FIG. 28 shows the effect of 10 mg (Pio10) and 30 mg (Pio30) of pioglitazone or its vehicle (0.0) on acquisition of food self-administration. Rats were divided into three groups. Animals (n=8/group) were treated twice a day. Statistical difference from controls (0.0 mg/kg/ml) was never significant.

Figure 29:
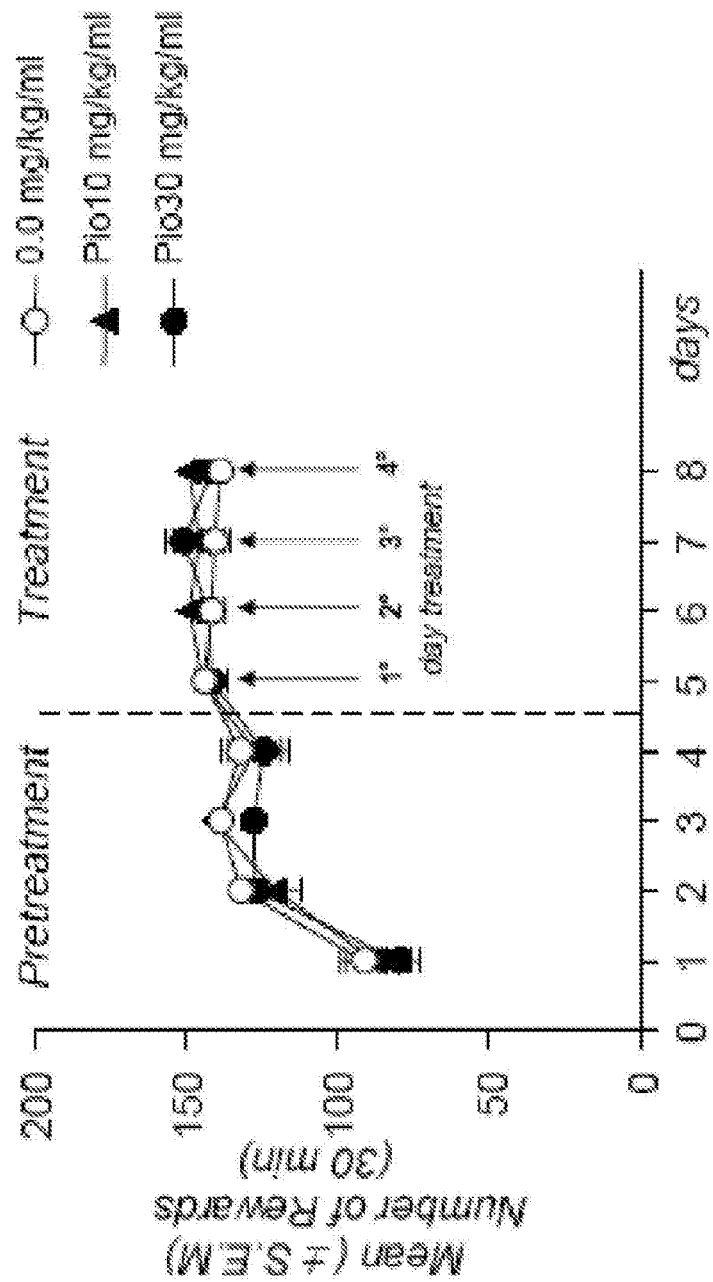

FIG. 29 shows the effect of 10 mg (Pio10) and 30 mg (Pio30) of pioglitazone or its vehicle (0.0) on food self-administration. Rats were divided into three groups (n=8/group). Rats were treated twice a day. Statistical difference from controls (0.0 mg/kg/ml) was never significant.

Figure 30:
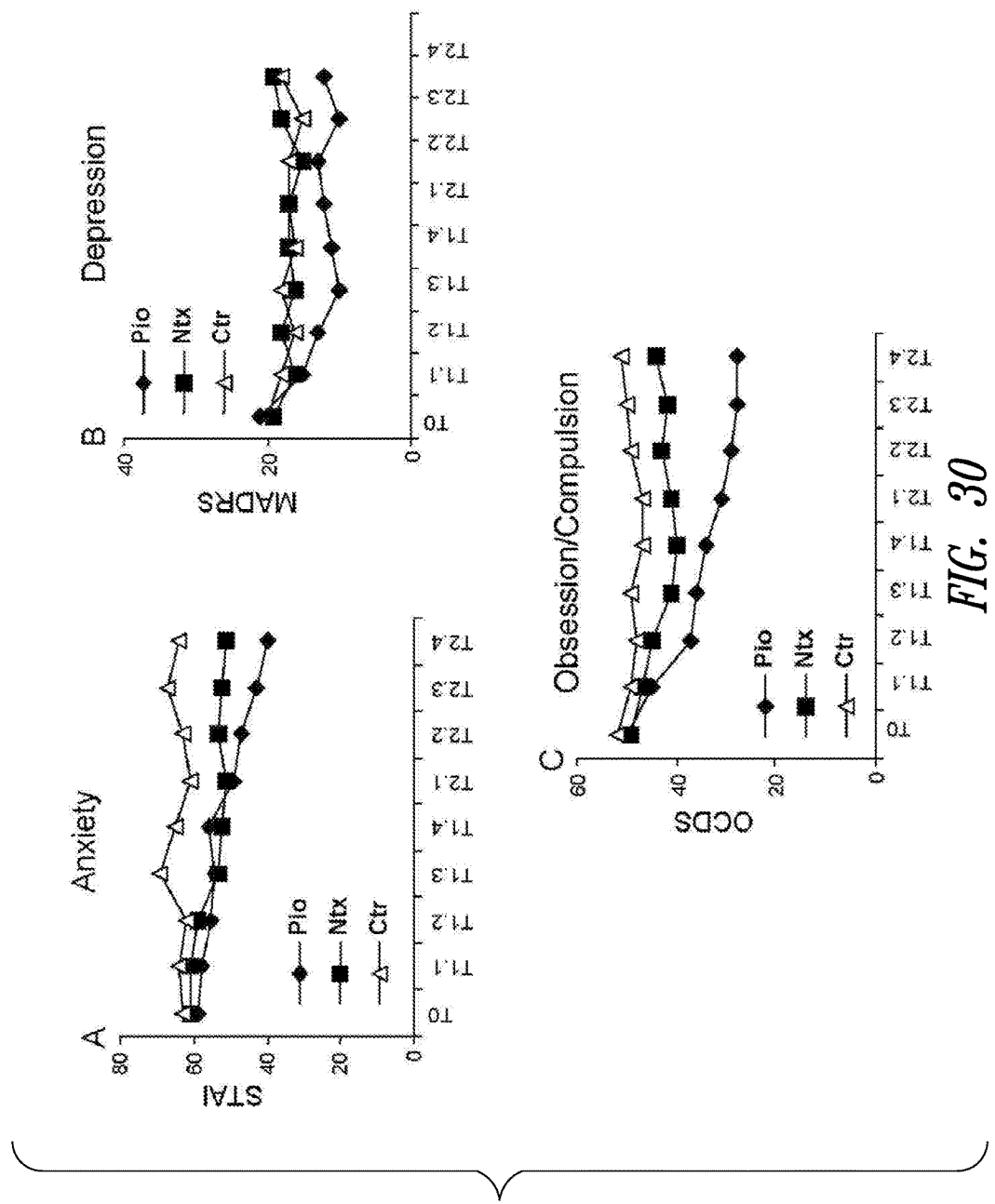

FIG. 30 shows the effect of treatment with pioglitazone (Pio) and naltrexone (Ntx) on anxiety (FIG. 30A); depression (FIG. 30B); and obsession/compulsion for alcohol (FIG. 30C) in alcoholic patients. Controls (Ctr) did not receive drug treatment. Abbreviations: Spielberger State-Trait Anxiety Inventory (STAI); Montgomery Asberg Depression Rating Scale (M.A.D.R.S 10 Item); and Obsessive Compulsive Drinking Scale (OCDS).

DETAILED DESCRIPTION

The present invention is based, in large part, upon the finding described herein that peroxisome proliferator-activated receptor gamma (PPARγ) agonists are useful in the treatment and prevention of addictions and relapse use of an addictive agent or behaviour. Accordingly, the present invention provides methods and related compositions, formulations, unit dosage forms and kits for the treatment and prevention of addiction and relapse use, which include one or more PPARγ agonists, alone or in combination with one or more additional therapeutic agents in which each of the PPARγ agonist and the additional therapeutic agent(s) contribute to the effective treatment or prevention of the addiction.

As demonstrated in the accompanying Examples, a variety of different thiazolidinediones (TZDs) were shown to reduce intake of an addictive agent in various models of addiction. For example, each of the TZDs, pioglitazone, ciglitazone, and rosiglitazone, significantly reduced ethanol consumption in rat models of alcohol addiction (Examples 1, 3, 7, and 8). The effect was evident for both acute and subchronic administration of a TZD (Examples 1 and 2). In addition, TZDs were shown to reduce cocaine use in a rat model of cocaine addiction (Example 23) and a rat model of nicotine addiction (Example 24). This effect of the PPARγ agonists was shown to be mediated by the activation of PPARγ receptors using two different PPARγ agonists (Examples 9 and 10). In addition, an observational study of human patients using pioglitazone for the treatment of diabetes confirmed that this PPARγ agonist was efficacious in reducing ethanol abuse (Example 22). These data establish that PPARγ agonists may be used to treat and prevent addiction to a variety of different addictive agents.

In addition, the accompanying Examples demonstrate that PPARγ agonists used in combination with a variety of different therapeutic agents substantially reduced intake of an addictive agent. For example, it is shown that acute or subchronic treatment with the TZD, pioglitazone, enhanced the inhibitor action of the opioid antagonist, naltrexone, on ethanol intake (Examples 2 and 4). These data demonstrate that the use of a PPARγ agonist in combination with an opioid antagonist would have increased, e.g., additive or synergistic, efficacy in treating or preventing addiction.

In addition to reducing use of an addictive agent, PPARγ agonists were also able to reduce or prevent relapse use, or reinstatement, of addictive agents. As described in Example 5, treatment with pioglitazone significantly reduced stress-induced reinstatement of alcohol use. Interestingly, however, it did not significantly reduce cue-induced reinstatement of alcohol use (Example 6). In contrast, the opioid antagonist, naltrexone, reduced cue-induced reinstatement of alcohol use, but not stress-induced reinstatement of alcohol use (Examples 12 and 11). The data support the concept that the combination of a PPARγ agonist and an opioid antagonist would have an enhanced ability to prevent relapse use of an addictive agent, since such a combination would prevent both stress-induced and cue-induced relapse use. In fact, treatment with the combination of the PPARγ agonist, pioglitazone, and the opioid antagonist, naltrexone, resulted in a significantly reduced reinstatement of both stress-induced and cue-induced alcohol use (Example 13).

PPARγ agonists also worked synergistically with other classes of therapeutic agents in reducing or preventing addiction and relapse use. For example, the TZD, pioglitazone, used in combination with a variety of different classes of antidepressants, including fluoxetine and mirtazapine, worked synergistically in reducing ethanol consumption in an animal model of ethanol addiction (Examples 14 and 15). Anti-epileptics, including topiramate, levetiracetam, and gabapentin, showed synergism in combination with a TZD in reducing ethanol intake (Examples 16-18), and antiemetics, including the serotonin-3 (5-HT3) receptor selective antagonist, ondansetron, and the corticotrophin releasing factor 1 receptor selective antagonist, antalarmin, also showed synergism in combination with a TZD in reducing alcohol consumption (Examples 19 and 20).

Interestingly, the experiments described in the accompanying Examples also showed that PPARγ agonists significantly reduced withdrawal symptoms in alcohol-addicted animals (Example 21).

In summary, the present invention demonstrates that treatment with PPARγ agonists represent a novel pharmacological approach for the treatment and prevention of addiction, since it reduces addictive agent consumption and recidivism associated to stress exposure.

In addition, considering that the physiopathology of addiction has features (i.e., drug craving, compulsive behaviour triggered by drug desire, withdrawal, relapse behaviour, neurological damages, cognitive impairment) common to all drugs of abuse it is reasonable to think that PPARγ agonists will be useful also for the treatment of dependence to other addictive agents or behaviours, including, e.g., opiates (morphine, heroin methadone), psychostimulants (cocaine, methamphetamine, and amphetamine related compounds in general), nicotine, gamma hydroxybutyrate (GHB), phencyclidine, and phencyclidine derivatives, etc.

PPARγ agonists showed efficacy also in combination with opioid antagonists; co-administration of the two drugs resulted in additivity with regard to the effect on ethanol drinking and expanded the efficacy of the opioid antagonist on stress induced reinstatement. In a co-administration regimen, it is of particular significance to note the neuroprotective anticonvulsant and withdrawal-reducing effect of TDZs, especially during the early treatment phase. In fact, opioid antagonists do not result in any amelioration of withdrawal symptoms and this, in general, may contribute to the early treatment drop out and low compliance often reported with these drugs.

The ability of TDZs to normalize hepatic function may also have positive consequences in exploitation of a combined treatment approach. In fact, the clinical condition of alcoholic patients is, in general, compromised, especially during the early detoxification phase. Thus, rapid recovery and amelioration from a pathological state could improve treatment retention.

A. Methods of Treating and Preventing Addictions Using PPARγ Agonist(s)

Thus, the present invention includes methods of treating or preventing an addiction, comprising providing one or more PPARγ agonists to a subject having an addiction or at risk for developing an addiction. In various embodiments, the subject is addicted to an addictive agent or behaviour, including, but not limited to, any of the addictive agents and behaviours described herein. The subject may be physically or physiologically dependent on the substance or behaviour; the subject may be psychologically dependent; or the subject may be both physically and psychologically dependent. The subject may be addicted to one or more than one addictive agent or behaviour.

As used herein, unless the context makes clear otherwise, "treat," and similar word such as "treatment," "treating" etc., is an approach for obtaining beneficial or desired results, including and preferably clinical results. Treatment can involve optionally either the reducing or amelioration of a disease or condition, (e.g., addiction, relapse use, withdrawal), or the delaying of the progression of the disease or condition (e.g., addiction relapse use, withdrawal).

As used herein, unless the context makes clear otherwise, "prevent," and similar word such as "prevention," "preventing" etc., is an approach for preventing the onset or recurrence of a disease or condition, (e.g., addiction, relapse use, withdrawal) or preventing the occurrence or recurrence of the symptoms of a disease or condition, or optionally an approach for delaying the onset or recurrence of a disease or condition or delaying the occurrence or recurrence of the symptoms of a disease or condition. Preventing also includes inhibiting the onset or recurrence of a disease or condition, or one or more symptoms thereof, and reducing the likelihood of onset or recurrence of a disease or condition, or one or more symptoms thereof.

Generally, a subject is provided with an effective amount of a PPARγ agonist. As used herein, an "effective amount" or a "therapeutically effective amount" of a substance, e.g., a PPARγ agonist, is that amount sufficient to affect a desired biological or psychological effect, such as beneficial results, including clinical results. For example, in the context of treating addiction using the methods of the present invention, an effective amount of a PPARγ agonist is that amount sufficient to cause the subject to reduce or discontinue use of an addictive agent.

According to certain embodiments of the present invention, a subject is provided with a PPARγ agonist alone, while in other embodiments, a subject is provided with a PPARγ agonist in combination with an additional therapeutic agent. It is understood that the effective amount of either or both of a PPARγ agonist and an additional therapeutic agent may be different when either is provided alone than when provided in combination. For example, when the PPARγ agonist and the additional therapeutic agent act synergistically, then a lower amount of the PPARγ agonist, a lower amount of the additional therapeutic agent, or lower amounts of both the PPARγ agonist or the additional therapeutic agent may be required to achieve the same therapeutic effect that would be provided by either the PPARγ agonist or the additional therapeutic agent alone. In other embodiments, the same amount of the PPARγ agonist and the additional therapeutic agent are used to provide an enhanced therapeutic effect relative to the therapeutic effect provided by either the PPARγ agonist or the additional therapeutic agent alone. As another example, data in the Examples below indicate that patients addicted to alcohol and treated with the PPARγ agonist pioglitazone exhibit decreased depression, and treatment of addicted patients with a combination of a PPARγ agonist and an antidepressant agent in accordance with the present invention may provide an enhanced antidepressive therapeutic effect as part of the treatment of the addictive disorder.

The subject may be any animal, including a mammal, and, particularly, a human.

In one aspect of the invention, the subject is first determined or diagnosed to have an addiction, or to be at risk of developing an addiction, by diagnostic testing, observation or analysis by a medical care provider. An effective amount of a PPARγ agonist, or an effective amount of a PPARγ agonist and one additional therapeutic agent, are then provided to the subject for treatment or prevention of the addiction. In another aspect of the invention, the subject is first determined or diagnosed to have an addiction, or to be at risk of developing an addiction, by diagnostic testing, observation or analysis by a medical care provider, but the subject has not been diagnosed or determined to have diabetes or other insulin disorder. An effective amount of a PPARγ agonist, or an effective amount of a PPARγ agonist and one additional therapeutic agent, are then provided to the subject for treatment or prevention of the addiction. The dosage of the PPARγ agonist, or the PPARγ agonist and the one additional therapeutic agent, may be specifically determined by the medical practitioner for treatment or prevention of the addiction rather than for any other disorder or disease.

In particular aspects, the subject is provided with a PPARγ agonist, alone or in combination with an additional therapeutic agent for the primary purpose of treating or preventing an addiction. In related aspects of the methods of the present invention, the subject has not previously been provided with a PPARγ agonist for the treatment or prevention of any disease or disorder other than an addiction. In particular, in certain embodiments, the subject has not previously been provided with a PPARγ agonist for the treatment of insulin resistance or diabetes. In a further related embodiment, the subject has not been diagnosed with insulin resistance or diabetes.

In various embodiments of the present invention, the subject may be provided with any PPARγ agonist, including any of the specific PPARγ agonists described below. In particular embodiments, the PPARγ agonist is a TZD, including any of the TZDs described below. In certain embodiments, the TZD is pioglitazone, ciglitazone, rosiglitazone or troglitazone.

In particular embodiments, the subject is suffering from or at risk for addiction to any physically addictive agent or addictive or compulsive behaviour, including, e.g., any of those described below. In particular embodiments, the subject is addicted to alcohol, cocaine, nicotine, marijuana, an opiate or other opioid agonist or methamphetamine or other psychostimulant, or phencyclidine and phencyclidine derivatives.

In particular embodiments, a subject is considered at risk of addiction or relapse to use of an addictive agent or practice of an addictive behaviour when the subject has previously been addicted to the same or a different addictive agent or addictive or compulsive behaviour. In certain embodiment, the subject is considered at risk of addiction or relapse to use of an addictive agent or practice of an addictive behaviour when the subject is psychologically addicted to an addictive agent or addictive or compulsive behaviour, even if the subject is no longer physically addicted.

In certain embodiments, the subject is addicted to or at risk of becoming addicted to a therapeutic agent provided to the patient to treat a disease or disorder, e.g., a pain medication. In a related embodiment, the subject may be at risk of abusing an addictive therapeutic agent, such as a pain medication. Abusing an addictive therapeutic agent, in certain embodiment, is understood to indicate using the agent for a reason different than or in addition to its prescribed use. In such a situation, a subject may be provided with both an addictive therapeutic agent and a PPARγ agonist, alone or in combination with an additional therapeutic agent. For example, a subject suffering from pain, or at risk of pain, may be provided with an opioid agonist and a PPARγ agonist or TZD, e.g., pioglitazone, to both provide analgesia and prevent or treat addiction to the opioid agonist. Because PPARγ agonists have been shown to reduce neuropatic pain and inflammatory responses (see, e.g., Oliveira A. et al., Antinociceptive and antiedematogenic activities of fenofibrate, an agonist of PPAR alpha, and pioglitazone, an agonist of PPAR gamma, *Eur J Pharmacol.* 561(1-3):194-201 (2007)), the PPARγ agonist may add to or enhance the analgesic affect of the opioid agonist.

In particular embodiments in which a subject is provided with both a PPARγ agonist and an opioid agonist, the PPARγ agonist is a TZD. In certain embodiments in which a subject is provided with both a PPARγ agonist and an opioid agonist, the PPARγ agonist is pioglitazone, rosiglitazone, ciglitazone, troglitazone, englitazone, rivoglitazone, or darglidazone. In particular embodiments in which a subject is provided with both a PPARγ agonist and an opioid agonist (or opioid), the opioid agonist is a phenanthrene, a phenylheptylamine, or a phenylpiperidine. In certain embodiments in which a subject is provided with both a PPARγ agonist and an opioid agonist, the opioid agonist is alfentanil, allylprodine, alphaprodine, anileridine, apomorphine, benzylmorphine, beta-hydroxy 3-methylfentanyl, bezitramide, carfentanil, clonitazene, codeine, desomorphine, dextromoramide, diacetylmorphine (heroin), diampromide, dihydrocodeine, dihydroetorphine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, etorphine, fentanyl, hydrocodone, hydromorphone, hydroxypethidine, isomethadone, ketobemidone, LMM, levorphanol, levophenacylmorphan, lofentanil, meperidine, metapon, metazocine, methadone, methadyl acetate, metopon, morphine, myrophine, narceine, nicomorphine, norlevorphanol, normethadone, normorphine, norpipanone, opium, oxycodone, oxymorphone, papaverine, phenadoxone, phenomorphan, phenoperidine, piminodine, piritramide, propheptazine, promedol, properidine, propoxyphene, remifentanil, sufentanil, thebaine, tildine, or tramadol, or any combination thereof.

Specific combinations of PPARγ agonists and opioid agonists contemplated by the present invention include, but are not limited to pioglitazone and codeine, pioglitazone and morphine, pioglitazone and noscapine, pioglitazone and hydrocodone, pioglitazone and hydromorphone, pioglitazone and oxycodone, pioglitazone and tramadol, pioglitazone and fentanyl, pioglitazone and propoxyphene, pioglitazone and methadone, ciglitazone and codeine, ciglitazone and morphine, ciglitazone and noscapine, ciglitazone and hydrocodone, ciglitazone and hydromorphone, ciglitazone and oxycodone, ciglitazone and tramadol, ciglitazone and fentanyl, ciglitazone and propoxyphene, ciglitazone and methadone, rosiglitazone and codeine, rosiglitazone and morphine, rosiglitazone and noscapine, rosiglitazone and hydrocodone, rosiglitazone and hydromorphone, rosiglitazone and oxycodone, rosiglitazone and tramadol, rosiglitazone and fentanyl, rosiglitazone and propoxyphene, rosiglitazone and methadone, englitazone and codeine, englitazone and morphine, englitazone and noscapine, englitazone and hydrocodone, englitazone and hydromorphone, englitazone and oxycodone, englitazone and tramadol, englitazone and fentanyl, englitazone and propoxyphene, englitazone and methadone, rivoglitazone and codeine, rivoglitazone and morphine, rivoglitazone and noscapine, rivoglitazone and hydrocodone, rivoglitazone and hydromorphone, rivoglitazone and oxycodone, rivoglitazone and tramadol, rivoglitazone and fentanyl, rivoglitazone and propoxyphene, rivoglitazone and methadone, darglidazone and codeine, darglidazone and morphine, darglidazone and noscapine, darglidazone and hydrocodone, darglidazone and hydromorphone, darglidazone and oxycodone, darglidazone and tramadol, darglidazone and fentanyl, darglidazone and propoxyphene, or darglidazone and methadone. In one particular embodiment, the subject is contacted with both pioglitazone and oxycodone. In another particular embodiment, the subject is contacted with both pioglitazone and hydrocodone. Any of these combinations may be administered to a subject in combination, or present in combination in a pharmaceutical composition, formulation, or kit of the present invention.

In various embodiments, the subject is provided with the PPARγ agonist at the same time that the subject is using an addictive agent, after the subject has discontinued use of an addictive agent, or before the subject begins using an addictive agent. In one particular embodiment, the subject is provided with the PPARγ agonist at the same time the subject is provided with an opioid agonist. For example, a subject being treated with an opioid agonist (e.g., oxycodone) for pain may be given a PPARγ agonist (e.g., pioglitazone) at the same time, in order to reduce the likelihood that the subject will become addicted to the opioid agonist. In particular embodiments, the PPARγ agonist and opioid agonist may be provided in a single co-formulation or composition. In one embodiment, the co-formulation or composition comprises both pioglitazone and oxycodone. In another embodiment, the co-formulation or composition comprises both pioglitazone and hydrocodone. In another particular embodiment, the subject is provided with the PPARγ agonist at the same time the subject is provided with nicotine or a nicotine containing substance. For example, a subject being treated with a controlled dosage of nicotine for purposes of eliminating or reducing the use of tobacco products may be given a PPARγ agonist (e.g., pioglitazone) at the same time, in order to increase the likelihood that the subject will reduce or cease use of the tobacco product. In particular embodiments, the PPARγ agonist and nicotone may be provided in a single co-formulation or composition. In one embodiment, the co-formulation or composition comprises both pioglitazone and nicotine.

1. Addictive Agents

The term addiction is used to describe a recurring compulsion by an individual to engage in some specific activity, despite harmful consequences to the individual's health, mental state or social life. The term is often reserved for drug addictions, but it is sometimes applied to other compulsions, such as problem gambling, and compulsive overeating. Factors that have been suggested as causes of addiction include genetic, biological/pharmacological and social factors.

The medical community now makes a careful theoretical distinction between physical or physiological dependence (characterized by symptoms of withdrawal) and psychological dependence (sometimes referred to simply as addiction). Addiction is now narrowly defined as "uncontrolled, compulsive use." If there is no harm being suffered by, or damage done to, the patient or another party, then clinically it may be considered compulsive, but to the definition of some it is not categorized as "addiction". In practice, the two kinds of addiction (physiological dependence and psychological dependence) are not always easy to distinguish. Addictions often have both physical and psychological components.

Physical dependence (or drug dependence) refers to a state resulting from habitual use of a drug, where negative physical withdrawal symptoms result from abrupt discontinuation. Examples of addictive agents for which a user may develop a physical dependence include nicotine, opioids, barbiturates, benzodiazepines, alcohol, i.e., ethyl alcohol, GHB, and methaqualone.

Commonly abused stimulants such as cocaine or amphetamine class drugs are not believed to cause significant physical dependence. However, their potential for extreme physiological addiction can compel the user to consume amounts which become physically damaging, but life-threatening withdrawal effects have not been observed.

As used herein, addictive agents includes any and all agents to which a subject can become addicted, either physically or psychologically, or both. As noted above, addiction includes addiction to chemical entities, such as drugs, e.g., ethyl alcohol, nicotine, or cocaine, as well as addiction to other behaviours, e.g., pathological gambling, pathological overeating, pathological use of electronic devices, e.g., BlackBerry®, pathological use of electronic video games, pathological use of electronic communication devices, pathological use of cellular telephones, addiction to pornography, sex addiction, obsessive compulsive disorder, compulsive spending, anorexia, bulimia, intermittent explosive disorder, kleptomania, pyromania, trichotillomania, compulsive overexercising, and compulsive overworking.

Addictive agents include addictive recreational drugs, as well as addictive medications. Examples of addictive agents include, but are not limited to, alcohol, e.g., ethyl alcohol, gamma hydroxybutyrate (GHB), caffeine, nicotine, *cannabis* (marijuana) and *cannabis* derivatives, opiates and other morphine-like opioid agonists such as heroin, phencyclidine and phencyclidine-like compounds, sedative ipnotics such as benzodiazepines, methaqualone, mecloqualone, etaqualone and barbiturates and psychostimulants such as cocaine, amphetamines and amphetamine-related drugs such as dextroamphetamine and methylamphetamine. Other examples include LSD, psilocybin, ecstasy and other hallucinogens. Examples of addictive medications include, e.g., benzodiazepines, barbiturates, and pain medications including alfentanil, allylprodine, alphaprodine, anileridine benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, OXYCONTIN®, oxymorphone, papaveretum, pentazocine, phenadoxone, phenomorphan, phenazocine, phenoperidine, piminodine, piritramide, propheptazine, promedol, properidine, propiram, propoxyphene sufentanil, tramadol, tilidine, salts thereof, mixtures of any of the foregoing, mixed μ-agonists/antagonists, and the like.

In certain embodiments, a subject may be addicted to an opioid agonist. The terms "opioid agonist," "opioid" and "opiate" are used interchangeably herein and are used to designate a group of drugs that are, to varying degrees, opium- or morphine-like in their properties. Their main use is for pain relief. These agents work by binding to opioid receptors, which are found principally in the central nervous system and the gastrointestinal tract. Opiates are also addictive agents. Opiates include, e.g., alfentanil, allylprodine, alphaprodine, anileridine, apomorphine, benzylmorphine, beta-hydroxy 3-methylfentanyl, bezitramide, carfentanil, clonitazene, codeine, desomorphine, dextromoramide, diacetylmorphine (heroin), diampromide, dihydrocodeine, dihydroetorphine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, etorphine, fentanyl, hydrocodone, hydromorphone, hydroxypethidine, isomethadone, ketobemidone, LMM, levorphanol, levophenacylmorphan, lofentanil, meperidine, metapon, metazocine, methadone, methadyl acetate, metopon, morphine, myrophine, narceine, nicomorphine, norlevorphanol, normethadone, normorphine, norpipanone, opium, oxycodone, oxymorphone, papaverine, phenadoxone, phenomorphan, phenoperidine, piminodine, piritramide, propheptazine, promedol, properidine, propoxyphene, remifentanil, sufentanil, thebaine, tildine, and tramadol.

Naturally occurring opiates include, e.g., codeine, morphine, noscapine, papaverine, and thebaine. Semi-synthetic opioids include, e.g., diacetylmorphine, hydrocodone, hydromorphone, levorphanol, metapon, nalorphine, naloxone, naltrexone, oxycodone, oxymorphone, and tramadol. Synthetic opioids include, e.g., ethoheptazine, fentanyl, levorphanol, meperidine, methadone, phenazocine, propoxyphene and sufentanil.

Three broad classifications of opiates are phenanthrenes, phenylheptylamines, and phenylpiperidines. Examples of phenanthrenes include codeine, etorpine, hydrocodone, hydromorphone, morphine, oxycodone, and oxymorphone. Examples of phenylheptylamines include dimepheptanol, dimenoxadol, dipipanone, isomethadone, methadone, methadyl acetate, and propoxyphene. Examples of phenylpiperidines include alfentanyl, alphaprodine, beta-promedol, carfentanyl, fentanyl, lofentanil, meperidine, properidine, and sufentanil.

Specific psychostimulants include, by way of example, amphetamine, cocaine, dextroamphetamine, methamphetamine, pemoline, and methylenedioxymethamphetamine.

While a subject may be addicted to a single addictive agent or behaviour, frequently, a subject is addicted to two or more addictive agents or behaviours. Addiction to two or more addictive agents or addictive behaviours is referred to as polyaddiction.

2. PPARγ Agonists

Peroxisome proliferator-activated receptors (PPARs) are ligand-activated transcription factors of the nuclear hormone receptor superfamily. At present three distinct PPAR isoforms, namely PPARα, PPARβ/δ and PPARγ, have been identified (Breidert et al., 2002; Feinstain et al. 2003). The PPARα receptor isoform is highly expressed in the liver and kidney and it regulates fatty acid catabolism; the PPARβ/δ is ubiquitously expressed and is involved in the regulation of different cellular processes including adipocytes, keratinocytes and oligodendrocytes differentiation. Finally, PPARγ receptors are predominantly expressed in adipose tissue and macrophages, where they are involved in adipocyte differentiation, regulation of sugar and lipid homeostasis and control of inflammatory responses (Heneka et al. 1999; Landreth and Heneka 2001; Harris and Phipps 2002).

The endogenous ligands of PPAR receptors belong to various classes of unsaturated fatty acid compounds that include leukotrienes, retinoic acid metabolites and prostaglandins. For example, the PPARγ receptor is mainly located in the cytoplasmatic fraction and is activated by the 15-deossi-$\Delta^{12-14}$-prostaglandin $J_2$ (Burstein 2005; Cernuda-Morollon, et al., 2002).

Recent studies have also shown that, in addition to various peripheral tissues, PPARδ/δ and PPARγ receptors are expressed in neurons, and olygodendrocytes (but not in astrocytes) of the central nervous system (CNS). The exact role of these receptors in the brain is not well understood yet (Kainu et al. 1994).

It is known that activation of PPARγ mediates neuroprotective responses against excitotoxic process and inflammatory damages (Butcher et al. 2002). Activation of these receptors is also associated with improvement of cognitive performances, and has protective potential against epileptic insults (Yu et al. 2008)

In 1997 a new class of drugs, the thiazolidinediones (TZDs), was developed in Japan, originally as anti-oxidants. Certain of these compounds were then approved for the clinical treatment of insulin resistance and type 2 diabetes.

At the molecular level, TDZs bind with high affinity and activate PPARγ receptors; this has been proposed as the major mechanism through which these molecules exert their therapeutic effects. At present, two TDZ compounds are used clinically to treat humans, pioglitazone (Actos®) and rosiglitazone (Avandia®). Pioglitazone and methods for synthesizing and formulating pioglitazone and pioglitazone compositions are further described in U.S. Pat. Nos. 4,687,777, 5,965,584 and 6,150,383, the disclosure of each of which is hereby incorporated by reference. Other compounds (i.e., ciglitazone, troglitazone, aleglitazar, muraglitazar, tesaglitazar, and ragaglitazar, etc.) are under development. Suitable PPARγ agonists for use in the present invention include selective PPARγ agonists such as ciglitazone, troglitazone, pioglitazone, rosiglitazone, englitazone, rivoglitazone and darglidazone.

Pioglitazone hydrochloride (Actos®) binds with high affinity PPARγ receptors with agonistic properties. Pioglitazone, together with rosiglitazone (Avandia®), is an approved anti-diabetic medication that acts primarily by decreasing insulin resistance. These two compounds also have positive effects on the vasculature; they lower hypertension and are effective in atherosclerosis and stroke (Lopez-Liuchi and Meier 1998; Bordet, Ouk et al. 2006). Rosiglitazone but not pioglitazone has been shown to increase the risk of congestive heart failure. Recently, the efficacy of these two agents in reducing brain inflammatory damage and improving cognition in Alzheimer's patients was also documented ((Landreth and Heneka 2001; Feinstein 2003); (Heneka and Landreth 2007; Kapadia, Yi et al. 2008)). Rosiglitazone binds to PPARγ receptors with higher affinity (40 to 100 times higher) than piolitazone, but pioglitazone crosses the blood brain barrier more easily (Young, Buckle et al. 1998; Breidert, Callebert et al. 2002). This may explain why pioglitazone appears to be more effective in modulating brain PPARγ receptor effects (Maeda, Kiguchi et al. 2007). The chemical structure of pioglitazone HCl is shown below.

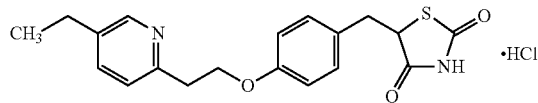 [SMILES: CCc1ccc(CCOc2ccc(CC3SC(=O)NC3=O)cc2)nc1 ; Cl]

An additional class of PPARγ agonists are the dual-acting PPARα/γ agonists. These dual-acting PPAR agonists are a group of compounds that activate nuclear transcription factors. By activating both PPARα and PPARγ receptors, they simultaneously reduce atherogenic triglycerides, raise cardioprotective HDI levels, and improve insulin resistance. Examples of dual-acting PPARα/γ agonists that may be suitable for use in the present invention include tesaglitazar, aleglitazar, muraglitazar, netoglitazone, naveglitazar, ragaglitazar, farglitazar, JTT-501, imiglitazar, chiglitazar, MK 767, LY 929, KRP-297, Compound 3q, 5-substituted 2-benzoylamino-benzoic acid derivatives, O-arylmandelic acid derivatives, azaindole-α-alkyloxy-phenylpropionic acid, oxime substituted with α-substituted-β-phenylpropionic acid derivatives with oxime, amide substituted with α-substituted-β-phenylpropionic acid derivatives, 2Alkoxydihydro cinnamate derivatives, TZD-18, α-Aryloxyphenol acetic acid derivatives, tricyclic-α-alkyloxyphenyl propionic acids, and LSN862, as described in Balakumar et al.

Other dual-acting PPARγ agonists that may be used according to the present invention include, but are not limited to, those that activate both PPARδ and PPARγ. One example of such dual PPAR gamma/delta agonist is DB959 (Dara BioSciences, Inc., Raleigh, N.C., USA). DB959 is a non-thiazolidinedione (non-TZD) and does not have PPAR-alpha activity. Another dual PPARγ/δ agonist is (R)-3-{2-ethyl-4-[3-(4-ethyl-2-pyridin-2-yl-phenoxy)]-phenyl}propionic, as described in Gonzalez et al. An additional example is (R)-3-{4-[3-(4-chloro-2-phenoxy-phenoxy)-butoxy]-2-ethyl-phenyl}-propionic acid, and related compounds, as described in Xu et al.

In addition, pan-PPAR agonists that activate PPARγ, PPARα, and PPARδ may be used in certain embodiments of the present invention. Examples of such pan-PPAR agonists include bezfibrate, carbazole-derived compounds, BPR1H036, PLX-204, GW-625019, GW 677954, and indeglitazar. Other examples include the amphipathic 3-phenyl-7-propylbenzisoxazoles described in Adams et al.

Additional PPARγ agonists that may be used according to the present invention include, but are not limited to, tesaglitazar, maraglitazar, peliglitazar, farglitazar, reglitazar, neviglitazar, oxeglitazar, edaglitazone, imiglitazar, and sipoglitazar, as well as those described in the following patents and patent applications: U.S. Pat. Nos. 6,294,580, 7,067,530, 6,582,738, 6,794,154, 4,812,570, 4,775,687, 4,725,610, 4,582,839, and 4,572,912; and U.S. Patent Application Publication Nos. US2002/006942, US2007/0299047, US2004/0077525, US2008/0045580, WO 2008/063842, the disclosures of which are hereby incorporated by reference. Examples of additional dual PPARγ agonists that may be used according to the present invention include, e.g., those described in U.S. Patent Application Nos. US2008/0131475, US2007/037882, US2006/0270722, US2006/0211749, US2006/0167045, and US2005/0014833, the disclosures of which are hereby incorporated by reference. Other suitable PPAR agonists are discussed in Shah et al, Evans et al., Feldman et al., Kasuga et al., and Rudolph et al.

It is understood that while certain embodiments of the present invention are described below with respect to selective PPARγ agonists, partial PPARγ agonists, dual agonists of PPARγ and PPARα, dual agonists of PPARγ and PPARδ, and pan agonists of PPARγ, PPARδ, and PPARα may be substituted for the selective PPARγ agonists to achieve other embodiments of the present invention.

B. Methods of Treating and Preventing Addiction Using PPARγ Agonist(s) in Combination with Other Therapeutic Agents As demonstrated in the accompanying Examples, PPARγ agonists may be effectively used in combination with one or more additional therapeutic agents to treat or prevent addiction, including addiction to one or more of the addictive agents described infra and compulsive or addictive behaviour. Accordingly, the present invention includes methods of treating or preventing an addiction, comprising providing to a subject addicted to, or at risk of becoming addicted to, an addictive agent one or more PPARγ agonist(s) and one or more additional therapeutic agent(s), in which each of the PPARγ agonist(s) and the additional therapeutic agent(s) contribute to the effective treatment or prevention of the addiction. In one embodiment, a subject is provided with or administered one PPARγ agonist and one additional therapeutic agent. In another embodiment, a subject is addicted to two or more addictive agents. As demonstrated by the Examples below, the combination of a PPARγ agonist and another therapeutic agent may have advantageous additive or synergistic efficacy in treating or preventing addiction or relapse use of an addictive agent. In some embodiments, the additional agent is another anti-addiction agent.

The PPARγ agonist and the additional therapeutic agent may be administered at the same time (i.e., concurrently), or either may be administered before the other (i.e., sequentially). In general, both the PPARγ agonist and the additional therapeutic agent are present in the subject at the same time for a duration of time and at levels sufficient to provide a therapeutic benefit to the subject, i.e., in the treatment or preventing of an addiction or the prevention of a relapse use (or reinstatement) of an addictive agent or compulsive or addictive behaviour. The PPARγ agonist and the additional therapeutic agent may be administered by the same or different routes of administration. Typically, the PPARγ agonist and the additional therapeutic agent are each provided to a subject according to a standard route of administration of a commercially available or other pharmaceutical composition. In one embodiment, the PPARγ agonist and the additional therapeutic agent are co-administered using a composition comprising both agents.

The additional therapeutic agent provided in combination with a PPARγ agonist may be any therapeutic agent that contributes to an aspect of the effective treatment or prevention of the addiction. For example, the additional therapeutic agent may be a drug used to treat an addiction or a drug used to alleviate side-effects associated with physiological withdrawal from an addictive agent. In addition, the additional therapeutic agent may be any drug that affects brain serotonin neurotransmission, such as selective serotonin reuptake inhibitors (SSRIs), and tricyclic and tetracyclic serotonin and norepinephrine reuptake inhibitors (SNRIs) as described below, and serotonin agonists such as sumatriptan, ergonovine, dihydroergotamine and buspirone. In certain embodiments, the additional therapeutic agent is an opioid antagonist, including mixed opioid partial agonist/antagonists, an antidepressant, an antiepileptic, an antiemetic, a corticotrophin-releasing factor-1 (CRF-1) receptor antagonist, a selective serotonin-3 (5-HT3) antagonist, a $5-HT_{2A/2C}$ antagonist such as mianserin, mirtazapine and ketanserin, or a cannabinoid-1 (CB1) receptor antagonist, including but not limited to those therapeutic agents specifically described infra.

In one embodiment, the addictive agent is alcohol and the additional therapeutic agent is an opioid antagonist or a mixed opioid antagonist/partial agonist. In a particular embodiment, the opioid antagonist is naltrexone. In another embodiment, the mixed opioid partial agonist/antagonist is buprenorphine. In a particular embodiment, the PPARγ agonist is pioglitazone and the additional therapeutic agent is naltrexone or buprenorphine.

In one embodiment, the addictive agent is alcohol, and the additional therapeutic agent is topiramate or levetiracetam. In a particular embodiment, the PPARγ agonist is pioglitazone and the additional therapeutic agent is topiramate or levetiracetam.

In one embodiment, the addictive agent is nicotine, and the additional therapeutic agent is an antidepressant. In a particular embodiment, the antidepressant is bupropion or sibutramine. In a particular embodiment, the PPARγ agonist is pioglitazone and the additional therapeutic agent is bupropion. In another particular embodiment, the PPARγ agonist is pioglitazone and the additional therapeutic agent is sibutramine.

In one embodiment, the addictive agent is nicotine, and the additional therapeutic agent is naltrexone.

In one embodiment, the addictive agent is cocaine, and the additional therapeutic agent is buprenorphine. In a particular embodiment, the PPARγ agonist is pioglitazone and the additional therapeutic agent is buprenorphine.

In one embodiment, the addictive agent is a psychostimulant and the additional therapeutic agent is an antidepressant. In a particular embodiment, the antidepressant is bupropion. In a particular embodiment, the PPARγ agonist is pioglitazone and the additional therapeutic agent is bupropion.

In one embodiment, the addictive agent is nicotine, and the additional therapeutic agent is an anti-epileptic. In a particular embodiment, the anti-epileptic is levetiracetam. Accordingly, in one embodiment, the PPARγ agonist is pioglitazone, and the anti-epileptic is levetiracetam. In another particular embodiment, the anti-epileptic agent is naltrexone. Accordingly, in one embodiment, the PPARγ agonist is pioglitazone, and the anti-epileptic is naltrexone.

In one embodiment, the subject is addicted to two or more addictive agents and the additional therapeutic agent is an opioid antagonist or a mixed opioid partial agonist/antagonist. In a particular embodiment, the mixed opioid partial agonist/antagonist is buprenorphine.

In one embodiment, the subject is addicted to both alcohol and nicotine, and the additional therapeutic agent is an anti-epileptic. In a particular embodiment, the PPARγ agonist is pioglitazone, and the anti-epileptic is naltrexone.

In particular embodiments, a subject is provided with a combination of: pioglitazone and naltrexone; ciglitazone and naltrexone; rosiglitazone and naltrexone; englitazone and naltrexone; rivoglitazone and naltrexone; darglidazone and naltrexone; pioglitazone and fluoxentine; ciglitazone and fluoxentine; rosiglitazone and fluoxentine; englitazone and fluoxentine; rivoglitazone and fluoxentine; darglidazone and fluoxentine; pioglitazone and mirtazapine; ciglitazone and mirtazapine; rosiglitazone and mirtazapine; englitazone and mirtazapine; rivoglitazone and mirtazapine; darglidazone and mirtazapine; pioglitazone and topiramate; ciglitazone and topiramate; rosiglitazone and topiramate; englitazone and topiramate; rivoglitazone and topiramate; darglidazone and topiramate; pioglitazone and levetiracetam; ciglitazone and levetiracetam; rosiglitazone and levetiracetam; englitazone and levetiracetam; rivoglitazone and levetiracetam; darglidazone and levetiracetam; pioglitazone and gabapentin; ciglitazone and gabapentin; rosiglitazone and gabapentin; englitazone and gabapentin; rivoglitazone and gabapentin; darglidazone and gabapentin; piolitazone and ondansetron; ciglitazone and ondansetron; rosiglitazone and ondansetron; englitazone and ondansetron; rivoglitazone and ondansetron; darglidazone and ondansetron; pioglitazone and antalarmin; ciglitazone and antalarmin; rosiglitazone and antalarmin; englitazone and antalarmin; rivoglitazone and antalarmin; darglidazone and antalarmin.

For treatment of alcohol addiction, combinations to be administered in accordance with the present invention include a PPARγ agonist and an opioid agonist or a mixed opioid antagonist/partial antagonist, a PPARγ agonist and an antidepressant, a PPARγ agonist and a CB1 receptor antagonist/inverse agonist, a PPARγ agonist and varenicicline, a PPARγ agonist and acamprosate, and a PPARγ agonist and disulfiram.

For treatment of a psychostimulant addiction, combinations to be administered in accordance with the present invention include, e.g., a PPARγ agonist and an antidepressant or a PPARγ agonist and a partial opioid agonist/antagonist, e.g., buprenorphine.

For treatment of nicotine addiction, combinations to be administered in accordance with the present invention include, e.g., a PPARγ agonist and an antidepressant, a PPARγ agonist and nicotine (as a replacement, in an oral, transcutaneous or other conventional formulation), a PPARγ agonist and an opioid antagonist, a PPARγ agonist and a CB1 receptor antagonist/inverse agonist, and a PPARγ agonist and varenicicline.

For treatment of polysubstance addiction, combinations to be administered in accordance with the present invention include, e.g., a PPARγ agonist and an opioid agonist or a mixed opioid antagonist/partial antagonist.

For treatment of gambling addiction, combinations to be administered in accordance with the present invention include, e.g., a PPARγ agonist and and an antidepressant or a PPARγ agonist and an agent affecting dopamine neurotransmission, e.g., a direct or indirect dopamine antagonist.

The effective amount of either or both of a PPARγ agonist and an additional therapeutic agent may be reduced when administered in combination that when either is provided alone. For example, when the PPARγ agonist and the additional therapeutic agent act additively or synergistically, then a lower amount of the PPARγ agonist, a lower amount of the additional therapeutic agent, or lower amounts of both the PPARγ agonist or the additional therapeutic agent may be required to achieve the same therapeutic effect that would be provided by either the PPARγ agonist or the additional therapeutic agent alone.

a. Opioid Antagonists

An opioid antagonist acts on one or more opioid receptors. At least three types of opioid receptors, mu, kappa, and delta opioid receptors, have been reported, and opioid antagonists are generally classified by their effects on the opioid receptors. Opioid antagonists may antagonize central receptors, peripheral receptors or both. Naloxone and naltrexone are commonly used opioid antagonist drugs that are competitive that bind to the opioid receptors with higher affinity than agonists, but that do not activate the receptors. This effectively blocks the receptor, preventing the body from responding to opiates and endorphins.

Many opioid antagonists are not pure antagonists but also produce some weak opioid partial agonist effects, and can produce analgesic effects when administered in high doses to opioid-naive individuals. Examples of such compounds include nalorphine, and levallorphan. However, the analgesic effects from these drugs are limited and tend to be accompanied by dysphoria, most likely due to action at the kappa opioid receptor. Since they induce opioid withdrawal effects in people who are taking, or have previously used, opioid full agonists, these drugs are considered to be antagonists.

Naloxone is one example of an opioid antagonist that has no partial agonist effects. Instead, it is a weak inverse agonist at mu opioid receptors, and is used for treating opioid overdose.

Specific examples of opioid antagonists that may be used according to the invention include alvimopan, binaltorphimine, buprenorphine, cyclazocine, cyclorphan, cypridime, dinicotinate, beta-funaltrexamine, levallorphan, methylnaltrexone, nalbuphine, nalide, nalmefene, nalmexone, nalorphine, nalorphine dinicotinate, naloxone, naloxonazine, naltrendol, naltrexone, naltrindole, oxilorphan, and pentazocine.

b. Antidepressants

Antidepressants are drugs used to treat depression. The three neurotransmitters believed to be involved in depression are serotonin, dopamine, and norepinephrine. Certain types of antidepressants increase the levels of one or more of these neurotransmitters in the brain by blocking their reabsorption.

Several different classes of antidepressants have been identified, including selective serotonin reuptake inhibitors (SSRIs), tricyclic and tetracyclic serotonin and norepinephrine reuptake inhibitors (SNRIs), norepinephrine reuptake inhibitors (NRIs), norepinephrine and dopamine reuptake inhibitors (NDRIs), azaspirones, monoamine oxidase inhibitors (MAOIs), and atypical antidepressants.

SSRIs include, e.g., cericlamine, citalopram, clomipramine, cyanodothiepin, dapoxetine, duloxetine, escitalopram, femoxetine, fluoxetine, fluvoxamine, ifoxetine, imipramine, indalpine, indeloxazine, litoxetine, lofepramine, mianserine, milnacipran, mirtazapine, nefazadone, nortriptyline, paroxetine, sertraline, sibutramine, tomoxetine, trazodone, venlafaxine, and zimeldine.

Amitriptyline, amoxapine, butriptyline, clomipramine, demexiptiline, desipramine, dibenzepin, dimetacrine, dothiepin, doxepin, imipramine, iprindole, lofepramine, maprotiline, melitracen, metapramine, mianserin, mirtazpine, nortriptyline, propizepine, protriptyline, quinupramine, setiptiline, tianeptine, and trimipramine are all tricyclic and tetracyclic antidepressants.

SNRIs include, e.g., amoxapine, atomoxetine, bicifadine, desipramine, desvenlafaxine, duloxetine, maprotiline, milnacipran, nefazodone, reboxetine, sibutramine, and venlafaxine.

Nisoxetine, nortriptyline, reboxetine, talsupram, and tomoxetine are all examples of NRIs.

NDRIs include, e.g., bupropion, hydroxybupropion, and tesofensine.

Azaspirones include, e.g., buspirone, gepirone, ipsapirone, tandospirone, and tiaspirone. Buspirone is an anxiolytic (partial agonist at 5-HT1 autoreceptors) that may be provided with an anti-depressant such as an SSRI.

Specific MAOIs include, e.g., amiflamine, brofaromine, clorgyline, alpha-ethyltryptamine, iproclozide, iproniazid, isocarboxazid, mebanazine, moclobemide, nialamide, pargyline, phenelzine, pheniprazine, pirlindole, safrazine, selegiline, toloxatone, and tranlcypromine.

Atypical antidepressants include, e.g., amesergide, amineptine, benactyzine, bupropion, clozapine, fezolamine, levoprotiline, lithium, medifoxamine, mianserin, minaprine, olanzapine, oxaflozane, oxitriptan, rolipram, teniloxazine, tofenacin, trazodone, tryptophan, and viloxazine.

c. Antiepileptics

The anticonvulsants, also called anti-epileptic drugs (AEDs) are a diverse group of drugs used in prevention of the occurrence of epileptic seizures and bipolar disorders. AEDs suppress the rapid and excessive firing of neurons that begins a seizure and/or prevents the spread of the seizure within the brain and offer protection against possible excitotoxic effects that may result in brain damage. Many anticonvulsants block sodium channels, calcium channels, AMPA receptors, or NMDA receptors.

Anti-epileptic agents include, but are not limited to, benzodiazepines, barbituates, valproates, GABA agents, iminostilbenes, hydantoins, NMDA antagonists, sodium channel blockers and succinimides.

Benzodiazepines include, e.g., alprazolam, chlordiazepoxide, cholrazepate, clobazam, clonazepam, diazepam, halazapam, lorazepam, oxazepam, and prazepam.

Barbiturates used as anti-epileptics include, e.g., amobarbital, mepobarbital, methylphenobarbital, pentobarbital, phenobarbital, and primidone.

Valproates used as anti-epileptics include, e.g., sodium valporate, valproic acid, valproate sem isodium, and valpromide.

Anti-epileptic GABA agents include, e.g., gabapentin, pregabalin, losigamone, pregabalin, retigabine, rufinamide, and vigabatrin.

Carbamazepine and oxcarbazepine are examples of iminostilbenes.

Hydantoins include, e.g., fosphenytoin sodium, mephenytoin, and phenytoin sodium.

NMDA antagonists such as harkoseramide are used as anti-epileptics.

Sodium channel blockers such as lamotrigine are also anti-epileptic agents.

Succinimides include, e.g., ethosuximide, methsuximide, and phensuximide.

Other anti-epileptic drugs include acetazolamide, briveracetam, CBD *cannabis* derivative, clomthiazole edisilate, divalproex sodium, felbamate, isovaleramide, lacosamide, lamotrigine, levetiracetam, methanesulphonamide, talampanel, tiagabine, topiramate, safinamide, seletracetam, soretolide, stiripentol, sultiam, valrocemide, and zonisamide.

d. Antiemetics

Anti-emetics are drugs effective against vomiting and nausea. Anti-emetics are typically used to treat motion sickness and the side effects of opioid analgesics, general anaesthetics, and chemotherapy.

Classifications of anti-emetics include, e.g., 5-hydroxytryptamine 3 (5-HT3) receptor antagonists, histamine receptor antagonists, dopamine receptor antagonists, muscarinic receptor antagonists, acetyl choline receptor antagonists, cannabinoid receptor antagonists, limbic system inhibitors, NK-1 receptor antagonists, corticosteroids, tachykinin antagonists, GABA agonists, cannabinoids, benzodiazepines, anticholinergics, and substance P inhibitors.

5-HT3 receptor antagonists include, e.g., alosetron, azasetron, bemesetron, cilansetron, dolasetron, granisetron, indisetron, itasetron, ondansetron, palonosetron, propisetron, ramosetron, renzapride, tropisetron, and zatosetron.

Coritcosteroid anti-emetics include dexamethasone and methylprednisolone.

Lymbic system inhibitors include alprazolam, lorazepam, and midazolam.

Dopamine receptor antagonists include diphenhydramine, dronabinol, haloperidol, metoclopramide, and prochlorperazine.

NK-1 receptor antagonists used as an anti-emetic include aprepitant and morpholine, and an example of a GABA agonist is propofol.

Thiethylperazine is a type of histamine receptor antagonist.

Cannabinoid receptor antagonists used as anti-emetics include dronabinol, nabilone, rimonabant, tanarabout, and tetrahydrocannabinol.

Examples of other anti-emetics include acetylleucine, monoethanolamine, alizapride, benzquinamide, bietanautine, bromopride, buclizine, chlorpromazine, clebopride, cyclizine, dimenhydrinate, dipheniodol, domperidone, dranisetron, meclizine, methalltal, metopimazine, oxypendyl, pipamazine, piprinhydrinate, scopolamine, thioproperzaine, and trimethobenzamide.

e. Cannabinoid Receptor Antagonists

The cannabinoid receptors are a class of the G-protein coupled receptor superfamily. Their ligands are known as cannabinoids. There are currently two known subtypes, CB1 which is expressed mainly in the brain, but also in the lungs, liver, and kidney, and CB2, which is mainly expressed in the immune system and in hematopoietic cells. It is also believed that there are novel cannabinoid receptors that is, non-CB1 and non-CB2, which are expressed in endothelial cells and in the CNS. Cannabinoid receptor antagonists may be selective for either the CB1 or CB2 receptor. The present invention contemplates the use of either or both CB1 and CB2 receptor antagonists.

Addictive agents (e.g., alcohol, opiates, Delta(9)-tetrahydrocannabinol (Delta(9)-THC) and psychostimulants, including nicotine) elicit a variety of chronically relapsing disorders by interacting with endogenous neural pathways in the brain. In particular, they share the common property of activating mesolimbic dopamine brain reward systems, and virtually all abused drugs elevate dopamine levels in the nucleus accumbens. Cannabinoid-1 (CB1) receptors are expressed in this brain reward circuit and modulate the dopamine-releasing effects of Delta(9)-THC and nicotine.

Rimonabant (SR141716), a CB1 receptor antagonist, blocks both the dopamine-releasing and the discriminative and rewarding effects of Delta(9)-THC in animals. Although CB1 receptor blockade is generally ineffective in reducing the self-administration of cocaine in rodents and primates, it reduces the reinstatement of extinguished cocaine-seeking behaviour produced by cocaine-associated conditioned stimuli and cocaine priming injections. Similarly, CB1 receptor blockade is effective in reducing nicotine-seeking behaviour induced by re-exposure to nicotine-associated stimuli. In human clinical trials, rimonabant was shown to block the subjective effects of Delta(9)-THC in humans and prevents relapse to smoking in ex-smokers.

Other examples of cannabinoid receptor CB1 antagonists include SR141716A (rimonabant), rosanabant, taranabant and CP-945598.

C. Methods of Treating and Preventing Relapse

Relapse use, or reinstatement, refers to the process of returning to the use of alcohol or another addictive agent or the practice of an addictive behaviour after a period of abstinence from, or limited or reduced use of, an addictive agent or practice of an addictive behaviour. In certain situations, relapse use of an addictive agent refers to the return to use of an addictive agent by a subject who has undergone physical withdrawal from the addictive agent. Typically, the subject will have undergone physical withdrawal from the addictive agent during a period of non-use or limited or reduced use of the addictive agent. In one embodiment, relapse use occurs in a subject who has previously undergone a treatment regime with an effective amount of an anti-addiction agent to reduce or eliminate use of an addictive agent, but who is no longer using an effective amount of the anti-addiction agent. Anti-addictive agents include any and all agents used to treat or prevent addiction or withdrawal symptoms.

Alcoholism, like many other addictions, is a chronic relapsing disorder characterized by high recidivism rates. Two major factors triggering relapse behaviour are stress and environmental conditioning experiences (O'Brien et al. 1997; Monti et al. 1993; Shaham et al. 1995), which probably facilitate relapse to alcohol-seeking via distinct brain mechanisms. For example, activation of the mesolimbic dopamine system via an opioid-dependent mechanism (or via direct alterations in dopamine transmission in the basolateral nucleus of amygdala) seems to mediate the effect of drug-associated cues (Liu and Wiess 2002; Ciccocioppo et al. 2001), and, extrahypothalamic CRF within the bed nucleus of the stria terminalis and median raphe nucleus is likely to mediate stress-induced reinstatement of drug-seeking behaviour (Erb et al 1998; Shaham et al. 1995; Lê et al. 2000).

Several lines of evidence suggest that molecular mechanisms underlying relapse to addiction are common to different classes of drugs of abuse. Drug craving and loss of control over drug taking behaviour associated to relapse are under the direct influence of stress and environmental conditioning stimuli; the two major factors affecting resumption to drug use.

Chronic drug abuse produces neuroadaptive changes not only within systems implicated in the acute reinforcing effects of ethanol, but also within other motivational systems, notably brain stress-regulatory mechanisms. Stress has an established role in the initiation and maintenance of drug abuse, and is a major determinant of relapse in abstinent individuals (Brown et al. 1995; Marlatt et al. 1985; McKay et al. 1995; Wallace 1989). The significance of stress in drug-seeking behaviour has also been amply documented in the animal literature. Physical, social, and emotional stress can facilitate acquisition or increase self-administration of cocaine (Goeders et al. 1995; Haney et al. 1995; Ramsey and VanRee 1993; Ahmed and Koob 1997), heroin, (Shaham and Stewart 2004), and ethanol (Nash et al. 1998; Mollenauer et al. 1993; Blanchard et al. 1987; Higley et al. 1991)) in rodents and nonhuman primates. Stressful stimuli have also been shown to elicit reinstatement of cocaine, heroin, and ethanol-seeking behaviour in drug-free animals following extinction (Ahmed and Koob 1997; Shaham 1993; Shaham and Stewart 1995; Ie et al. 1998) and these findings provide experimental support for a role of stress in relapse.

Traditionally, stress-related drug-seeking behaviour has been thought to be mediated via activation of the hypothalamic-pituitary-adrenal (HPA) axis. However, growing evidence suggests that the non-neuroendocrine corticotropin-releasing factor (CRF) system in the central nucleus of the amygdala (CeA) may play a significant independent role in the regulation of addictive behaviour associated with stress. The CeA is rich in CRF immunoreactive cell bodies, terminals, and receptors, and this neuronal CRF system has been implicated in the mediation of behavioural and emotional responses to stressful stimuli (Dunn and Berridge 1990; Koob et al. 1994). For example, immobilization stress elevates extracellular CRF levels in the CeA (Merlo Pich et al. 1995; Merali et al. 1998) while intra-CeA injection of the CRF receptor antagonist, α-helical CRF9-41, reduces behavioural signs of anxiety produced by social and environmental stressors (Heinrichs et al. 1992; Swiergiel et al. 1993). Anxiety and stress-like symptoms are central to drug and alcohol withdrawal syndromes. Considering the evidence on a role of CRF neurons in the CeA in the regulation of emotional and anxiogenic effects of stress, it is likely that anxiogenic and stress-like consequences of withdrawal from drugs of abuse may be mediated by the CRF system in the CeA as well.

Changes in the regulation of the activity of the CRF system within the CeA may represent a critical neuroadaptive mechanism responsible for the development of dependence and compulsive drug-seeking behaviour.

The data discussed above identify neuroadaptive changes in brain circuitries and perturbations in stress systems as an important element in compulsive drug-seeking behaviour and dependence. Another important factor in the long-lasting addictive potential of drugs of abuse is the conditioning of their rewarding actions with specific environmental stimuli. Environmental cues repeatedly associated with the subjective effects of drugs of abuse including alcohol can evoke drug craving (Childress et al. 1988; Ehrman et al. 1992; Monti et al. 1993; Pomerleau et al. 1983; Stormark et al. 1995) or elicit automatic behavioural responses (Miller and Gold 1994; Tiffany and Carter 1998) that ultimately may lead to relapse. Learned responses to drug-related stimuli may, therefore, contribute critically to the high rates of relapse associated with cocaine and other drug addiction.

Data from operant response-reinstatement models developed to investigate drug-seeking behaviour associated with exposure to drug-related environmental cues in rats indicate that discriminative stimuli predictive of cocaine (Weiss et al. 2000), ethanol (Katner et al. 1999; Katner and Weiss 1999), or heroin (Gracy et al. 2000) availability reliably elicit strong recovery of extinguished drug-seeking behaviour in the absence of further drug availability. The response-reinstating effects of these stimuli show remarkable resistance to extinction with repeated exposure and, in the case of cocaine, can still be observed after several months of forced abstinence. Additionally, in the case of ethanol, drug-seeking behaviour induced by ethanol-predictive discriminative stimuli was found to be enhanced in genetically alcohol-preferring P rats compared to Alcohol Nonpreferring (NP) and nonselected Wistar rats (Weiss and Ciccocioppo 1999). This observation demonstrates that genetic predisposition toward heightened ethanol intake is reflected also by a greater susceptibility to the motivating effects of ethanol cues (i.e., enhanced drug-seeking under conditions where behaviour is not directly reinforced by ethanol itself). Together, these findings strongly support the hypothesis that learned responses to drug-related stimuli are a significant factor in long-lasting vulnerability to relapse.

In humans, relapse risk involves multiple determinants that are likely to interact. For example, exposure to drug cues may augment vulnerability to relapse imparted by protracted withdrawal symptoms resulting from neuroadaptive changes in dependent individuals. Interactive effects exacerbating relapse risk may also exist between the motivating effects of stress and drug-related cues. Recent work addressing these issues has confirmed that additive interactions between the response-reinstating effects of ethanol-associated cues and stress can indeed be demonstrated, and that these effects are enhanced in rats with a history of ethanol dependence (Liu and Weiss 2000).

In experimental laboratories, reinstatement of drug seeking is obtained with administration of the α-2 adrenoreceptor antagonist yohimbine, which, increasing brain noradrenaline cell firing and release, acts as a pharmacological stressor. Footshock stress and yohimbine-induced reinstatement of drug-seeking behaviours both represent valid experimental models to investigate stress-induced alcohol relapse (Lee et al. 2004; Lê et al. 2000).

As shown in the accompanying Examples, PPARγ agonists significantly reduce stress-induced relapse use of an addictive agent (Example 5). In addition, in human patients, pioglitazone, a TZD, consistently reduced OCDS score (Example 22). Obsession for alcohol and the urge to drink (which are measured by OCDS scale) are the major predictors of relapse. These data indicate, therefore, that pioglitazone has anti-relapse properties.

Interestingly, the results showed that pioglitazone did not significantly prevent relapse elicited by conditioning factors. Interestingly, various reports have shown that the nonselective opiate receptor antagonist naltrexone reduces the urge to drink elicited by presentation of alcohol cues in human alcoholics (Monti et al. 1993) and decreases the efficacy of an alcohol cue to reinstate extinguished responding at a previously drug-paired lever in rats (Katner et al. 1999). However, naltrexone does not reduce relapse behaviour elicited by stress ((Le A. D. Psychopharmacology 1998).

These findings suggest that the use of a combination of pioglitazone and naltrexone should result in a synergistic action to reduce relapse behaviour elicited by both stress and conditioning factors.

Accordingly, the present invention provides treatment methods and drug combinations that protect individuals from the effects of more than a single environmental risk factor (i.e., stress and environmental conditioning factors).

In one embodiment, the present invention provides a method of treating or preventing stress-induced relapse use of an addictive agent, comprising providing a PPARγ agonist to a subject who has undergone physiological withdrawal from an addictive agent.

In a related embodiment, the invention includes a method of treating or preventing relapse use of an addictive agent or practice of an addictive or compulsive behaviour, comprising providing an effective amount of a peroxisone proliferator-activated receptor gamma (PPARγ agonist) to a subject who previously reduced or eliminated use of an addictive agent or practice of an addictive or compulsive behaviour in response to exposure to an effective amount of another anti-addiction treatment, wherein the subject is no longer exposed to an effective amount of the anti-addiction treatment. The anti-addiction treatment may be an anti-addiction drug or may be a non-pharmacologic therapy such as counseling, psychotherapy or hypnosis therapy. The relapse use may be triggered by stress.

In certain embodiments, the subject is no longer exposed to an effective amount of an anti-addiction agent because the subject has become tolerant to the agent, such that the blood plasma concentration of the anti-addiction agent that was previously effective in treating the addiction is no longer effective. In other embodiments, the subject is no longer exposed to an effective amount of an anti-addiction agent because the subject is now exposed to a lower blood plasma concentration of the anti-addiction agent, and this lower blood plasma concentration is not effective.

In certain embodiments of the methods of the present invention, the subject has undergone a period of abstinence from, or limited or reduced use of, the addictive agent or practice of the addictive or compulsive behaviour. This period of abstinence or limited or reduced use may be, e.g., at least 24 hours, at least 48 hours, at least 3 days, at least 5 days, at least one week, at least 2 weeks, at least 1 month, at least 2 months, at least 4 months, at least 6 months, at least 9 months, at least one year, at least 2 years, or at least 5 years.

In another embodiment, the present invention includes a method of treating or preventing relapse use of an addictive agent, comprising providing a PPARγ agonist and an opioid antagonist to a subject who has undergone physiological withdrawal from the addictive agent.

In a further embodiment, the present invention includes a method of treating or preventing relapse use of an addictive agent, comprising providing a PPARγ agonist and a CB1 antagonist, e.g., disulfiram, topiramate, levetiracetam, SSRIs, or ondansetron, to a subject who has undergone physiological withdrawal from the addictive agent.

In particular embodiments, the relapse use is triggered by stress, an environmental conditioning factor, or both. Examples of suitable PPARγ agonists are TDZs, such as pioglitazone, etc. One example of a suitable opioid receptor antagonist is naltrexone.

While the methods of the present invention may be practiced in subjects addicted to a single addictive agent, they may also be used in subjects addicted to two or more addictive agents. Similarly, while these methods may be used to prevent relapse use of the addictive agent from which the subject has undergone withdrawal, they may also be adapted to prevent relapse use or the commencement of use of an addictive agent different than the one from which the subject has undergone physiological withdrawal.

D. Methods of Reducing Withdrawal Symptoms and Treating Depression/Anxiety

Withdrawal, also known as withdrawal/abstinence syndrome, refers to the characteristic signs and symptoms that appear when a drug or addictive agent that causes physical dependence is regularly used for a long time and then suddenly discontinued or decreased in dosage. Withdrawal symptoms can vary significantly among individuals, but there are some commonalties. Brain dysfunction associated with withdrawal is often characterized by depression, anxiety and craving, and, if extreme, can help drive the individual to continue the drug despite significant harm—the definition of addiction—or even to suicide.

Increased heart rate and/or blood pressure, sweating, and tremors are common signs of withdrawal. More serious symptoms such as confusion, seizures, and visual hallucinations indicate a serious emergency and the need for immediate medical care. Alcohol, opiates, benzodiazepines, and barbiturates are the only commonly abused substances that can be fatal in withdrawal. Abrupt withdrawal from other drugs, such as nicotine or psychostimulants, can exaggerate mild to moderate neurotoxic side effects due to hyperthermia and generation of free radicals, but life-threatening complications are very rare.

As demonstrated in the accompanying Examples, PPARγ agonists reduce withdrawal symptoms (Example 21). In addition, they decreased anxiety and depression, which is also associated with withdrawal (Example 22). These data demonstrate that PPARγ agonists may be successfully used to reduce withdrawal symptoms, including depression and anxiety, thus making withdrawal easier for subjects and encouraging them to complete the withdrawal process.

The present invention includes a method of reducing one or more withdrawal symptoms associated with reduced or discontinued use of an addictive agent, comprising providing an effective amount of a peroxisome proliferator-activated receptor gamma (PPARγ) agonist to a subject undergoing physiological withdrawal from an addictive agent. In particular embodiments, the addictive agent is alcohol, an opioid agonist, such as morphine, or nicotine. In certain embodiments, the PPARγ agonist is a TZD, e.g., pioglitazone.

The PPARγ agonist may be provided to the subject before the subject begins withdrawal and/or during the withdrawal process. In a related method, a subject is provided with a PPARγ agonist over a period of time during which the subject uses a reduced amount of an addictive agent. For example, the subject may begin using a PPARγ agonist at the same time that they cease using or begin using a reduced amount of an addictive agent. In one embodiment, the subject uses a step-wise reduced amount of an addictive agent at the same time as a PPARγ agonist, until physical withdrawal is completed. The subject may then discontinue use of the PPARγ agonist or continue use of the PPARγ agonist to prevent relapse. Therefore, in related embodiments, the present invention contemplates delivering an addictive agent in combination with a PPARγ agonist, e.g., to reduce the likelihood of developing addiction, or to reduce withdrawal symptoms. In particular embodiments, the PPARγ agonist, e.g., pioglitazone, is delivered in combination with nicotine or an opioid agonist. The PPARγ agonist and the addictive agent may be delivered separately or in a single formulation or via a single delivery means. For example, both nicotine and a PPARγ agonist, such as pioglitazone, may be delivered via a transdermal patch, an oral lozenge, or a chewing gum delivery system. Transdermal patches, oral lozenges, and chewing gum containing nicotine are frequently used for the delivery of nicotine to subjects attempting to reduce nicotine use. By including a PPARγ agonist in combination with the nicotine in the transdermal patch, lozenge, or chewing gum, it is believed that the subject will suffer less nicotine withdrawal symptoms. In addition, this may facilitate greater compliance and more rapid reduction in nicotine use. The same principal applies to other addictive agents, including, e.g., opioid agonists. In addition, intranasal spray, an atomizer, or an inhalation device may be used to deliver nicotine or another addictive agent in combination with a PPAR agonist, such as a PPARγ agonist like pioglitazone.

In one particular embodiment, the addictive agent is nicotine, and the subject reduces or discontinues use of nicotine over a period of time during which the subject is provided with a PPARγ agonist, such as a TZD, e.g., pioglitazone, alone or in combination with another therapeutic agent. PPARγ agonist and nicotine combinations in the form of a transdermal patch, lozenge, chewing gum or other delivery vehicle may be prescribed in reducing dosages, or decreasing dosages may be kitted together, to permit tapering off of use of the drug product.

E. Pharmaceutical Compositions, Routes of Administration, Unit Dosage Forms, and Kits The present invention has established the efficacy of using combinations of a PPARγ agonist, e.g., a TZD such as pioglitazone, in combination with one or more additional therapeutic agents, such as opioid antagonists, antidepressents, antiepileptics, antiemetics, and CB1 receptor antagonists. Thus, the present invention further includes compositions comprising one or more PPARγ agonists and one or more additional therapeutic agents, such as opioid antagonists, mixed opioid antagonists/partial agonist, antidepressents, antiepileptics, antiemetics, CRF1 receptor antagonists and CB1 receptor antagonists.

The present invention has also established the efficacy of using a PPARγ agonist, e.g., a TZD such as pioglitazone, in combination with an addictive therapeutic agent, e.g., to prevent or reduce the likelihood that a subject treated with an addictive therapeutic agent will become addicted to it. Examples of addictive therapeutic agent include, but are not limited to, therapeutic opioid agonists, such as pain medications. Thus, the present invention includes methods involving contacting a subject with both an addictive therapeutic agent and one or more PPARγ agonists, as well as pharmaceutical compositions, and unit dosage forms thereof, comprising one or more PPARγ agonists and one or more addictive therapeutics agents, e.g., an opioid agonist such as, e.g., oxycodone or hydrocodone. In particular embodiments, the PPARγ agonist is pioglitazone, and the addictive therapeutic agent is oxycodone, or the PPARγ agonist is pioglitazone, and the addictive therapeutic agent is hydrocodone.

The present invention has further established the efficacy of using a PPARγ agonist, e.g., a TZD such as pioglitazone, in combination with an addictive agent, e.g., to prevent or reduce withdrawal symptoms as a subject stops use or reduces use of the addictive agent. Examples of such addictive agent include, but are not limited to, therapeutic opioid agonists, such as pain medications, nicotine, and alcohol. Thus, the present invention includes methods involving contacting a subject with both an addictive agent and one or more PPARγ agonists, as well as pharmaceutical compositions, and unit dosage forms thereof, comprising one or more PPARγ agonists and one or more addictive agents, e.g., an opioid agonist such as, e.g., oxycodone or hydrocodone, nicotine, or alcohol. In particular embodiments, the PPARγ agonist is pioglitazone, and the addictive therapeutic agent is nicotine.

In particular embodiments, the composition comprises one PPARγ agonist and one additional therapeutic agent. In one particular embodiment, a pharmaceutical composition comprises a TZD and one additional therapeutic agent. In certain embodiments, the additional therapeutic agent is an opioid antagonist or a mixed opioid antagonist/partial agonist. In one embodiment, the opioid antagonist is naltrexone. In another embodiment, the mixed opioid partial agonist/antagonist is buprenorphine. In certain embodiments, the additional therapeutic agent is an antidepressant. In a particular embodiment, the antidepressant is bupropion. In certain embodiments, the additional therapeutic agent is an antiepileptic, an antiemetic, or an opioid antagonist or a mixed opioid partial agonist/antagonist. In further embodiments, the additional therapeutic agent is an opioid agonist.

In particular embodiments, the present invention provides a composition comprising both an addictive agent, such as nicotine, an opioid agonist, or alcohol, and a PPAR agonist, e.g., a TZD such as pioglitazone. Such compositions may be in any suitable form. For instance, a composition comprising both nicotine and a PPAR agonist, such as pioglitazone, may be, e.g., a transdermal patch comprising both agents, a lozenge comprising both agents, or a chewing gum comprising both agents. Examples of transdermal patches comprising a PPARγ agonist are provided in U.S. Pat. No. 6,011,049. Examples of a PPARγ agonist delivered using patches, lozenges, or chewing gum are described in PCT Publication Nos. WO2007/075847, WO03/026586, and WO 05/107713, each of which is incorporated by reference with respect to its description of PPARγ agonist formulations, dosages, and delivery methods.

Dosages of PPAR agonist present in such a combination may be readily determined depending upon the route of administration, in order to provide a suitable dosage over the course of administration. In one embodiment wherein pioglitazone is administered in combination with nicotine, e.g., both present in a transdermal patch, the dosage of pioglitazone may be, e.g., between 5-45 mg per day, between 5-15 mg per day, between 10-15 mg per day, or about 5, about 10, or about 15 mg per day. In certain embodiments, the dosage of pioglitazone is less than or equal to 15 mg per day or less than or equal to 10 mg per day. In certain embodiments, glitazones are administered at doses from about 5 mg to about 2500 mg per day, and more typically from about 50 mg to about 1500 mg per day. In one embodiment, the glitazone is troglitazone, and it is used at doses from about 100 mg to about 1000 mg per day. In another embodiment, the glitazone is rosiglitazone, and it is used at doses of about 5 mg to about 10 mg per day. In another embodiment, the glitazone is pioglitazone, and it is used at doses of about 50 mg to about 200 mg per day.

In particular embodiments of pharmaceutical compositions, and unit dosage forms thereof, comprising both a PPAR agonist and an opioid agonist, the PPAR agonist is a PPARγ agonist, e.g., a TZD. In certain embodiments, the PPARγ agonist is pioglitazone, rosiglitazone, ciglitazone, troglitazone, englitazone, rivoglitazone, or darglidazone. In particular embodiments, the opioid agonist is a phenanthrene, a phenylheptylamine, or a phenylpiperidine. In certain embodiments, the opioid agonist is alfentanil, allylprodine, alphaprodine, anileridine, apomorphine, benzylmorphine, beta-hydroxy 3-methylfentanyl, bezitramide, carfentanil, clonitazene, codeine, desomorphine, dextromoramide, diacetylmorphine (heroin), diampromide, dihydrocodeine, dihydroetorphine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, etorphine, fentanyl, hydrocodone, hydromorphone, hydroxypethidine, isomethadone, ketobemidone, LMM, levorphanol, levophenacylmorphan, lofentanil, meperidine, metapon, metazocine, methadone, methadyl acetate, metopon, morphine, myrophine, narceine, nicomorphine, norlevorphanol, normethadone, normorphine, norpipanone, opium, oxycodone, oxymorphone, papaverine, phenadoxone, phenomorphan, phenoperidine, piminodine, piritramide, propheptazine, promedol, properidine, propoxyphene, remifentanil, sufentanil, thebaine, tildine, or tramadol, or any combination thereof.

In various embodiments, the composition comprises: pioglitazone and naltrexone; ciglitazone and naltrexone; rosiglitazone and naltrexone; englitazone and naltrexone; rivoglitazone and naltrexone; darglidazone and naltrexone; pioglitazone and fluoxentine; ciglitazone and fluoxentine; rosiglitazone and fluoxentine; englitazone and fluoxentine; rivoglitazone and fluoxentine; darglidazone and fluoxentine; pioglitazone and mirtazapine; ciglitazone and mirtazapine; rosiglitazone and mirtazapine; englitazone and mirtazapine; rivoglitazone and mirtazapine; darglidazone and mirtazapine; pioglitazone and topiramate; ciglitazone and topiramate; rosiglitazone and topiramate; englitazone and topiramate; rivoglitazone and topiramate; darglidazone and topiramate; pioglitazone and levetiracetam; ciglitazone and levetiracetam; rosiglitazone and levetiracetam; englitazone and levetiracetam; rivoglitazone and levetiracetam; darglidazone and levetiracetam; pioglitazone and gabapentin; ciglitazone and gabapentin; rosiglitazone and gabapentin; englitazone and gabapentin; rivoglitazone and gabapentin; darglidazone and gabapentin; piolitazone and ondansetron; ciglitazone and ondansetron; rosiglitazone and ondansetron; englitazone and ondansetron; rivoglitazone and ondansetron; darglidazone and ondansetron; pioglitazone and antalarmin; ciglitazone and antalarmin; rosiglitazone and antalarmin; englitazone and antalarmin; rivoglitazone and antalarmin; darglidazone and antalarmin.

In additional embodiments, the composition comprises pioglitazone and codeine, pioglitazone and morphine, pioglitazone and noscapapine, pioglitazone and hydrocodone, pioglitazone and hydromorphone, pioglitazone and oxycodone, pioglitazone and tramadol, pioglitazone and fentanyl, pioglitazone and propoxyphene, pioglitazone and methadone, ciglitazone and codeine, ciglitazone and morphine, ciglitazone and noscapapine, ciglitazone and hydrocodone, ciglitazone and hydromorphone, ciglitazone and oxycodone, ciglitazone and tramadol, ciglitazone and fentanyl, ciglitazone and propoxyphene, ciglitazone and methadone, rosiglitazone and codeine, rosiglitazone and morphine, rosiglitazone and noscapapine, rosiglitazone and hydrocodone, rosiglitazone and hydromorphone, rosiglitazone and oxycodone, rosiglitazone and tramadol, rosiglitazone and fentanyl, rosiglitazone and propoxyphene, rosiglitazone and methadone, englitazone and codeine, englitazone and morphine, englitazone and noscapapine, englitazone and hydrocodone, englitazone and hydromorphone, englitazone and oxycodone, englitazone and tramadol, englitazone and fentanyl, englitazone and propoxyphene, englitazone and methadone, rivoglitazone and codeine, rivoglitazone and morphine, rivoglitazone and noscapapine, rivoglitazone and hydrocodone, rivoglitazone and hydromorphone, rivoglitazone and oxycodone, rivoglitazone and tramadol, rivoglitazone and fentanyl, rivoglitazone and propoxyphene, rivoglitazone and methadone, darglidazone and codeine, darglidazone and morphine, darglidazone and noscapapine, darglidazone and hydrocodone, darglidazone and hydromorphone, darglidazone and oxycodone, darglidazone and tramadol, darglidazone and fentanyl, darglidazone and propoxyphene, or darglidazone and methadone. In a particular embodiment, the composition comprises both pioglitazone and oxycodone.

The compositions of the present invention may be administered to a subject as a pharmaceutical composition or formulation. In particular embodiments, pharmaceutical compositions of the present invention may be in any form which allows for the composition to be administered to a subject. For example, the composition may be in the form of a solid, liquid or gas (aerosol). In particular embodiments, the compositions may be provided using drug delivery systems suitable for delivering by any appropriate route of administration, including, e.g., intranasal sprays or inhalation devices. Typical routes of administration include, without limitation, oral, topical, parenteral, transdermal, intranasal, inhalation, sublingual, rectal, vaginal, and intranasal. The term parenteral as used herein includes subcutaneous injections, intravenous, intramuscular, epidural, intrasternal injection or infusion techniques.

Pharmaceutical compositions used according to the present invention comprise a PPAR agonist (e.g., a PPARg agonist), another therapeutic agent, and a pharmaceutically acceptable diluent, excipient, or carrier. "Pharmaceutically acceptable carriers" for therapeutic use are well known in the pharmaceutical art, and are described, for example, in *Reminqtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id. The compositions may contain common excipients and carriers such as starch, sucrose, talc, gelatin, methylcellulose, and magnesium stearate.

Pharmaceutical compositions of the invention are generally formulated so as to allow the active ingredients contained therein to be bioavailable upon administration of the composition to a subject. Compositions that will be administered to a subject may take the form of one or more dosage units, where for example, a tablet, capsule or cachet may be a single dosage unit, and a container comprising a combination of agents according to the present invention in aerosol form may hold a plurality of dosage units. The compositions may be made for oral administration, for instance as tablets or capsules, but also may be in the form of aqueous suspensions or solutions, suppositories, slow release forms, for example employing an osmotic pump, transdermal patch, or the like. In certain embodiments, a transdermal patch may comprise a unit dosage form of a PPARγ agonist in combination with either another therapeutic agent or an addictive agent, as described infra.

In particular embodiments, the composition comprising a PPARγ agonist and another therapeutic agent is administered in one or more doses of a tablet formulation, typically for oral administration. The tablet formulation may be, e.g., an immediate release formulation, a controlled release formulation, or an extended release formulation, e.g., a depot formulation. In particular embodiments, extended release formulations of the invention release at least 80% of the active ingredients in vivo over a period of greater than 24 hours, greater than 48 hours, greater than one week, greater than one month, or even greater than 2 or 4 months. Extended release formulations of the invention therefore allow for less frequency of dosing to the mammal in need thereof than other more immediate or controlled release formulations.

In one embodiment, a tablet formulation comprises an effective amount of a composition comprising a PPARγ agonist and another therapeutic agent. In particular embodiments, a tablet comprises about 1, 5, 10, 20, 30, 50 100, 150, 200, 250, or 300 mg of a PPARγ agonist, such as pioglitazone, and about 1, 5, 10, 20, 30, 50 100, 150, 200, 250, or 300 mg of another therapeutic agent.

The present invention further includes unit dosage forms of pharmaceutical compositions comprising a PPARγ agonist and another therapeutic agent. Each unit dosage form comprises a therapeutically effective amount of a pharmaceutical composition of the present invention, when used in the recommended amount. For example, a unit dosage form may include a therapeutically effective amount in a single tablet, or a unit dosage form may include a therapeutically effective amount in two or more tablets, such that the prescribed amount comprises a therapeutically effective amount.

As noted above, the present invention includes compositions (including delivery vehicles) comprising both nicotine and a PPARγ agonist, such as pioglitazone. In particular embodiments, the invention includes a transdermal patch suitable for drug delivery, which patch comprises both nicotine and a PPARγ agonist, such as pioglitazone. In particular embodiments, the patch provides for continued or controlled release of both nicotine and the PPARγ agonist. In one embodiment, the transdermal patch provides for 16 or 24 hour release of nicotine and the PPARγ agonist, e.g., pioglitazone. In one embodiment, the dosage of pioglitazone released over 16 to 24 hours is between 5-45 mg, between 5-15 mg, between 10-15 mg, or about 5, about 10, or about 15 mg. In certain embodiments, the dosage of pioglitazone released over the 16-24 hours is less than or equal to 15 mg or less than or equal to 10 mg. In particular embodiments, it is about 15 mg per 16 or 24 hours. In certain embodiments, the dosage of nicotine released over 16-24 hours is between 5 and 25 mg, e.g., about 21 mg, 14 mg or 7 mg.

A number of the PPARγ agonists and other therapeutic agents described herein are approved for human use at particular dosages. The present invention contemplates using these agents at their approved dosages or at other effective dosages. Since the combination of a PPARγ agonist and another therapeutic agent has been demonstrated to have synergistic efficacy, it is understood that effective amounts of one or both agents may be reduced when provided together, as compare to the effective amount of each when provided alone. In particular embodiments, a PPARγ agonist is provided to a subject in an amount in the range of 0.1-1000 mg/day, 1-1000 mg/day, 10-100 mg/day, or 25-50 mg/day. In one embodiment, pioglitazone is provided to a patient at about 30 mg/day.

Table 1 lists representative agents used in the present invention and provides the daily dosages at which these agents are conventionally administered to adults for other indications, which dosages are believed to be useful for administration in accordance with the methods of the present invention in the treatment or prevention of addiction and relapse use or practice. Dosages listed are oral unless otherwise indicated. It is believed that the dosages of these agents may be reduced when delivered in combinations of a PPARγ agonist and an additional therapeutic agent in accordance with the present invention for the treatment or prevention of addiction or for the treatment or prevention of relapse use. These reductions may be up to 10% of conventional dosages, or up to 20% of conventional dosages, or up to one third of conventional dosages, up to one half of conventional dosages or up to two thirds of conventional dosages. For example, pioglitazone is most commonly dosed at 30 mg per day for treatment of diabetes, which dosage was found to be effective for the treatment of alcoholism (Example 22). When combined with 50 mg/day naltrexone in accordance with the present invention for treatment of addiction, it is believed therapeutic effect may be seen at 10-15 mg per day of pioglitazone.

TABLE 1

| Therapeutic Agent | Exemplary Dosage Applied as Single Agent |
| --- | --- |
| Pioglitazone | 15-45 mg |
| Rosiglitazone | 2-8 mg |
| Troglitazone | 200-600 mg |
| Rimonabant | 10-20 mg |
| Buprenorphine | 0.3 mg (IV or IM) |
|  | 12-16 mg (sublingual) |
| Naltrexone | 25-50 mg |
| Fluoxetine | 20-80 mg |
| Mirtazipine | 15-45 mg |
| Topiramate | 400 mg |
| Levetiracetam | 1,000-6,000 mg |
| Gabapentin | 900-1,800 mg |
| Ondansetron | 8-24 mg |
| Bupropion | 200-400 mg |
| Butorphanol | 0.5-4 mg (IM or IV), |
|  | 1-2 mg (nasal spray) |
| Codeine | 30-240 mg |
| Dextropopoxyphene | 65-240 mg |
| Diamorphine | 5-60 mg |
| Morphine | 15-200 mg |
| Fentanyl | 2.0-100 μg/kg or 0.15-7.5 mg (IM or IV), |
|  | 12.5-100 μg/hr (transdermal patch), 0.2-1.6 |
|  | mg (oral lozenge), 0.1-1.6 mg (buccal tablets) |
| Oxycodone | 5-10 mg |
| Hydrocodone | 5-100 mg |
| Hydromorphone | 2-25 mg |
| Levorphanol | 2-3 mg |
| Meptazocine | 75-600 mg |
| Meperidine | 13-200 mg |
| Methadone | 10-120 mg |

In one embodiment, a unit dosage form of a pharmaceutical composition of the present invention comprises about 15-45 mg of pioglitazone and about 25-50 mg of naltrexone. This unit dosage form may consist of one or more tablets. In one particular embodiment, a unit dosage form of a pharmaceutical composition of the present invention comprises about 30 mg of pioglitazone and about 50 mg of naltrexone. This unit dosage form may consist of one or more tablets.

In one embodiment, a unit dosage form of a pharmaceutical composition of the present invention comprises about 15-45 mg of pioglitazone and about 5-10 mg of oxycodone. In another embodiment, a unit dosage form of a pharmaceutical composition of the present invention comprises about 15-45 mg of pioglitazone and about 5-100 mg of hydrocodone. In another embodiment, a unit dosage form of a pharmaceutical composition of the present invention comprises about 15-45 mg of pioglitazone and about 0.5-4.0 mg (IM or IV) or about 1.0-2.0 mg (nasal spray) of butorphanol. In another embodiment, a unit dosage form of a pharmaceutical composition of the present invention comprises about 15-45 mg of pioglitazone and about 30-240 mg of codeine. In another embodiment, a unit dosage form of a pharmaceutical composition of the present invention comprises about 15-45 mg of pioglitazone and about 65-240 mg of dextropopoxyphene. In another embodiment, a unit dosage form of a pharmaceutical composition of the present invention comprises about 15-45 mg of pioglitazone and about 5-60 mg of diamorphine. In another embodiment, a unit dosage form of a pharmaceutical composition of the present invention comprises about 15-45 mg of pioglitazone and about 15-200 mg of morphine. In another embodiment, a unit dosage form of a pharmaceutical composition of the present invention comprises about 15-45 mg of pioglitazone and about 0.3 mg of fentanyl, which may be in the form of a transmucosal lozenge. In another embodiment, a unit dosage form of a pharmaceutical composition of the present invention comprises about 15-45 mg of pioglitazone and about 2-25 mg of hydromorphone. In another embodiment, a unit dosage form of a pharmaceutical composition of the present invention comprises about 15-45 mg of pioglitazone and about 2.0 mg of levorphanol. In another embodiment, a unit dosage form of a pharmaceutical composition of the present invention comprises about 15-45 mg of pioglitazone and about 75-600 mg of meptazocine. In another embodiment, a unit dosage form of a pharmaceutical composition of the present invention comprises about 15-45 mg of pioglitazone and about 13-200 of meperidine. In another embodiment, a unit dosage form of a pharmaceutical composition of the present invention comprises about 15-45 mg of pioglitazone and about 10-120 mg of methadone.

In one embodiment, a unit dosage form of a pharmaceutical composition of the present invention comprises about 2-8 mg of rosiglitazone and about 5-10 mg of oxycodone. In another embodiment, a unit dosage form of a pharmaceutical composition of the present invention comprises about 2-8 mg of rosiglitazone and about 5-100 mg of hydrocodone. In another embodiment, a unit dosage form of a pharmaceutical composition of the present invention comprises about 2-8 mg of rosiglitazone and about 0.5-4.0 mg (IM or IV) or about 1.0-2.0 mg (nasal spray) of butorphanol. In another embodiment, a unit dosage form of a pharmaceutical composition of the present invention comprises about 2-8 mg of rosiglitazone and about about 30-240 mg of codeine. In another embodiment, a unit dosage form of a pharmaceutical composition of the present invention comprises about 2-8 mg of rosiglitazone and about 65-240 mg of dextropopoxyphene. In another embodiment, a unit dosage form of a pharmaceutical composition of the present invention comprises about 2-8 mg of rosiglitazone and about 5-60 mg of diamorphine. In another embodiment, a unit dosage form of a pharmaceutical composition of the present invention comprises about 2-8 mg of rosiglitazone and about 15-200 mg of morphine. In another embodiment, a unit dosage form of a pharmaceutical composition of the present invention comprises about 2-8 mg of rosiglitazone and about 0.3 mg of fentanyl. In another embodiment, a unit dosage form of a pharmaceutical composition of the present invention comprises about 2-8 mg of rosiglitazone and about 2-25 mg of hydromorphone. In another embodiment, a unit dosage form of a pharmaceutical composition of the present invention comprises about 2-8 mg of rosiglitazone and about 2.0 mg of levorphanol. In another embodiment, a unit dosage form of a pharmaceutical composition of the present invention comprises about 2-8 mg of rosiglitazone and about 75-600 mg of meptazocine. In another embodiment, a unit dosage form of a pharmaceutical composition of the present invention comprises about 2-8 mg of rosiglitazone and about 13-200 of meperidine. In another embodiment, a unit dosage form of a pharmaceutical composition of the present invention comprises about 2-8 mg of rosiglitazone and about 10-120 mg of methadone.

The various unit dosage forms described above comprising both a PPARγ agonist and an opioid agonist may be altered to replace pioglitazone or rosiglitzeon with another PPARγ agonist at an acceptable dosage, such as, e.g., troglitazone at about 200-600 mg.

Certain combinations of PPARγ agonists and other therapeutic agents may not be readily adaptable to coformulation. For example, one of the agents may be more amenable to intravenous administration, while another of the agents may be more amenable to oral administration. Or, the serum half life of the two agents may be such that one must be administered more frequently than the other. Accordingly, the present invention contemplates kits comprising one or more unit dosage forms of a PPARγ agonist and one or more unit dosage forms of another therapeutic agent, such that the two unit dosage forms may be provided to a subject in a therapeutically effective manner. In particular embodiments, a kit comprises unit dosage forms of pioglitazone and naltrexone; ciglitazone and naltrexone; rosiglitazone and naltrexone; englitazone and naltrexone; rivoglitazone and naltrexone; darglidazone and naltrexone; pioglitazone and fluoxentine; ciglitazone and fluoxentine; rosiglitazone and fluoxentine; englitazone and fluoxentine; rivoglitazone and fluoxentine; darglidazone and fluoxentine; pioglitazone and mirtazapine; ciglitazone and mirtazapine; rosiglitazone and mirtazapine; englitazone and mirtazapine; rivoglitazone and mirtazapine; darglidazone and mirtazapine; pioglitazone and topiramate; ciglitazone and topiramate; rosiglitazone and topiramate; englitazone and topiramate; rivoglitazone and topiramate; darglidazone and topiramate; pioglitazone and levetiracetam; ciglitazone and levetiracetam; rosiglitazone and levetiracetam; englitazone and levetiracetam; rivoglitazone and levetiracetam; darglidazone and levetiracetam; pioglitazone and gabapentin; ciglitazone and gabapentin; rosiglitazone and gabapentin; englitazone and gabapentin; rivoglitazone and gabapentin; darglidazone and gabapentin; piolitazone and ondansetron; ciglitazone and ondansetron; rosiglitazone and ondansetron; englitazone and ondansetron; rivoglitazone and ondansetron; darglidazone and ondansetron; pioglitazone and antalarmin; ciglitazone and antalarmin; rosiglitazone and antalarmin; englitazone and antalarmin; rivoglitazone and antalarmin; darglidazone and antalarmin.

In one embodiment, the present invention includes a kit comprising unit dosage forms of a PPARγ agonist and unit dosage forms of nicotine. In one embodiment, the unit dosage forms of nicotine comprise a plurality of different unit dosage forms of nicotine, wherein the different dosage forms of nicotine represent decreasing amount that may be taken one after the other over a period of time, so as to overcome addiction and effectuate withdrawal from the nicotine. In particular embodiments, the PPARγ agonist is pioglitazone. The unit dosage forms of nicotine may be present, e.g., in the form of a transdermal or skin patch, gum, or a lozenge.

EXAMPLES

The following examples describe a number of studies performed to demonstrate the effect of various PPARγ agonists for treating addiction and preventing relapse for a variety of addictive agents. Certain examples describe studies demonstrating the effect of PPARγ agonists used in combination with other therapeutic agents to treat alcohol addiction. These studies were performed using well-validated laboratory animal models for alcohol abuse and cocaine abuse.

Most of the studies described in Examples 1-21 were conducted using male, genetically selected alcohol-preferring rats, referred to as Marchigian Sardinian alcohol-preferring (msP) rats. These animals were bred at the Department of Pharmacological Sciences and Experimental Medicine of the University of Camerino (Marche, Italy) for 60 generations from Sardinian alcohol-preferring rats of the $13^{th}$ generation, provided by the Department of Neurosciences of the University of Cagliari, Italy. At the time of the experiments, their body weight ranged between 300 and 350 g. They were housed in a room on a reverse 12-hourlight/dark cycle (lights off at 9:00 a.m.), temperature of 20-22° C. and humidity of 45-55%. The rats were offered free access to tap water and food pellets (4RF18, Mucedola, Settimo Milanese, Italy). In the operant self-administration experiments, male heterogeneous Wistar rats (Charles River, Germany) were used.

Experiments were performed at 9:30 a.m., which is the beginning of the dark phase of the light/dark cycle. Separate groups of animals were used in each experiment. All procedures were conducted in adherence to the *European Community Council Directive for Care and Use of Laboratory Animals* and the *National Institutes of Health Guide for the Care and Use of Laboratory Animals*.

Pioglitazone, rosiglitazone, fluoxetine, mirtazapine, topiramate, gabapentine, ondansetrone, and levetiracetam was purchased from commercial sources. Yohimbine and ciglitazone were purchased from SIGMA SRL (Mi, Italy). Naltrexone and GW9662 were obtained from TOCRIS (U.K).

Prior to administration, pioglitazone was suspended in distilled water, and the resulting suspension was maintained under constant agitation until administration. The drug was given orally (OS) via gavage procedure in a volume of 1.0 ml/kg. Yohimbine was dissolved in distilled water and was administered intraperitoneally (IP) in a volume of 1.0 ml/kg. Naltrexone hydrochloride was dissolved in distilled water and administered IP in a volume of 1.0 ml/kg. Rosiglitazone, fluoxetine, mirtazapine, topiramate, gabapentin and levetiracetam were suspended in distilled water, and resulting suspensions were maintained under constant agitation until administration. These drugs were given orally (OS) via gavage procedure in a volume of 1.0 ml/kg. Yohimbina was dissolved in distilled water and was administered intraperitoneally (IP) in a volume of 1.0 ml/kg. GW9662 was prepared in 5% DMSO and 5% TWIN 80 and was given either IP (1 ml/kg) or intacerebroventricularly (ICV, 1 μl/rat). Antalarmin was prepared in 10% TWIN 80 and was given IP (1 ml/kg). Ondansetron was prepared in aqueous solution and was given IP (1 ml/kg).

At the beginning of the experiments, msP rats were allowed free choice between water and 10% (v/v) alcohol 24 h/day for at least 15 days. The fluids were offered in graduated drinking tubes equipped with metallic drinking spouts. The position (to the right or left) of alcohol and water drinking tubes was changed daily to avoid the development of side preference. Water and food were available ad libitum, while alcohol access was either restricted to 2 hours/day (Examples 1 and 2) or was available 24 hours/day (Examples 3 and 4). Alcohol, water and food intakes were measured.

Training and testing were conducted in standard operant chambers (Med Associate) located in sound-attenuating, ventilated environmental cubicles. Each chamber was equipped with a drinking reservoir (volume capacity: 0.30 ml) positioned 4 cm above the grid floor in the centre of the front panel of the chamber, and two retractable levers located 3 cm to the right or to the left of the drinking receptacle. Auditory and visual stimuli were presented via a speaker and a light located on the front panel. A microcomputer controlled the delivery of fluids, presentation of auditory and visual stimuli, and recording of the behavioural data.

Rats were trained to self-administer 10% alcohol (v/v) in 30-min. daily sessions on a fixed-ratio 1 schedule of reinforcement, in which each response resulted in delivery of 0.1 ml of fluid as previously described (Economidou et al. 2006). For the first 3 days, rats were allowed to lever-press for a 0.2% (w/v) saccharin solution, and then trained to self-administer 10% alcohol by fading the saccharine (Weiss et al. 1993). During the first 6 days of training, rats were allowed to lever-press for a 5.0% (v/v) alcohol solution containing 0.2% (w/v) saccharin. Starting on day 7, the concentration of alcohol was gradually increased from 5.0% to 8.0% and finally to 10.0% (w/v), while the concentration of saccharin was correspondingly decreased to 0%.

Cue-induced reinstatement of alcohol-seeking behaviour experimental procedures consisted of three phases: (1) conditioning phase; (2) extinction phase; and (3) reinstatement phase, as described below.

For the conditioning phase, at the completion of the fading procedure (see above), in 30 min daily sessions, animals were trained to discriminate between 10% alcohol and water. Beginning with self-administration training at the 10% alcohol concentration, discriminative stimuli (SD) predictive of alcohol versus water availability were presented during the alcohol and water self-administration sessions, respectively. The discriminative stimulus for alcohol consisted of the odour of an orange extract ($S^+$) whereas water availability (i.e. no reward) was signalled by an anise extract ($S^-$). The olfactory stimuli were generated by depositing six to eight drops of the respective extract into the bedding of the operant chamber. In addition, each lever-press resulting in delivery of alcohol was paired with illumination of the chamber's house light for 5 sec ($CS^+$). The corresponding cue during water sessions was a 5 second tone (70 dB) ($CS^-$). Concurrently with the presentation of these stimuli, a 5 sec. time-out period was in effect, during which responses were recorded but not reinforced. The olfactory stimuli serving as $S^+$ or $S^-$ for alcohol availability were introduced one minute before extension of the levers and remained present throughout the 30-min. sessions. The bedding of the chamber was changed and bedding trays were cleaned between sessions. During the first three days of the conditioning phase, the rats were given alcohol sessions only. Subsequently, alcohol and water sessions were conducted in random order across training days, with the constraint that all rats received a total of 10 alcohol and 10 water sessions.

For the extinction phase, after the last conditioning day, rats were subjected to 30-min extinction sessions for 15 consecutive days. During this phase, sessions began by extension of the levers without presentation of the SD. Responses at the lever activated the delivery mechanism but did not result in the delivery of liquids or the presentation of the response-contingent cues (house light or tone).

The reinstatement testing phase began the day after the last extinction session. This test lasted 30-min under conditions identical to those during the conditioning phase, except that alcohol and water were not made available. Sessions were initiated by the extension of both levers and presentation of either the alcohol $S^+$ or water $S^-$ paired stimuli. The respective SD remained present during the entire session and responses at the previously active lever were followed by activation of delivery mechanism and a 5-sec presentation of $CS^+$ in the $S^+$ condition or the $CS^-$ (tone) in the $S^-$ condition. Rats were tested under the $S^-/CS^-$ condition on day 1 and under $S^+/CS^+$ condition on day 2.

Stress-induced reinstatement of alcohol-seeking experimental procedures consisted of three phases: (1) training phase; (2) extinction phase; and (3) reinstatement phase, as described below.

For the training phase, after completion of the fading procedure, msP rats were trained to self-administer 10% (v/v) alcohol for 15 days in 30-min daily sessions under a FR1 schedule of reinforcement. During the infusion, a stimulus house light was turned on for 5 s (time out; TO). Lever presses during the TO period were counted, but did not lead to further infusions.

For the extinction phase, after the last alcohol self-administration session, animals were subjected to 30-min extinction sessions for 15 consecutive days. Responses at the lever activated the delivery mechanism but did not result in the delivery of alcohol.

For the reinstatement phase, the day after the last extinction session, rats were injected with yohimbine (1.25 mg/kg) and after 30 minutes were placed in the operant chamber and lever presses was monitored for 30 min. It is known that administration of the α-2 adrenoreceptor antagonist yohimbine, increasing brain noradrenaline cell firing and release, acts as a pharmacological stressor and facilitates relapse to alcohol seeking (Le et al. 2005).

Analysis of variance (ANOVA) of data was used to evaluate the results. When appropriate, ANOVA was followed by post-hoc tests. In particular, the effect of acute administration of pioglitazone, naltrexone or their combination on alcohol intake (Examples 1 and 2) was evaluated by mean of a two-way ANOVA with two within factors (time and treatment). The effect of chronic administration of pioglitazone, naltrexone or their combination on alcohol intake (Examples 3 and 4) was evaluated by mean of a three-way ANOVA with one between factor (treatment) and two between factors (days and hours). The effect of pioglitazone on reinstatement of alcohol seeking (Examples 5 and 6) was evaluated by mean of a one-way ANOVA with repeated measures using drug dose as a within subject factor. Alcohol self-administration (Example 7) in Wistar rats was studied by one-way ANOVA with one within factor (dose). Post hoc analysis was carried out using the Newman-Keuls test.

Example 1

Effect of Acute Pioglitazone Administration on Voluntary Ethanol Intake

The effect of acute pioglitazone administration on voluntary ethanol intake was demonstrated by first training rats to drink 10% (w/v) alcohol for 24 hours a day (free choice between water and ethanol). After acquisition of a stable baseline of ethanol intake (6-8 g/kg bw; daily), alcohol access was restricted to 2 hours a day at the beginning of the dark phase. Water and food were freely available.

Once stable ethanol drinking baseline was reached (also under limited access conditions), rats (n=7) were tested for the effect of pioglitazone (0.0, 10.0, 30.0 mg/kg) using a within subject counterbalanced Latine square design where each animal received all drug doses. Before starting the treatment, rats were trained to gavage administration procedures for three days, during which they received vehicle (distilled water).

Treatments were carried out at intervals of at least three days. Before each ethanol drinking experiment, msP rats received two doses of pioglitazone or vehicle at 12 hours and at 1 hour before access to ethanol. Drinking experiments were conducted right at the beginning of the dark cycle. Alcohol, water and food intakes were monitored at 30, 60, 90 and 120 minutes after ethanol was made available.

Figure 1:
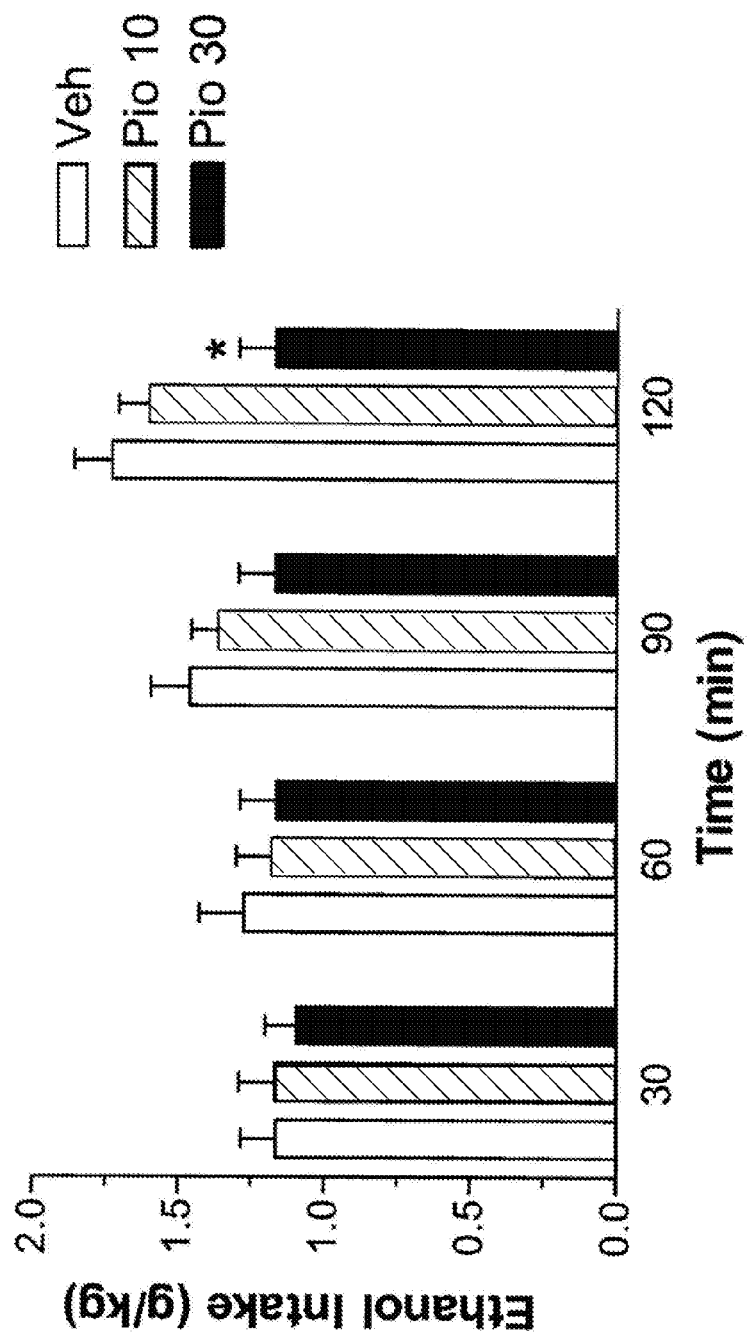
FIG. 1 is a graph depicting the effect of acute administration of 10.0 or 30.0 mg/kg of pioglitazone (Pio 10 and Pio 30, respectively) on alcohol intake in Marchigian Sardinian alcohol-preferring (msP) rats. Controls were treated with vehicle only (Veh). Values represent the mean±sem of alcohol intake. Significant difference from controls is indicated: *p<0.05.

Analysis of variance revealed the absence of a significant treatment effect on ethanol intake $F(2,6)=1.22$ NS]. However, a significant treatment time interaction was detected $[F(6,18)=6.87\ p<0.01]$. As shown in FIG. 1, post-hoc tests revealed that acute treatment with 30 mg/kg of pioglitazone significantly reduced ethanol consumption at 2 hours but not at 30, 60, or 90 minutes. The selectivity effect was demonstrated by the lack of significant effects on water and food consumption (data not shown).

Example 2

Effect of Acute Pioglitazone Plus Naltrexone Administration on Voluntary Ethanol Intake In this experiment, the effect of the co-administration of pioglitazone and naltrexone on alcohol consumption was examined to demonstrate that PPARγ agonists could enhance the inhibitory action of opioid antagonists on ethanol intake. The dose of naltrexone used in these studies (0.25 mg/kg) was previously shown to be marginally effective in reducing ethanol intake in msP rats under the same experimental conditions (Ciccocioppo et al. 2007).

The msP rats (n=8) were prepared for the study as described in Example 1. After acquisition of a stable baseline of ethanol intake, alcohol access was restricted to 2 hours a day at the beginning of the dark phase. Water and food were freely available. Animals were tested for the effect of the combination between pioglitazone (0.0, 10.0, 30.0 mg/kg) given at 12 hours and at 1 hour before access to ethanol and naltrexone (0.0 and 0.25 mg/kg) injected 2 minutes after the second pioglitazone administration. The experiment was conducted using a within subject counterbalanced Latine square design where each animal received all drug doses.

These experiments were conducted at the beginning of the dark cycle and alcohol, and water and food intakes were monitored at 30, 60, 90 and 120 minutes after ethanol was made available. Water and food intakes were not significantly modified by the various treatments.

Figure 2:
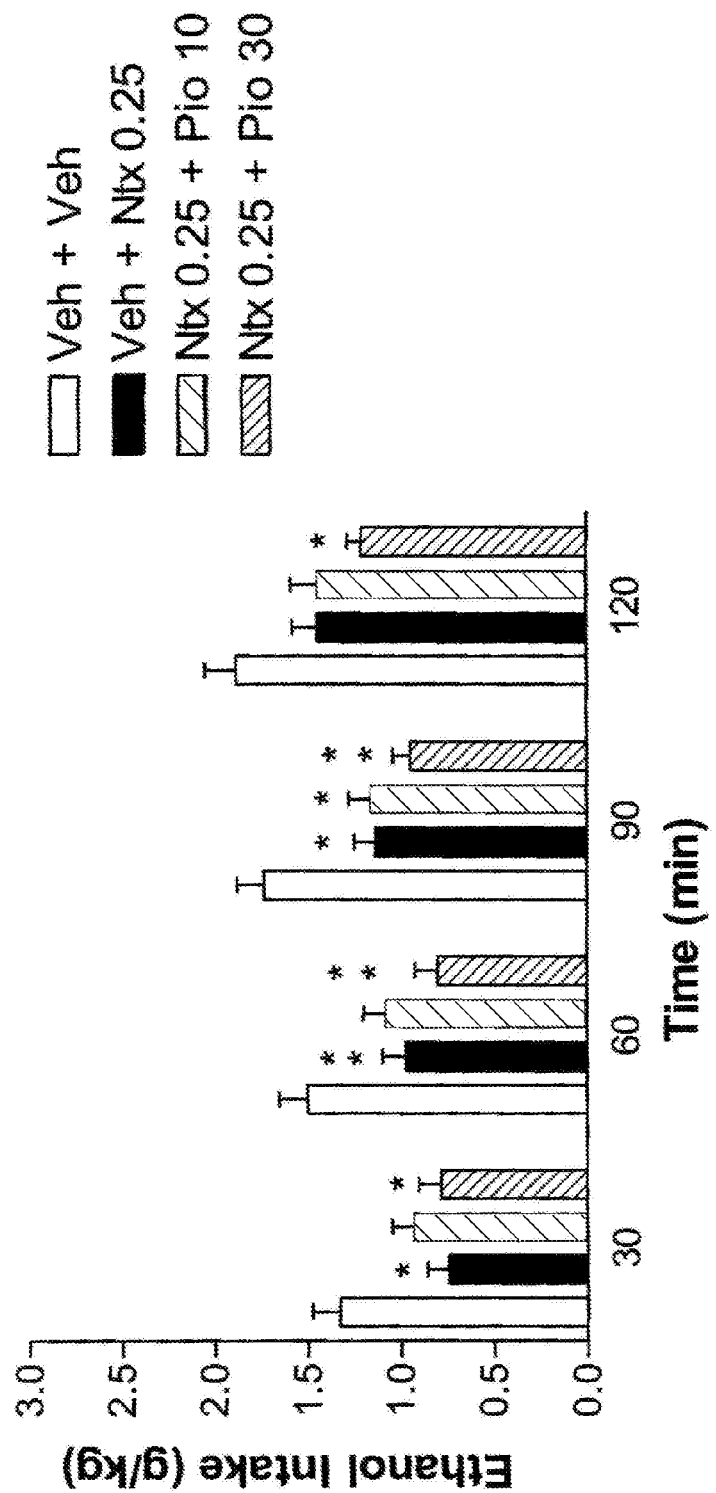
FIG. 2 is a graph depicting the effect of acute administration of 0.25 mg/kg of naltrexone (Ntx) alone or in combination with 10.0 or 30.0 mg/kg of pioglitazone (Pio 10 and Pio 30, respectively) on alcohol intake in msP rats. Controls were treated with drugs' vehicles (Veh+Veh). Values represent the mean±sem of alcohol intake. Significant difference from controls is indicated: **p<0.01 and *p<0.05.

Analysis of variance revealed a significant overall effect of treatment $[F(3,7)=5.95\ p<0.01]$ on alcohol intake. As shown in FIG. 2, post-hoc tests demonstrated that both naltrexone alone and naltrexone+piolgitazone significantly reduced ethanol intake at 30, 60, and 90 minutes. At 120 minutes, the treatments with naltrexone alone and naltrexone+pioglitazone (10 mg/kg) did not show significant effects. In contrast, compared to controls, the co-administration of naltrexone+pioglitazone (30 mg/kg) showed a significant effect also at 120 minutes (p<0.05). This data suggests that co-administration of the two drugs results in an enhancement of their effects, or could result in an increased duration of naltrexone effect.

Example 3

Effect of Subchronic Pioglitazone Administration on Voluntary Ethanol Intake

The effect of subchronic pioglitazone administration was demonstrated using rats trained to drink 10% (v/v) alcohol for 24 hours a day (free choice between water and ethanol) until a stable baseline of ethanol intake was reached. At this point, msP rats (N=9/group) were tested for the effect of pioglitazone (0.0, 10.0, or 30.0 mg/kg) on ethanol intake using a between subject design, in which each group of animals received a different dose of drug. Before starting the treatment, rats were trained to gavage administration procedures for three days, during which they received vehicle (distilled water).

Pioglitazone treatment was continued for seven consecutive days, and drug (or vehicle) was administered twice a day at 12 hour and at 1 hour before the beginning of dark period of the light/dark cycle. Alcohol, water and food intakes were monitored at 2, 8 and 24 hours. Fluids and food intakes were monitored for three additional days after the end of the drug treatment period.

Figure 3A:
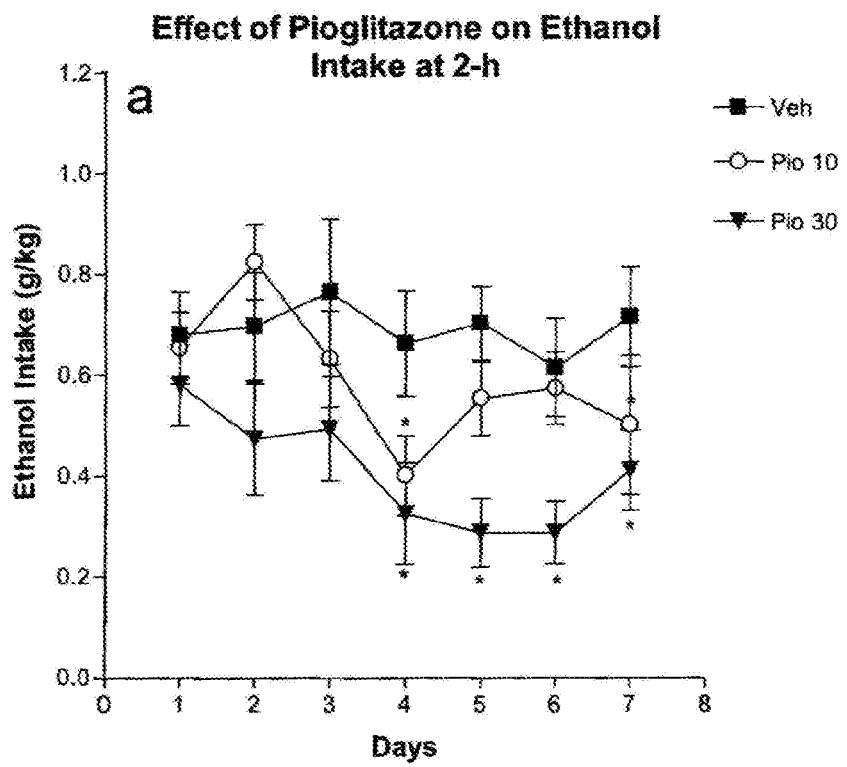
FIGS. 3A-3D are graphs demonstrating the effect of subchronic administration of 10.0 or 30.0 mg/kg of pioglitazone (Pio 10 and Pio 30, respectively) on alcohol intake in msP rats. Controls were treated with drug vehicle (Veh). The values shown in FIGS. 3A-3C represent the mean±sem of daily alcohol intake measured at: 2 hours (FIG. 3A); 8 hours (FIG. 3B); and 24 hours (FIG. 3C) from the beginning of the dark phase of the daily light/dark cycle.
Figure 3B:
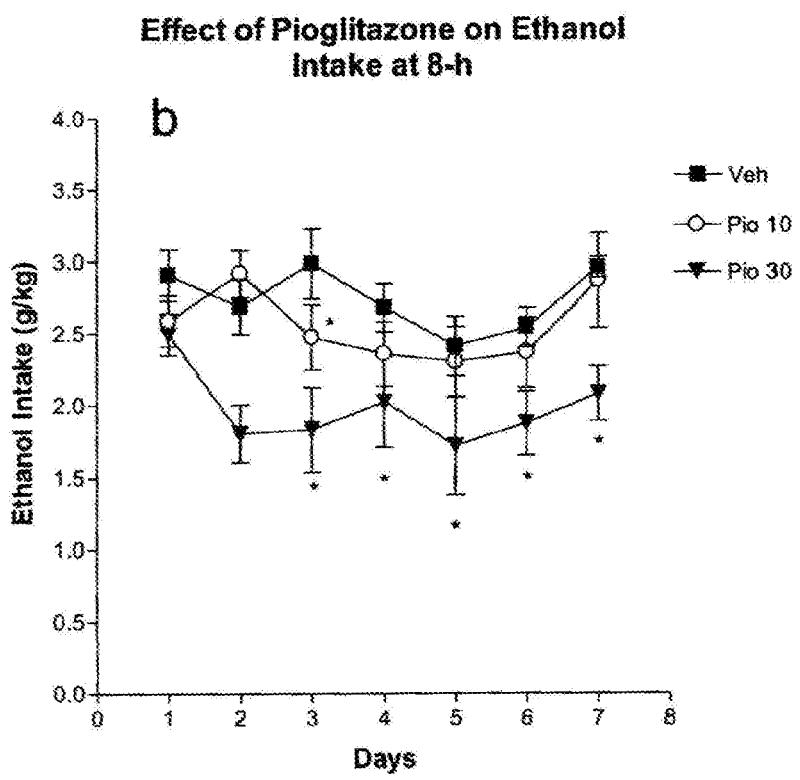
Figure 3C:
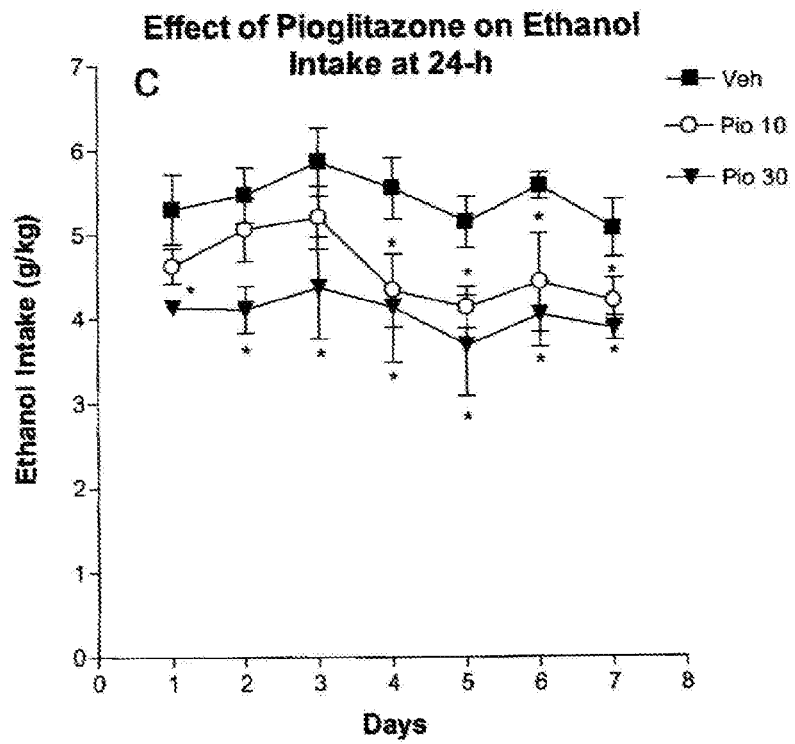

Sub-chronic (7 days) pioglitazone administration significantly reduced voluntary ethanol intake in msP rats. Analysis of variance revealed a significant overall effect of treatment $[F(2,33)=9.51;\ p<0.01]$. As shown by post-hoc tests, the effect appeared from the first day of treatment at the highest drug dose (FIGS. 3A, 3B and 3C). The effect progressively increased during treatment, and starting from the $4^{th}$ day of treatment, both drug doses (10 and 30 mg/kg) significantly reduced ethanol intake.

Figure 3D:
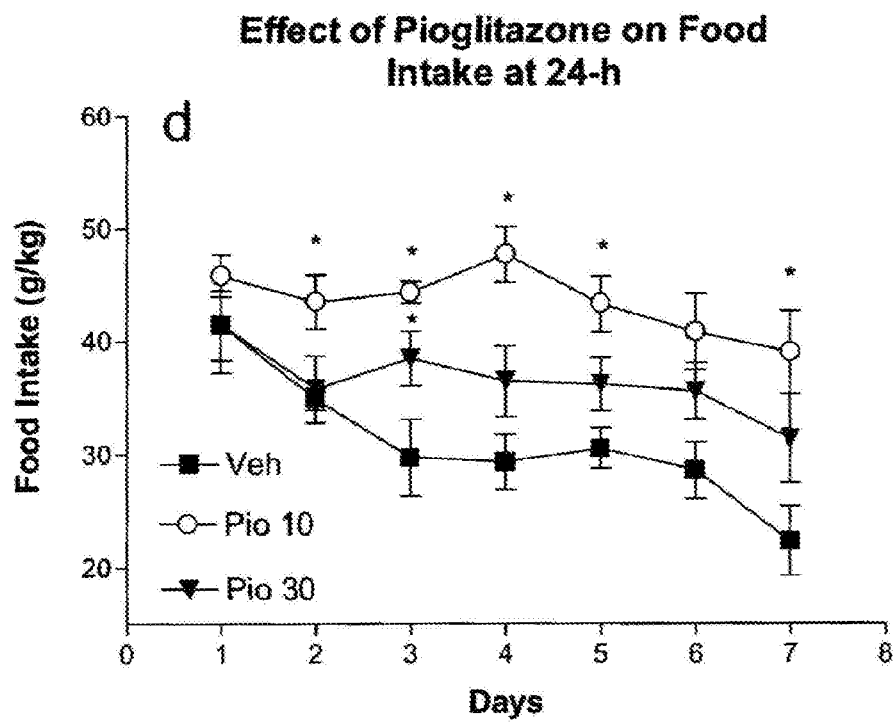

During treatment, water consumption was rather low and was not significantly affected by drug treatment. Conversely, food intake (FIG. 3D) was significantly increased by pioglitazone $[F(2,33)=7.34\ p<0.01]$. The effect was higher after administration of the lowest dose (10 mg/kg) of drug. At the end of the treatment, rats gradually recovered from the effect of the drug and ethanol intake and progressively returned at pre-treatment levels (data not shown).

Example 4

Effect of Chronic Pioglitazone Plus Naltrexone Administration on Voluntary Ethanol Intake The effect of chronic co-administration of pioglitazone and naltrexone on alcohol consumption was studied to evaluate if PPARγ agonists could also enhance the inhibitory action of opioid antagonists on ethanol intake after repeated treatments. As in the studies described in Example 2, a naltrexone dose (0.25 mg/kg) previously shown to be marginally effective in reducing ethanol intake in msP rats was used (Ciccocioppo et al. 2007). According to a between-subject design, four groups of msP rats (N=9/group) were prepared as described in Example 3. Specifically, once a stable baseline of daily ethanol consumption was reached, different groups of msP rats were tested for the effect of pioglitazone in combination with naltrexone. For seven consecutive days, msP rats received pioglitazone treatments (0.0, 10.0, or 30.0 mg/kg) at 12 hour and at 1 hour before the beginning of the dark of the light/dark cycle, while naltrexone (0.0 and 0.25 mg/kg) was injected 2 minutes after the second pioglitazone administration. Alcohol, water and food intakes were monitored at 2, 8 and 24 hours. Fluids and food intakes were monitored for three additional days after the end of the drug treatment period.

Figure 4A:
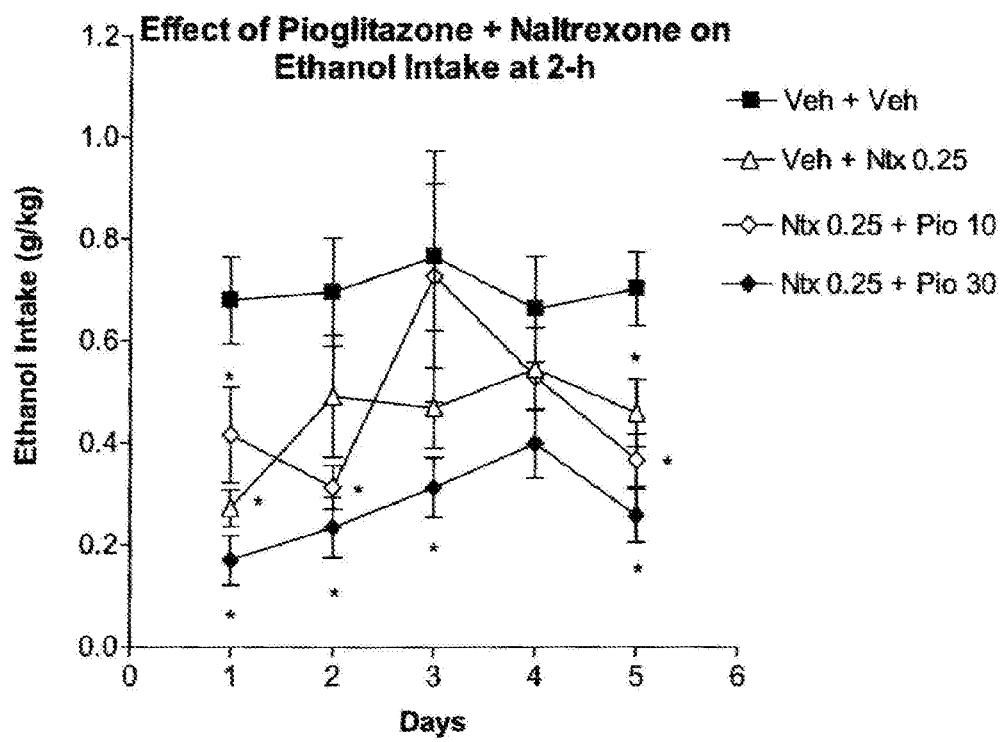
FIGS. 4A-4D are graphs demonstrating the effect of subchronic administration of 0.25 mg/kg of naltrexone (Ntx) alone or in combination with 10.0 or 30.0 mg/kg of pioglitazone (Pio 10 and Pio 30, respectively) on alcohol intake in msP rats. Controls were treated with drug vehicle (Veh+Veh). The values shown in FIGS. 4A-4C represent the mean±sem of daily alcohol intake measured at: 2 hours (FIG. 4A); 8 hours (FIG. 4B); and 24 hours (FIG. 4C) from the beginning of the dark phase of the daily light/dark cycle.
Figure 4B:
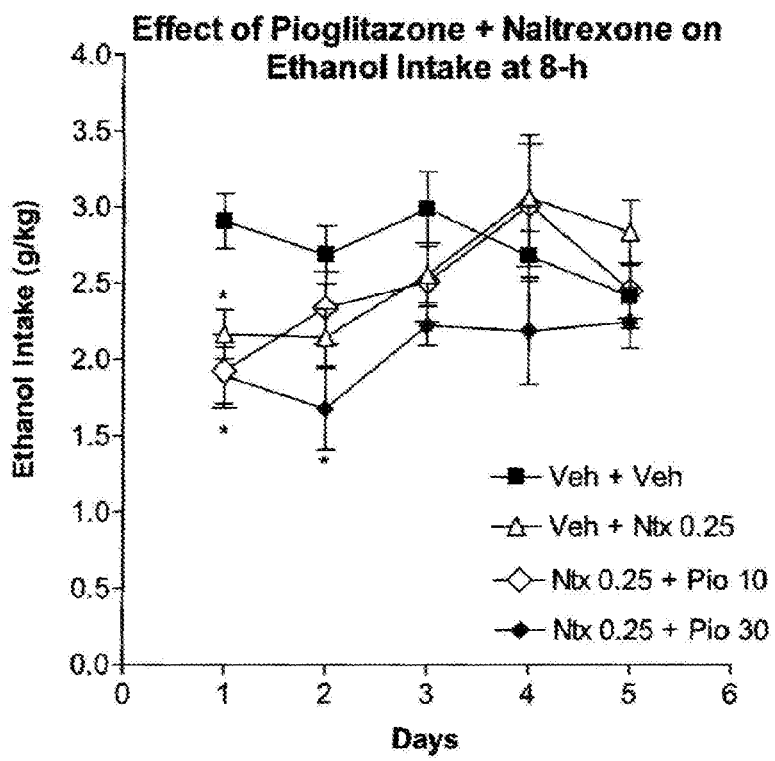
Figure 4C:
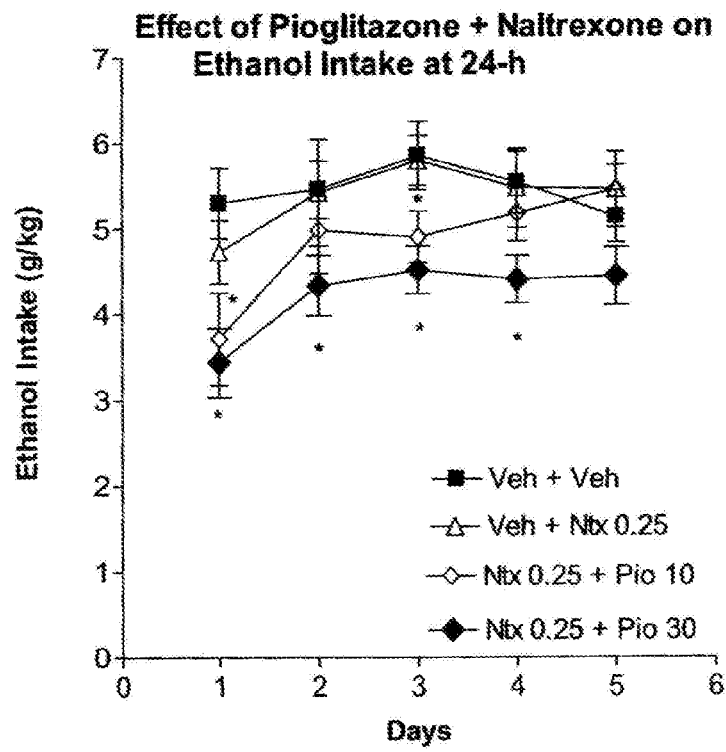

Sub-chronic (7 days) administration of naltrexone or naltrexone+pioglitazone significantly reduced voluntary ethanol intake in msP rats. Analysis of variance revealed a significant overall effect of treatment [$F(3,32)=9.59$ $p<0.01$]. As shown by post-hoc tests (FIGS. 4A, 4B and 4C), naltrexone significantly reduced ethanol intake at 2 hours ($p<0.05$) but not at 8 and 24 hours. In addition, the effect progressively decayed during treatment days. Animals treated with pioglitazone plus naltrexone, instead, significantly reduced their drinking at all time points tested (2, 8 and 24 hours). This effect remained significant for the entire period of treatment. These results indicate that pioglitazone and naltrexone co-administration may result in additive or synergistic effects on ethanol consumption.

Figure 4D:
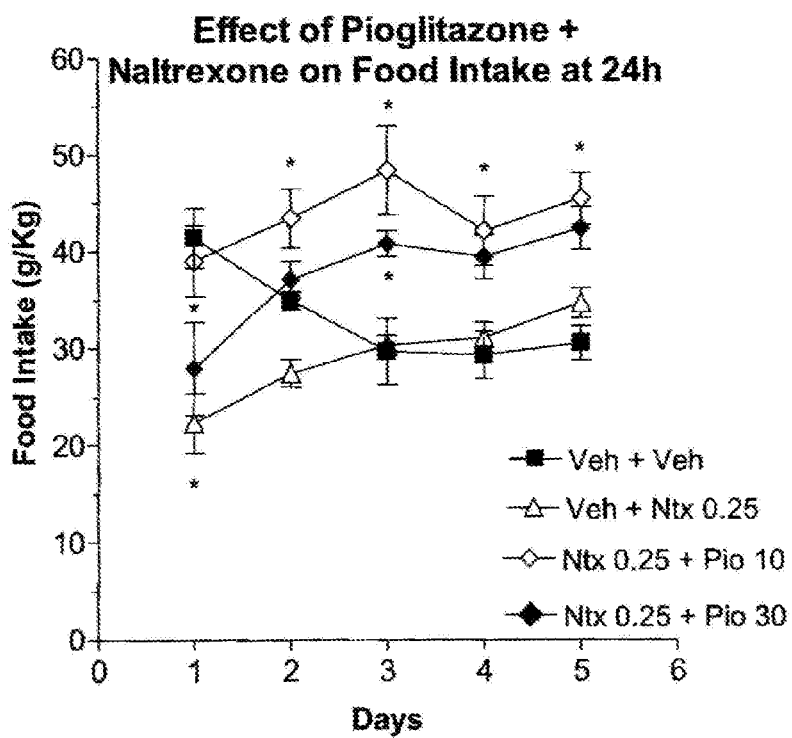

During treatment, water consumption was rather low and was not significantly affected by drug treatment. Conversely, food intake was significantly increased by pioglitazone [$F(3,32)=5.34$ $p<0.05$] (FIG. 4D). The effect was higher after administration of the lowest dose (10 mg/kg) of drug. Post hoc comparisons showed that on the first day naltrexone alone significantly reduced food consumption. Conversely, the combination of pioglitazone plus naltrexone resulted in an increase of food intake toward vehicle treated controls (data not shown). At the end of the treatment, rats gradually recovered from the effect of the drug and ethanol intake progressively returned at pre-treatment levels.

Example 5

Effect of Acute Pioglitazone Administration on Yohimbine-Induced Reinstatement of Alcohol Seeking Stress and anxiety are major factors in resuming alcohol use in former abstinent alcoholics. Yohimbine, an α-2 adrenoreceptor antagonist that increases brain noradrenaline cell firing (Aghajanian and VanderMaelen 1982) and release (Abercrombie, Keller et al. 1988), and acts as a pharmacological stressor (Holmberg, Gershon et al. 1962; Le, Harding et al. 2000; Lee, Tiefenbacher et al. 2004), is known to increase alcohol craving in humans and to resume extinguished alcohol seeking in rats. This pharmacological stressor was used to investigate the effect of pioglitazone or of naltrexone on the reinstatement of drug seeking in rats previously trained to alcohol self-administration.

To demonstrate the effect of TZDs on stress-induced relapse to alcohol seeking, following acquisition of a stable baseline of 10% ethanol, responding msP rats (n=10) were subjected to an extinction period (14 days) during which ethanol responding progressively decreased. The day after the last extinction session, rats were subjected to the reinstatement test. The animals were treated OS with pioglitazone (0.0, 10.0, or 30.0 mg/kg) at 12 hours and 1 hour before the reinstatement test. Yohimbine (1.25 mg/kg, IP) was given 30 min after the last pioglitazone administration.

Animals received all drug treatments according to a counterbalance Latin square design. A 3-day interval, during which animals were subjected to extinction sessions, was allowed between drug tests. In the reinstatement test, active and inactive lever responses were recorded.

Figure 5:
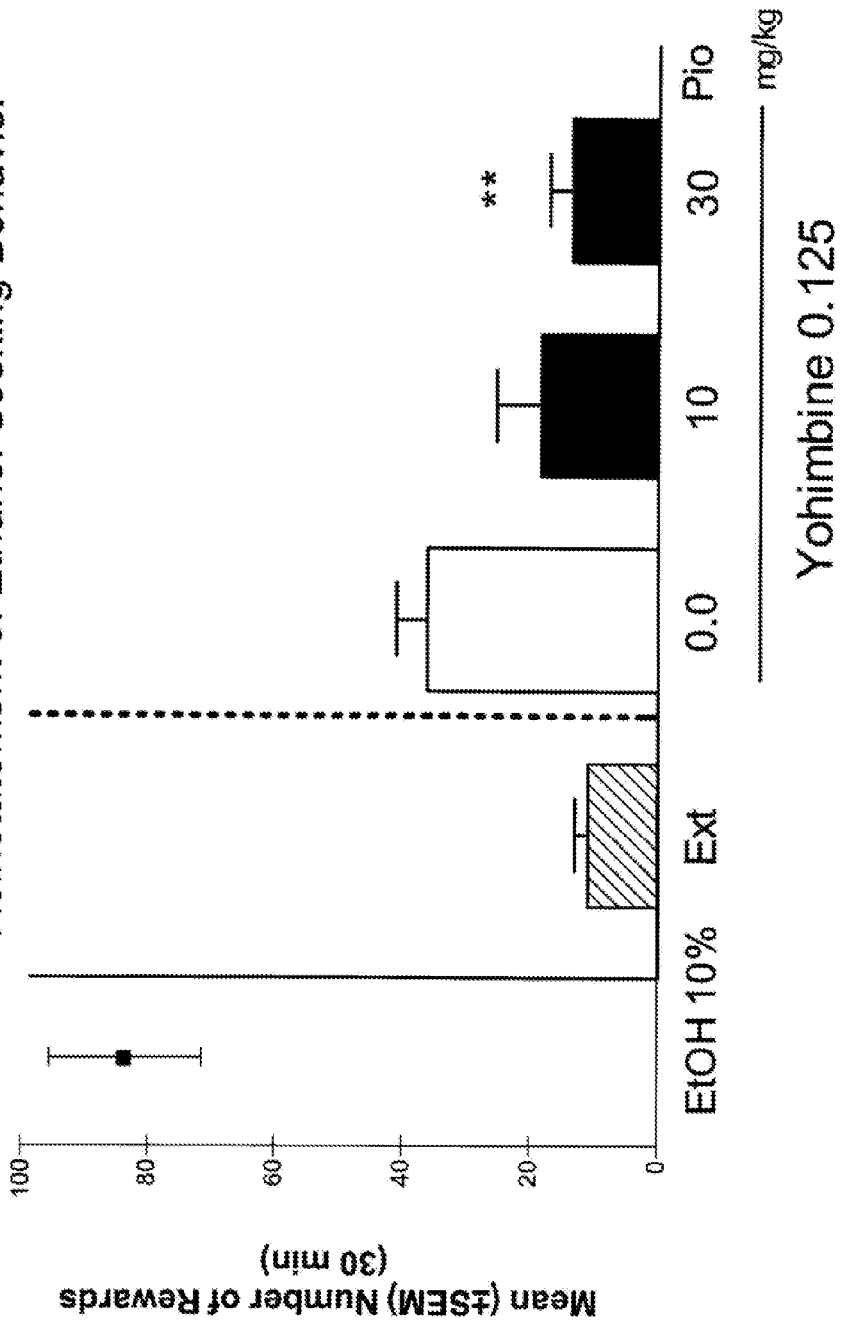
FIG. 5 is a bar graph depicting the effect of pioglitazone on yohimbine-induced reinstatement of ethanol seeking behaviour. Compared to extinction (Ext), yohimbine elicited a significant reinstatement of responding that was markedly reduced by pre-treatment with 10.0 and 30.0 mg/kg of pioglitazone (Pio 10 and 30, respectively). Values represent the mean (±SEM) number of responses at the active lever. Significant difference from controls (pioglitazone vehicle; Veh) is indicated: **P<0.05.

A stable baseline of responding for 10% (v/v) alcohol was established in 15 days. Following this alcohol self-administration phase, extinction training began. During the extinction phase, responding progressively decreased, and the last extinction day values were 16.1±3.9. The intraperitoneal administration of the alpha-2 adrenoceptor antagonist yohimbine at the dose of 1.25 mg/kg significantly reinstated the operant response for alcohol $F(1,18)=22.78$ $p<0.01$]. As shown by the analysis of variance, pre-treatment with pioglitazone significantly reduced the effect of yohimbine [$F(2,9)=12.21$, $p<0.01$] (FIG. 5). Post-hoc analysis demonstrated a significant inhibition of reinstatement following administration of 30 mg/kg of pioglitazone ($p<0.01$).

At the lowest dose (10 mg/kg), pioglitazone showed a clear trend ($p=0.07$) to an inhibition of yohimbine effect. Analysis of inactive lever responding revealed absence of treatment effects at this lever. This indicated the selectivity of the effect of yohimbine in eliciting reinstatement of alcohol seeking.

Example 6

Effect of Acute Pioglitazone Administration on Cue-Induced Reinstatement of Alcohol Seeking Like stress, environmental condition factors have been shown to have significant role in eliciting alcohol craving in abstinent individuals. Here, using a well validated animal model of cue-induced relapse the effect of pioglitazone on conditioned reinstatement of alcohol seeking was investigated.

msP rats (n=14) were trained to operantly self-administer 10% ethanol or water in 30 min daily session on an FR-1 schedule of reinforcement, where each response resulted in delivery of 0.1 ml of fluid. Ethanol availability was signalled by the odor of an orange extract, which served as a discriminative stimulus. In addition, each lever press resulting in delivery of ethanol was paired with illumination of the house light for 5 s ($S^+/CS^+$). For water, anise odor and a 5 sec white noise were employed as discriminative and contiguous cues ($S^-/CS^-$), respectively. Rats were than subjected to daily extinction sessions, during which lever presses progressively decreased.

The reinstatement test was conducted by re-exposing them to the conditioned stimuli predictive of ethanol or water availability but in the absence of the fluids. Pioglitazone (0.0, 10.0, 30.0 mg/kg) was given 12 hours and 1 hour before the reinstatement test. Experiments were conducted at the beginning of the dark phase of the light/dark cycle. Animals received all drug treatments according to a counterbalance Latin square design, and a 3-day interval was allowed between reinstatement sessions. In the reinstatement test, active and inactive lever responses were recorded.

Figure 6:
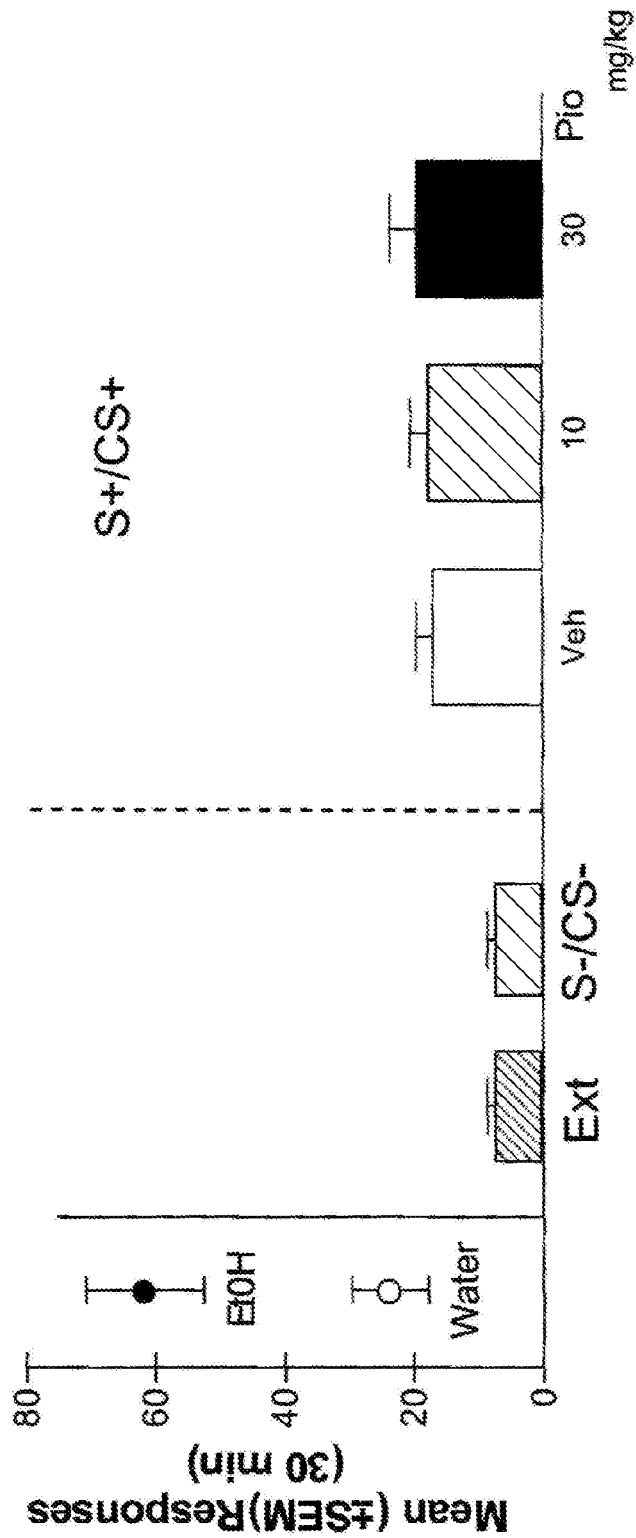
FIG. 6 is a bar graph depicting the lack of effect of pioglitazone on cue-induced reinstatement of ethanol seeking behaviour. Values shown represent the mean (±SEM) number of responses at the active or inactive levers. Conditioning: responses of the last 10% alcohol (filled circle) and water (open circle) session of the discrimination phase. Extinction (EXT): responses during the last day of this phase. Reinstatement: responses in rats exposed to stimuli predictive of alcohol ($S^+$/$CS^+$) or water ($S^-$/$CS^-$) availability. Significant difference from Ext is indicated: **P<0.01.

Throughout the conditioning phase, in which animals discriminated between alcohol or water availability, rats responded at a higher level for alcohol. ANOVA showed a significant overall effect of conditioning [$F(1.28)=41.89$, $p<0.01$]. On the last day of the discrimination period, animals reached a lever pressing response of about 60 in 30 min., while the response for water was 20. During extinction, lever pressing progressively decreased to 5.87±1.07 of the last extinction day. In the reinstatement test, the ANOVA showed that cues had a significant overall effect on alcohol-seeking [$F(1.28)=30.4$, $p<0.01$]. A more detailed analysis showed a robust reinstatement of responding under the $S^+/CS^+$ ($p<0.01$) but not under the $S^-/CS^-$ compared with the last day of extinction. As shown in FIG. 6, conditioned reinstatement of alcohol-seeking was not significantly modified by pre-treatment with pioglitazone. Responses at the inactive lever were not influenced by the treatment (data not shown).

Example 7

Effect of Ciglitazone Administration on Ethanol Self-Administration in Wistra Rats This study was performed to demonstrate the the effect of pioglitazone on ethanol intake extends also to other PPARγ agonists. The effect of ciglitazone, a structurally different TDZ, on ethanol-self-administration was determined. In addition, to verify that the effect observed with pioglitazone extends to other experimental alcohol intake models, these studies were performed in heterogeneous Wistar rats under operant self-administration conditions.

Wistra rats (n=7) were trained to self-administer ethanol 30 min/day under FR1 schedule of reinforcement. Once a stable level of responding was reached, in a within subject counterbalance order (Latin square design), rats were treated with ciglitazone (0.0, 5.0 or 20.0 mg/kg) given IP 30 minutes before the beginning of the self-administration session. The number of responses to the active and inactive levers were recorded. A 3-day interval was allowed between self-administration sessions.

Figure 7:
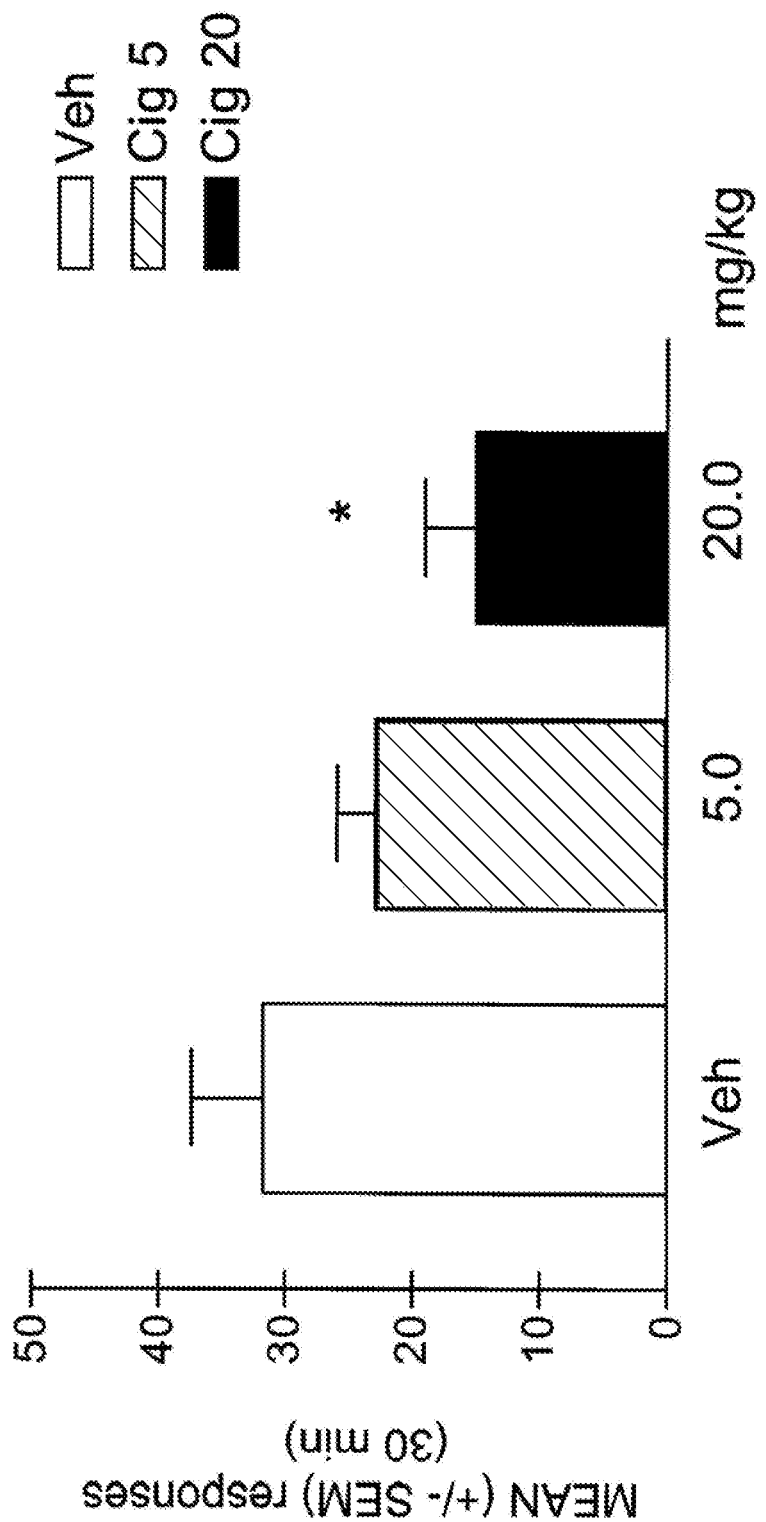
FIG. 7 is a graph depicting the effect of treatment with ciglitazone 5.0 (Cig 5) or 20.0 mg/kg (Cig 20) or its vehicle (Veh) on FR1 ethanol self-administration in Wistar rats.

During ethanol self-administration, Wistar rats acquired robust operant alcohol responding. At the end of this phase, rats pressed the alcohol lever an average of 30-35 times in 30-min. At this point, animals were treated with ciglitazone IP. Results showed that ciclitazone treatment significantly reduced ethanol self-administration [$F(2,6)=5.87$ $p<0.05$]. Responding at the inactive lever was very low and was not affected by drug treatment [$F(2,6)=1.52$ NS]. Post hoc tests showed that ethanol self-administration was significantly reduced following administration of the highest dose of drug (FIG. 7).

Example 8

Effect of Acute Rosiglitazone Administration on Voluntary Ethanol Intake

The ability of another TZD, rosiglitazone, to reduce ethanol intake was demonstrated. MsP rats were first trained to drink 10% (w/v) alcohol for 24 hours a day (free choice between water and ethanol). Once stable ethanol drinking baseline was reached (6-8 g/kg/day), rats (n=28) were tested for the effect of rosiglitazone (0.0, 7.5 and 15 mg/kg) using a between subject design. Before starting the treatment, rats were trained to gavage administration procedures for three days, during which they received vehicle (distilled water). Rosiglitazone was given twice, at 12 hours and 1 hour before access to ethanol. Drinking experiments started at the beginning of the dark cycle. Alcohol, water and food intakes were monitored at 2, 8 and 24 hours after ethanol was made available.

Analysis of variance revealed a significant treatment effect on ethanol intake [$F(2,18)=0.4$ $p<0.05$]. As shown in FIG. 8, post-hoc Newman-Keuls tests revealed that acute treatment with 15 mg/kg of rosiglitazone significantly reduced ethanol consumption at 2 hours ($p<0.05$). Inhibition of ethanol drinking was highly significant at 24 hours ($p<0.01$). The selectivity effect was demonstrated by the lack of significant effects on water and food consumption (data not shown). Follow-up studies showed that treatment with 5 or 15 mg/kg of rosiglitazone increased food consumption at 24 hours [$F(2,25)=13.11$ $p<0.01$].

Example 9

Effect of IP Administration of the PPARγ Antagonist GW9662 on Pioglitazone-Induced Reduction of Ethanol Intake This experiment demonstrated that the effect of pioglitazone on ethanol intake was mediated by activation of PPARγ receptors. After acquisition of a stable baseline of ethanol intake, msP rats (n=22) were tested for the effect of GW9662 on pioglitazone-induced reduction of ethanol intake. Rats were treated with 30 mg/kg of pioglitazone given OS 1 hour before access to ethanol. GW9662 was administered IP 30 min after pioglitazone administration, and additional 30 min were awaited before giving ethanol access to rats. Before starting the treatment, rats were trained to gavage and IP administration procedures for three days. Experiment was conducted in a between subject design (n=22). Another group of msP rats (n=22) received GW9662 alone to demonstrate the effect of PPARγ blockade on ethanol consumption. Drinking experiments started at the beginning of the dark cycle. Alcohol, water and food intakes were monitored at 2, 8 and 24 hours after ethanol was made available.

As shown in FIG. 9A, analysis of variance revealed that blockade of PPARγ receptors by GW9662 did not modify ethanol drinking in msP rats [$F(2,18)=0.40$ NS]. However, analysis of variance revealed a significant treatment effect on ethanol intake $F(3,24)=18.64$ $p<0.01$] following administration of pioglitazone (FIG. 9B). Newman-Keuls tests revealed that treatment with 30 mg/kg of pioglitazone significantly reduced ethanol consumption at 8 and 24 hours ($p<0.01$). Further experiments also showed that treatment with 30 mg/kg of pioglitazone significantly reduced ethanol consumption at 2 hours ($p<0.05$; data not shown). Pretreatment with GW9662 blocked the effect of pioglitazone in a dose related manner. Water and food consumption were not affected by drug treatments (data not shown).

Example 10

Effect of ICV Administration of the PPARγ Antagonist GW9662 on Pioglitazone-Induced Reduction of Ethanol Intake This experiment demonstrated that the effect of pioglitazone on ethanol intake is mediated by activation of brain PPARγ receptors. For this purpose, msP rats (n=6) were treated with GW9662 (5 µg/rat) ICV to selectively block brain PPARγ receptors, while pioglitazone (30 mg/kg) was given OS. The experiment was conduced using a within subject counterbalanced Latine square design, where each animal received all drug doses.

The drinking experiments were conducted at the beginning of the dark cycle, and alcohol, water and food intakes were monitored at 2, 8 and 24 hours after ethanol was made available.

Analysis of variance revealed a significant treatment effect on ethanol intake $F(3,5)=12.93$ $p<0.001$]. As shown in FIG. 10, post-hoc Newman-Keuls tests revealed that treatment with 30 mg/kg of pioglitazone significantly reduced ethanol consumption at 2 hours ($p<0.05$) 8 hours ($p<0.05$) and at 24 hours ($p<0.01$). ICV administration of GW9662 did not significantly affect ethanol intake per se. However it completely prevented the effect of pioglitazone. Water and food consumption were not affected by drug treatments (data not shown).

Example 11

Effect of Acute Naltrexone Administration on Yohimbine-Induced Reinstatement of Alcohol Seeking The inability of naltrexone to reduce yohimbine-induced reinstatement of alcohol use was demonstrated. Following acquisition of a stable baseline of 10% ethanol, responding msP rats (n=10) were subjected to an extinction period (14 days) during which ethanol responding progressively decreased. The day after the last extinction session, rats were subjected to the reinstatement test.

To determine whether naltrexone was able to prevent the effect of the pharmacological stressor yohimbine, animals (n=7) were treated IP with the opioid antagonist (0.0, 0.25 and 1.0 mg/kg) 1 hour before the reinstatement test. Yohimbine (1.25 mg/kg, IP) was given 30 min after naltrexone administration. Animals received all drug treatments according to a counterbalance Latin square design. A 3-day interval, during which animals were subjected to extinction sessions, was allowed between drug tests. In the reinstatement test, active and inactive lever responses were recorded.

A stable baseline of responding for 10% (v/v) alcohol was established in 15 days. Following this alcohol self-administration phase, extinction training began. During the extinction phase, responding progressively decreased. The intraperitoneal administration of the alpha-2 adrenoceptor antagonist yohimbine at the dose of 1.25 mg/kg significantly reinstated the operant response for alcohol $F(1,8)=19.99$ $p<0.01$]. As shown by the analysis of variance, pre-treatment with naltrexone did not significantly reduce the effect of yohimbine [$F(2,8)=0.46$, NS] (FIG. 11). Analysis of inactive lever responding revealed absence of treatment effects at this lever (data not shown). This indicates the selectivity of the effect of yohimbine in eliciting reinstatement of alcohol seeking.

Example 12

Effect of Acute Naltrexone Administration on Cue-Induced Reinstatement of Alcohol Seeking The ability of naltrexone to reduce cue-induced reinstatement of alcohol seeking was demonstrated. In this experiment, msP rats (n=9) were trained to operantly self-administer 10% ethanol or water in 30 min daily session on an FR-1 schedule of reinforcement, where each response resulted in delivery of 0.1 ml of fluid. Ethanol availability was signalled by the odor of an orange extract, which served as a discriminative stimulus. In addition, each lever press resulting in delivery of ethanol was paired with illumination of the house light for 5 s ($S^+/CS^+$). For water, anise odor and a 5 sec white noise were employed as discriminative and contiguous cues ($S^-/CS^-$), respectively. Rats were than subjected to a daily extinction sessions during which lever presses progressively decreased.

Reinstatement tests were conducted by re-exposing them to the conditioned stimuli predictive of ethanol or water availability, but in the absence of the fluids. Naltrexone (0.0, 0.25 and 1.0 mg/kg) was given one hour before the reinstatement test. Experiments were conducted at the beginning of the dark phase of the light/dark cycle. Animals received all drug treatments according to a counterbalance Latin square design, and a 3-day interval was allowed between reinstatement sessions. In the reinstatement test, active and inactive lever responses were recorded.

Throughout the conditioning phase, in which animals discriminated between alcohol or water availability, rats responded at a higher level for alcohol. During extinction, lever pressing progressively decreased. In the reinstatement test, the ANOVA showed that cues had a significant overall effect on alcohol-seeking [$F(1,8)=36.31$, $p<0.01$]. A more detailed analysis showed a robust reinstatement of responding under the $S^+/CS^+$ ($p<0.01$) but not under the $S^-/CS^-$ compared with the last day of extinction. As shown in FIG. 12, conditioned reinstatement of alcohol-seeking was significantly reduced by naltrexone [$F(2,8)=15.90$; $p<0.01$]. Post-hoc analysis revealed that both doses (0.25 and 1.0 mg/kg) of the opioid antagonist tested significantly reduced reinstatement of ethanol seeking ($p<0.01$). Responses at the inactive lever were not influenced by the treatment (data not shown).

Example 13

Effect of Co-Administration of Pioglitazone and Naltrexone on Yohimbine- and Cue-Induced Reinstatement of Alcohol Seeking The combined effect of a PPARγ agonist, pioglitazone, and an opioid antagonist, naltrexone, on various inducers of reinstated alcohol seeking was determined.

For yohimbine-induced reinstatement of ethanol seeking, after acquisition of a stable baseline of 10% ethanol responding, msP rats (n=9) were subjected to an extinction period (14 days) during which ethanol responding progressively decreased. The day after the last extinction session, rats were subjected to the reinstatement test.

To evaluate whether combination of naltrexone plus pioglitazone was able to prevent the effect of the pharmacological stressor yohimbine, animals were treated IP with the opioid antagonist (1.0 mg/kg) and OS with the TDZ (30 mg/kg) 1 hour before the reinstatement test. Yohimbine (1.25 mg/kg, IP) was given 30 min after naltrexone/pioglitazone administration. Animals received all drug treatments according to a counterbalance Latin square design. A 3-day interval, during which animals were subjected to extinction sessions, was allowed between drug tests. In the reinstatement test, active and inactive lever responses were recorded.

For cue-induced reinstatement of alcohol seeking, another group of msP rats (n=10) were trained to operantly self-administer 10% ethanol or water in 30 min daily session on an FR-1 schedule of reinforcement, where each response resulted in delivery of 0.1 ml of fluid. Ethanol availability was signalled by the odor of an orange extract, which served as a discriminative stimulus. In addition, each lever press resulting in delivery of ethanol was paired with illumination of the house light for 5 s ($S^+/CS^+$). For water, anise odor and a 5 sec white noise were employed as discriminative and contiguous cues ($S^-/CS^-$), respectively. Rats were then subjected to a daily extinction sessions, during which lever presses progressively decreased.

A reinstatement test was conducted by re-exposing them to the conditioned stimuli predictive of ethanol or water availability, but in the absence of the fluids. Naltrexone (1.0 mg/kg) and pioglitazone were co-administered 1 hour before the reinstatement test. Experiments were conducted at the beginning of the dark phase of the light/dark cycle. Animals received all drug treatments according to a counterbalance Latin square design and a 3-day interval was allowed between reinstatement sessions. In the reinstatement test, active and inactive lever responses were recorded.

For yohimbine-induced reinstatement of alcohol seeking, rats reached a stable baseline of responding for 10% (v/v) alcohol in 15 days. Following this time period, alcohol self-administration phase extinction training began. During the extinction phase, responding progressively decreased. The intraperitoneal administration of the alpha-2 adrenoceptor antagonist yohimbine at the dose of 1.25 mg/kg significantly reinstated the operant response for alcohol $F(1,8)=12.86$ $p<0.01$]. As shown by the analysis of variance, pre-treatment with naltrexone plus pioglitazone significantly reduced the effect of yohimbine [$F(2,8)=5.71$, $p<0.01$] (FIG. 13A). Analysis of inactive lever responding revealed absence of treatment effects at this lever.

For cue-induced reinstatement of alcohol seeking, msP rats rapidly learned to discriminate between alcohol or water availability; rats responded at a higher level for alcohol. During extinction, lever pressing progressively decreased. In the reinstatement test, the ANOVA showed that cues had a significant overall effect on alcohol-seeking [$F(1,9)=31.83$, $p<0.01$]. A more detailed analysis showed a robust reinstatement of responding under the $S^+/CS^+$ ($p<0.01$) but not under the $S^-/CS^-$ compared with the last day of extinction. As shown in FIG. 13B, conditioned reinstatement of alcohol-seeking was significantly reduced by co-administration of naltrexone and pioglitazone [$F(2,9)=16.58$; $p<0.01$]. Responses at the inactive lever were not influenced by the treatment (data not shown).

Example 14

Effect of Acute Pioglitazone Plus Fluoxetine Administration on Voluntary Ethanol Intake In this experiment, the effect of the co-administration of pioglitazone and fluoxetine on alcohol consumption was studied to demonstrate that co-treatment with PPARγ agonists, e.g., TZDs, and antidepressants, e.g., selective serotonin uptake inhibitors, has synergistic effects on ethanol intake inhibition. For this purpose, a low dose of fluoxetine (3.0 mg/kg, OS) that did not reduce ethanol intake in msP rats in a pilot study was used. Also, a pioglitazone dose (10 mg/kg, OS) was chosen that does not significantly affect alcohol intake per se.

MsP rats were first trained to drink 10% (w/v) alcohol for 24 hours a day (free choice between water and ethanol). Once a stable ethanol drinking baseline was reached (6-8 g/kg/day), in a between subject design, msP rats (n=34) were tested for the effect of pioglitazone, fluoxetine or their combination. Rats treated with drug vehicles served as a control. Before starting the treatment, rats were trained to gavage administration for three days, during which they received drugs vehicle (distilled water). Pioglitazone and fluoxetine were given twice, at 12 hours and 1 hour before access to ethanol. Drinking experiments started at the beginning of the dark cycle. Alcohol, water, and food intakes were monitored at 2, 8 and 24 hours after ethanol was made available.

Analysis of variance revealed a significant overall effect of treatment [$F(3,30)=5.37$ $p<0.01$] on alcohol intake. As shown in FIG. 14, post-hoc tests demonstrated that a low dose of pioglitazone alone or fluoxetine alone did not significantly modify ethanol intake in msP rats. However, co-administration of the two agents resulted in a marked inhibition of ethanol consumption at 2 and 8 hours ($p<0.01$), as well as at 24 hours ($p<0.05$). These data suggest that co-administration of the two drugs exert synergistic inhibitory actions on ethanol drinking.

A modest, nonsignificant trend to an increase of food intake was observed following drug treatment (data not shown). Water consumption was very low and was not modified by drug administration (data not shown).

Example 15

Effect of Acute Pioglitazone Plus Mirtazapine Administration on Voluntary Ethanol Intake The effect of the co-administration of pioglitazone and mirtazapine on alcohol consumption was studied to demonstrate that co-treatment with PPARγ agonists and this antidepressant had synergistic effects on ethanol intake inhibition. For this purpose, a low dose of mirtazapine (5.0 mg/kg, OS) that did not reduce ethanol intake in msP rats in a pilot study was used. Also, a pioglitazone dose (10 mg/kg, OS) was chosen such that it did not significantly affect alcohol intake per se.

MsP rats were first trained to drink 10% (w/v) alcohol for 24 hours a day (free choice between water and ethanol). Once stable ethanol drinking baseline was reached (6-8 g/kg/day), in a between subject design, msP rats (n=34) were tested for the effect of pioglitazone, mirtazapine or their combination. Rats treated with drug vehicles served as a control. Before starting the treatment, rats were trained to gavage administration for three days, during which they received drugs vehicle (distilled water). Pioglitazone and mirtazapine were given twice, at 12 hours and 1 hour before access to ethanol. Drinking experiments started at the beginning of the dark cycle. Alcohol, water and food intakes were monitored at 2, 8 and 24 hours after ethanol was made available.

Analysis of variance revealed a significant overall effect of treatment [$F(3,30)=12.50$ $p<0.01$] on alcohol intake. As shown in FIG. 15, post-hoc tests demonstrated that a low dose of pioglitazone alone or mirtazapine alone did not significantly modify ethanol intake in msP rats. However, co-administration of the two agents resulted in a marked inhibition of ethanol consumption at 2 and 8 hours ($p<0.05$); a significant reduction of ethanol intake at 2 hours was also reported for pioglitazone alone ($p<0.05$). These data suggest that co-administration of the two drugs exert synergistic inhibitory actions on ethanol drinking.

A nonsignificant trend to an increase of food intake was observed following drug treatments (data not shown). Water consumption was very low and was not modified by drug administration (data not shown)

Example 16

Effect of Acute Pioglitazone Plus Topiramate Administration on Voluntary Ethanol Intake In this experiment, the effect of the co-administration of pioglitazone and topiramate on alcohol consumption was studied to demonstrate that co-treatment with PPARγ agonists and this antiepileptic has synergistic effects on ethanol intake inhibition. For this purpose, a low dose of topiramate (30.0 mg/kg, OS) that did not reduce ethanol intake in msP rats in a pilot study was used. Also, a pioglitazone dose (10 mg/kg, OS) was chosen such that it did not significantly affect alcohol intake per se.

MsP rats were first trained to drink 10% (w/v) alcohol for 24 hours a day (free choice between water and ethanol). Once stable ethanol drinking baseline was reached (6-8 g/kg/day), in a between subject design, msP rats (n=34) were tested for the effect of pioglitazone, topiramate or their combination. Rats treated with drug vehicles served as a control. Before starting the treatment, rats were trained to gavage administration for three days, during which they received drugs vehicle (distilled water). Pioglitazone and topiramate were given twice, at 12 hours and 1 hour before access to ethanol. Drinking experiments started at the beginning of the dark cycle. Alcohol, water and food intakes were monitored at 2, 8 and 24 hours after ethanol was made available.

Analysis of variance revealed a significant overall effect of treatment [$F(3,30)=4.35$ $p<0.01$] on alcohol intake. As shown in FIG. 16, post-hoc tests demonstrated that a low dose of pioglitazone alone or topiramate alone did not significantly modify ethanol intake in msP rats. However, co-administration of the two agents resulted in a marked inhibition of ethanol consumption at 2, 8 and 24 hours ($p<0.05$); a significant reduction of ethanol intake at 2 hours was also reported for topiramate alone ($p<0.05$). These data suggest that co-administration of the two drugs exert synergistic inhibitory actions on ethanol drinking.

A nonsignificant trend to an increase of food intake was observed following drug treatments (data not shown). Water consumption was very low and was not modified by drug administration (data not shown).

Example 17

Effect of Acute Pioglitazone Plus Levetiracetam Administration on Voluntary Ethanol Intake The effect of the co-administration of pioglitazone and levetiracetam on alcohol consumption was studied to demonstrate that co-treatment with PPARγ agonists and this antiepileptic has synergistic effects on ethanol intake inhibition. For this purpose, a low dose of levetiracetam (100.0 mg/kg, OS) that did not reduce ethanol intake in msP rats in a pilot study was used. Also, a pioglitazone dose (10 mg/kg, OS) was chosen, such that it did not significantly affect alcohol intake per se.

MsP rats were first trained to drink 10% (w/v) alcohol for 24 hours a day (free choice between water and ethanol). Once stable ethanol drinking baseline was reached (6-8 g/kg/day), in a between subject design, msP rats (n=33) were tested for the effect of pioglitazone, levetiracetam or their combination. Rats treated with drug vehicles served as a control. Before starting the treatment, rats were trained to gavage administration for three days, during which they received drugs vehicle (distilled water). Pioglitazone and levetiracetam were given twice, at 12 hours and 1 hour before access to ethanol. Drinking experiments started at the beginning of the dark cycle. Alcohol, water and food intakes were monitored at 2, 8 and 24 hours after ethanol was made available.

Analysis of variance revealed a significant overall effect of treatment [$F(3,29)=3.76$ $p<0.05$] on alcohol intake. As shown in FIG. 17, post-hoc tests demonstrated that a low dose of pioglitazone alone or levetiracetam alone did not significantly modify ethanol intake in msP rats. Conversely, co-administration of the two agents resulted in a marked inhibition of ethanol consumption at 2 hours ($p<0.01$), as well as at 8 and 24 hours ($p<0.05$). These data suggest that co-administration of the two drugs exerts synergistic inhibitory actions on ethanol drinking.

Food and water consumption was not modified by drug administration (data not shown).

Example 18

Effect of Acute Pioglitazone Plus Gabapentin Administration on Voluntary Ethanol Intake The effect of the co-administration of pioglitazone and gabapentin on alcohol consumption was studied to demonstrate that co-treatment with PPARγ agonists and this antiepileptic has synergistic effects on ethanol intake inhibition. For this purpose, a low dose of gabapentin (60.0 mg/kg, OS) that did not reduce ethanol intake in msP rats in a pilot study was used. Also a pioglitazone dose (10 mg/kg, OS) was chosen, such that it did not significantly affect alcohol intake per se.

MsP rats were first trained to drink 10% (w/v) alcohol for 24 hours a day (free choice between water and ethanol). Once stable ethanol drinking baseline was reached (6-8 g/kg/day), in a between subject design, msP rats (n=36) were tested for the effect of pioglitazone, gabapentin or their combination. Rats treated with drug vehicles served as a control. Before starting the treatment, rats were trained to gavage administration for three days, during which they received drugs vehicle (distilled water). Pioglitazone and topiraate were given twice, at 12 hours and 1 hour before access to ethanol. Drinking experiments started at the beginning of the dark cycle. Alcohol, water and food intakes were monitored at 2, 8 and 24 hours after ethanol was made available.

Analysis of variance revealed a significant overall effect of treatment [$F(3,7)=3.31$ $p<0.05$] on alcohol intake. As shown in FIG. 18, post-hoc tests demonstrated that a low dose of pioglitazone alone or gabapentin alone did not significantly modify ethanol intake in msP rats. Conversely, co-administration of the two agents resulted in a marked inhibition of ethanol consumption at 2 and 8 hours ($p<0.05$). These data suggest that co-administration of the two drugs exerts synergistic inhibitory actions on ethanol drinking.

A nonsignificant trend to an increase of food intake was observed following drug treatments (data not shown). Water consumption was very low and was not modified by drug administration (data not shown).

Example 19

Effect of Acute Pioglitazone Plus Ondansetron Administration on Voluntary Ethanol Intake The effect of the co-administration of pioglitazone and ondansetron on alcohol consumption was studied to demonstrate that co-treatment with PPARγ agonists and this serotonin-3 (5-HT3) receptor selective antagonist have synergistic effects on ethanol intake inhibition. For this purpose, a low dose of ondansetron (1.0 mg/kg, IP) that did not reduce ethanol intake in msP rats in a pilot study was used. Also, a pioglitazone dose (10 mg/kg, OS) was chosen, such that it did not significantly affect alcohol intake per se.

MsP rats were first trained to drink 10% (w/v) alcohol for 24 hours a day (free choice between water and ethanol). Once stable ethanol drinking baseline was reached (6-8 g/kg/day), in a between subject design, msP rats (n=36) were tested for the effect of pioglitazone, ondansetron, or their combination. Rats treated with drug vehicles served as a control. Before starting the treatment, rats were trained to gavage administration for three days, during which they received drugs vehicle (distilled water). Pioglitazone and ondansetron were given twice, at 12 hours and 1 hour before access to ethanol. Drinking experiments started at the beginning of the dark cycle. Alcohol, water and food intakes were monitored at 2, 8 and 24 hours after ethanol was made available.

Analysis of variance revealed a nonsignificant overall effect of treatment [$F(3,32)=2.73$ $p<0.05$], but a significant treatment time interaction on alcohol intake was observed [$F(6,64)=2.29$ $p<0.0.5$]. As shown in FIG. 19, post-hoc tests demonstrated that a low dose of pioglitazone alone or ondansetron alone did not significantly modify ethanol intake in msP rats. However, co-administration of the two agents resulted in a marked inhibition of ethanol consumption at 24 hours ($p<0.05$). Water and food consumption was very low and was not modified by drug administration (data not shown). These data suggest that co-administration of the two drugs exerts synergistic inhibitory actions on ethanol drinking.

Example 20

Effect of Acute Pioglitazone Plus Antalarmin Administration on Voluntary Ethanol Intake The effect of the co-administration of pioglitazone and antalarmin on alcohol consumption was studied to demonstrate that co-treatment with PPARγ agonists and this corticotrophin releasing factor CRF1 receptor selective antagonist has synergistic effects on ethanol intake inhibition. For this purpose, a low dose of antalarmin (15.0 mg/kg, IP) that modestly reduced ethanol intake in msP rats in a pilot study was used. Also, a pioglitazone dose (10 mg/kg, OS) was chosen, such that it did not significantly affect alcohol intake per se.

MsP rats were first trained to drink 10% (w/v) alcohol for 24 hours a day (free choice between water and ethanol). Once stable ethanol drinking baseline was reached (6-8 g/kg/day), in a between subject design, msP rats (n=32) were tested for the effect of pioglitazone, antalarmin or their combination. Rats treated with drug vehicles served as a control. Before starting the treatment, rats were trained to gavage administration for three days during which they received drugs vehicle (distilled water). Pioglitazone and antalarmin were given twice, at 12 hours and 1 hour before access to ethanol. Drinking experiments started at the beginning of the dark cycle. Alcohol, water and food intakes were monitored at 2, 8 and 24 hours after ethanol was made available.

Analysis of variance revealed a significant overall effect of treatment [$F(3,28)=3.29$ $p<0.05$] on alcohol intake. As shown in FIG. 20, post-hoc tests demonstrated that a low dose of pioglitazone alone or antalarmin alone did not significantly modify ethanol intake in msP rats. However, co-administration of the two agents resulted in a marked inhibition of ethanol consumption at 8 ($p<0.01$) and 24 hours ($p<0.05$); a significant reduction of ethanol intake at 8 hours was also reported for antalarmin alone ($p<0.05$). These data suggest that co-administration of the two drugs exerts synergistic inhibitory actions on ethanol drinking.

Water and food consumption was not modified by drug administration (data not shown).

Example 21

Effect of Pioglitazone Administration on Alcohol Withdrawal

The effect of pioglitazone administration on alcohol withdrawal was determined in rats. Male Wistar rats were subjected to a six days of intermittent alcohol intoxication. During the dark phase, rats received 4 oral administration of 2.5-3.0 g/kg of 20% ethanol. The first ethanol dose was given at the beginning of the dark phase. The other 3 daily doses were administered at intervals of 3 hours. Rats were not injected during the light phase of the light/dark cycle. Targeted blood alcohol levels were 250-300 mg/dl. After 6 days of this treatment, rats undergo to spontaneous withdrawal, which generally appears between 8 and 14 hours after the last ethanol injection. Pioglitazone (0.0, 10 and 30 mg/kg) was administered twice, 12 hours and 1 hour before rating withdrawal symptoms. Behavioural signs of withdrawal included: (1) presence of the ventromedial distal flexion response; (2) tail stiffness/rigidity; and (3) tremors (Schulteis et al. 1995). Each sign was rated during a 3-5 min observation period on a scale of 0-2 (Macey et al., 1996; Schulteis, et al., 1995). All signs were cumulated to yield an overall withdrawal severity score.

Twelve hours after the last ethanol administration, animals treated with pioglitazone vehicle showed marked withdrawal symptoms. The analysis of variance showed an overall effect of pioglitazone treatment that reduced tail rigidity [$F(4,25)=11.98$ $p<0.001$] (FIG. 21). Post hoc tests revealed that alcohol withdrawal signs were significantly reduced after administration of both 10 mg/kg and 30 mg/kg of pioglitazone, with a highly significant effect of tail rigidity ($p<0.01$), tremors ($p<0.01$), and ventromedial limb retraction ($p<0.01$). Interestingly, while measuring withdrawal score, two out of the 7 animals of vehicle treated groups showed convulsion. Conversely, none of the 12 rats treated with pioglitazone showed seizures. These data suggest that pioglitazone not only helps to reduce ethanol drinking (see previous experiments), but it also possesses the ability to reduce or control alcohol withdrawal syndrome and related symptoms, including seizures.

Example 22

Effect of Pioglitazone on Alcohol Abuse in Humans

An observational study of human patients using pioglitazone (Actos®) for the treatment of diabetes was performed to demonstrate that PPARγ agonists, alone or in combination with opioid antagonists, are effective in reducing ethanol abuse.

A total of 12 patients were enrolled in the study. 4 patients (2 male and 2 female) received only psychotherapy (Control; CRT); 4 patients (male) received naltrexone 50 mg/day (NTX)+psychotherapy; and 4 patients (3 male and 1 female) received pioglitazone 30 mg/day (Actos®; ACT)+psychotherapy. The patients' ages ranged from 25 to 45 years old. All patients had previous unsuccessful experiences of alcohol detoxification. No major psychiatric comorbidity was identified. Patient treated with Actos® were all diagnosed with diabetes.

Patients were instructed to record in a personal logbook the number of drinks per day and the time of the day drinks occurred. At the end of the study, the logbooks were returned to the clinical personnel who analyzed the data. Immediately before beginning treatment and on a weekly basis, patients were interviewed and subjected to the Spielberger State-Trait Anxiety Inventory (STAI), the Montgomery Asberg Depression Rating Scale (M.A.D.R.S 10 Item) and the Obsessive Compulsive Drinking Scale (OCDS) questioners to score anxiety, depression and alcohol craving, respectively (Bruno 1989; Janiri, Gobbi et al. 1996) (Cador, Cole et al. 1993; Anton, Moak et al. 1996).

In addition, biochemical parameters to ascertain alcohol detoxification and to measure recovery of physiological functions (i.e., hepatic function) were monitored monthly. Hematological parameters measured included: mean corpuscular volume (MCV); gamma-GT; aspartate aminotransferase (AST); alanine aminotransferase (ALT); and carbohydrate-deficient transferring (CDT). MCV and CDT are biomarkers for ethanol consumption, and GGT, ALT and AST are biomarkers for hepatic functionality.

Data were analyzed by analysis of variance followed by Newman-Keuls post hoc tests when appropriate.

Statistical analysis revealed an overall significant effect of pharmacological treatments on the number of daily drinks. Both naltrexone and pioglitazone significantly reduced daily ethanol intake and increased the number of abstinence days. Nonparametric Krustall Wallis test showed that naltrexone was more effective than pioglitazone on the first two weeks of treatment (P<0.05). Over time the effect of pioglitazone progressively increased and from month 2 week 2 (T2.2) to month 2 week 4 (T2.4) it was significantly higher than that of naltrexone (p<0.001). The number of abstinence days was significantly different in drug treated patients compared to control. The highest effect was observed in patients treated with pioglitazone. The number of abstinence days in the pioglitazone treated group was significantly higher to that of naltrexone treated patients during the second month of therapy (T 2.1, T2.2, T2.3 and T2.4). No changes in daily alcohol consumption were observed in the group subjected to only psychotherapy. Follow-up evaluation continued for 9 months before interrupting the therapy. Results showed that all participants except pioglitazone treated patients dropped out from the treatment.

Blood tests showed that at recruitment all twelve participants had plasma levels of MCV, CDT, GGT, ALT and AST reflecting a situation compatible with long term excessive alcohol drinking. However, results demonstrated a rapid normalization of all blood parameters in patients treated with pioglitazone (ACT), as shown in Table 2.

TABLE 2

Mean value of blood tests

|  | T0 | | | T1 = 4 weeks | | | T2 = 8 weeks | | |
| --- | --- | --- | --- | --- | --- | --- | --- | --- | --- |
|  | ACT | NTX | CTR | ACT | NTX | CTR | ACT | NTX | CTR |
| MCV | 102.26 | 101.96 | 102.78 | 99.82 | 101.96 | 103.26 | 91.37 | 97.96 | 104.87 |
| GGT | 192.21 | 167.38 | 173.58 | 86.7 | 91.35 | 181.67 | 38.26 | 42.9 | 179.47 |
| ALT | 51.6 | 62.7 | 58.7 | 45.6 | 52.8 | 52 | 24.9 | 41.8 | 55.9 |
| AST | 69.2 | 49.3 | 82.1 | 51.9 | 41.5 | 78.4 | 29.3 | 38.3 | 77 |
| CDT | 3.2 | 3.6 | 3.8 | 2.9 | 3.0 | 3.7 | 2.1 | 2.5 | 3.1 |

The decrease of MCV and CDT indicated that patients' ethanol drinking progressively decreased over the two-months of drug treatment. The decrease in GGT, ALT and AST reflected normalisation of hepatic function. In naltrexone treated patients (NTX), a decrease in MCV and CDT was also observed, but to a lesser extent compared to the pioglitazone group. Hepatic parameters were also ameliorated by naltrexone, but again the effect of pioglitazone was more pronounced. The Control group that received only psychotherapy did not show any improvement during the 2-month treatment.

Statistical analysis revealed an overall effect of treatment for all blood parameters measured (MCV, $[F(2,9)=89.7$ $P<0.0001]$; GGT; $[F(2,9)=5328$ $P<0.0001]$; ALT $[F(2,9)=52.57$ $P<0.0001]$; AST $[F(2,9)=771$ $P<0.0001]$; CDT $[F(2,9)=26.54$ $P<0.0001])$. Post hoc tests revealed that for all the five biomarkers a statistical difference (P<0.001) exists between controls (psychotherapy alone) and patients treated with naltrexone (P<0.001) or with pioglitazone (P<0.001). Pioglitazone was more effective than naltrexone in reducing the values of MCV (P<0.001), GGT (P<0.001) and ALT (p<0.001). No significant difference between naltrexone and pioglitazone were detected for CDT and AST.

Results also showed a progressive decrease in anxiety score during treatment. Pioglitazone showed the highest effect, as shown in Table 3 and FIG. 30A. In control patients, (psychotherapy alone) anxiety did not diminish during treatment.

TABLE 3

Anxiety Score obtained using The STAY-Y1 scale (mean score values)

|  | ACT | NTX | CTR |
| --- | --- | --- | --- |
| T = 0 | 59 | 61 | 63 |
| T = 1.1 | 58 | 61 | 64 |
| T = 1.2 | 55 | 59 | 62 |
| T = 1.3 | 54 | 53 | 69 |
| T = 1.4 | 56 | 52 | 65 |
| T = 2.1 | 49 | 51 | 61 |
| T = 2.2 | 47 | 53 | 63 |
| T = 2.3 | 43 | 52 | 67 |
| T = 2.4 | 40 | 51 | 64 |

T = 0 corresponds to the beginning of the treatment; T = 1.1 corresponds to month 1, week 1; T = 1.2 corresponds to month 1, week 2, etc.

The analysis of variance revealed an overall effect of treatment ($[F(2,9)=142.86$ $P<0.0001]$). Post hoc tests revealed statistically significant difference between controls and patients treated with naltrexone (P<0.001) or with pioglitazone (P<0.001). Pioglitazone was more effective than naltrexone, and a significant difference between pioglitazone and naltrexone was also observed (p<0.001)

Results also showed a progressive decrease in obsessive compulsive score for alcohol. The effect was extremely robust for pioglitazone, as shown in Table 4 and FIG. 30C. In control patients, OCDS remained at pre-treatment level.

TABLE 4

Obsessive compulsive drinking scale (OCDS) (mean score values)

|  | ACT | NTX | CTR |
| --- | --- | --- | --- |
| T = 0 | 50 | 49 | 52 |
| T = 1.1 | 45 | 47 | 49 |
| T = 1.2 | 37 | 45 | 48 |
| T = 1.3 | 36 | 41 | 49 |
| T = 1.4 | 34 | 40 | 47 |
| T = 2.1 | 31 | 41 | 47 |
| T = 2.2 | 29 | 43 | 49 |

TABLE 4-continued

Obsessive compulsive drinking scale (OCDS) (mean score values)

|  | ACT | NTX | CTR |
|---|---|---|---|
| T = 2.3 | 28 | 42 | 50 |
| T = 2.4 | 28 | 44 | 51 |

T = 0 corresponds to the beginning of the treatment; T = 1.1 corresponds to month 1, week 1; T = 1.2 corresponds to month 1, week 2, etc.

The analysis of variance revealed an overall effect of treatment ([F(2,9)=329.27 P<0.0001]). Post hoc tests revealed statistically significant difference between controls and patients treated with naltrexone (P<0.001) or with pioglitazone (P<0.001). Pioglitazone was more effective than naltrexone, and a significant difference between pioglitazone and naltrexone was also observed (p<0.001).

The initial Score in the MADRS scale indicated that this patient population did not have severe co-morbid depression. During treatment with pioglitazone, the depression score decreased starting from the second week of treatment, as shown in Table 5 and FIG. 30B. At week 3, it reached the plateau. However, a floor effect might have contributed to rapid plateau.

TABLE 5

Depression Scale M.A.D.R.S (mean score values)

|  | ACT | NTX | CTR |
|---|---|---|---|
| T = 0 | 21 | 19 | 20 |
| T = 1.1 | 15 | 16 | 18 |
| T = 1.2 | 13 | 18 | 19 |
| T = 1.3 | 10 | 16 | 17 |
| T = 1.4 | 11 | 17 | 19 |
| T = 2.1 | 12 | 17 | 21 |
| T = 2.2 | 13 | 15 | 19 |
| T = 2.3 | 10 | 18 | 19 |
| T = 2.4 | 12 | 19 |  |

T = 0 corresponds to the beginning of the treatment; T = 1.1 corresponds to month 1, week 1; T = 1.2 corresponds to month 1, week 2, etc.

The analysis of variance revealed an overall effect of treatment ([F(2,9)=42.12 P<0.0001]). Post hoc tests revealed statistically significant difference between controls and patients treated with pioglitazone (P<0.001) but not naltrexone. Pioglitazone was significantly different also from naltrexone (p<0.001)

In summary, the blood parameters determined during the course of this study indicated normalization of different alcohol drinking related markers in patients treated with pioglitazone or naltrexone. The effect was more robust with pioglitazone. Patients under psychotherapy alone did not show improvements during treatment. This indicates that the difference between Controls and Drug treated patients depended upon the pharmacological intervention.

High comorbidity exists between alcohol abuse, anxiety and depression. The symptoms of these mood-related disorders tend to exacerbate during early alcohol detoxification phase, thus contributing to reduced patients compliance. In this respect, it is highly relevant that pioglitazone reduces anxiety and depressive symptoms in alcoholic patients. This could also explain why after two months of drug administration, all 4 patients under pioglitazone were still in treatment, whereas 2 patients of the control group and 1 of the naltrexone the group dropped out. It is also highly relevant that pioglitazone consistently reduced OCDS score. Obsession for alcohol and the urge to drink (which are measured by OCDS scale) are the major predictors of relapse. These data indicate, therefore, that pioglitazone has anti-relapse properties.

The absence of a placebo treatment in the control (psychotherapy alone) group may have contributed to the high efficacy of drug treatments, since the effect of naltrexone was higher that that normally reported in controlled randomized clinical trials. However, placebo effect cannot account for the difference between pioglitazone and naltrexone efficacy. In fact, in this case, both groups of patients received pharmacological medications in association with psychotherapy. Based on this consideration, while it cannot be ruled out that the effect of pioglitazone could have been over estimated to some extent in these studies, it is evident that this drug has a significant efficacy in controlling alcohol abuse, and its effect may be superior to naltrexone.

Example 23

Effect of Pioglitazone on Cocaine Self-Administration

The ability of pioglitazone to reduce cocaine use was demonstrated in a rat model of cocaine addiction. Cocaine hydrochloride (obtained from the National Institute on Drug Abuse, Bethesda, Md.) was dissolved in sterile physiological saline at a concentration of 0.25 mg/0.1 ml. Drug or vehicle solution was infused at a volume of 0.1 ml over 4 s. Pioglitazone obtained from a commercial source was suspended in distilled water, and the resulting suspension was maintained under constant agitation until administration. Pioglitazone was given orally (OS) via gavage procedure 12 hours and 1 hour before the beginning of cocaine self-administration.

Male Wistar rats weighing between 180 and 200 g at the time of arrival in the lab were used. The rats were housed in groups of three in a humidity- and temperature-controlled (22° C.) vivarium on a 12 h:12 h reverse light/dark cycle (on, 17:00; off, 05:00) with ad libitum access to food and water. One week after arrival, rats were subjected to surgery, and a silastic catheter was implanted into the right jugular vein.

Rats (n=6) were trained to self-administer cocaine in 2-h daily sessions on a fixed-ratio 5 schedule of reinforcement, in which each response resulted in delivery of 0.25 mg/0.1 ml of fluid cocaine solution. Cocaine self-administration training continued until a stable baseline of responding was reached (less than 10% variation for 3 consecutive days calculated for each single rat). At this point, drug testing begun.

In a within subject counterbalance order (Latin square design), rats were treated with pioglitazone (0.0, 10.0 or 30.0 mg/kg) given OS 12 hours and 1 hour before the beginning of the self-administration session. The number of responses to the active and inactive levers was recorded. A 3-day interval was allowed between drug testing. During these intervals, cocaine self-administration was continued to re-establish baseline lever responses.

The effect of pioglitazone administration on cocaine self-administration was evaluated by mean of a one-way within factor ANOVA followed by Newman-Keuls post hoc test.

Treatment with pioglitazone significantly reduced cocaine self-administration [F(2,5)=13.189 p<0.01]. Post hoc tests revealed a significant (p<0.01) reduction of cocaine self-administration at both 10.0 and 30.0 mg/kg of pioglitazone (FIG. 22A). Responses at the left inactive lever were very low and were not modified by pioglitazone treatment (FIG. 22B).

Example 24

Effect of Pioglitazone on Nicotine Use

The ability of PPARγ agonists and antidepressant to reduce nicotine use was demonstrated in an animal model of nicotine addiction.

Bupropion hydrochloride (Sigma, Milan, Italy) was dissolved in saline. Nicotine tartrate (Sigma, Milan, Italy) was dissolved in isotonic saline at a concentration of 0.03 mg/0.1 ml free base. The pH of the nicotine solution was adjusted to 7 with dilute NaOH. Drug or vehicle solution was infused at a volume of 0.1 ml over 4 s. Pioglitazone was obtained from commercial source; it was suspended in distilled water, and the resulting suspension was maintained under constant agitation until administration. Pioglitazone was given orally (OS) via gavage procedure at 12 hours and 1 hour before the beginning of nicotine self-administration.

Male Long Evans rats weighing between 180 and 200 g at the time of arrival in the lab were used. The rats were housed in groups of three in a humidity- and temperature-controlled (22° C.) vivarium on a 12 h:12 h reverse light/dark cycle (on, 17:00; off, 05:00) with ad libitum access to food and water. One week after arrival, the rats were subjected to surgery, and a silastic catheter was implanted into the right jugular vein.

Rats (n=9) were trained for one week to self-administer cocaine in 2-h daily sessions on a fixed-ratio 5 schedule of reinforcement, in which each five response resulted in delivery of 0.25 mg/0.1 ml of fluid cocaine solution. After the successful completion of cocaine training, rats were allowed to self-administer nicotine at the 0.03 mg/kg/infusion dose by switching the delivery of cocaine for the delivery of a nicotine infusion. Nicotine self-administration training continued until stable baseline of responding was established (less than 20% variation for 3 consecutive days calculated for each single rat). At this point, drug testing began.

In a within subject counterbalance order (Latin square design), rats were treated with pioglitazone (0.0 and 30.0 mg/kg) given OS 12 hours and 1 hour before the beginning of the self-administration session. The number of responses to the active and inactive levers was recorded. A 3-day interval was allowed between drug testing. During these intervals, nicotine self-administration was continued to re-establish lever responses baseline.

The effect of pioglitazone administration on nicotine self-administration was evaluated by mean of a paired t-test. Statistical significance was set at P<0.05

After a few training days, rats acquired robust operant responding for nicotine. As shown in FIG. 23A, treatment with 30 mg/kg pioglitazone significantly reduced nicotine self-administration [$t_{df8}$=−2.70 p<0.05]. Responses at the left inactive lever was very low and were not modified by pioglitazone treatment (FIG. 23B). These results demonstrate that PPARγ agonists are effective in reducing nicotine use.

Example 25

Effect of Pioglitazone and Selected Therapeutic Agents on Nicotine Use

The ability of PPARγ agonists in combination with other therapeutic agents, such as bupropion, nicotine replacement formulations, naltrexone, varenicicline, and CB1 receptor antagonist/inverse agonists, e.g., rimonabant, rosonabant, taranabant, and CP-945598, to synergistically reduce nicotine use is determined in a rat model of nicotine addiction.

Experiments are conducted using operant self-administration paradigms, essentially as described in Example 23 (see also Bruijnzeel and Markou, 2003; Rauhut et al 2003). Briefly, male Wistar rats are implanted with a permanent silastic catheter into the right jugular vein for intravenous nicotine self-administration (0.03 mg/infusion). Using operant self-administration chambers, rats are trained to self-infuse nicotine under a fixed ratio 5 schedule of reinforcement (five lever presses to obtain one nicotine infusion). Nicotine self-administration training is continued until stable baseline of responding is established. At this point, drug testing is begun.

In a within subject counterbalance order (Latin square design), rats are treated with pioglitazone (predicted dose range 5-30.0 mg/kg) or with other PPRγ agonists in combination with bupropion, nicotine (replacement formulations; i.e., nicotine patches), naltrexone, varenicicline, or rimonabant. To evaluate synergism between PPRAγ agonists and these latter drugs, the lowest effective dose for each of the compounds is tested in association with the PPARγ agonist. A dose range for bupropion is 10-100 mg/given OS; a dose range for naltrexone is 0.25-2.5 mg/kg given IP; a dose range for varenicline is 0.25-2.5 mg/kg given IP; and a dose range for rimonabant is (0.1-3.0 mg/kg given IP) (Bruijnzeel and Markou, 2003; Rauhut et al. 2003; Steensland P et al. 2007; Cohen et al. 2005). The number of responses to the active and inactive leversis recorded. A 3-day interval is allowed between drug testing. During these intervals, nicotine self-administration is continued to re-establish lever responses baseline.

Data is analyzed by analysis of variance followed by post-hoc tests (Newman-Keuls or Dunnets) where appropriate. Statistical significance is set at P<0.05. It is expected that these experiments will demonstrate that the combination of a PPARγ agonist and any of the listed drugs will act synergistically in reducing nicotine self-administration, thereby demonstrating the efficacy of using PPARγ and any of these drugs to treat addiction.

Example 26

Effect of Pioglitazone and Antidepressants or Opioid Agonist/Antagonist Partial Agonists on Cocaine Use The ability of PPARγ agonists in combination with antidepressants, bupropion, fluoxetine, or the opioid parial agonist agonist/antagonist, buprenorphine, to synergistically reduce cocaine use is determined in a rat model of cocaine addiction.

Experiments are conducted using operant self-administration paradigms as described in Example 23 (see also Glatz et al. 2002; Peltier et al. 1993). Briefly, male Wistar rats are implanted with a permanent silastic catheter into the right jugular vein for intravenous cocaine self-administration (0.25 mg/infusion). Using operant self-administration chambers, rats are trained to self-infuse cocaine under a fixed ratio 5 schedule of reinforcement (five lever presses to obtain one cocaine infusion). Cocaine self-administration training is continued until stable baseline of responding is established. At this point, drug testing is begun.

In a within subject counterbalance order (Latin square design), rats are treated with pioglitazone (predicted dose range 5-30.0 mg/kg) or with another PPRγ agonist in combination with bupropion, fluoxetine, or buprenorphine. To evaluate synergism between PPRAγ agonists and these latter drugs, the lowest effective dose for each of the compound is tested in association. A dose range for bupropion is 10.0-100.0 mg/kg given OS; a dose range for fluoxetine is 3.0-15.0 mg/kg given OS; and a dose range for buprenorphine is 0.1-5.0 mg/kg given IP (Glatz et al. 2002; Peltier et al. 1993; Sorge et al. 2005). The number of responses to the active and inactive levers are recorded. A 3-day interval is allowed between drug testing. During these intervals, nicotine self-administration is continued to re-establish lever responses baseline.

Data is analyzed by analysis of variance followed by post-hoc tests (Newman-Keuls or Dunnets) where appropriate. Statistical significance is set at P<0.05. It is expected that these experiments will demonstrate that the combination of a PPARγ agonist and any of the listed drugs will act synergistically in reducing cocaine self-administration, thereby demonstrating the efficacy of using PPARγ and any of these drugs to treat addiction.

Example 27

Effect of Pioglitazone on Development of Opiate Addiction

The ability of PPARγ agonists to reduce opiate use and prevent opiate addiction is determined in a rat model of opiate addiction.

Experiments are conducted using a conditioned place preference apparatus and a well established procedure to study morphine induced conditioned place preference (Ciccocioppo et al. 2000). Briefly, using a two-chamber place conditioning apparatus, male Wistar rats are trained to associate morphine effects to one side of the box and saline to the other side. Multiple groups of rats are used, and the experiment is conducted in a between subject design. Animals are pretreated with pioglitazone vehicle before the injection of morphine vehicle. Control group receive morphine and pioglitazone vehicles in both compartments.

The rats are conditioned during a conditioning phase of six days. Every other day, for three times, rats receive subcutaneous injections of 3 mg/kg of morphine or its vehicle. Pioglitazone (5.0-30.0 mg/kg) is injected one hour before morphine. During conditioning, the guillotine door remains closed, and the rats are confined for 1 h in one compartment of the box. The day following the last conditioning session, rats are allowed to explore the entire box for 15 min, and the time spent in each compartment is measured.

Place preference score (referred to as Δ time) for each rat is obtained by subtracting the time spent in the compartment associated with morphine vehicle to the time spent in the compartment associated to morphine injections. The Δ time values are submitted to statistical analysis. Data is analyzed by analysis of variance followed by post-hoc tests (Newman-Keuls or Dunnets) where appropriate. Statistical significance is set at P<0.05.

It is predicted that morphine will elicit a marked conditioned place preference, and treatment with pioglitazone will reduce the acquisition of morphine-induced place conditioning (see for review; Sanchis-Segura and Spanagel 2006) These results will demonstrate the ability of PPARγ agonists to prevent the development of addiction to opioids and more specifically to morphine.

Example 28

Effect of Pioglitazone Administration on Yohimbine-Induced Reinstatement of Nicotine Seeking Stress and anxiety are major factors in resuming nicotine use in former abstinent users. As described in Examples 5 and 11 for alcohol, the α-2 adrenoreceptor antagonist yohimbine was used to resume extinguished nicotine seeking in rats, in order to investigate the effect of pioglitazone on the reinstatement of drug seeking in rats previously trained to nicotine self-administration. Briefly, following acquisition of a stable baseline of IV nicotine self-administration (30 µg/0.1 ml/infusion), male Long Evans rats (n=8) were subjected to an extinction period of 5 days. During extinction, lever presses were no longer contingently associated to nicotine delivery; hence, operant responding rapidly decreased.

The day after the last extinction session, rats were subjected to the reinstatement test. To evaluate the effect of pioglitazone on yohimbine-induced reinstatement in counterbalanced order (Latin square), 12 and 1 hour (9 p.m and 8 a.m) before the beginning of the test, rats were administered pioglitazone or its vehicle. Yohimbine (2.0 mg/kg/ml) was administered to all animals at 30 min after the second pioglitazone administration, which corresponds to 30 min prior to the start of the reinstatement session. Reinstatement experiments and relative drug treatments were performed every third day. Between reinstatements, extinction baseline was re-established. The number of operant responses at both active and inactive lever was recorded.

Statistical analysis of variance revealed an overall significant effect of treatment [F $(4,7)$=12.153; P<0.01]. Post hoc Newman-Keuls test (FIG. 24) revealed a significant reinstatement of responding in yohimbine treated rats compared to extinction (p<0.001). At all doses tested (5.0, 10.0 and 30.0 mg/kg), pioglitazone significantly (p<0.001) decreased yohimbine-induced reinstatement of nicotine seeking. Responses at the inactive lever were not significantly modified by treatments [F $(4,7)$=2.358; NS]. These results suggest that PPARγ agonists may be used to treat nicotine addiction.

Example 29

Clinical Evaluation of Pioglitazone as a Treatment for Nicotine Addiction

Millions of people are addicted to nicotine worldwide, but despite the enormous health problems associated with tobacco smoking, very few medications are available to facilitate smoking cessation. Most therapies developed for nicotine addiction have shown only moderate success in reducing smoking and in preventing relapse, leading to a high failure rate in attempts to quit smoking. Classical testaments include the use of nicotine replacement products, anti-depressants (e.g., bupropione (Amfebutamone®, Wellbutrin®, Zyban®)), and behavioral therapy.

Recently a new medication, namely varenicline (Chantix®), which selectively targets the alpha4beta2 nicotinic acetylcholine receptors where it acts as a partial agonist, has been developed. Clinical evidence suggests that this agent has an improved efficacy profile compared to previously existing treatments. Nevertheless, after approximately one year from its commercialization, serious concerns about side effects associated with varenicline treatment are emerging.

In particular, positive associations between varenicline treatment, suicidal ideation, paranoia, and irritability have been described (Kohen and Kremen 2007; Morstad, Kutscher et al. 2008).

To provide clinical proof-of-concept of the efficacy of pioglitazone in the treatment of nicotine addiction, a pilot study in heavy tobacco smokers was conducted. For this purpose a three-arm study (3-4 patients per arm) was designed, where one group of subjects was treated with pioglitazone (15-30 mg/daily escalating doses), another group was treated with varenicline (dose titrated from 0.5 to 2.0 mg/day according to manufacturer instruction), and the third group received bupropione (150 mg/kg). Data were recorded for two months, during which patients were seen by the physician every other week. Patients were instructed to record in a personal logbook the number of cigarettes per day and the time of the day smoking occurred. At the end of the study, the logbooks were returned to the clinical personnel who analyzed the data. Every other week, participants were interviewed and subjected to the Spielberger State-Trait Anxiety Inventory (STAI), the Montgomery Asberg Depression Rating Scale (M.A.D.R.S 10 Item), and to a Visual Analogic Scale (VAS) to measure nicotine craving. During the first month of treatment, every two weeks, ACTH and cortisol levels were also monitored to evaluate HPA activation before and during treatment.

At recruitment, all participants completed the eight item Fagerström Tolerance Questionnaire (FTQ; Fargestrom Addicitive Bhaviour (1978)) to obtain data on nicotine dependence severity and were interviewed to register their sociodemographic characteristics. As shown in Table 6, patients were matched for duration of nicotine use and dependence, social status, etc. The Fargestrom scale revealed that all participants were severe smokers (Table 7).

Results

Daily Smoking:

Statistical analysis (ANOVA) revealed an overall significant effect of pharmacological treatments on the percent of weekly smoked cigarettes (Table 8). All four patients treated with pioglitazone completed the treatment. One of the subjects reached complete abstinence, two other subjects almost reached abstinence (97% inhibition of smoking), and one showed a marked reduction (75%) of smoking. The three participants receiving varenicline also showed a robust overall smoking reduction (95%), with one of them reaching complete abstinence. One of the patients treated with bupropione dropped out after four weeks of treatment. Prior to his dropping out, the inhibition of smoking in this patient was very modest (20%). The other two buporpione treated patients completed the treatment program, and after 10 weeks of drug administration, smoking was reduced by about 40%. Post hoc tests revealed a significant difference between pioglitazone and varenicline compared to bupropione ($p<0.05$), while no significant differences were identified between pioglitazone and varenicline. Together, these data suggest that pioglitazone and varenicline have comparable efficacy in lowering smoking, while bupropione is much less effective.

Biochemical Markers:

Blood tests showed that at recruitment all 10 participants had comparable plasma ACTH and cortisol levels, which were within a normal range. Treatments did not affect hormonal levels, suggesting that none of the drugs under investigation had effects on the stress axis activity (Table 9).

Anxiety:

The analysis of variance revealed a nonsignificant effect treatment ($[F(2,6)=0.68$ NS]) but a significant effect of time ($[F(5,10)=15.66$ $P<0.01]$), reflecting a progressive decrease in anxiety score over treatment weeks. STAI score (FIG. 25A) was significantly reduced in patients treated with pioglitazone and varenicline, but not with bupropione.

Depression:

The MADRS questioner score was low, and was not significantly affected by drug treatment ($[F(2,6)=3.11$ NS]). MADRS score remained at the same level throughout the 10 observation weeks (FIG. 25B).

Craving:

Results showed a progressive decrease in craving score measured with the visual analogic craving scale. Anova did not show any significant effect of treatment ($[F(2,6)=2.33$ NS]), while a significant effect of time ($[F(5,10)=72.37$ $P<0.001]$) and of treatment×time interaction ($[F(5,30)=30.63$ $P<0.001]$) was observed. As shown in FIG. 25C, craving progressively decreased over treatment. The highest reduction was observed in the varenicline and pioglitazone treated groups. Bupropione was less effective.

TABLE 6

Characteristics of the study participants on admission to treatment.

|  | Pioglitazone 15-30 mg 4 patients | Varenicline 3 patients | Bupropione 3 patients |
|---|---|---|---|
| Age | 49 ± 3.4 | 52 ± 4.2 | 46 ± 6.4 |
| Male sex | 3 | 2 | 3 |
| Female Sex | 1 | 1 | 0 |
| Married | All | All | All |
| Education (Years) | 9.3 ± 1.5 | 8.7 ± 2.4 | 9.3 ± 1.5 |
| Employed | All | 2 | 2 |
| Duration of nicotine use | 23 ± 7.8 | 21 ± 4.7 | 25 ± 3.7 |
| Living situation: with family | 100% | 100% | 100% |

TABLE 7

Evaluation of nicotine dependence severity using the Fargestrom Scale at recruitment (T = 0). Dependence score: Modest (0-2); Intermediate (3-4); High (5-6); severe (7-10)

| Pio | Patient 1 | Patient 2 | Patient 3 | Patient 4 |
|---|---|---|---|---|
| T = 0 | 5 | 8 | 10 | 9 |
| Var | Patient 1 | Patient 2 | Patient 3 | |
| T = 0 | 9 | 8 | 9 | |
| Bup | Patient 1 | Patient 2 | Patient 3 | |
| T = 0 | 7 | 10 | 9 | |

Pioglitazone (Pio); Varenicline (Var); Bupropione (Bup).

TABLE 8

Percent inhibition of smoking recorded every two weeks. T = 0 correspond to baseline data expressed as 100% and is a measure of smoking before entering the treatment. Patients were then visited after 2, 4, 6 8 and 10 weeks of treatment (T = 2-10).

| Pio | Patient 1 | Patient 2 | Patient 3 | Patient 4 |
|---|---|---|---|---|
| T = 0 | 100 | 100 | 100 | 100 |
| T = 2 | 27 | 24 | 25 | 23 |
| T = 4 | 49 | 39 | 44 | 41 |
| T = 6 | 57 | 46 | 66 | 53 |

TABLE 8-continued

Percent inhibition of smoking recorded every two weeks. T = 0 correspond to baseline data expressed as 100% and is a measure of smoking before entering the treatment. Patients were then visited after 2, 4, 6 8 and 10 weeks of treatment (T = 2-10).

| | | | | |
|---|---|---|---|---|
| T = 8 | 72 | 68 | 84 | 67 |
| T = 10 | 100 | 75 | 98 | 96 |

| Var | Patient 1 | Patient 2 | Patient 3 |
|---|---|---|---|
| T = 0 | 100 | 100 | 100 |
| T = 2 | 34 | 22 | 38 |
| T = 4 | 46 | 47 | 54 |
| T = 6 | 61 | 63 | 62 |
| T = 8 | 80 | 87 | 79 |
| T = 10 | 93 | 100 | 94 |

| Bup | Patient 1 | Patient 2 | Patient 3 |
|---|---|---|---|
| T = 0 | 100 | 100 | 100 |
| T = 2 | 100 | 100 | 100 |
| T = 4 | 20 | 18 | 15 |
| T = 6 | 28 | 20 | 21 |
| T = 8 | 34 | — | 34 |
| T = 10 | 40 | — | 45 |

Pioglitazone (Pio); Varenicline (Var); Bupropione (Bup).

TABLE 9

Plasma Adrenocorticotropic Hormone (ACTH) and Cortisol (CORT) levels in patients treated with Pioglitazone (Pio) Varenicline (Var) or bupropione (Bup). ACTH and Cortisol levels are expressed as pg/dl and μg/l, respectively. Blood samples were taken between 6:00 and 10:00 a.m.

| | Patient 1 | | Patient 2 | | Patient 3 | | Patient 4 | |
|---|---|---|---|---|---|---|---|---|
| Pio | ACTH | CORT | ACTH | CORT | ACTH | CORT | ACTH | CORT |
| T = 0 | 36 | 17 | 43 | 13 | 35 | 19 | 32 | 20 |
| T = 2 | 39 | 16 | 41 | 15 | 38 | 20 | 39 | 18 |
| T = 4 | 37 | 17 | 39 | 16 | 41 | 17 | 37 | 21 |
| T = 6 | | | | | | | | |
| T = 8 | | | | | | | | |
| T = 10 | | | | | | | | |

| | Patient 1 | | Patient 2 | | Patient 3 | |
|---|---|---|---|---|---|---|
| Var | ACTH | CORT | ACTH | CORT | ACTH | CORT |
| T = 0 | 39 | 21 | 41 | 19 | 47 | 17 |
| T = 2 | 36 | 20 | 40 | 17 | 46 | 20 |
| T = 4 | 40 | 18 | 38 | 18 | 41 | 24 |

| | Patient 1 | | Patient 2 | | Patient 3 | |
|---|---|---|---|---|---|---|
| Bup | ACTH | CORT | ACTH | CORT | ACTH | CORT |
| T = 0 | 38 | 20 | 54 | 21 | 44 | 24 |
| T = 2 | 35 | 19 | 52 | 24 | 41 | 23 |
| T = 4 | 37 | 17 | 51 | 29 | 40 | 21 |

Pioglitazone (Pio); Varenicline (Var); Bupropione (Bup)

The studies described herein showed that pioglitazone markedly reduces nicotine consumption and reinstatement of nicotine seeking elicited by administration of the pharmacological stressor, yohimbine. Importantly, results of proof-of-concept clinical study confirmed this effect of pioglitazone. Of the four heavy smokers receiving pioglitazone, three reached almost complete abstinence after two months of treatment. The fourth patient showed a 75% reduction. Psychometric tests revealed that none of the patients treated had comorbid anxiety or depression. During treatment, despite drastic reduction of smoking, rebound anxiety or depression was not observed. Higher efficacy of pioglitazone was observed in comparison to bupropione, while a comparable profile of efficacy was observed with varenicline.

Example 30

Effect of Pioglitazone on Morphine-Induced Analgesic Tolerance

To induce tolerance to morphine-induced analgesia, twice daily injections of a constant dose of morphine were administered to mice as previously described (Contet et al. 2008; Mamiya et al., 2001). 49 male CD mice (Charles River, Calco, Italy, weighing 28-30 g at the beginning of the experiment, were employed. All animals were handled for three days before the beginning of the treatment and behavioral tests. Experimental subjects were housed in common cages in rooms with artificial 12:12 h light/dark cycle (lights off at 9:00 a.m.), with constant temperature (20-22° C.) and humidity (45-55%). During the experiments, animals were offered free access to tap water and food pellets (4RF18, Mucedola, Settimo Milanese, Italy). Experiments were conducted during the dark phase of the light/dark cycle. All procedures were conducted in adherence to the *European Community Council Directive for Care and Use of Laboratory Animals*.

Mice were divided into 6 groups. Group 1 (n=8) received drug vehicles (veh/veh). Group 2 (n=9) received pioglitazone vehicle plus 30 mg/kg morphine. Group 3 (n=8) and Group 4 (n=8) received 10 or 30 mg/kg of pioglitazone followed by morphine vehicle. Group 5 (n=8) and Group 6 (n=7) received 10 or 30 mg/kg of pioglitazone followed by morphine. Animals were treated twice daily (between 9:00 and 10:00 a.m. and 9:00 and 10:00 p.m.).

Morphine hydrochloride was purchased from Salars (Milano, Italy). Morphine (30 mg/kg) was dissolved in NaCl 9% and was injected intraperitoneally (IP) twice a day at the indicated doses in a volume of 0.2 ml per mice. Pioglitazone was purchased from commercial sources (pharmacy). It was dissolved in distilled water and was administered per o.s. at the doses of 10 mg/kg and 30 mg/kg in a volume of 0.6 ml per mice.

Two different tests were used to monitor analgesic responses. The tail-flick test was performed 45 min after the morning injection of morphine, and the tail-immersion test was performed 45 min after the evening injection of morphine. These tests were chosen, because they involve a spinally-mediated reflex response and can be repeated several times on the same animal (Le Bars et al., 2001).

For the tail-flick test, each mouse was gently restrained in a soft tissue pocket, and the tail (1 cm from the tip) was exposed to a hot light beam. Latency for tail-flick was measured with a 6 seconds cut-off time. For the tail-immersion test, each mouse was restrained in a soft tissue pocket, and the distal half of the tail dipped into a water bath set at 52 C.°. Latency for removing the tail from the hot water was measured with a 10 seconds cut-off time.

In the tail-flick test, overall ANOVA revealed a significant effect of treatment [F (5,43)=44.37: $p<0.0001$]. As shown in FIG. 26 (upper panel), Newman-Keuls test revealed that morphine significantly increased the time to tail-flick on day 1, 3 and 5 ($p<0.01$). The analgesic effect of morphine progressively decreased, and non significant difference from controls were found on test days 7 and 9. Conversely, in mice treated with morphine plus pioglitazone, the difference between treated rats and controls remained significant for the whole duration of the experiment. This suggests that the development of morphine tolerance was substantially reduced by the combination. Analgesic responses in mice treated with pioglitazone alone did not differ from controls.

In the tail-immersion test, overall ANOVA revealed a significant effect of treatment [F (5.43)=87.89: $p<0.0001$]. As shown in FIG. 26 (lower panel), Newman-Keuls test revealed that morphine significantly increased the time to tail-flick on day 1, 3, 5, and 7($p<0.01$). The analgesic effect of morphine progressively decreased, and on test day 9, it was marginally significant. The combination of morphine with pioglitazone elicited a very potent analgesic effect that did not decay over time and remained highly significant for the whole duration of drug self-administration. Again, these data suggest that development of morphine tolerance was substantially reduced by the combination.

Example 31

Effect of Pioglitazone on Heroin Self-Administration

To test the effect of pioglitazone on heroin acquisition, 20 male Wistar rats (Charles River, Calco, Italy) were employed. At the beginning of the experiments, the animals' body weights ranged between 250 and 280 g. Rats were handled once daily for 5 min for one week before the beginning of the experiments, Experimental subjects were housed in common cages in rooms with artificial 12:12 h light/dark cycle (lights off at 9:00 a.m.), constant temperature (20-22° C.) and humidity (45-55%). During the experiments, animals were offered free access to tap water and food pellets (4RF18, Mucedola, Settimo Milanese, Italy). Experiments were conducted during the dark phase of the light/dark cycle. All procedures were conducted in adherence to the *European Community Council Directive for Care and Use of Laboratory Animals.*

The rats were divided into two groups. The first group (n=10) was treated twice daily (12 hours and 1 hour prior to the heroin operant session). The second group (n=10) was administered pioglitazone vehicle. Heroin self-administration sessions took place between 9:00 and 11:00 a.m. Sessions consisted of 2 hours heroin self-administration under an FR1 schedule of reinforcement where each lever pressing delivered an infusion of 0.1 ml of fluid. To avoid heroine overdosing, immediately after lever activation, the cue light above the active lever was on for 20 seconds, during which time lever presses did not activate the pump (TO=20 sec).

Heroine hydrochloride was purchased from Salars (Milano, Italy). Heroine was dissolved in NaCl 9% at a concentration of 10 µg/0.1 ml for infusion and given intravenously (IV). Pioglitazone was purchased from commercial sources (pharmacy). It was dissolved in distilled water and was administered per o.s. at the doses of 10 mg/kg and 30 mg/kg in a volume of 0.6 ml per mice.

Animals were anesthetized by intramuscular injection of 100-150 µl of a solution containing tiletamine cloridrate (58.17 mg/ml) and zolazepam cloridrate (57.5 mg/ml).

For IV surgery, incisions were made to expose the right jugular vein and the scull, and a catheter made from silicon tubing (I.D.=0.020 inches, O.D.=0.037 inches) was subcutaneously positioned between these two points. After insertion into the vein, the proximal end of the catheter was anchored to the muscles underlying the vein with surgical silk. The distal end of the catheter was attached to a stainless-steel cannula bent at a 90° angle. The cannula was inserted in a support made by dental cement on the scull of the animals, fixed with screws and covered with a plastic cap. For one week after surgery, rats were daily treated with 0.2 ml of the antibiotic Sodium Cefotaxime (262 mg/ml). For all the duration of the experiments, catheters were daily flushed with 0.2-0.3 ml of heparinized saline solution.

Body weights were monitored every day, and catheter patency was confirmed approximately every 3 days with an injection of 0.2-0.3 ml of thiopental sodium (250 mg/ml) solution. Patency of the catheter was assumed if there was an immediate loss of reflexes. Self administration experiments began one week after surgery.

The self-administration stations consisted of operant conditioning chambers (Med Associate Inc.) enclosed in sound-attenuating, ventilated environmental cubicles. Each chamber was equipped with two retractable levers located in the front panel of the chamber. Heroin was delivered by a plastic tube that was connected with the catheter before the beginning of the session. An infusion pump was activated by responses on the right or active lever, while responses on the left or inactive lever were recorded but did not result in any programmed consequences. Activation of the pump resulted in a delivery of 0.1 ml of fluid. An IBM compatible computer controlled the delivery of fluids and recording of the behavioral data.

In the pioglitazone vehicle treated group, heroin self-administration progressively increased over days. Conversely, in rats pre-treated with pioglitazone, operant responding for cocaine remained extremely low. This effect was reflected by a significant overall difference as demonstrated by Anova [F (1, 18)=18.714: $p<0.001$]. As shown in FIG. 27, statistical analysis showed that pioglitazone significantly decreased acquisition of heroin self-administration. Post-hoc comparisons confirmed a significant difference between control and the pioglitazone treated rats from day 3 to day 8. Inactive control lever was not affected by drug treatment [$F(1,18)=3.579$; $p>0.05$)].

Opiate drugs are the major pharmacological remedy used for pain treatment. However, it is important to recognize that abuse and addiction are potential side effects from chronic use of these compounds. Examples 30 and 31 demonstrated that the PPARγ agonist, pioglitazone, reduces development of morphine tolerance and prevents the acquisition of opioid addiction (e.g., heroine self-administration). Based on these finding, it is predicted that during chronic use of an opioid agent, the combination with pioglitazone would result in reduced risk of escalating morphine (or any other opiate agonist) doses and would prevent the development of opiate addiction.

PPARγ agonists have been shown to also possess intrinsic anti-inflammatory properties and reduce neuropatic pain. Hence, in addition to reducing morphine tolerance and addiction, they could also expand the analgesic profile of opioids.

Finally, combining the two active ingredients in the same formulation should prevent the possibility of inappropriate use of the opiate agents. Diversion risk in this case is limited, because as shown by the present data, opioid agonists lose their addictive potential when combined with PPARγ agonists.

Example 32

Effect of Pioglitazone on Acquisition of Food

To test the effect of pioglitazone on food pellets acquisition, three groups of Wistar rats were used. The first two groups (n=8/group) were treated twice a day (12 hours and 1 hour prior to the food operant session) with pioglitazone at 10 and 30 mg, respectively. The third group (n=8) was administered with drug vehicle. Food self-administration sessions took place between 9:00 and 10:00 a.m. Pioglitazone treatment was continued for the whole acquisition period (14 days). To increase rats' motivation for food pellet self-administration, rats were food-restricted and maintained at 80% of their normal body weight. Sessions consisted of 30-min food self-administration under an FR1 schedule of reinforcement, where each lever pressing delivered 45 mg food pellets. Immediately after lever activation, the cue light above the active lever was turned on for 10 seconds, during which time lever presses did not activate the feeder (TO=10 sec).

Results showed no effect of treatment [$F(2, 21)=0.748$: NS]. As shown in FIG. 28, all rats groups rapidly acquired operant responding for food and no significant differences were observed between pioglitazone and vehicle treated rats. Inactive control lever was also not affected by drug treatment [$F(2,21)=0.793$; $p>0.05$)] (data not shown).

Example 33

Effect of Pioglitazone on Food Self-Administration

To test the effect of pioglitazone on food self-administration, Wistar rats (n=24) were used. The rats were trained to self-administer food pellets under a fixed ratio FR1 (TO 10 sec) schedule of reinforcement for 30 min a day. Each lever pressing delivered 45 mg food pellets. During TO, lever presses were recorded but not reinforced with food delivery. The rats were trained to food self administer for several days, until a stable baseline of reinforcements was established. At this point, for four consecutive days (pretreatment), they were subjected to vehicle injection to habituate them to the drug administration procedure. At this point, drug pioglitazone treatment (10 and 30 mg/kg/ml) was begun. A third group of rats received drug vehicle and served as a control. Drug treatment was performed every day, twice daily for 4 consecutive days. The number of active operant responses at both active and inactive levers were recorded.

Results showed that on the first pretreatment day in all groups of rats, food intake was lower than that recorded during the rest of the study, because animals were not familiar with the injection procedure yet. Drug treatment started when all rats were trained to the administration procedure, and statistical evaluation of the results demonstrated no effect of treatment [$F(2, 21)=0.87$: NS]. As shown in FIG. 29, all rats showed a high rate of operant responding for food, and no differences were observed between pioglitazone and vehicle treated rats. Inactive control lever was also not affected by drug treatment ($F(2,21)=0.89$; NS; data not shown).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

REFERENCES

Abercrombie, E. D., R. W. Keller, Jr., et al. (1988). Characterization of hippocampal norepinephrine release as measured by microdialysis perfusion: pharmacological and behavioral studies. *Neuroscience* 27(3): 897-904.

Adams, A. D., et al. (2003). Amphipathic 3-phenyl-7-propylbenzisoxazoles; human PPAR gamma, delta, and alpha agonists. Bioorg. Med. Chem. Lett. 13(5):931-935.

Administration, S. A. a. M. H. S. (2003). Substance Abuse and Mental Health Services Administration, Overview of Findings from the 2002 National Survey on Drug Use and Health, Substance Abuse and Mental Health Services Administration Rockville, Md. Office of Applied Studies.

Aghajanian, G. K. and C. P. VanderMaelen (1982). alpha 2-adrenoceptor-mediated hyperpolarization of locus coeruleus neurons: intracellular studies in vivo. *Science* 215 (4538): 1394-6.

Ahmed, S. H. and Koob, G. F., Cocaine—but not food-seeking behaviour is reinstated by stress after extinction, *Psychopharmacology,* 132, 289, 1997.

Ang E, Chen J, Zagouras P, Magna H, Holland J, Schaeffer E, et al. (2001). Induction of nuclear factor-kappaB in nucleus accumbens by chronic cocaine administration. *J. Neurochem.* 79:221-224.

Anton, R. F., D. H. Moak, et al. (1996). The obsessive compulsive drinking scale: A new method of assessing outcome in alcoholism treatment studies. *Arch Gen Psychiatry* 53(3): 225-31.

Asanuma M., Cadet J. L. (1998). Methamphetamine-induced increase in striatal NF-kappaB DNA-binding activity is attenuated in superoxide dismutasetrangenic mice. *Brain Res Mol Brain Res* 60:305-30, 9.

Association, A. P. (1994). Diagnostic and Statistical Manual of Mental Disorders, Fourth Edition. Washington, D.C., American Psychiatric Association.

Balakumar, P., et al. (2007). PPAR dual agonists: are they opening Pandora's Box?. *Pharmacol Res* 56(2):91-98.

Barroso, I., Gurnell, M., Crowley, V. E. Agostani, M., Schwabe, J. W., Soos, M. A., Maslen, G. L., Williams, T. D. Lewis, H., Schafer, A. J., et al., *Dominant negative mutations in human PPARgamma associated with severe insulin resistance, diabetes mellitus and hypertension.* Nature. 1999; 402:880-3.

Blanchard, R. J., Hori, K., Tom, P., and Blanchard, C., Social structure and ethanol consumption in laboratory rats, Pharmacol. *Biochem. Behav.,* 28, 437, 1987.

Bordet, R., T. Ouk, et al. (2006). PPAR: a new pharmacological target for neuroprotection in stroke and neurodegenerative diseases. *Biochem Soc Trans* 34(Pt 6): 1341-6.

Bowers M. S., Kalivas P. W. (2003). Forebrain astroglial plasticity is induced following withdrawal from repeated cocaine administration. *Eur J Neurosci* 17:1273-1278.

Breidert T., Callebert J., Heneka M. T., Landreth G. E., Launary J. M., Hirsch E. C.: Protectiv action of the peroxisome proliferator-activated receptor gamma agonist pioglitazone in a mouse model of Parkinson's disease. *J Neurochem* 2002; 82:615-624.

Brown S. A., Vik P. W., Patterson T. L., et al. Stress, vulnerability and adult alcohol relapse. *J Studies Alcohol* 1995; 56:538.

Bruijnzeel A. W., Markou A. Characterization of the effects of bupropion on the reinforcing properties of nicotine and food in rats. *Synapse.* 2003; 50: 20-8.

Bruno, F. (1989). Buspirone in the treatment of alcoholic patients. *Psychopathology* 22(Suppl 1): 49-59.

Bucther, S. P., Hensshall, D. C., Teramura, Y, Iwasaki, K., Sharkey, J., 1997. Neuroprotetive actions of FK501 in experimentala stroke: in vivo evidence against an antiexcitotoxic mechanism. *J Neurosci.* 17, 6939-694.

Burstein S. PPAR-gamma: a nuclear receptor with affinity for cannabinoids. *Life Sci.* 2005; 77:1674-84.

Cador, M., B. J. Cole, et al. (1993). Central administration of corticotropin releasing factor induces long-term sensitization to D-amphetamine. *Brain Res* 606(2): 181-6.

Cernuda-Morollon, E, Rodriguez-Pascual, F., Klatt, lamas, Perez-Sala, D., 2002. PPAR agonists amplify iNOS expression while inhibiting NF-kappaB: implications for mesangial cell activation by cytokines. *J. Am. Soc. Nephrol.* 13, 2223-2231.

Childress, A. R., Ehrman, R. N., McLellan, A. T., and O'Brien, C. P., Conditioned craving and arousal in cocaine addiction: A preliminary report, in NIDA Research Monograph 81, US Government Printing Office, Washington, D.C., 1988, 74.

Chinetti G, Fruchart J. C., Staels B. (2000). Peroxisome proliferator-activated receptors (PPARs): nuclear receptors at the crossroads between lipid metabolism and inflammation. *Inflamm Res* 49: 497-505.

Ciccocioppo R., Angeletti S., Sanna P. P., Weiss F., Massi M. Effect of nociceptin/orphanin FQ on the rewarding properties of morphine. *Eur J Pharmacol.* 2000; 404: 153-9.

Ciccocioppo R., Katner S. N., Weiss F. Relapse induced by alcohol-associated environmental stimuli after extinction in rats. *Alcohol Clin Exp Res* 1999-c; 23(Suppl):52A.

Ciccocioppo R., Panocka I., Polidori C., Regoli D., Massi M. Effect of nociceptin on alcohol intake in alcohol-preferring rats. *Psychopharmacology* 1999-a; 141:220-4.

Ciccocioppo R., Sanna P. P., Weiss F. Cocaine-predictive stimulus induces drug-seeking behaviour and neural activation in limbic brain regions after multiple months of abstinence: reversal by D(1) antagonists. *Proc Natl Acad Sci USA* 2001-b; 98(4):1976-81.

Cohen C., Perrault G., Griebel G., Soubrié P. Nicotine-associated cues maintain nicotine-seeking behavior in rats several weeks after nicotine withdrawal: reversal by the cannabinoid (CB1) receptor antagonist, rimonabant (SR141716). *Neuropsychopharmacology.* 2005; 30:145-55.

Compton, W. M. and N. D. Volkow (2006). Abuse of prescription drugs and the risk of addiction. *Drug Alcohol Depend* 83 Suppl 1: S4-7.

Compton, W. M. and N. D. Volkow (2006). Major increases in opioid analgesic abuse in the United States: concerns and strategies. *Drug Alcohol Depend* 81(2): 103-7.

Contet C, Filliol D, Matifas A, Kieffer B L (2008). Morphine-induced analgesic tolerance, locomotor sensitization and physical dependence do not require modification of mu opioid receptor, cdk5 and adenylate cyclase activity. *Neuropharmacology.* 54(3):475-86.

Mamiya T, Noda Y, Ren X, Nagai T, Takeshima H, Ukai M, Nabeshima T (2001). Morphine tolerance and dependence in the nociceptin receptor knockout mice. *J Neural Transm.* 108(12):1349-6.

Crews F., Nixon K., Kim D., Joseph J., Shukitt-Hale B., Qin L., Zou J. 2006. BHT blocks NF-kappaB activation and ethanol-induced brain damage. *Alcohol Clin Exp Res.* 30:1938-49.

Cristiano L., Cimini A., Moreno S., Ragnelli A. M., Paola Ceru M. (2005). Peroxisome proliferator-activated receptors (PPARs) and related transcription factors in differentiating astrocyte cultures. *Neuroscience* 131: 577-587.

Crosby M. B., Zhang J., Nowing T. M, Svenson J. L., Nicol C. J., Gonzalez F. J. et al. (2006). Inflammatory modulation of PPAR gamma expression and activity. *Clin Immunol* 118:276-283 [E-pub 2005 November 2021].

De Souza E. B. Corticotropin-releasing factor receptors: physiology, pharmacology, biochemistry and role in central nervous system and immune disorders. *Psychoneuroendocrinology* 1995; 20(8):789-819.

Deeb, S., Fajas, L., Nemoto, M., Laakso, M., Fujimoto, W. & Auwerk, J., (1998) *Nat Genet.* 20, 284-287.

Delva, J., J. M. Wallace, Jr., et al. (2005). The epidemiology of alcohol, marijuana, and cocaine use among Mexican American, Puerto Rican, Cuban American, and other Latin American eighth-grade students in the United States: 1991-2002. *Am J Public Health* 95(4): 696-702.

Di Chiara G., Imperato A. Drugs abused by humans preferentially increase synaptic dopamine concentrations in the mesolimbic system of freely moving rats. *Proc Natl Acad Sci USA.* 1988; 85(14):5274-8.

Dunn, A. J. and Berridge, C. W., Physiological and behavioural responses to corticotropin-releasing factor administration: is CRF a mediator of anxiety or stress responses?, *Brain Res Brain Res Rev,* 15, 71, 1990.

Ehrman, R. N., Robbins, S. J., Childress, A. R., and O'Brien, C. P., Conditioned responses to cocaine-related stimuli in cocaine abuse patients, *Psychopharmacology,* 107, 523, 1992.

Erb Suzanne, Shaham Yavin, Stewart Jane. The Role of Corticotropin-Releasing Factor and Corticosterone in Stress- and Cocaine-Induced Relapse to Cocaine Seeking in Rats. *J Neurosci* 1998; 18(14):5529-3

Evans, J. L. et al. (2005). Novel approach to treat insulin resistance, type 2 diabetes, and the metabolic syndrome: simultaneous activation of PPARalpha, PPARgamma, and PPARdelta. *Curr Diabetes Rev* 1(3):299-307.

Feinstein D. L. (2003). Therapeutic potential of peroxisome proliferator-activated receptor agonists for neurological disease. *Diabetes Technol Ther* 5: 67-73.

Feinstein D. L., Galea E., Gavrilyuk V., Brosnan C. F., Whitacre C. C., Dumitrescu-Ozimek L., Landreth G. E., Pershdsingh H. A., Heneka M. T: peroxisomeproliferator-activated receptor-gamma agonists prevent experimental autoimmune encephalomyelitis. *Ann Neuronal* 2002; 51:694-702.

Feldman, P. L., et al. (2008). PPAR modulators and PPAR pan agonists for metabolic diseases: the next generation of drugs treating peroxisome proliferator-activated receptors? *Curr Top Med Chem* 8(9):728-749.

Furumaka, S., et al. Increased oxidative stress in obesity and its impact on metabolic syndrome. *J. Clin. Invest.* 114: 1752-1761.

Glatz A. C., Ehrlich M., Bae R. S., Clarke M. J., Quinlan P. A., Brown E. C., Rada P., Hoebel B. G. Inhibition of cocaine self-administration by fluoxetine or D-fenfluramine combined with phentermine. *Pharmacol Biochem Behav.* 2002; 71:197-204.

Goeders, N. E. and Guerin, G. F., Non-contingent electric shock facilitates the acquisition of intravenous cocaine self-administration in rats, *Psychopharmacology*, 114, 63, 1994.

Gonzalez, I. C., et al. (2007). Design and synthesis of a novel class of dual PPARgamma/delta agonists. *Bioorg. Med Chem Lett.* 17(4):1052-1055.

Gonzalez-Zalueta, M., Ensz, L. M., Mukhina, G., Lebovitz, R. M., Zwacka, R. M., Engelhardt, J. F., Oberley, L. W., Dawson, V. L., Dawson, T. M., 1998. Manganese superoxide dismutase protects nNOS neurons from NMDA and nitric oxide-mediated neurotoxicity. *J. Neurosci.* 18, 2040-2055.

Gracy, K. N., Dankiewicz, L. A., Weiss, F., and Koob, G. F., Heroin-specific cues reinstate heroin-seeking behaviour in rats after prolonged extinction, Pharmacol. *Biochem. Behav.*, 65, 489, 2000.

Haney, M., Maccari, S., Le Moal, M., Simon, H., and Piazza, P. V., Social stress increases the acquisition of cocaine self-administration in male and female rats, *Brain Res.*, 698, 46, 1995.

Harris S. G., Phipps R. P.: Prostaglandin D(2), its metabolite 15-d-PGJ(2), and peroxisome proliferator-activated receptor gamma agonists induce apoptosis in transformed, but not normal, human T lineage cells. *Immunology* 2002; 105:23-34.

Heinrichs, S. C., Merlo Pich, E., Miczek, K. A., Britton, K. T., and Koob, G. F., Corticotropin-releasing factor reduces emotionality in socially defeated rats via direct neurotropic action, *Brain Res.*, 581, 190, 1992.

Heneka M. T., Feinstein D. L., Gleichamann M., Wullner U., Klockgether T: Peroxide proliferator-activated receptor gamma agonists protect cerebellar granule cells from cytokine-induced apoptotic cell death by inhibition of inducible nitric oxide synthase. *J Neuroimmunol* 1999; 100:156-168.

Higley, J. D., Hasert, M. F., Suomi, S. J., and Linnoila, M., Nonhuman primate model of alcohol abuse: effect of early experience, personality, and stress on alcohol consumption., *Proc. Natl. Acad. Sci. USA*, 88, 7261, 1991.

Hofmann C., Lorenz K., Braithwaite S. S. et al. Altered gene expression for tumor necrosis factor-γ and its receptors during drug and dietary modulation of insulin resistance. *Endocrinology* 1994; 134:264-270.

Hollenberg, A. N., Susulic, V. S., Madura, J. P., Zhang, B., Moller, D. E., Tontonoz, P., Sarraf, P., Spielgelman, (1997) *J. Biol. Chem.* 272, 5283-5290.

Holmberg, G., S. Gershon, et al. (1962). Yohimbine as an autonomic test drug. *Nature* 193: 1313-4.

Hotta, K., et al. 2001. Circulating concentrations of the adipocyte protein adiponectin are decreased in parallel with reduced insulin sensitivity during the progression to type 2 diabetes in rhesus monkeys. *Diabetes.* 50:1126-1133.

Hu, E., Liang, P., and Spiegelman, B. M. (1996) Adipo Q is a novel adipose-specific gene dysregulated in obesity. *J. Biol. Chem.* 271: 10697-10703.

Hwang, J., Kleinhenz, D. J., Lassegue, B., Griendling, K. K., Dikalov, S., Hart, C. M., 2005. Peroxisome proliferator-activated receptor-gamma ligands regulate endothelial membrane superoxide production *Am. J. Physiol.: Cell Physiol.* 288, C899-C905.

Janiri, L., G. Gobbi, et al. (1996). Effects of fluoxetine at antidepressant doses on short-term outcome of detoxified alcoholics. *Int Clin Psychopharmacol* 11(2): 109-17.

Jiang C, Ting A. T., Seed B. (1998) PPARγ agonists inhibit production of monocyte inflammatory cytokines. *Nature* 391:82-86.

Kainu T, Wikstrom A. C., Gustafsson J. A., Pelto-Huikko M.: Localization of the peroxisome proliferator-activated receptor in the brain. *Neuroreport* 1994; 5:2481-2485.

Kapadia, R., J. H. Yi, et al. (2008). Mechanisms of anti-inflammatory and neuroprotective actions of PPAR-gamma agonists. *Front Biosci* 13: 1813-26.

Kasuga, J., et al. (2008). Improvement of the transactivation activity of phenylpropanoic acid-type peroxisome proliferator-activated receptor pan agonists: effect of introduction of fluorine at the linker part. *Bioorg. Med Chem Lett.* 18(16):4525-4528.

Katner, S. N., Magalong, J. G., and Weiss, F., Reinstatement of alcohol-seeking behaviour by drug-associated discriminative stimuli after prolonged extinction in the rat, *Neuropsychopharmacology*, 20, 471, 1999.

Katner S. N. and Weiss F. Ethanol-associated olfactory stimuli reinstate ethanol-seeking behaviour after extinction and modify extracellular dopamine levels in the nucleus accumbens. *Alcohol Clin Exp Res* 1999; 23:1751.

Kielian, T., Drew, P. D., 2003. Effects of peroxisome proliferator-activated receptor-gamma agonists on central nervous system inflammation. *J. Neurosci. Res.* 71, 315-325.

Kliwer, S. A., Lenhard, J. M., Willson, T. M., Patel, I., Morris, D. C., Lehmann, J. M., 1995. A prostaglandin J2 metabolite binds peroxisome proliferator-activated receptor-gamma and promotes adipocyte differentiation. *Cell* 83, 813-819.

Kohen, I. and N. Kremen (2007). Varenicline-induced manic episode in a patient with bipolar disorder. *Am J Psychiatry* 164(8): 1269-70.

Koob G. F., Heinrichs S. C., Menzaghi F., et al. Corticotropin releasing factor, stress and behaviour. *Semin Neurosci* 1994; 6:221.

Koob G. F., Sanna P. P., Bloom F. E. Neuroscience of addiction. *Neuron* 1998; 21:467-76.

Koob G. F. Drugs of abuse: Anatomy, pharmacology and function of reward pathways. *Trends Pharmacol Sci* 1992; 13:177-84.

Kubota, N., et al., Pioglitazone ameliorates insulin resistance and diabetes by both adiponectin dependent and independent pathways. *J. Biol. Chem.* 281:8748-8755.

Landreth, G. (2006). PPARgamma agonists as new therapeutic agents for the treatment of Alzheimer's disease. *Exp Neurol* 199(2): 245-8.

Landreth, G., Q. Jiang, et al. (2008). PPARgamma agonists as therapeutics for the treatment of Alzheimer's disease. *Neurotherapeutics* 5(3): 481-9.

Landreth, G. E. and M. T. Heneka (2001). Anti-inflammatory actions of peroxisome proliferator-activated receptor gamma agonists in Alzheimer's disease. *Neurobiol Aging* 22(6): 937-44.

Le A. D., Harding S., Juzytsch W., Watchus J., Shalev U., Shaham Y. The role of corticotrophin-releasing factor in stress-induced relapse to alcohol-seeking behaviour in rats. *Psychopharmacology (Berl)* 2000; 150(3):317-24.

Le A. D, Harding S., Juzytsch W., Funk D., Shaham Y. Role of alpha-2 adrenoceptors in stress-induced reinstatement of alcohol seeking and alcohol self-administration in rats. *Psychopharmacology* (Berl). 2005; 179:366-73.

Le Bars, D., Gozariu, M., Cadden, S. W., 2001. Animal models of nociception. *Pharmacol. Rev.* 53, 597-652.

Lee B., Tiefenbacher S., Platt D. M., Spealman R. D. Pharmacological blockade of alpha2-adrenoceptors induces reinstatement of cocaine-seeking behavior in squirrel monkeys. *Neuropsychopharmacology.* 2004; 29:686-93.

Letteron P., Fromenty B., Terris B. Acute and chronic hepatic steatosis lead to in vivo lipid peroxidation in mice. *J Hepatol* 1996; 24:200-208.

Levine J. A., Harris M. M., Morgan M. Y. Energy expenditure in chronic abuse. *Eur. J. Clin. Invest.* 2000; 30:779-787.

Liu, X. and Weiss, F., Reinstatement of ethanol-seeking behaviour by stress- and drug-related cues in rats with a history of ethanol dependence, *Soc. Neurosci. Abstr.* 26, 786, 2000.

Liu X., Weiss F. Reversal of ethanol-seeking behaviour by D1 and D2 antagonists in an animal model of relapse: differences in antagonist potency in previously ethanol-dependent versus nondependent rats. *J Pharmacol Exp Ther* 2002; 300(3):882-9.

Lopez-Liuchi, J. V. and C. A. Meier (1998). PPARgamma: from adipose tissue to the atherosclerotic plaque. *Eur J Endocrinol* 139(4): 363-4.

Maeda, K., et al. 1996. cDNA cloning and expression of a novel adipose specific collagen-like factor, apM1 (Adipose most abundant Gene transcript 1). *Biochem. Biophys. Res. Commun.* 221: 286-289.

Maeda, N., et al. 2001. PPARγ ligands increase expression and plasma concentrations of adiponectin, an adipose derived protein. *Diabetes.* 50:2094-2099.

Maeda, T., N. Kiguchi, et al. (2007). Peroxisome proliferator-activated receptor gamma activation relieves expression of behavioral sensitization to methamphetamine in mice. *Neuropsychopharmacology* 32(5): 1133-40.

Mao, X., et al. 2006. APPL1 binds to adiponectin receptors and mediates adiponectin signalling and function. *Nat. Cell Biol.* 8:516-523.

Marlatt, G. A., Relapse prevention: introduction and overview of the model, in Relapse Prevention: Maintenance Strategies in the Treatment of Addictive Behaviours, Guilford, London, 1985, 3.

McKay, J. R., Rutherford, M. J., Alterman, A. I., Cacciola, J. S., and Kaplan, M. R., An examination of the cocaine relapse process, *Drug Alcohol Dep.*, 38, 35, 1995.

McCusker C. G., Brown K. The cue-responsivity phenomenon in dependent drinkers: 'personality' vulnerability and anxiety as intervening variables. *Br J Addict* 1991; 86:905-12.

McEwen B. S., Magarinos A. M., Reagan L. P. 2002. Studies of hormone action in the hippocampal formation: possible relevance to depression and diabetes. *J Psychosom Res.;* 53(4):883-90.

Merali, Z., McIntosh, J., Kent, P., Michaud, D., and Anisman, H., Aversive and Appetitive Events Evoke the Release of Corticotropin—Releasing Hormone and Bombesin-Like Peptides at the Central Nucleus of the Amygdala, *J. Neurosci.*, 18, 4758, 1998.

Merlo Pich, E., Lorang, M. T., Yeganeh, M., De Fonseca, F. R., Raber, J., Koob, G. F., and Weiss, F., Increase of extracellular corticotropin-releasing factor-like immunoreactivity levels in the amygdala of awake rats during restraint stress and ethanol withdrawal as measured by microdialysis, *J. Neurosci.*, 15, 5439, 1995.

Miller, N. S. and Gold, M. S., Dissociation of "conscious desire" (craving) from and relapse in alcohol and cocaine dependence, *Ann. Clin. Psychiatry,* 6, 99, 1994.

Mollenauer, S., Bryson, R., Robinson, M., Sardo, J., and Coleman, C., EtOH Self-administration in anticipation of noise stress in C57BL/6J mice, *Pharmacol. Biochem. Behav.,* 46, 35, 1993.

Monti P. M., Rohsenow D. J., Rubonis A. V., Niaura R. S., Sirota A. D., Colby S. M., Abrams D. B. Alcohol cue reactivity: effects of detoxification and extended exposure. *J Stud Alcohol* 1993; 54:235-45.

Morstad, A. E., E. C. Kutscher, et al. (2008). Hypomania with agitation associated with varenicline use in bipolar II disorder. *Ann Pharmacother* 42(2): 288-9.

Nash, J., Jr. and Maickel, R. P., The role of the hypothalamic-pituitary-adrenocortical axis in post-stress induced ethanol consumption by rats, *Prog Neuropsychopharmacol Biol Psychiatry,* 12, 653, 1988.

Nishikawa T, Mataga N, Takashima M, Toru M (1993). Behavioural sensitization and relative hyperresponsiveness of striatal and limbic dopaminergic neurons after repeated MHET treatment. *Eur J Pharmacol* 88: 195-203.

O'Brien C P (1997). A range of research-based pharmacotherapies for addiction. *Science* 278: 66-70.

Oliveira A. et al., Antinociceptive and antiedematogenic activities of fenofibrate, an agonist of PPAR alpha, and pioglitazone, an agonist of PPAR gamma, *Eur J Pharmacol.* 561(1-3):194-201 (2007).

Panocka I, Ciccocioppo R, Mosca M, Polidori C, Massi M. Effects of the dopamine D1 receptor antagonist SCH 39166 on the ingestive behaviour of alcohol-preferring rats. *Psychopharmacology* (Berl) 1995; 120(2):227-35.

Park, E. J., Park, S. Y., Jou, I., 2003 15d-PGJ2 and rosiglitazone suppress janus kinase-STAT inflammatory signaling through induction of suppressor of cytokine signaling 1 (SOCS1) and SOCS3 in glia. *J. Biol. Chem.* 278, 14747-14752.

Peltier R, Schenk S. Effects of serotonergic manipulations on cocaine self-administration in rats. *Psychopharmacology* (Berl). 1993; 110:390-4.

Pomerleau, O. F., Fertig, J., Baker, L., and Cooney, N., Reactivity to alcohol cues in alcoholics and non-alcoholics: Implications for the stimulus control analysis of drinking, *Addict. Behav.,* 8, 1, 1983.

Ramsey, N. F. and Van Ree, M., Emotional but not physical stress enhances intravenous cocaine self-administration in drug naive rats, *Brain Res.*, 608, 216, 1993.

Rauhut A. S., Neugebauer N., Dwoskin L. P., Bardo M. T. Effect of bupropion on nicotine self-administration in rats. *Psychopharmacology* (Berl). 2003; 169:1-9.

Rudolph, J., et al. (2007). Indanylacetic acid derivatives carrying 4-thiazolyl-phenoxy tail groups, a new class of potent PPAR alpha/gamma/delta pan agonists: synthesis, structure-activity relationship, and in vivo efficacy. *J Med Chem* 50(5):984-1000.

Sanchis-Segura C., Spanagel R. Behavioural assessment of drug reinforcement and addictive features in rodents: an overview. *Addict Biol.* 2006; 11:2-38.

Shaham, Y., Immobilization stress-induced oral opioid self-administration and withdrawal in rats: role of conditioning factors and the effect of stress on "relapse" to opioid drugs, *Psychopharmacology*, 111, 477, 1993.

Shaham Y and Stewart J. Stress reinstates heroin-seeking in drug-free animals: an effect mimicking heroin, not withdrawal. *Psychopharmacology* 1995; 119:334.

Shah, P., et al. (2008). CoMFA analysis of dual/multiple PPAR activators. *Eur J Med Chem* 43(12):2784-2791.

Shalev U., Yap J., Shaham Y. 2001 Leptin attenuates acute food deprivation-induced relapse to heroin seeking. *J Neurosci.* 15; 21(4):RC129.

Siegal, H. A., R. G. Carlson, et al. (2003). Probable relationship between opioid abuse and heroin use. *Am Fam Physician* 67(5): 942, 945.

Sorensen T. I., Orholm M., Bentsen K. D., Hoybye G., Eghoje K., Christoffersen P. 1984 Prospective evaluation of alcohol abuse and alcoholic liver injury in men as predictors of development of cirrhosis. *Lancet.* 2(8397): 241-4.

Sorge R. E., Rajabi H., Stewart J. Rats maintained chronically on buprenorphine show reduced heroin and cocaine seeking in tests of extinction and drug-induced reinstatement. *Neuropsychopharmacology.* 2005; 30:1681-92.

Souza S. C., Yamamoto M. T., Franciosa M. D., Lien P., BRL 49653 blocks the lipolytic actions of tumor necrosis factor-$\alpha$: a potential new insulin sensitizing mechanism for thiazolidinediones. *Diabetes* 1998; 47:691-695.

Steensland P., Simms J. A., Holgate J., Richards J. K., Bartlett S. E. Varenicline, an alpha4beta2 nicotinic acetylcholine receptor partial agonist, selectively decreases ethanol consumption and seeking. *Proc Natl Acad Sci USA.* 2007; 104:12518-23.

Stormark, K. M., Laberg, J. C., Bjerland, T., Nordby, H., and Hugdahl, K., Autonomic cued reactivity in alcoholics: The effect of olfactory stimuli, *Addict. Behav.*, 20, 571, 1995.

Substance Abuse and Mental Health Services Administration (2003). Substance Abuse and Mental Health Services Administration, Emergency Department Trends From the Drug Abuse Warning Network, Final Estimates 1995-2002, Substance Abuse and Mental Health Services Administration, Rockville, Md. Office of Applied Statistics.

Substance Abuse and Mental Health Services Administration (2004). Substance Abuse and Mental Health Services Administration, Mortality Data from the Drug Abuse Warning Network, 2002, Substance Abuse and Mental Health Services Administration, Rockville, Md. Office of Applied Statistics.

Swiergiel, A. H., Takahashi, L. K., and Kalin, N. H., Attenuation of stress-induced behaviour by antagonism of corticotropin-releasing factor receptors in the central amygdala in the rat, *Brain Res*, 623, 229, 1993.

Takehara T., Nakamura T., Protective effect of hepatocyte growth factor on in vitro hepatitis in primary cultured hepatocytes. *Biomed. Res.* 1991; 12:335-338.

Tiffany, S. T. and Carter, B. L., Is craving the source of compulsive drug use?, J Psychopharmacol, 12, 23, 1998.

Tsuchida, A., et al. 2005. Peroxisome proliferator-activated receptor (PPAR) alpha activation increases adiponectin receptors and reduces obesity related inflammation in adipose tissue: comparison of activation of PPARalpha, PPARgamma, and their combination. *Diabetes.* 54:3358-3370.

Volpicelli J. R., Alterman A. I., Hayashida M., O'Brien C. P. Naltrexone in the treatment of alcohol dependence. *Arch Gen Psychiatry* 1992; 49:876-880.

Wallace, B. C., Psychological and environmental determinants of relapse in crack cocaine smokers, *J Subst Abuse Treat*, 6, 95, 1989.

Weiss, F. and Ciccocioppo, R., Environmental stimuli potently reinstate alcohol-seeking behaviour: Effect of repeated alcohol intoxication, *Soc. Neurosci. Abstr.*, 25, 1081, 1999.

Weiss F., Ciccocioppo R., Parsons L. H., Katner S., Liu X., Zorrilla E. P., Valdez G. R., Ben-Shahar O., Angeletti S., Richter R. R. Compulsive drug-seeking behaviour and relapse. Neuroadaptation, stress, and conditioning factors. *Ann N Y Acad Sci* 2001; 937:1-26.

Weiss F., Lorang M. T., Bloom F. E., Koob G. F. Oral alcohol self-administration stimulates dopamine release in the rat nucleus accumbens: genetic and motivational determinants. *J Pharmacol Exp Ther* 1993; 267:250-8.

Weiss, F., Maldonado-Vlaar, C. S., Parsons, L. H., Kerr, T. M., Smith, D. L., and Ben-Shahar, O., Control of cocaine-seeking behaviour by drug-associated stimuli in rats: Effects on recovery of extinguished operant responding and extracellular dopamine levels in amygdala and nucleus accumbens, *Proc. Natl. Acad. Sci. USA,* 97, 4321, 2000.

Wise R. A. Drug activation of brain reward pathways. *Drug Alcohol Depend* 1998; 51:13-22.

Wu Z., Bucher N. L., Farmer S. R. (1996). Induction of peroxisome proliferator-activated receptor-gamma during the conversion of 3t3 fibroblasts into adipocytes is mediated by C/EBPbeta, C/EPBdelta, and glucocorticoids. *Mol Cell Biol* 16: 4128-4136.

Xu, Y., et al. (2006). Design and synthesis of dual peroxisome proliferator-activated receptors gamma and delta agonists as novel euglycemic agents with a reduced weight gain profile. *J Med Chem* 49(19):5649-5652.

Yamauchi, T., et al. 2001. The fat derived hormone adiponectin reverses insulin resistance associated with both lipoatrophy and obesity. *Nat. Med.* 7:941-946.

Yamauchi, T., et al. 2003. Cloning of adiponectin receptors that mediate antidiabetic metabolic effects. *Nat. Med.* 423:762-769.

Young, P. W., D. R. Buckle, et al. (1998). Identification of high-affinity binding sites for the insulin sensitizer rosiglitazone (BRL-49653) in rodent and human adipocytes using a radioiodinated ligand for peroxisomal proliferator-activated receptor gamma. *J Pharmacol Exp Ther* 284(2): 751-9.

Yu X, Shao X. G., Sun H., Li Y. N., Yang J., Deng Y. C., Huang Y. G. Activation of cerebral peroxisome proliferator-activated receptors gamma exerts neuroprotection by inhibiting oxidative stress following pilocarpine-induced status epilepticus. *Brain Res.* 2008; 1200C:146-58.

Yu, J. G., et al. 2002. The effect of thiazolidinediones on plasma adiponectin levels in normal, obese, and type 2 diabetic subjects. *Diabetes.* 51:2968-2974.

Zalcman S., Savina I., Wise R. A. (1999). Interleukin-6 increases sensitivity to the locomotor-stimulating effects of amphetamine in rats. *Brain Res* 847: 276-283.

Zhao, M. L., Brosnan, C. F, Lee, S. C., 2004. 15-Deoxy-delta (12-14)-PGJ2 inhibits astrocyte IL-1 signaling: inhibition of NF-kappaB and MAP kinase pathways and suppression of cytokine and chemokine expression. *J. Neuroimmunol.* 153, 132-142.

The invention claimed is:

1. A method of treating or reducing the likelihood of an addiction, comprising:
   determining that a subject has an addiction to an addictive agent or to the practice of an addictive or compulsive behavior;
   determining that the subject has (a) undergone a period of abstinence from or limited or reduced use of the addictive agent, or (b) undergone a period of abstinence from or limited or reduced practice of the addictive or compulsive behavior; and
   providing to the subject an amount of an agonist of a peroxisome proliferator-activated receptor gamma (PPARγ agonist) effective to reduce the reward action from practice of the addiction, wherein the PPARγ agonist is a thiazolidinedione (TZD) and wherein the PPARγ agonist is effecting for treating or preventing relapse use of the addictive agent or practice of the addictive or compulsive behavior.

2. The method of claim 1, wherein the subject is addicted to an addictive agent.

3. The method of claim 2, wherein the subject is addicted to an addictive agent selected from the group consisting of: alcohol, nicotine, marijuana, a marijuana derivative, an opioid agonist, a benzodiazepine, a barbiturate, and a psychostimulant.

4. The method of claim 3, wherein the addictive agent is nicotine.

5. The method of claim 3, wherein the addictive agent is an opioid agonist is selected from the group consisting of: morphine, methadone, fentanyl, sufentanil, and diacetylmorphine (heroin), alfentanil, allylprodine, alphaprodine, anileridine, apomorphine, benzylmorphine, beta-hydroxy 3-methylfentanyl, bezitramide, carfentanil, clonitazene, codeine, desomorphine, dextromoramide, diampromide, dihydrocodeine, dihydroetorphine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, etorphine, hydrocodone, hydromorphone, hydroxypethidine, isomethadone, ketobemidone, LMM, levorphanol, levophenacylmorphan, lofentanil, meperidine, metopon, metazocine, methadyl acetate, metapon, myrophine, narceine, nicomorphine, norlevorphanol, normethadone, normorphine, norpipanone, opium, oxycodone, oxymorphone, papaverine, phenadoxone, phenomorphan, phenoperidine, piminodine, piritramide, propheptazine, promedol, properidine, propoxyphene, remifentanil, thebaine, tildine, tramadol, noscapine, nalorphine, naloxone, naltrexone, phenazocine and propoxyphene.

6. The method of claim 3, wherein the addictive agent is a psychostimulant selected from the group consisting of cocaine, amphetamine or and an amphetamine derivative.

7. The method of claim 1, wherein the subject is addicted to an addictive or compulsive behavior.

8. The method of claim 7, wherein the addictive or compulsive behavior is selected from the group consisting of: pathological gambling, pathological overeating, pathological use of electronic devices, pathological use of electronic video games, pathological use of electronic communication devices, pathological use of cellular telephones, addiction to pornography, sex addiction, obsessive compulsive disorder, compulsive spending, anorexia, bulimia, intermittent explosive disorder, kleptomania, pyromania, trichotillomania, compulsive overexercising, and compulsive overworking.

9. The method of claim 1, wherein the TZD is selected from the group consisting of: pioglitazone, rosiglitazone, ciglitazone, troglitazone, englitazone, rivoglitazone and darglidazone.

10. The method of claim 9, wherein the TZD is pioglitazone.

11. The method of claim 1, further comprising providing an additional therapeutic agent, wherein each of the PPARγ agonist and the additional therapeutic agent contribute to the effective treatment or prevention of the addiction.

12. The method of claim 11, wherein said additional therapeutic agent is selected from the group consisting of: an opioid antagonist, a mixed opioid partial agonist/antagonist, an antidepressant, an antiepileptic, an antiemetic, a corticotrophin-releasing factor-1 (CRF-1) receptor antagonist, a selective serotonin-3 (5-HT3) antagonist, a 5-HT2A/2C antagonist, and a cannabinoid-1 (CB1) receptor antagonist.

13. The method of claim 11, wherein the additional therapeutic agent is an opioid antagonist selected from the group consisting of naltrexone and nalmefene.

14. The method of claim 11, wherein the additional therapeutic agent is an antidepressant selected from the group consisting of fluoxetine, mirtazapine, and bupropion.

15. The method of claim 11, wherein the additional therapeutic agent is an antiepileptic selected from the group consisting of benzodiazepines, barbituates, valproates, GABA agents, iminostilibenes, hydantoins, NMDA antagonists, sodium channel blockers and succinamides.

16. The method of claim 11, wherein the additional therapeutic agent is a CRF-1 receptor antagonist that is antalarmin.

17. The method of claim 11, wherein the additional therapeutic agent is a selective serotonin-3 (5-HT3) antagonist that is ondansetron.

18. The method of claim 11, wherein the additional therapeutic agent is a cannabinoid-1 (CB1) receptor antagonist selected from the group consisting of rimonabant and tanarabant.

19. The method of claim 11, wherein the additional therapeutic agent is a mixed opioid agonist/antagonist that is buprenorphine.

20. The method of claim 1, wherein the subject previously reduced or eliminated use of the addictive agent or practice of the addictive or compulsive behaviour in response to treatment with an effective amount of an anti-addiction treatment, and wherein the subject is no longer exposed to an effective amount of the anti-addiction treatment.

* * * * *

UNITED STATES PATENT AND TRADEMARK OFFICE
CERTIFICATE OF CORRECTION

PATENT NO. : 10,064,850 B2  
APPLICATION NO. : 15/231239  
DATED : September 4, 2018  
INVENTOR(S) : Roberto Ciccocioppo Page 1 of 1

It is certified that error appears in the above-identified patent and that said Letters Patent is hereby corrected as shown below:

In the Specification

| Column | Line | Error |
|---|---|---|
| 13 | 45 | "nicotine addition" should read --nicotine addiction-- |
| 14 | 4 | "nicotine addition" should read --nicotine addiction-- |
| 21 | 67 | "analgesic affect" should read --analgesic effect-- |
| 23 | 30 | "nicotone" should read --nicotine-- |
| 25 | 61 | "PPARδ/δ" should read --PPARβ/δ-- |
| 26 | 60 | "HDI levels" should read --HDL levels-- |
| 34 | 31 | "Ie et al." should read --Le et al.-- |
| 41 | 38 | "Reminqtons" should read --Remingtons-- |
| 54 | 51 | "experiment was conduced" should read --experiment was conducted-- |
| 66 | 7 | "higher that that" should read --higher than that-- |
| 68 | 19 | "PPRγ" should read --PPARγ-- |
| 68 | 22 | "PPRAγ" should read --PPARγ-- |
| 68 | 31 | "inactive leversis" should read --inactive levers is-- |
| 68 | 51 | "opioid parial" should read --opioid partial-- |
| 69 | 1 | "PPRγ" should read --PPARγ-- |
| 69 | 3 | "PPRAγ" should read --PPARγ-- |
| 70 | 57 | "testaments include" should read --treatments include-- |
| 71 | 49 | "buporpione" should read --bupropion-- |

Signed and Sealed this  
Eighth Day of October, 2019

Andrei Iancu  
*Director of the United States Patent and Trademark Office*